United States Patent
Newell et al.

(10) Patent No.: US 7,510,710 B2
(45) Date of Patent: Mar. 31, 2009

(54) COMPOSITIONS OF UCP INHIBITORS, FAS ANTIBODY, A FATTY ACID METABOLISM INHIBITOR AND/OR A GLUCOSE METABOLISM INHIBITOR

(75) Inventors: Martha Karen Newell, Colorado Springs, CO (US); Evan Newell, Toronto (CA); Elizabeth Villobos-Menvey, Monument, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 11/031,109

(22) Filed: Jan. 7, 2005

(65) Prior Publication Data

US 2006/0140953 A1 Jun. 29, 2006

Related U.S. Application Data

(60) Provisional application No. 60/534,896, filed on Jan. 8, 2004, provisional application No. 60/535,077, filed on Jan. 8, 2004, provisional application No. 60/566,746, filed on Apr. 29, 2004.

(51) Int. Cl.
*A61K 39/395* (2006.01)
*A61K 31/675* (2006.01)
*A01N 43/04* (2006.01)

(52) U.S. Cl. .......... 424/146.1; 424/450; 424/130.1; 424/138.1; 424/141.1; 514/27; 514/43; 514/79

(58) Field of Classification Search .......... None
See application file for complete search history.

(56) References Cited

U.S. PATENT DOCUMENTS

| 4,724,234 A | 2/1988 | Cone, Jr. |
| 4,935,450 A | 6/1990 | Cone, Jr. |
| 5,556,754 A | 9/1996 | Singer et al. |
| 5,585,363 A | 12/1996 | Scanlon et al. |
| 5,587,397 A | 12/1996 | Fox |
| 5,739,159 A | 4/1998 | Wolf |

(Continued)

FOREIGN PATENT DOCUMENTS

EP 0 239 400 9/1987

(Continued)

OTHER PUBLICATIONS

Cabrero et al., Biochemica et Biophysica Acta. 2001; 1532:195-202.*

(Continued)

*Primary Examiner*—Gary B Nickol
*Assistant Examiner*—Cherie M. Woodward
(74) *Attorney, Agent, or Firm*—Wolf Greenfield & Sacks, PlC.

(57) ABSTRACT

Systems and methods for treating inflammatory and proliferative diseases, and wounds, using as a pharmacon a UCP and/or Fas antibody or other inhibitor, or combination thereof, and a therapeutically acceptable amount of a fatty acid metabolism inhibitor and/or a therapeutically acceptable amount of a glucose metabolism inhibitor, optionally in combination with one or more chemotherpeutic agents. In preferred embodiments, the invention combines an antibody against UCP and/or Fas antigen with an oxirane carboxylic acid, represented by etomoxir, and/or with a 2-deoxyglucose compound, represented by 2-deoxy-D-glucose. The systems and methods of the invention can be used to treat drug-resistant or multi-drug resistant cancers.

6 Claims, 59 Drawing Sheets

U.S. PATENT DOCUMENTS

| | | | |
|---|---|---|---|
| 6,133,946 | A | 10/2000 | Cavallaro et al. |
| 6,140,067 | A | 10/2000 | Anderson et al. |
| 6,331,559 | B1 | 12/2001 | Bingham et al. |
| 6,416,958 | B2 | 7/2002 | Vidovic |
| 6,569,853 | B1 | 5/2003 | Borisy et al. |
| 6,582,713 | B2 | 6/2003 | Newell et al. |
| 6,670,330 | B1 | 12/2003 | Lampidis et al. |
| 6,846,816 | B2 | 1/2005 | Borisy et al. |
| 6,951,887 | B2 | 10/2005 | Bingham et al. |
| 7,160,865 | B2 | 1/2007 | Lampidis et al. |
| 2002/0107234 | A1 | 8/2002 | Bingham et al. |
| 2003/0150022 | A1 | 8/2003 | Martha et al. |
| 2003/0212138 | A1 | 11/2003 | Obukowicz |
| 2004/0005291 | A1 | 1/2004 | Rogers et al. |
| 2004/0116407 | A1 | 6/2004 | Borisy et al. |
| 2005/0020682 | A1 | 1/2005 | Newell et al. |
| 2005/0042224 | A1 | 2/2005 | Newell |
| 2005/0043250 | A1 | 2/2005 | Lampidis et al. |
| 2005/0074882 | A1 | 4/2005 | Newell |
| 2005/0158333 | A1 | 7/2005 | Newell et al. |
| 2005/0202559 | A1 | 9/2005 | Pownall et al. |
| 2006/0025351 | A1 | 2/2006 | Lampidis et al. |
| 2006/0140953 | A1 | 6/2006 | Newell et al. |
| 2006/0247199 | A1 | 11/2006 | Newell et al. |

FOREIGN PATENT DOCUMENTS

| | | |
|---|---|---|
| WO | WO 87/00751 | 2/1987 |
| WO | WO 95/15161 | 6/1995 |
| WO | WO 98/02579 | 1/1998 |
| WO | WO 98/31396 | 7/1998 |
| WO | WO 98/45313 | 10/1998 |
| WO | WO 98/45438 | 10/1998 |
| WO | WO 00/47617 | 8/2000 |
| WO | WO 00/78941 | 12/2000 |
| WO | WO 01/34145 | 5/2001 |
| WO | WO 03/031643 | 4/2003 |
| WO | WO 03/037323 | 5/2003 |
| WO | WO 2004/111199 | 12/2004 |

OTHER PUBLICATIONS

Alberts et al., Eds. The Cell. Fourth Ed., 2002, Garland Science Press, at pp. 856, 857, 1396.*
Strieleman et al., J Biol Chem. Nov. 5, 1985; 260(25):13402-13405.*
Clement et al., EMBO J. Jan. 15, 1996; 15(2):216-225.*
Kuhajda et al., PNAS USA. Mar. 28, 2000; 97(7): 3450-3454; Epub Mar. 14, 2000.*
Huppertz et al., J Biol Chem. Apr. 20, 2001; 276(16):12520-12529.*
Dulloo et al., (Biochemical Society Transactions. 2001; 29(6):785-791.*
Li et al., Endocrinology. Apr. 2002; 143(4):1371-1377.*
Patane et al., Diabetes. Sep. 2002; 51:2749-2756.*
Samec et al., Pflugers Arch—Eur J Physiol. 1999; 438:452-457.*
Harper et al., FASEB J. Oct. 2002;16(12):1550-7.*
Koop et al., Biochem J 1993; 295:165-170.*
Healy et al., Clinical Science. Aug. 2002; 103:179-189.*
Li et al., Endocrinology. Apr. 2002; 143(4)1371-1377 (previously cited in the Office Action of Nov. 27, 2006).*
Kaplan et al., Cancer Res. Feb. 1, 1990;50(3):544-51, Abstract Only.*
Baselga et al. J.Natl.Canc.Inst. Aug. 18, 1993;85(16):1327-33, Abstract Only.*
Tschmelitsch et al. Canc.Res. Jun. 1, 1997;57(11):2181-6, Abstract Only.*
Timmer et al., J Pathol. Feb. 2002;196(2):125-34, Abstract Only.*
Mills et al., J Biol Chem. Jul. 26, 2002;277(30):27385-92. Epub May 14, 2002, Abstract Only.*
Ohta et al., J Neurooncol. Oct. 1997; 35(1):7-11, Abstract only.*
Abdel-aleem et al., Horm Metab Res. 1994;26:99-91.*
Venkatesan et al., Metabolism. Jan. 1996;45(1):92-100.*
Agrawal S., et al., "Antisense therapeutics: is it as simple as complementary base recognition?," Molecular Med. Today, vol. 6, pp. 72-81 (2000).
Arsenijevic et al., "Disruption of the uncoupling rpotein-2 gene in mice reveals a role in immunity and reactive oxygen species production," Nat. Genet., Dec; 26(4):435-9 (2000).
Asoh et al., "Expression of the apoptosis-mediator Fas is enhanced by dysfunctional mitochondria," J. Biochem (Tokyo), Sep; 120(3):600-7 (1996).
Babu et al., "Genetic control of multisystem autoimmune disease in encephalomycarditis virus infected BALB/cCUM and BALB/cBYJ mice," Curr Top Microbiol Immunol. 122:154-61 (1985).
Bach et al., "Insulin-dependent diabetes mellitus as an autoimmune disease," Endocr Rev. Agu; 15(4):516-42 (1994).
Baggetto, "Deviant energetic metabolism of glycolytic cancer cells," Biochimie. Nov; 74(11):959-74 (1992).
Berg, S.L. et al, "Pharmacokinetics of taxol and doxorubicin administered alone and in combination by continuous 72-hour infusion," J. Nat. Cancer Inst., 86(2):143-145 (1994).
Bhushan et al., "Drug resistance results in alterations in expression of immune recognition molecules and failure to express Fas (CD95)," Immunol. Cell Biol. Agu; 76(4):350-6 (1998).
Billingham et al., "Activity acquired tolerance of foreign cells," Nature Oct. 3:172(4379):603-6 (1953).
Birnboim et al., "Levels of DNA stand breaks and superoxide in phorbol ester-treated human granulocytes," J. Cell Biochem Aug. 1; 66(2):219-28 (1997).
Bitar, M.S. "Co-Adminstration of Etomoxir and RU-486 Mitigates Insulin Resistance in Hepatic and Muscular Tissues of STZ-Induced Diabetic Rats," Hormone and Metabolic Research, vol. 33(10) Jan. 1 p. 577-584 (2001).
Black et al., "Glycolytic enzyme inhibitor therapy in human malignant neoplasia," Cancer Res. May 1;9:314-319 (1949).
Bohme et al., "Transgenic mice with I-A on islet cells are normoglycemic but immunologically intolerant," Science, Jun. 9; 244(4909):1179-83 (1989).
Bonfoco et al., "Inducible nonlymphoid expression of Fas ligand is responsible for superantigen-induced peripheral deletion of T cells," Immunity, Nov; 9(5):711-20 (1998).
Bouillaud, F. et al., "A sequence related to a DNA recognition element is essential for the inhibition of nucleotides of proton transport through the mitochondrial uncoupling protein," The EMBO Journal, vol. 13, No. 8, pp. 1990-1997 (1994).
Branch, A., "A good antisense molecule is hard to find," Trends in Biochem. Sci., vol. 23, pp. 45-50 (1998).
Bristol Myers Squibb product information for TAXOL (paclitaxel), Mar. 2003, Bristol Meyers Squibb, Princeton, NJ 6 pages.
Bull et al., "Mode of Action of Liver Tumor Induction by Trichloroethylene and Its Metabolites, Trichloroacetate and Dichloroacetate," vol. 108 p. 241-259 (2000).
Caldwell et al., "Evaluation of methods for the isolation of plasma membranes displaying guanosine 5'-triphosphate-dependence for the regulation of adenylate cyclase activity: potential application to study of other guanosine 5'-triphosphate-dependent transduction systems," Anal. Biochem. Nov. 15; 175(1): 177-90 (1988).
Calkins et al., "UNL Beef Cattle Reports. University of Nebraska Cooperative Extension MP17," Beef, Feb. (1999) 3 pages.
Cambier et al., "Ia binding ligands and cAMP stimulate nuclear translocation of PKC is B lymphocytes," Nature, Jun. 18-24; 327(6123):629-32 (1987).
Carrel et al, "Recombinant interferon-γ can induce the expression of HLA-DR and -DC on DR-negative melanoma cells and enhance the expression of HLA-ABC and tumor-associated antigens," Eru. J. Immunol. 15(2):118-123 (1985).
Chien et al., "Fas-induced B cell apoptosis requires an increase in free cytosolic magnesium as an early event," J Biol. Chem., Mar. 12; 274(11): 7059-66 (1999).
Chirila, T. et al., "The use of synthetic polymers for delivery of therapeutic antisense oligodeoxynucleotides," Biomaterials, vol. 23, pp. 321-342 (2002).
Chisari et al., "Molecular pathogenesis of hepatocellular carcinoma in hepatits B virus trangenic mice," Cell, Dec. 22;59(6): 1145-56 (1989).

Conceicao-Silva et al., "The resolution of lesions induced by Leishmania major in mice requires a functional Fas (APO-1, CD95) pathway of cytotoxicity," Eur. J. Immunol. Jan; 28(1): 237-45 (1998).
Constantini et al., "Mitochondrion as a Novel Target of Anticancer Chemotherapy," J of Nat'l Cancer Inst., vol. 92, p. 1042-1053 (2000).
Cosgrove et al., "Evaluation of the functional equivalence of major histocompatibility complex class II A and E complexes," J. Exp. Med., Aug. 1; 176(2):629-34 (1992).
Cosgrove et al., "Mice lacking MHC class II molecules,"Cell, Sep. 6; 66(5):1051-66 (1991).
Cossarizza et al., "Mitochondrial modifications during rat thymocyte apoptosis: a study at the single cell level," Exp. Cell Res. Sep; 214(1): 323-30 (1994).
Craighead et al., "Diverse patterns of immune and non-immune-mediated disease in EMC M-variant-infected mice," J. Autoimmun. Apr;3 Suppl. 1:27-9 (1990).
Creech et al., "MHC genes modify systemic autoimmune disease. The role of the I-E locus," J. Immunol. Jan 15; 156(2):812-7 (1996).
Crump et al., "Gemcitabine, dexamethasone, and cisplatin in patients with recurrent or refractory aggressive histology B-cell non-Hodgkin lymphoma: a Phase II study by the National Cancer Institute of Canada Clinical Trials Group (NCIC-CTG)," Cancer 101(8): 1835-1842 (2004).
Dang et al., "Oncogenic alterations of metabolism," Trends Biochem Sci. Feb; 24(2): 68-72 (1999).
Denis-Pouxviel et al., "Regulation of mitochondrial hexokinase in cultured HT 29 human cancer cells. An ultrastructural and biochemical study," Biochim Biophys Acta. Sep. 3; 902(3):335-48 (1987).
Desbarats et al, "Fas (CD95) expression and death-mediating function are induced by CD4 cross-linking on CD4+ T cells," PNAS Oct. 1;93(20):11014-8 (1996).
Desbarats et al., "Newly discovered role for Fas ligand in the cell-cycle arrets of CD4+ T cells," Nat. Med. Dec; 4(12):1377-82 (1998).
Durig et al., "Lactic acidosis and hypoglycemia in a patient with high-grade non-Hodgkin's lymphoma and elevated circulating TNF-alpha," Ann. Hematol. vol. 72 pp. 97-99 (Abstract Only) (1996).
Elipoulos, A.G. et al, "CD40 Stimulation Augments Apoptosis in Carcinoma Cell Lines," J. Cellular Biochem, (supplemental 19B), Abstract B8-123, p. 271 (1995).
Fantin et al., A novel mitochondriotoxic small molecule that selectively inhibits tumor cell growth, Cancer Cell, vol. 2, p. 29-42 (2002).
Fanciulli et al., "Effect of the antiumor drug lonidamine on glucose metabolism of adriamycin-sensitive and -resistant human breast cancer cells," Oncology Res., 8(3):111-120 (1996).
Fleury et al., "Uncoupling protein-2: a novel gene linked to obesity and hyperinsulinemia," Nat. Genet. Mar; 15(3):269-72 (1997).
Freedman et al., "gamma delta T-cell-human glial cell interactions. II. Relationship between heat shock protein expression and susceptibility to cytolysis," J. Neuroimmunol. Apr; 74(1-2):143-8 (1997).
Fujihashi et al., "gamma/delta T cell-deficient mice have impaired mucosal immunoglobulin A responses," J. Exp. Med. Apr. 1; 183(4): 1929-35 (1996).
Garban et al., "Signal transduction via human leucocyte antigen class II molecules distinguishes between cord blood, normal, and malignant adult B lymphocytes,"Exp. Hematol. Aug;26(9):874-84 (1998).
Garlid et al., "The mechanism of proton transport mediated by mitochondrial uncoupling proteins," FEBS Lett. Oct. 30; 438(1-2):10-14 (1998).
Genestier et al., "Caspase-dependent ceramide production in Fas- and HLA class I-mediated peripheral T cell apoptosis," J Biol Chem. Feb. 27; 273(9):5060-6 (1998).
Golshani-Hebroni et al., "Hexokinase binding to mitochondria: a basis for proliferative energy metabolism," J. Bioenerg. Biomembr. Aug; 29(4):331-8 (1997).
Gonzalez-Barroso et al., "The uncoupling protein UCPI does not increase the proton conductance of the inner mitochondrial membrane by functioning as a fatty acid anion transporter," J. Biol. Chem, Jun. 19; 273(25):15528-32 (1998).
Gorer et al., "The genetic and antigenic basis of tumour transplantation," J Pathol. 44:691-7 (1937).
Gray et al., "Mitochondrial evolution," Science Mar. 5; 283(5407):1476-81 (1999).

Greiner et al., "Glucose is essential for proliferation and the glycolytic enzyme induction that provokes a transition to glycolytic energy production," J Biol. Chem Dec. 16; 269(50):31484-90 (1994).
Harper et al., "Use of top-down elasticity analysis to identify sides of thyroid hormone-induced thermogenesis," Proc Soc Exp Biol Med. Mar;208(3):228-37 (1995).
Harrington-Brock et al., "Mutagenicity of three disinfection by-products: di- and trichloroacetic acid and chloral hydrate in L5178Y/TK +/− (−)3.7.2c mouse lymphoma cells," Mutation Research, vol. 413, No. 3, pp. 265-276 (Abstract) (1998).
Hatefi et al., "Nicotinamide nucleotide transhydrogenase: a model for utilization of substrate binding energy for proton translocation," FASEB J. Mar; 10(4):444-52 (1996).
Haynes et al, "Helper-inducer T-lymphocytes mediate diabetes in EMC-infected BALB/c By J mice," Diabetes Jul; 36(7):877-81 (1987).
Helander et al., "Molecular Cloning and Characterization of the Human Mitochondrial 2,4-Dienoyl-CoA Reductase Gene (DECR)," Genomics 46 1997; 112-119.
Hermesh et al., "Mitochondria uncoupling by a long chain fatty acyl analogue," J. Biol Chem, Feb. 13; 237(7):3937-42 (1998).
Hess et al,. "Cooperation of glycolytic enzymes," Adv. Enzyme Regul. 7:149-67 (1969).
Hess et al., "A novel function of CD40: induction of cell death in transformed cells," J. Exp. Med., 183:159-167 (1996).
Hosokawa et al, "Beta-cell hypersensitivity to glucose following 24-h exposure of rat islets to fatty acids," Diabetologia Apr; 40(4):392-7 (1997).
Huber et al, "Differential Th1 and TH2 cell responses in male and female BALB/c mice infected with coxsackievirus group B type 3," J. Virol. Aug; 68(8):5126-32 (1994).
Huber et al, "Modulation of cytokine expression by CD4+ T cells during coxsackievirus B3 infections of BALB/c mice initiated by cells expressing the gamma delta + T-cell receptor," J. Virol. May; 70(5):3039-44 (1996).
Ianniello, G.P. et al., "Cisplatin, epirubicin, and vindesine with or without Ionidamine in the treatment of inoperable nonsmall cell lung carcinoma: a multicenter randomized clinical trial," 78(1):63-69 (1996).
Johnson et al., "Relationships between drug activity in NCI preclinical in vitro and in vivo models and early clinical trials," British J. of Cancer, 84(10): 1424-1431 (2001).
Kang et al., "Fas ligand expression in islets of Langerhans does not confer immune privilege and instead targets them for rapid destruction," Nat Med. Jul; 3 (7):738-43 (1997).
Kaplan et al, "Effects of 2-deoxyglucose on drug-sensitive and drug-resistant human breast cancer cells: toxicity and magnetic resonance spectrocopy studies of metabolism," Cancer Res. Feb. 1; 50(3):544-51 (1990).
Kennedy et al., "Effects of depletion of mitochondrial DNA in metabolism secretion coupling in INS-1 cells," Diabetes Mar;47(3):374-80 (1998).
Kiberstis et al. "Mitochondria make a comeback," Science Mar. 5;283(5407):1475 (1999).
Korshunov et al., "Fatty acids as natural uncouplers preventing generation of O2.- and H2O2 by mitochondria in the resting state," FEBS Lett. Sep. 18; 435(2-3):215-8 (1998).
Kubota et al., "Phase II study of concurrent chemotherapy and radiotherapy for unresectable stage III non-small-cell lung cancer: long-term follow-up results. Japan Clinical Oncology Group Protocol 8902," Ann. Oncol. vol. 11; pp. 445-450 (Abstract Only) (2000).
Larrouy et al., "Kupffer cells are a dominant site of uncoupling protein 2 expression in rat liver," Biochem Biophys Res. Commun. Jun. 27;235(3):760-4 (1997).
Lefracois et al., "Extrathymic sselection of TCR gamma delta + T cells by class II major histocompatibility complex molecules," Cell Oct. 19;63(2):333-40 (1990).
Le Meur et al., "Correcting an immune-response deficiency by creating E alpha gene transgenic mice," Nature Jul. 4-10;316(6023):34-42 (1985).
Le Meur et al., "Restricted assembly of MHC class II molecules in transgenic mice," J Immunol. Jan. 1;142(1):323-7 (1989).

Lee et al, "HLA-DR-mediated signals for hematopoiesis and induction of apoptosis involve but are not limited to a nitric oxide pathway," Blood Jul. 1;90(1):217-25 (1997).

Lissoni et al., "Ten-year survival results in metastatic renal cell cancer patients treated with monoimmunotherapy with subcutaneous low-dose interleukin-2," Anticancer Res., vol. 22, pp. 1061-1064 (Abstract Only) (2002).

Lobato, M. et al., "Intracellular antibodies and challenges facing their use as therapeutic agents," Trends in Molecular Medicine, vol. 9, No. 9, pp. 390-396 (2003).

Logan et al, "A glycyl radical site in the crystal structure of a class III ribonculetode reductase," Science, Mar. 5;283(5407):1499-504 (1999).

Loudon et al, "An attenuated variant of Coxackievirus B3 preferentially induces immunoregulatory T cells in vivo," J. Virol. Nov;65(11):5813-9 (1991).

Luft et al., "Mitochondrial medicine," J. Intern Med. Nov; 238(5):405-21 (1995).

Luhder et al., "Major histocompatibility complex class II molecules can protect from diabetes by positively selecting T cells with additional specificities," J Exp Med. Feb. 2;187(3):379-87 (1998).

Mackaness et al., "The J. Burns Amberson Lecture The Induction and expression of cell-mediated bypersensitivity in the lung," Am. Rev. Respir Dis. Dec;104(6):813-28 (1971).

Marzo et al., "Bax and adenine nucleotide translocator cooperate in the mitochondrial control of apoptosis," Science Sep. 25;281(5385):2027-31 (1998).

Maruricio et al., "Apoptosis and the pathogenesis of IDDM a question of life and death," Diabetes Oct;47(10):1537-43 (1998).

Meuer et al., "Cellular signalling in T lymphocytes," Immunol. Today Aug;10(8):S23-5 (1989).

Meyer et al., "Giant cell myocarditis due to coxsackie B2 virus infection," Cardiology, May-Jun.; 88(3):296-9 (1997).

Mieza et al., "Selective reduction of V alpha 14+ NK T cells associated with disease development in autoimmune-prone mice," J. Immunol. May 15;156(10):4035-40 (1996).

Mills et al., "Regulation of cellular oncosis by uncoupling protein 2," J Biol Chem Jul. 26; 277(30):27385-92 2002 Epub May 14 (2002).

Molero et al, "Recovery of polyols from flexible polyurethane foam by "split-phase" glycolysis: Glycol influence," Polymer Degradation and Stability, Feb; 9 1(2):221 (2006).

Morimoto et al., "Overcoming tumor necrosis factor and drug resistance of human tumor cell lines by combination treatment with anti-Fas antibody and drugs or toxins," Cancer Res. Jun. 1;53(11):2591-6 (1993).

Nakamoto et al., "Immune pathogenesis of hepatocellular carcinoma," J Exp Med Jul. 20;188(2):341-50 (1998).

Negre-Salvayre et al., "A role for uncoupling protein-2 as a regulator of mitochondrial bydrogen peroxide generation," FASEB J. Aug; 11(10):809-15 (1997).

Newell et al., "Does the oxidative/glycolytic ratio determine proliferation or death in immune recognition," Ann NY Acad Sci., 887:77-82 (1999).

Newell et al., "The effects of chemotherapeutics on cellular metabolism and consequent immune recognition," J Immune Based Ther Vaccines, Feb. 2;2(1):3 (2004).

Newell et al., "Ligation of major histocompatibility complex class II molecules mediates apoptotic cell death in resting B lymphocytes," PNAS USA Nov. 15;90(22):10459-63 (1993).

Newell et al., "Death of mature T cells by separate ligation of CD4 and the T-cell receptor for antigen," Nature Sep. 20;347(6290):286-9 (1990).

Newell et al., "Biochemical characterizatoin of proteins that co-purify with class II antigens of the murine MHC," J Immunol. Mar. 15;140-(6):1930-8 (1998).

Newell et al, "Studies with glycolysis-deficient cells suggest that production of lactic acid is not the only cause of tumor acidity," PNAS; vol. 90; pp. 1127-1131 (1993).

Palu, G. et al., "In pursuit of new developments for gene therapy of human diseases," J of Biotech, vol. 68 pp. 1-13 (1999).

Pecqueur et al., "Uncoupling protein 2, in vivo distribution, induction upon oxidative stress, and evidence for translation regulation," J Biol. Chem, Mar. 23;276(12):8705-12, Epub Nov. 29, 2000 (2001).

Posada et al, "Human multidrug resistant KB cells overexpress protein kinase C: involvement in drug resistance," Cancer Communication; 1(5):285-292 (1989).

Posselt et al., "Induction of donor-specific unresponsiveness by intrathymic islet transplantation," Science Sep. 14;249(4974):1293-5 (1990).

Reyes et al., "The proinflammatory cytokine network: interactions in the CNS and blood of rhesus monkeys," Am J. Physiol. Jan;274(1 Pt 2): R139-44 (1998).

Roe et al., "2,4-Dienoyl-Coenzyme A Reductace Deficiency: A Possible New Disorder of Fatty Acid Oxidation," J. Clin. Invest. 85, May 1990; 1703-1707.

Ruiz-Ruiz et al., "Activation of protein kinase C attenuates early signals in Fas-mediated apoptosis," Eur J. Immunol. Jun; 27(6):1442-50 (1997).

Rustenbeck et al., "Energetic requirement of insulin secretion distal to calcium influx," Diabetes, Aug;46(8):1305-11 (1997).

Saraste et al., "Oxidative phosphorylation at the fin siecle," Science, Mar. 5;283(5407):1488-93 (1999).

Satoh et al, "Changes in mitochondrial membrane potential during oxidative stress-induced apoptosis in PC12 cells," J. Neurosci Res Nov. 1;50(3):413-20 (1997).

Sausville et al., "Contributions of human tumor xenografts to anti-cancer drug development," Cancer Research, vol. 66; pp. 3351-3354 (2006).

Saydjari et al., "2-Deoxy-D-glucose inhibits the antitumor effects of alpha-difluoromethylornithine on the growth of colon cancer in vivo," Invest New Drugs Jul;7(2-3):131-8 (1989).

Scaffidi et al, "Two CD95 (APO-1/Fas) signaling pathways," EMBO J. Mar. 16;17(6):1675-87 (1998).

Schattner et al, "CD40 ligation induces Apo-1/Fas expression on human B lymphocytes and facilitates apoptosis through the Apo-1/Fas pathway," J Exp Med. Nov. 1;182(5):1557-65 (1995).

Schild et al., "The nature of major histocompatibility complex recognition by gamma delta T cells," Cell, Jan. 14;76(1):29-37 (1994).

Schrezenmeier et al., "Inactivation of a T cell receptor-associated GTP-binding protein by antibody-induced modulation of the T cell receptor/CD3 complex," J Exp Med. Aug. 1;168(2):817-22 (1988).

Sciorati et al., "Autocrine nitric oxide modulates CD95-induced apoptosis in gammadelta T lymphocytes," J Biol. Chem. Sep. 12;272(37):23211-5 (1997).

Shoukry and Schultz; "Significance of the Reductase-dependent Pathway for the β-Oxidation of Unsaturated Fatty Acids with Odd-numbered Double Bonds," J. Biol. Chem. 273(12) 1998; 6892-6899.

Skerrett et al, "New transplant method evades immune attack," Science Sep. 14;249(4974):1248 (1990).

Snell et al., "Some recollections of Peter Gorer and his work on this fiftieth anniversary of his discovery of H-2," Immunogenetics 24(6):339-40 (1986).

Snell et al, "The Novel Lectures in Immunology. Lecture for the Nobel Prize for Physiology or Medicine," Studies in histocompatibility, Scand J Immunol. Oct; 36(4):513-26 (1992).

Stacpoole et al., "Controlled Clinical Trial of Dichloroacetate for Treatment of Congential Lactic Acidosis in Children," Pediatrics, May; 117(5): 1519-1532 (2006).

Stacpoole et al., "Clinical Pharmacology and Toxicology of Dichloroacetate," Environmental Health Perspectives, Aug.; 106(4): 989-994 (1998).

Stacpoole et al., "Treatment of congenital Lactic acidosis with dichloroacetate," Archives of Disease in Childhood, 77:535-541 (1997).

Street et al., "Interferon-gamma enhances susceptibility of cervical cancer cells to lysis by tumor-specific cytotoxic T cells," Gynecol Oncol. May;65(2):265-72 (1997).

Summerfield et al, "Lymphocyte apoptosis during classical swine fever; implication of activation-induced cell death," J Virol. Mar;72(3):1853-61 (1998).

Suzuki et al., "Maximal proliferation of cytotoxic T lymphocytes requires reverse signaling through Fas ligand," J. Ex Med Jan. 5;187(1):123-8 (1998).

Taneja et al., "Expression of the H2-E molecule mediates protection to collagen-induced arthritis in HLA-DQ8 transgenic mice: role of cytokines," Int Immunol. Aug;9(8):1213-9 (1997).

Tansan, S. et al., "Augmentation of vincristine cytotoxicity by megestrol acetate," Cancer Chemother. Pharmacol., 39:333-40 (1997).

Tao et al, "Effect of dichloroacetic acid and trichloroacetic acid on DNA methylation in liver and tumors of female B6C3F1 mice," Toxicological Sciences, vol. 43, No. 2, pp. 139-144 (Abstract) (1998).

Teruya et al., "Pancreatic islet function in nondiabetic and diabetic BB rats," Diabetes Sep; 42(9):1310-7 (1993).

Thupari et al., "Fatty acid synthase inhibition in human breast cancer cells leads to malonyl-CoA-induced inhibition of fatty acid oxidation and cytotoxicity," Biochem Biophys Res Commun Jul. 13;285(2):217-23 (2001) Erratum in: Biochem Biophys Res Commun Jul. 12;295(2):570 (2002).

Tian et al., "Attenuated of inducible Th2 immunity with autoimmune disease progression," J. Immunol. Nov. 15; 161(10):5399-403 (1998).

Truman et al., "HLA class II-mediated death is induced via Fas/Fas ligand interactions in human splenic B lymphocytes," Blood Mar. 15;89(6):1996-2007 (1997).

Truman et al., "HLA-class II signaling mediates cellular activation and programmed cell death," Exp Hematol. Oct;24(12):1409-15 (1996).

Vidal-Puig et al., "Uncoupling expectation," Nat Genet. Dec;26(4):387-8 (2000).

Wallace et al., "Mitochondrial diseases in man and mouse," Science Mar. 5;283(5407):1482-8 (1999).

Wang et al., "Effects of cisplatin and taxol on inducible nitric oxide synthase, gastrin and somatostatin in gastrointestinal toxicity," AntiCancer Drugs; 8(9): 853-858 (1997).

Wang and Schultz, "β-Oxidation of polyunsaturated fatty acids with conjugated double bonds," Biochem J. 264 1989, 47-52.

Wilkens et al., "ATP synthase's second stalk comes into focus," Nature May 7;393(6680):29 (1998).

Yaffe et al., "The machinery of mitochondrial inheritance and behavior," Science Mar 5;283(5407):1483-7 (1999).

Zhang et al., "LAT: the ZAP-70 tyrosine kinase substrate that links T cell receptor to cellular activation," Cell Jan. 9;92(1):83-92 (1998).

Zhelev et al., "Phenothiazines suppress proliferation and induce apoptosis in cultured leukemic cells without any influence on the viability of normal lymphocytes," Phenothiazines and leukemia, Cancer Chemother Pharmacol. Mar; 53(3):267-75 2004; Epub, Dec. 9 (2003).

Zinkernagel et al., "The discovery of MHC restriction," Immunol Today Jan; 18(1):14-7 (1997).

* cited by examiner

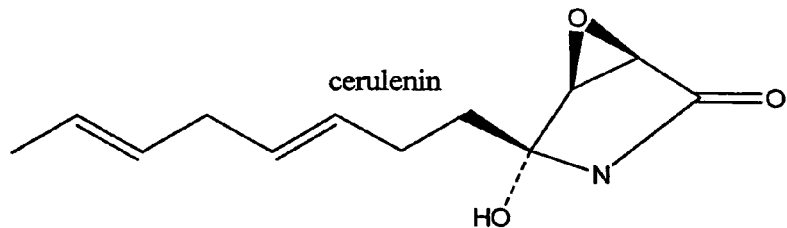
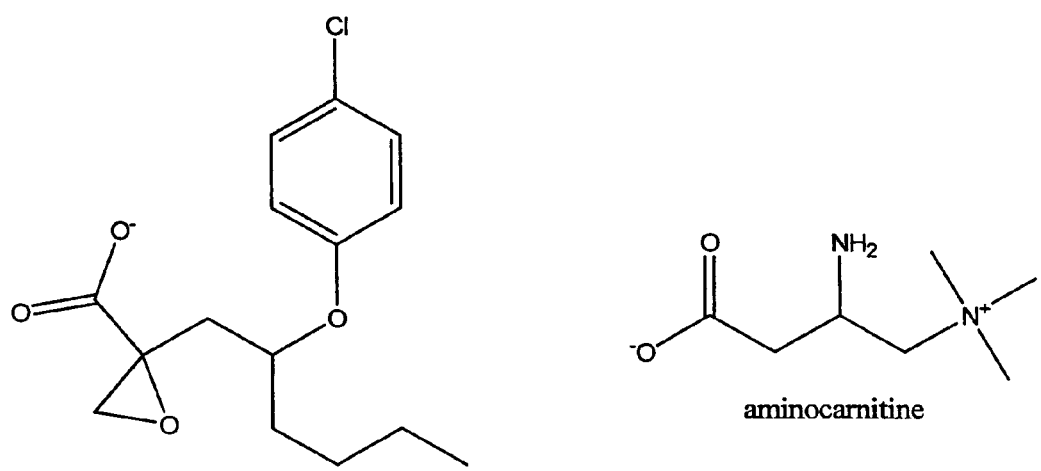
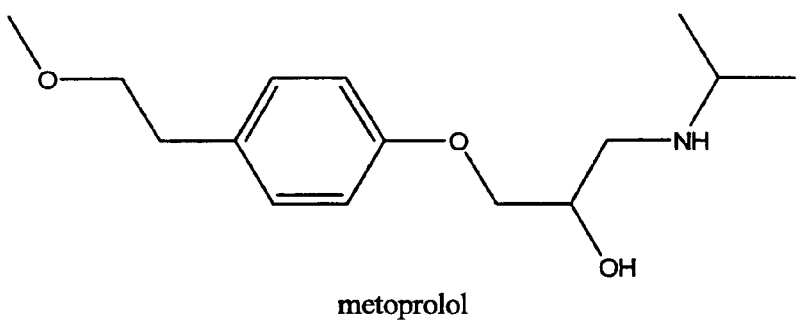
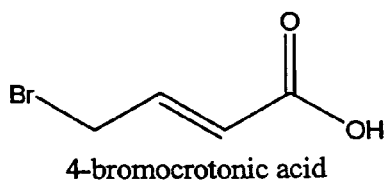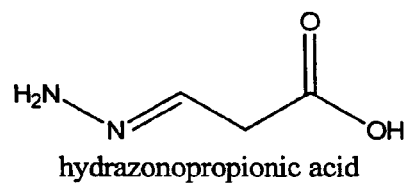
FIG. 1A

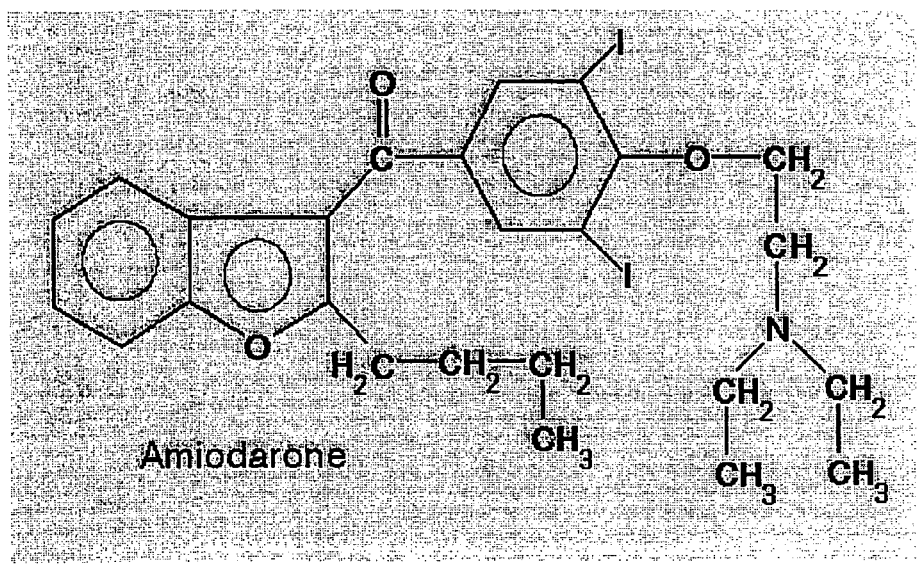
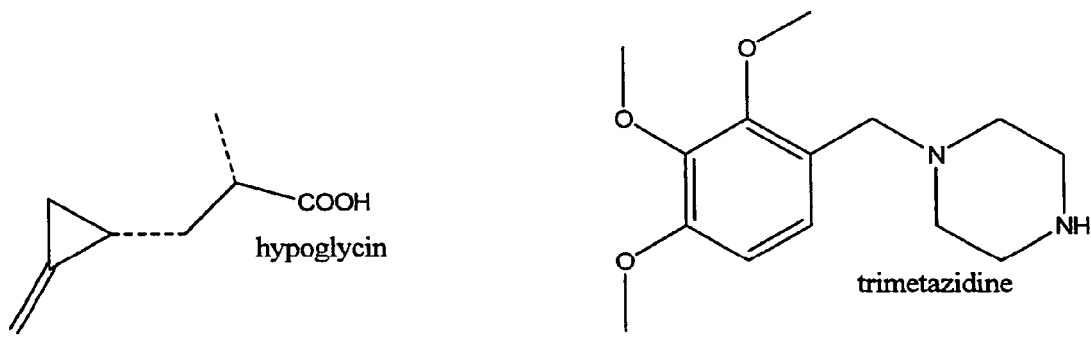
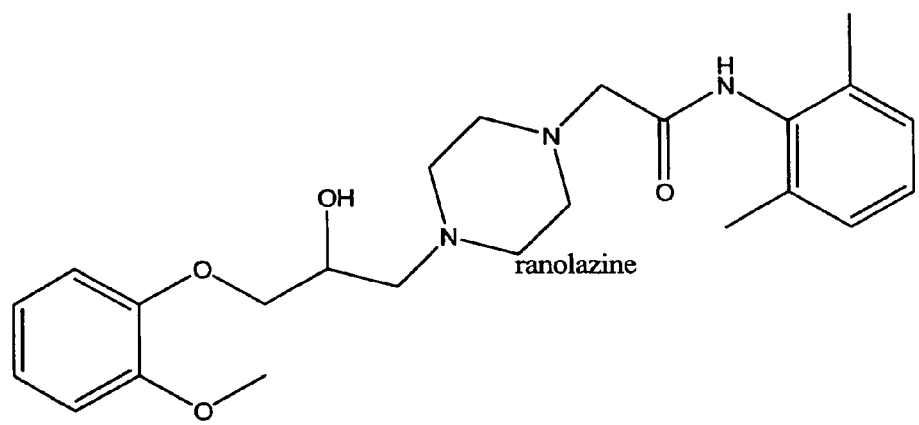
FIG. 1B

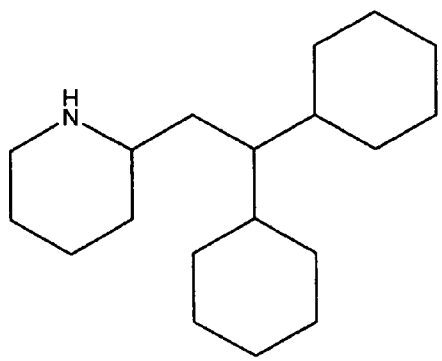
perhexiline
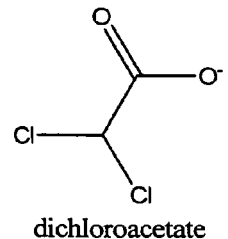
dichloroacetate
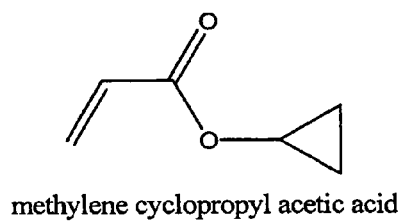
methylene cyclopropyl acetic acid
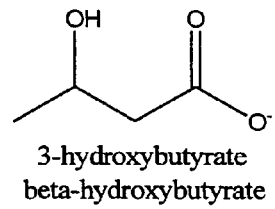
3-hydroxybutyrate
beta-hydroxybutyrate
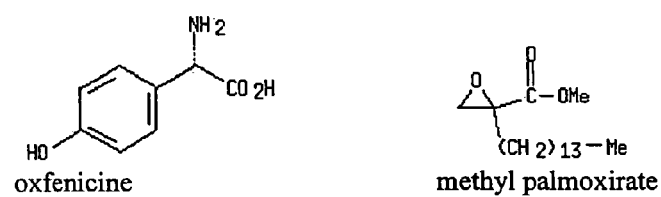
oxfenicine        methyl palmoxirate
5-(tetradecyloxy)-2-furoic acid
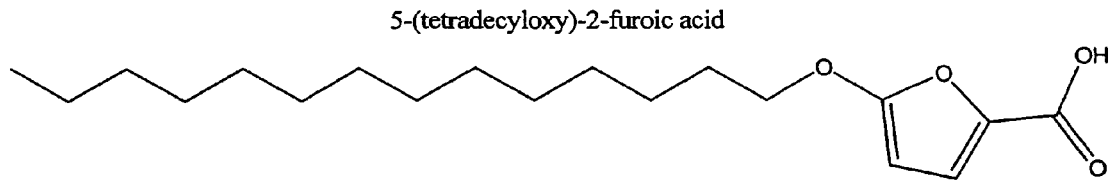
FIG.1C FIG. 2A
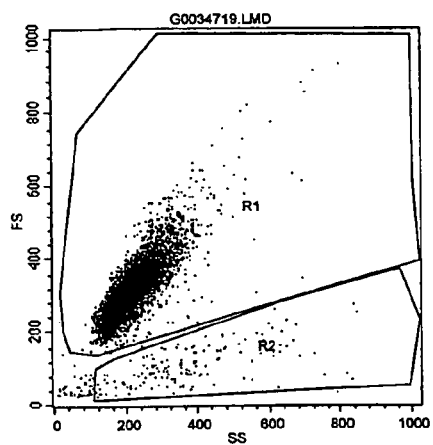
L1210 No Treatment
7.0 Hours
1.7 % Death
FIG. 2B
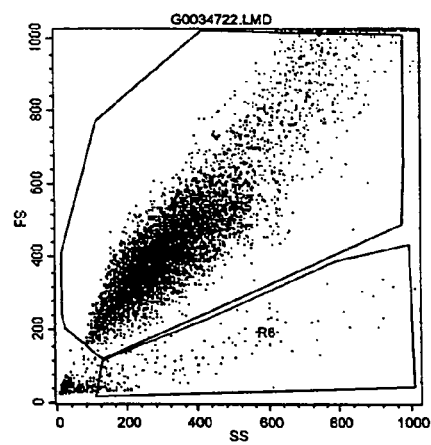
L1210 DDP No Treatment
7.0 Hours
1.4 % Death
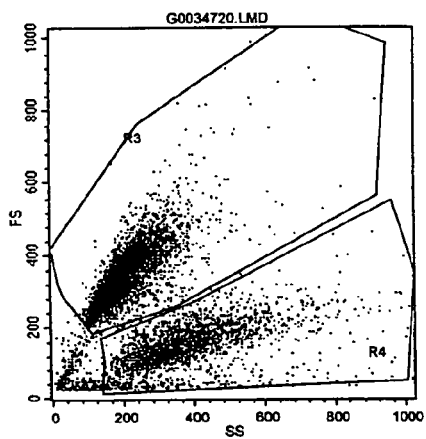
L1210 @ 25ug/mL Cerulenin
7.0 Hours
27 % Death
FIG. 2C
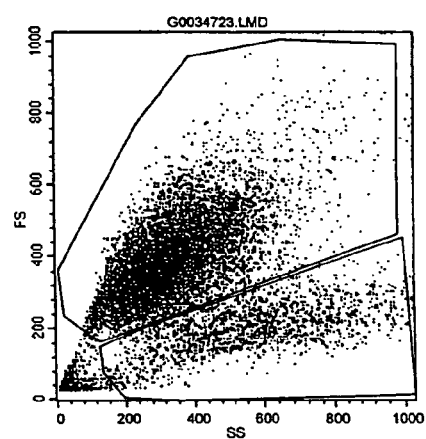
L1210 DDP @ 25ug/mL Cerulenin
7.0 Hours
14 % Death
FIG. 2D L1210 No Treatment
24 Hours
2.3 % Death L1210 DDP No Treatment
24 Hours
2.0 % Death L1210 @ 25ug/mL Cerulenin
24 Hours
89 % Death L1210 DDP @ 25ug/mL Cerulenin
24 Hours
92 % Death HL60   No Stn HL60    No Stn HL60 Treated Cells HL60    MDR Cells    No Stn HL60    MDR Cells   Treated Cells

B16F1 Melanoma Data
Treated (or not) with Etomoxir for 48 Hours
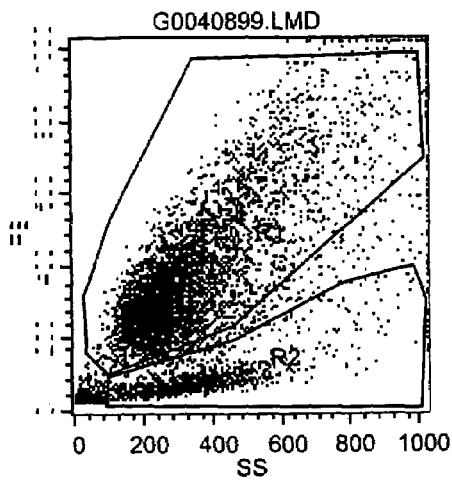
B16F1 Melanoma Cells
Untreated
Percent Death = 19%
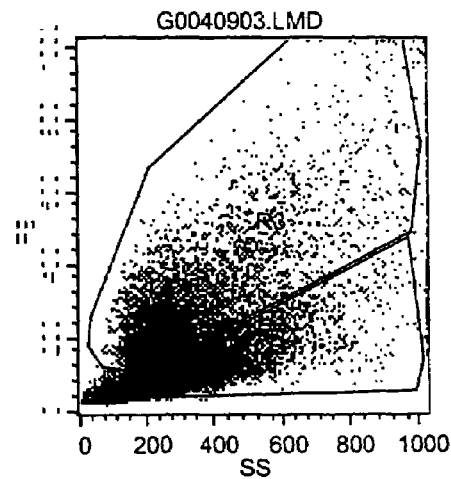
B16F1 Melanoma Cells
100ug/mL Etomoxir
Percent Death = 65%
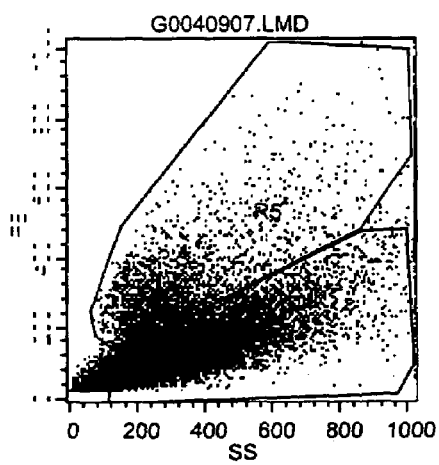
B16F1 Melanoma Cells
25ug/mL Etomoxir
Percent Death = 89.5%
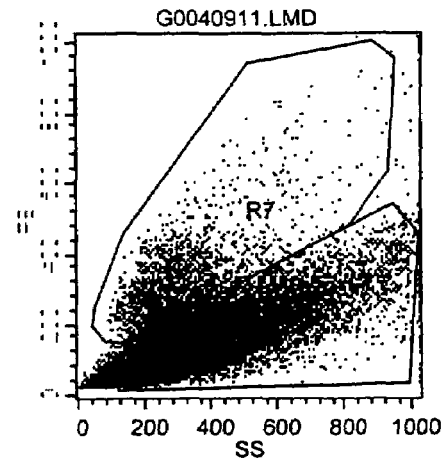
B16F1 Melanoma Cells
500ug/mL Etomoxir
Percent Death = 91.3%
FIG. 15

A-204 Rhabdomyosarcoma Data
Treated (or not) with Etomoxir for 24, 48, & 72 Hours

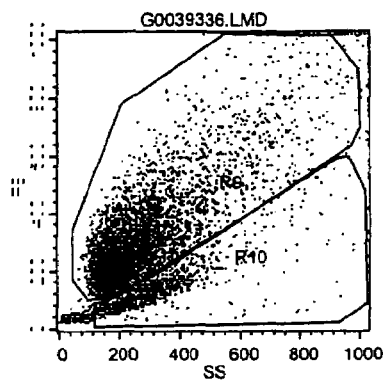

A-204 Rhabdomyosarcoma Cells
Untreated
Percent Death = 17%

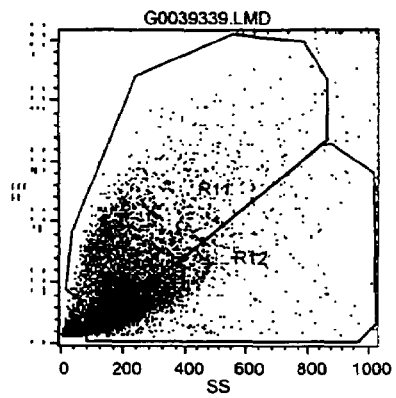

A-204 Rhabdomyosarcoma Cells
250ug/mL Etomoxir 24 Hrs
Percent Death = 66%

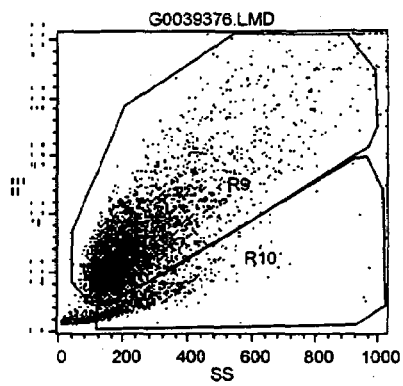

A-204 Rhabdomyosarcoma Cells
Untreated
Percent Death = 10%

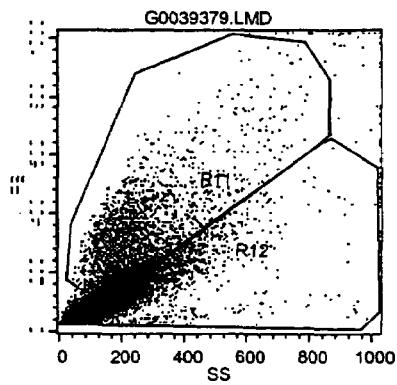

A-204 Rhabdomyosarcoma Cells
250ug/mL Etomoxir 48 Hrs
Percent Death = 69%

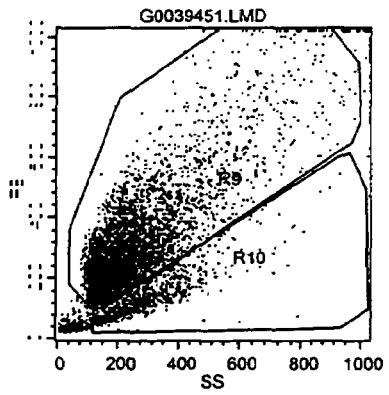

A-204 Rhabdomyosarcoma Cells
Untreated
Percent Death = 13%

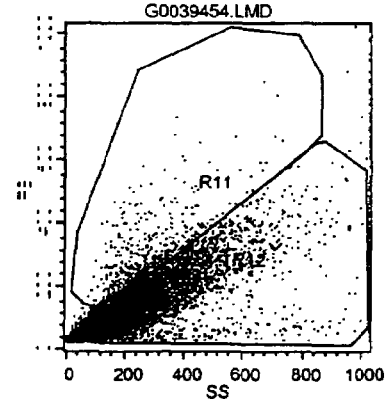

A-204 Rhabdomyosarcoma Cells
250ug/mL Etomoxir 72 Hours
Percent Death = 94%

FIG. 24

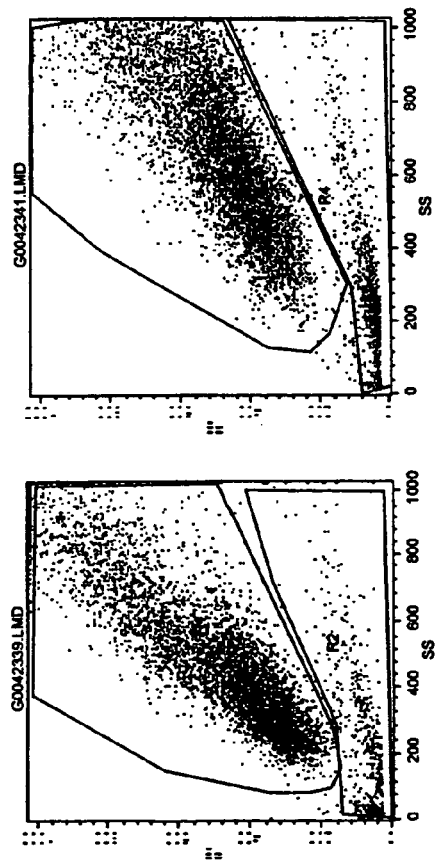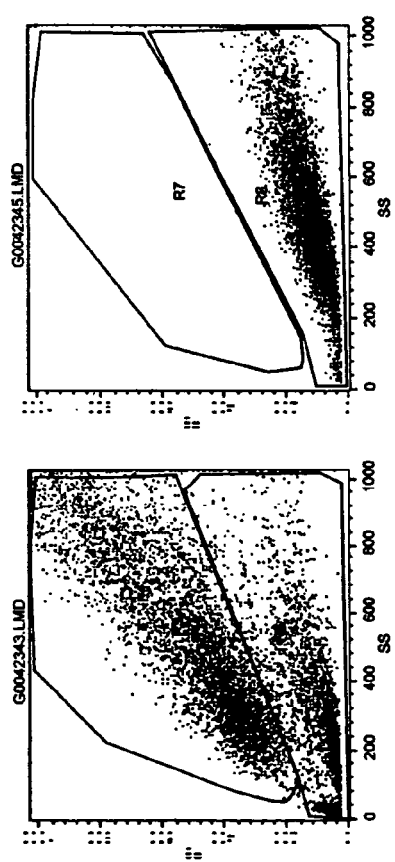
No Treatment = 9% Death
Eto Treatment = 14% Death
2D Treatment = 38% Death
Both Treatments = 100% Death
FIG. 31
HL60 MDR Cells Treated or not with Etomoxir, 2-Deoxyglucose, or Both
48 Hours No Treatment = 36% Death
Eto Treatment = 64% Death
2D Treatment = 63% Death
Both Treatments = 68% Death
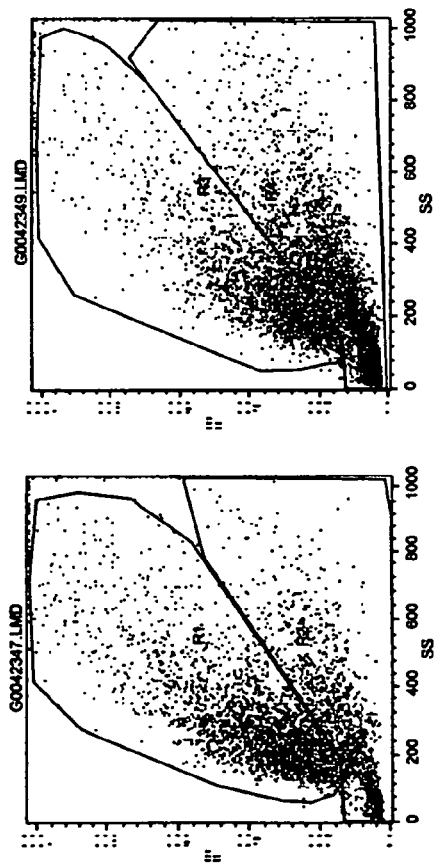
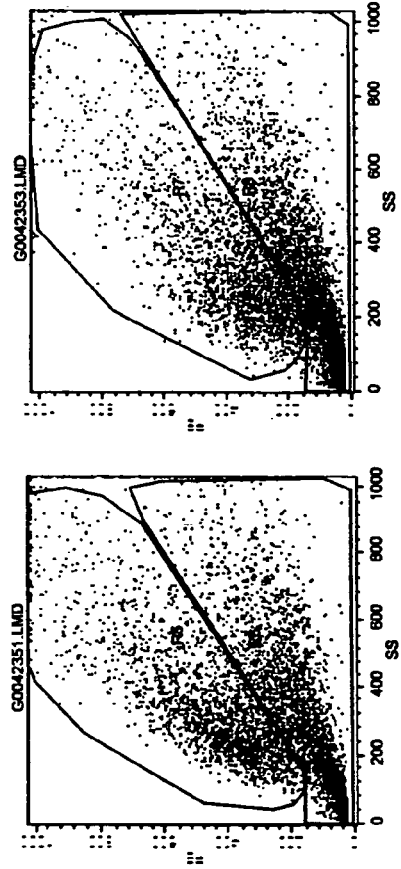
FIG. 33
RD Cells Treated or not with Etomoxir, 2-Deoxyglucose, or Both
48 Hours

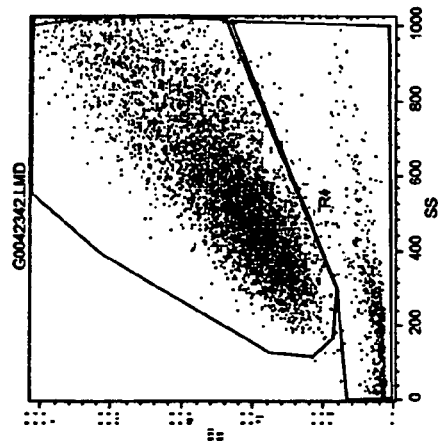
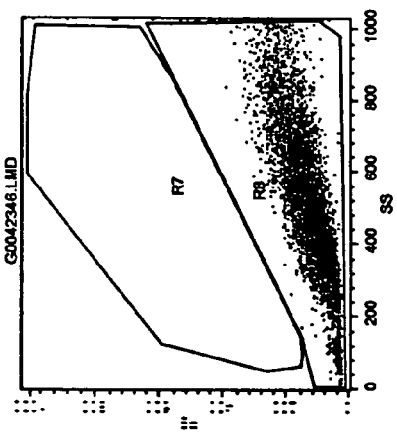
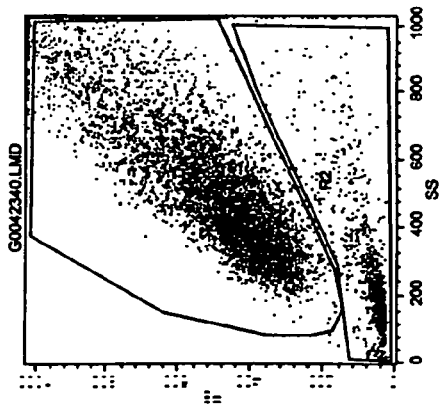
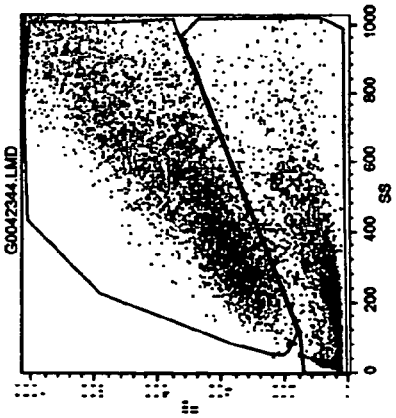
FIG. 35
No Treatment = 16% Death
Eto Treatment = 9% Death
2D Treatment = 36% Death
Both Treatments = 100% Death
HL60 MDR Cells Treated or not with Etomoxir, 2-Deoxyglucose, or Both AND with anti-UCP2 antibody
48 Hours No Treatment = 52% Death
Eto Treatment = 69% Death
2D Treatment = 62% Death
Both Treatments = 65% Death
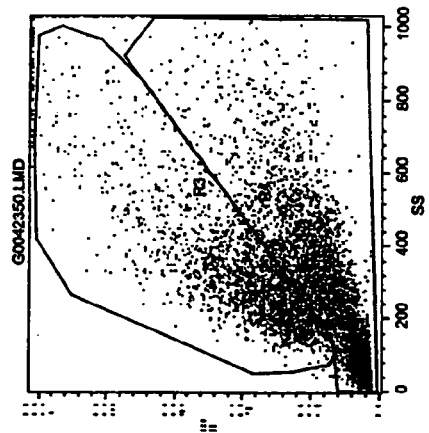
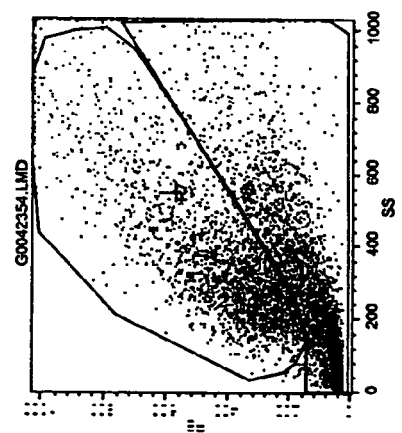
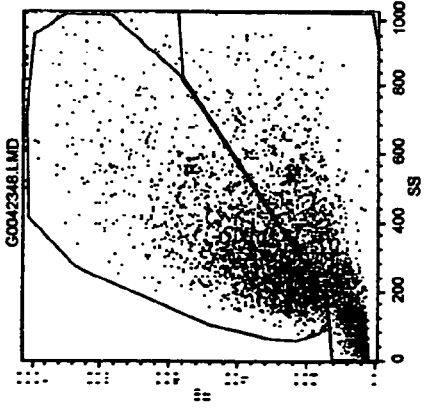
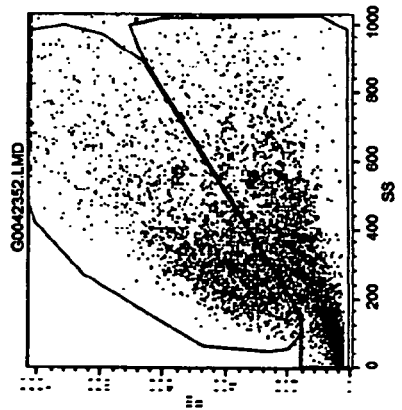
FIG. 37
RD Cells Treated or not with Etomoxir, 2-Deoxyglucose, or Both
AND with anti-UCP2 antibody
48 Hours

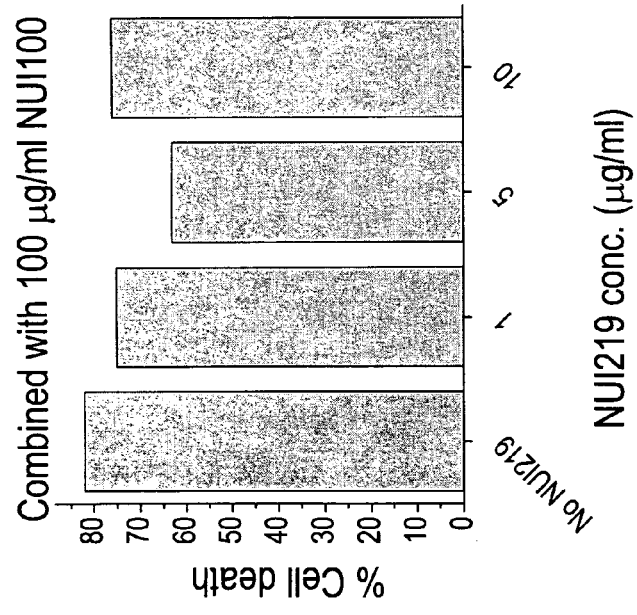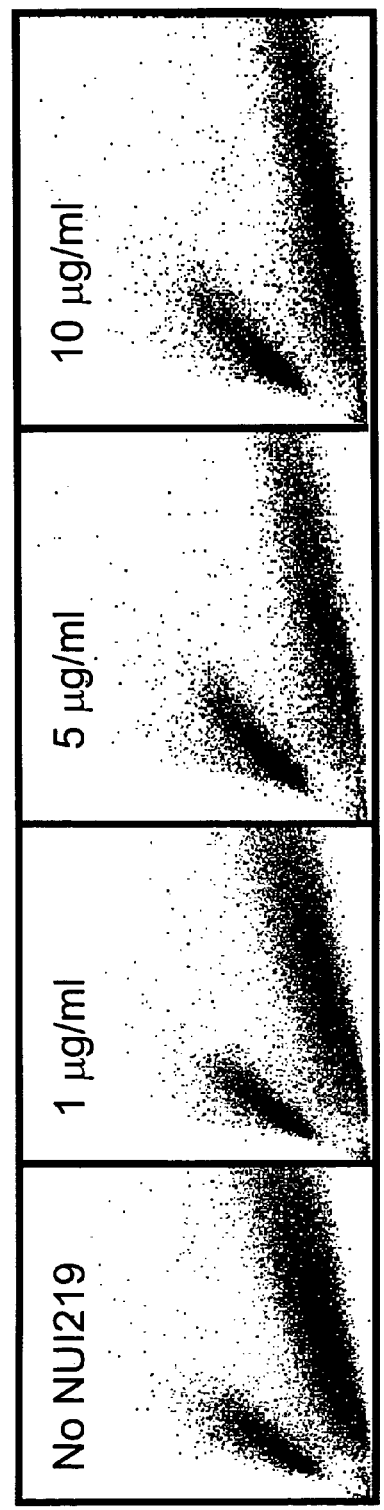
FIG. 44

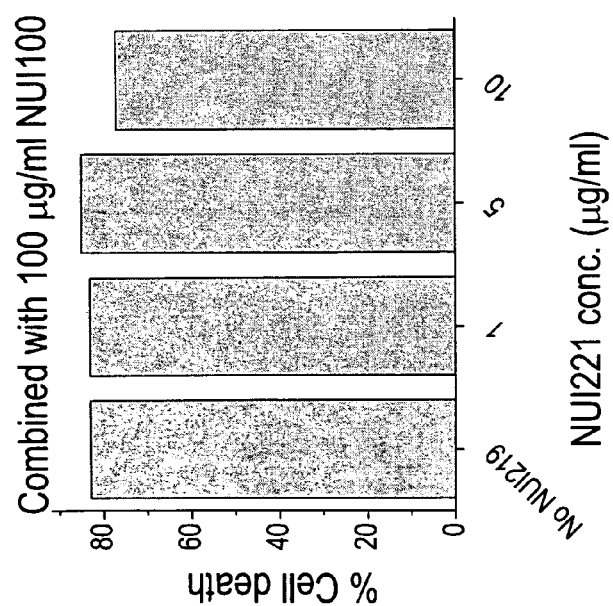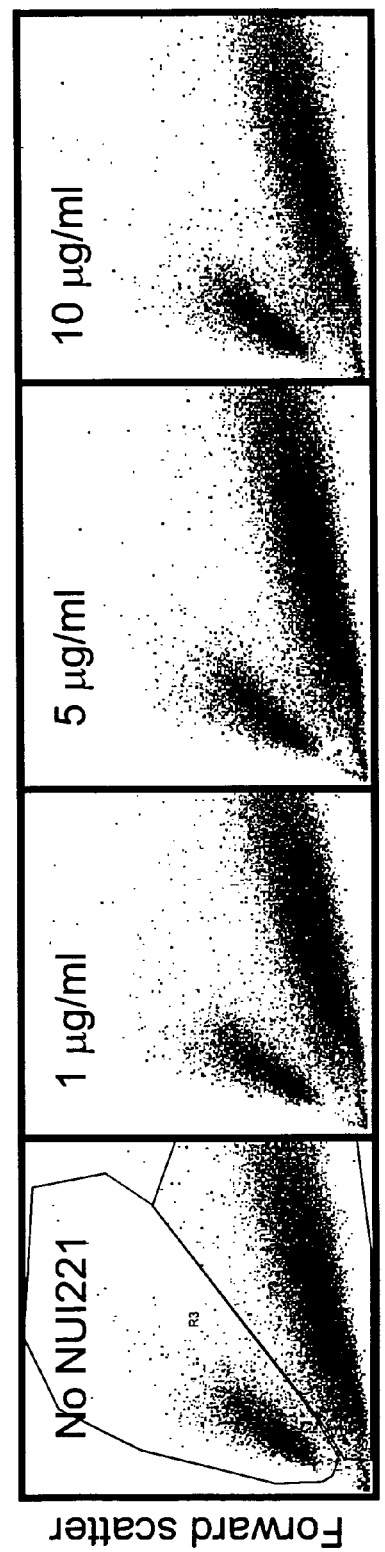
FIG. 45

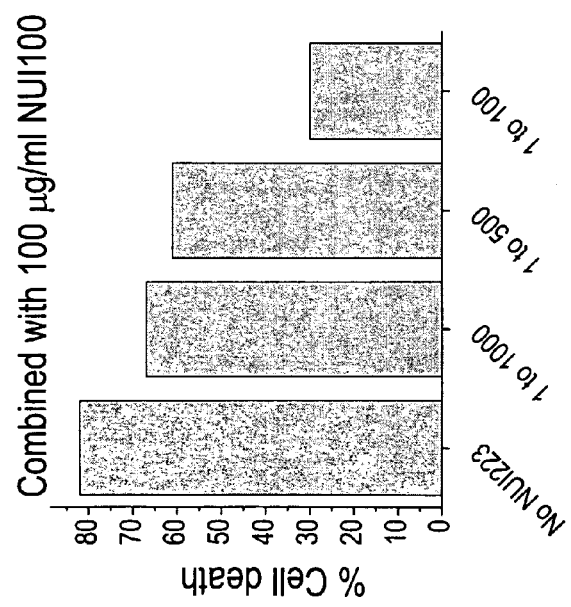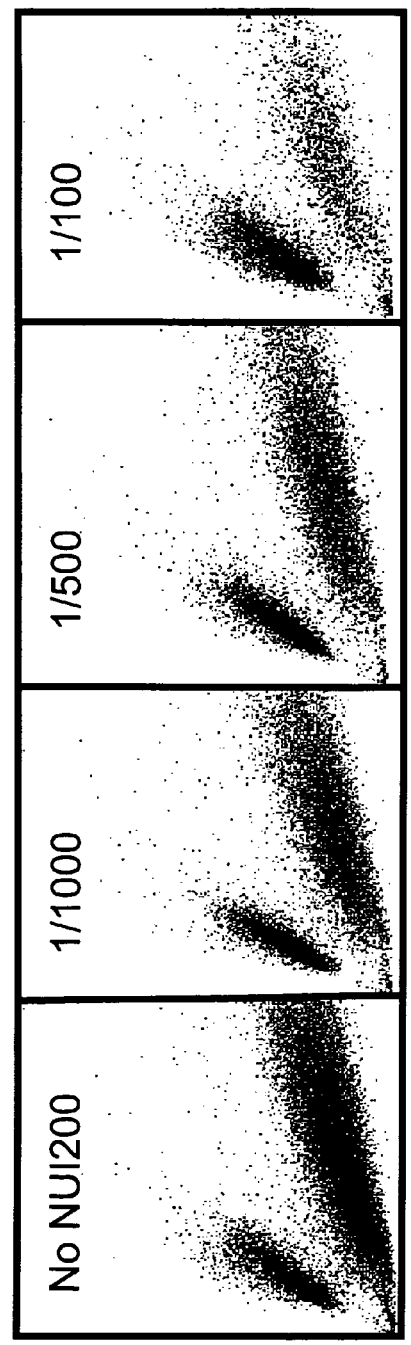
FIG. 46

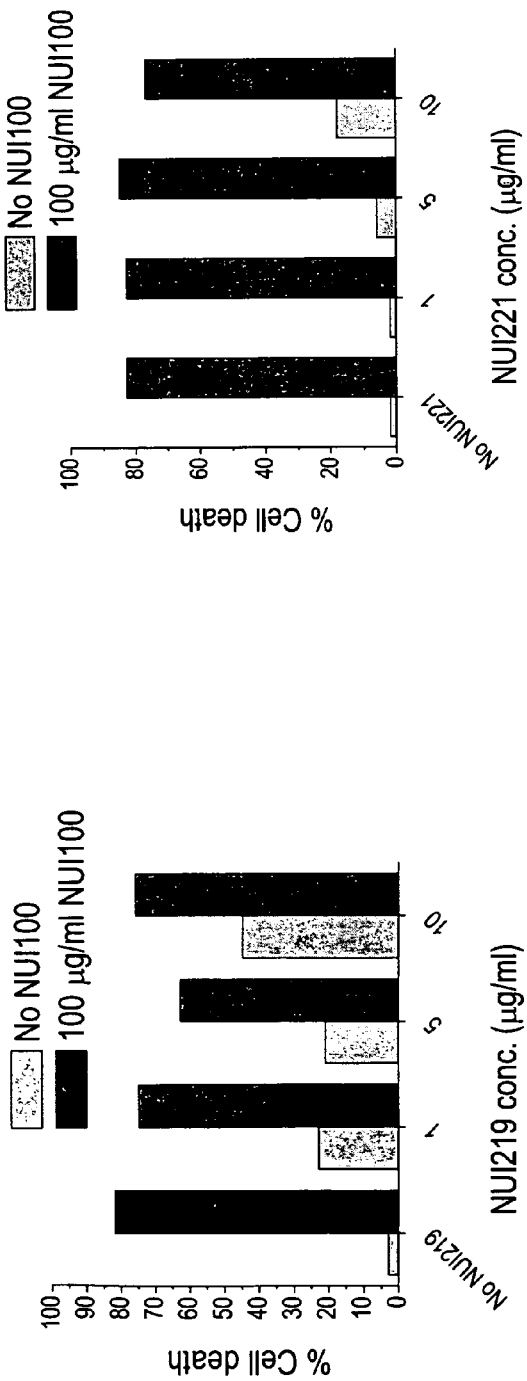
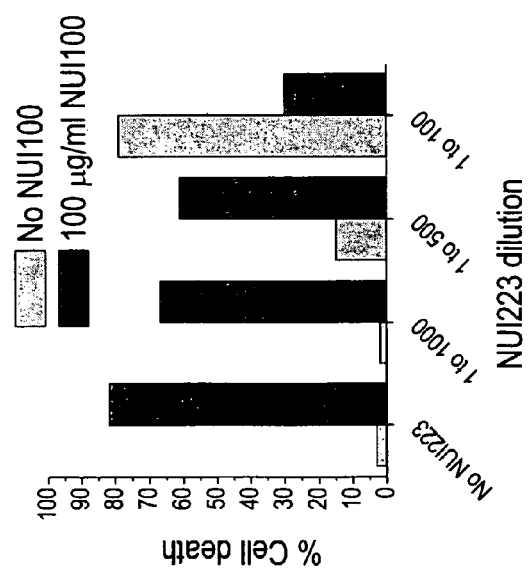
FIG. 47

SEQUENCE LISTING

<160> NUMBER OF SEQ ID NOS: 19

<210> SEQ ID NO 1
<211> LENGTH: 924
<212> TYPE: DNA
<213> ORGANISM: Homo sapiens

<400> SEQUENCE: 1

```
atgggggcc tgacagcctc ggacgtacac ccgaccctgg gggtccagct cttctcagct      60
ggaatagcgg cgtgcttggc ggacgtgatc accttcccgc tggacacggc caaagtccgg    120
ctccaggtcc aaggtgaatg cccgacgtcc agtgttatta ggtataaagg tgtcctggga    180
acaatcaccg ctgtggtaaa aacagaaggg cggatgaaac tctacagcgg gctgcctgcg    240
gggcttcagc ggcaaatcag ctccgcctct ctcaggatcg gcctctacga cacggtccag    300
gagttcctca ccgcagggaa agaaacagca cctagtttag aagcaagat tttagctggt     360
ctaacgactg gaggagtggc agtattcatt gggcaaccca cagaggtcgt gaaagtcaga    420
cttcaagcac agagccatct ccacggaatc aaacctcgct acacgggac ttataatgcg     480
tacagaataa tagcaacaac cgaaggcttg acgggtcttt ggaaagggac tactcccaat    540
ctgatgagaa gtgtcatcat caattgtaca gagctagtaa catatgatct aatgaaggag    600
gcctttgtga aaacaacat attagcagat gacgtcccct gccacttggt gtcggctctt     660
atcgctggat tttgcgcaac agctatgtcc tccccggtgg atgtagtaaa accagatt      720
attaattctc caccaggaca gtacaaaagt gtgcccaact gtgcaatgaa agtgttcact    780
aacgaaggac caacggcttt cttcaagggg ttggtacctt ccttcttgcg acttggatcc    840
tggaacgtca ttatgtttgt gtgctttgaa caactgaaac gagaactgtc aaagtcaagg    900
cagactatgg actgtgccac ataa                                            924
```

<210> SEQ ID NO 2
<211> LENGTH: 307
<212> TYPE: PRT
<213> ORGANISM: Homo sapiens

<400> SEQUENCE: 2

```
Met Gly Gly Leu Thr Ala Ser Asp Val His Pro Thr Leu Gly Val Gln
  1               5                  10                  15

Leu Phe Ser Ala Gly Ile Ala Ala Cys Leu Ala Asp Val Ile Thr Phe
             20                  25                  30

Pro Leu Asp Thr Ala Lys Val Arg Leu Gln Val Gln Gly Glu Cys Pro
         35                  40                  45

Thr Ser Ser Val Ile Arg Tyr Lys Gly Val Leu Gly Thr Ile Thr Ala
     50                  55                  60

Val Val Lys Thr Glu Gly Arg Met Lys Leu Tyr Ser Gly Leu Pro Ala
 65                  70                  75                  80

Gly Leu Gln Arg Gln Ile Ser Ser Ala Ser Leu Arg Ile Gly Leu Tyr
                 85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Val Ala Val
        115                 120                 125

Phe Ile Gly Gln Pro Thr Glu Val Val Lys Val Arg Leu Gln Ala Gln
    130                 135                 140
```

-continued

| Ser | His | Leu | His | Gly | Ile | Lys | Pro | Arg | Tyr | Thr | Gly | Thr | Tyr | Asn | Ala |
| 145 | | | | 150 | | | | | 155 | | | | | 160 | |

| Tyr | Arg | Ile | Ile | Ala | Thr | Thr | Glu | Gly | Leu | Thr | Gly | Leu | Trp | Lys | Gly |
| | | | 165 | | | | | 170 | | | | | 175 | | |

| Thr | Thr | Pro | Asn | Leu | Met | Arg | Ser | Val | Ile | Ile | Asn | Cys | Thr | Glu | Leu |
| | | | 180 | | | | | 185 | | | | | 190 | | |

| Val | Thr | Tyr | Asp | Leu | Met | Lys | Glu | Ala | Phe | Val | Lys | Asn | Asn | Ile | Leu |
| | | | 195 | | | | | 200 | | | | | 205 | | |

| Ala | Asp | Asp | Val | Pro | Cys | His | Leu | Val | Ser | Ala | Leu | Ile | Ala | Gly | Phe |
| | 210 | | | | | 215 | | | | | 220 | | | | |

| Cys | Ala | Thr | Ala | Met | Ser | Ser | Pro | Val | Asp | Val | Lys | Thr | Arg | Phe |
| 225 | | | | | 230 | | | | | 235 | | | | 240 |

| Ile | Asn | Ser | Pro | Pro | Gly | Gln | Tyr | Lys | Ser | Val | Pro | Asn | Cys | Ala | Met |
| | | | | 245 | | | | | 250 | | | | | 255 | |

| Lys | Val | Phe | Thr | Asn | Glu | Gly | Pro | Thr | Ala | Phe | Phe | Lys | Gly | Leu | Val |
| | | | 260 | | | | | 265 | | | | | 270 | | |

| Pro | Ser | Phe | Leu | Arg | Leu | Gly | Ser | Trp | Asn | Val | Ile | Met | Phe | Val | Cys |
| | | 275 | | | | | 280 | | | | | 285 | | | |

| Phe | Glu | Gln | Leu | Lys | Arg | Glu | Leu | Ser | Lys | Ser | Arg | Gln | Thr | Met | Asp |
| | 290 | | | | | 295 | | | | | 300 | | | | |

Cys Ala Thr
305

<210> SEQ ID NO 3
<211> LENGTH: 1105
<212> TYPE: DNA
<213> ORGANISM: Homo sapiens

<400> SEQUENCE: 3

```
gttcctctat ctcgtcttgt tgctgattaa aggtgcccct gtctccagtt tttctccatc      60
tcctgggacg tagcaggaaa tcagcatcat ggttgggttc aaggccacag atgtgccccc     120
tactgccact gtgaagtttc ttggggctgg cacagctgcc tgcatcgcag atctcatcac     180
ctttcctctg gatactgcta aagtccggtt acagatccaa ggagaaagtc aggggccagt     240
gcgcgctaca gccagcgccc agtaccgcgg tgtgatgggc accattctga ccatggtgcg     300
tactgagggc ccccgaagcc tctacaatgg gctggttgcc ggcctgcagc gccaaatgag     360
ctttgcctct gtccgcatcg gcctgtatga ttctgtcaaa cagttctaca ccaagggctc     420
tgagcatgcc agcattggga gccgcctcct agcaggcagc accacaggtg ccctggctgt     480
ggctgtggcc cagcccacgg atgtggtaaa ggtccgattc caagctcagg cccgggctgg     540
aggtggtcgg agataccaaa gcaccgtcaa tgcctacaag accattgccc gagaggaagg     600
gttccggggc ctctggaaag ggacctctcc caatgttgct cgtaatgcca ttgtcaactg     660
tgctgagctg gtgacctatg acctcatcaa ggatgccctc ctgaaagcca acctcatgac     720
agatgacctc ccttgccact tcacttctgc ctttgggcag gcttctgca ccactgtcat     780
cgcctcccct gtagacgtgg tcaagacgag atacatgaac tctgccctgg ccagtacag     840
tagcgctggc cactgtgccc ttaccatgct ccagaaggag gggccccgag ccttctacaa     900
agggttcatg ccctccttc tccgcttggg ttcctggaac gtggtgatgt tcgtcaccta     960
tgagcagctg aaacgagccc tcatggctgc ctgcacttcc cgagaggctc ccttctgagc    1020
ctctcctgct gctgacctga tcacctctgg ctttgtctct agccgggcca tgctttcctt    1080
ttcttccttc tttctcttcc ctccg                                          1105
```

<210> SEQ ID NO 4
<211> LENGTH: 309
<212> TYPE: PRT
<213> ORGANISM: Homo sapiens

<400> SEQUENCE: 4

```
Met Val Gly Phe Lys Ala Thr Asp Val Pro Thr Ala Thr Val Lys
1               5                   10                  15

Phe Leu Gly Ala Gly Thr Ala Ala Cys Ile Ala Asp Leu Ile Thr Phe
                20                  25                  30

Pro Leu Asp Thr Ala Lys Val Arg Leu Gln Ile Gln Gly Glu Ser Gln
                35                  40                  45

Gly Pro Val Arg Ala Thr Ala Ser Ala Gln Tyr Arg Gly Val Met Gly
    50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
                100                 105                 110

His Ala Ser Ile Gly Ser Arg Leu Leu Ala Gly Ser Thr Thr Gly Ala
                115                 120                 125

Leu Ala Val Ala Val Ala Gln Pro Thr Asp Val Val Lys Val Arg Phe
    130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
                180                 185                 190

Glu Leu Val Thr Tyr Asp Leu Ile Lys Asp Ala Leu Leu Lys Ala Asn
                195                 200                 205

Leu Met Thr Asp Asp Leu Pro Cys His Phe Thr Ser Ala Phe Gly Ala
    210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
                260                 265                 270

Phe Met Pro Ser Phe Leu Arg Leu Gly Ser Trp Asn Val Val Met Phe
                275                 280                 285

Val Thr Tyr Glu Gln Leu Lys Arg Ala Leu Met Ala Ala Cys Thr Ser
    290                 295                 300

Arg Glu Ala Pro Phe
305
```

<210> SEQ ID NO 5
<211> LENGTH: 1132
<212> TYPE: DNA
<213> ORGANISM: Homo sapiens

<400> SEQUENCE: 5

```
tcctgggatg agccctagg  gagcccctgt gctgccccctg ccgtggcagg actcacagcc      60
ccaccgctgc actgaagccc agggctgtgg agcagcctct ctccttggac ctcctctcgg     120
```

-continued

```
ccctaaaggg actgggcaga gccttccagg actatggttg gactgaagcc ttcagacgtg    180
cctcccacca tggctgtgaa gttcctgggg gcaggcacag cagcctgttt tgctgacctc    240
gttacctttc cactggacac agccaaggtc cgcctgcaga tccagggggga gaaccaggcg    300
gtccagacgg cccggctcgt gcagtaccgt ggcgtgctgg caccatcct gaccatggtg    360
cggactgagg gtccctgcag cccctacaat gggctggtgg ccggcctgca gcgccagatg    420
agcttcgcct ccatccgcat cggcctctat gactccgtca agcaggtgta caccccaaa    480
ggcgcggaca actccagcct cactacccgg attttggccg gctgcaccac aggagccatg    540
gcggtgacct gtgcccagcc cacagatgtg gtgaaggtcc gatttcaggc agcatacac    600
ctcgggccat ccaggagcga cagaaaatac agcgggacta tggacgccta cagaaccatc    660
gccagggagg aaggagtcag gggcctgtgg aaaggaactt tgcccaacat catgaggaat    720
gctatcgtca actgtgctga ggtggtgacc tacgacatcc tcaaggagaa gctgctggac    780
taccacctgc tcactgacaa cttcccctgc cactttgtct ctgcctttgg agccggcttc    840
tgtgccacag tggtggcctc cccggtggac gtggtgaaga cccggtatat gaactcacct    900
ccaggccagt acttcagccc cctcgactgt atgataaaga tggtggccca ggagggcccc    960
acagccttct acaaggggtg agcctcctcc tgcctccagc actccctccc agagaacagg   1020
ggcttctttc ttttcgaatg tggctaccgt gggtcaacct gggatgtagc ggtgaagagt   1080
acagatgtaa atgccacaaa gaagaagttt aaaaaaccat gcaaaaaaaa aa           1132
```

<210> SEQ ID NO 6
<211> LENGTH: 275
<212> TYPE: PRT
<213> ORGANISM: Homo sapiens

<400> SEQUENCE: 6

```
Met Val Gly Leu Lys Pro Ser Asp Val Pro Thr Met Ala Val Lys
1               5                  10                  15

Phe Leu Gly Ala Gly Thr Ala Ala Cys Phe Ala Asp Leu Val Thr Phe
            20                  25                  30

Pro Leu Asp Thr Ala Lys Val Arg Leu Gln Ile Gln Gly Glu Asn Gln
        35                  40                  45

Ala Val Gln Thr Ala Arg Leu Val Gln Tyr Arg Gly Val Leu Gly Thr
    50                  55                  60

Ile Leu Thr Met Val Arg Thr Glu Gly Pro Cys Ser Pro Tyr Asn Gly
65                  70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
    130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190
```

```
Asn Cys Ala Glu Val Val Thr Tyr Asp Ile Leu Lys Glu Lys Leu Leu
        195                 200                 205

Asp Tyr His Leu Leu Thr Asp Asn Phe Pro Cys His Phe Val Ser Ala
        210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
            260                 265                 270

Tyr Lys Gly
        275

<210> SEQ ID NO 7
<211> LENGTH: 25
<212> TYPE: PRT
<213> ORGANISM: Unknown
<220> FEATURE:
<223> OTHER INFORMATION: P-cadherin

<400> SEQUENCE: 7

Phe Ile Leu Pro Ile Leu Gly Ala Val Leu Ala Leu Leu Leu Leu
1               5                   10                  15

Thr Leu Leu Ala Leu Leu Leu Val
            20                  25

<210> SEQ ID NO 8
<211> LENGTH: 26
<212> TYPE: PRT
<213> ORGANISM: Unknown
<220> FEATURE:
<223> OTHER INFORMATION: CD2

<400> SEQUENCE: 8

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 9
<211> LENGTH: 22
<212> TYPE: PRT
<213> ORGANISM: Unknown
<220> FEATURE:
<223> OTHER INFORMATION: CD40

<400> SEQUENCE: 9

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 10
<211> LENGTH: 20
<212> TYPE: PRT
<213> ORGANISM: Unknown
<220> FEATURE:
<223> OTHER INFORMATION: Contactin

<400> SEQUENCE: 10

Ile Ser Gly Ala Thr Ala Gly Val Pro Thr Leu Leu Leu Gly Leu Val
1               5                   10                  15
```

Leu Pro Ala Pro
            20

<210> SEQ ID NO 11
<211> LENGTH: 24
<212> TYPE: PRT
<213> ORGANISM: Unknown
<220> FEATURE:
<223> OTHER INFORMATION: IL-4 receptor

<400> SEQUENCE: 11

Leu Leu Leu Gly Val Ser Val Ser Cys Ile Val Ile Leu Ala Val Cys
1               5                   10                  15

Leu Leu Cys Tyr Val Ser Ile Thr
            20

<210> SEQ ID NO 12
<211> LENGTH: 24
<212> TYPE: PRT
<213> ORGANISM: Unknown
<220> FEATURE:
<223> OTHER INFORMATION: Mannose receptor

<400> SEQUENCE: 12

Val Ala Gly Val Val Ile Ile Val Ile Leu Leu Ile Leu Thr Gly Ala
1               5                   10                  15

Gly Leu Ala Ala Tyr Phe Phe Tyr
            20

<210> SEQ ID NO 13
<211> LENGTH: 25
<212> TYPE: PRT
<213> ORGANISM: Unknown
<220> FEATURE:
<223> OTHER INFORMATION: M-CSF receptor

<400> SEQUENCE: 13

Phe Leu Phe Thr Pro Val Val Ala Cys Met Ser Ile Met Ala Leu
1               5                   10                  15

Leu Leu Leu Leu Leu Leu Leu Leu Leu
            20                  25

<210> SEQ ID NO 14
<211> LENGTH: 30
<212> TYPE: PRT
<213> ORGANISM: Unknown
<220> FEATURE:
<223> OTHER INFORMATION: PDGFR beta-chain

<400> SEQUENCE: 14

Val Val Val Ile Ser Ala Ile Leu Ala Leu Val Val Leu Thr Ile Ile
1               5                   10                  15

Ser Leu Ile Ile Leu Ile Met Leu Trp Gln Lys Lys Pro Arg
            20                  25                  30

<210> SEQ ID NO 15
<211> LENGTH: 26
<212> TYPE: PRT
<213> ORGANISM: Unknown
<220> FEATURE:
<223> OTHER INFORMATION: PDGFR alpha-chain

<400> SEQUENCE: 15

Glu Leu Thr Val Ala Ala Ala Val Leu Val Leu Leu Val Ile Val Ser
1               5                   10                  15

```
Ile Ser Leu Ile Val Leu Val Val Thr Trp
            20                  25

<210> SEQ ID NO 16
<211> LENGTH: 24
<212> TYPE: PRT
<213> ORGANISM: Unknown
<220> FEATURE:
<223> OTHER INFORMATION: P-selectin

<400> SEQUENCE: 16

Leu Thr Tyr Phe Gly Gly Ala Val Ala Ser Thr Ile Gly Leu Ile Met
1               5                   10                  15

Gly Gly Thr Leu Leu Ala Leu Leu
            20

<210> SEQ ID NO 17
<211> LENGTH: 34
<212> TYPE: PRT
<213> ORGANISM: Rattus rattus

<400> SEQUENCE: 17

Val Lys Cys Gly Gly Ile Ser Leu Leu Val Gln Asn Thr Ser Trp Leu
1               5                   10                  15

Leu Leu Leu Leu Leu Ser Leu Ser Phe Leu Gln Ala Thr Asp Phe Ile
            20                  25                  30

Ser Leu

<210> SEQ ID NO 18
<211> LENGTH: 23
<212> TYPE: PRT
<213> ORGANISM: Unknown
<220> FEATURE:
<223> OTHER INFORMATION: TNFR-1

<400> SEQUENCE: 18

Thr Val Leu Leu Pro Leu Val Ile Phe Phe Gly Leu Cys Leu Leu Ser
1               5                   10                  15

Leu Leu Phe Ile Gly Leu Met
            20

<210> SEQ ID NO 19
<211> LENGTH: 23
<212> TYPE: PRT
<213> ORGANISM: Unknown
<220> FEATURE:
<223> OTHER INFORMATION: VCAM-1

<400> SEQUENCE: 19

Leu Leu Val Leu Tyr Phe Ala Ser Ser Leu Ile Ile Pro Ala Ile Gly
1               5                   10                  15

Met Ile Ile Tyr Phe Ala Arg
            20
```

COMPOSITIONS OF UCP INHIBITORS, FAS ANTIBODY, A FATTY ACID METABOLISM INHIBITOR AND/OR A GLUCOSE METABOLISM INHIBITOR

RELATED APPLICATIONS

This application claims the benefit of: U.S. Provisional Patent Application Ser. No. 60/534,896 filed Jan. 8, 2004, entitled "Systems and Methods for Treating Cancers and Wounds" by M. Karen Newell et al.; U.S. Provisional Patent Application Ser. No. 60/535,077, entitled "Systems and Methods for Treating Cancers and Wounds With Oxirane Carboxylic Acids" by M. Karen Newell; and U.S. Provisional Patent Application Ser. No. 60/566,746, entitled "Systems and Methods for Treating Human Inflammatory and Proliferative Diseases, With a Combination of Fatty Acid Metabolism Inhibitors and Glucose metabolism Inhibitors and/or UCP and/or Fas Antibodies" by M. Karen Newell.

FEDERALLY SPONSORED RESEARCH

This invention was sponsored by the NIH, Grant No. RO1 GM62562. The Government may have certain rights to this invention.

FIELD OF INVENTION

The field of the invention generally relates to systems and methods for treating inflammatory and proliferative diseases, and wounds, using a UCP and/or Fas antibody or other inhibitor, optionally with a fatty acid metabolism inhibitor and/or a glucose metabolism inhibitor, further optionally in combination with one or more chemotherpeutic agents.

BACKGROUND

Normal tissue develops, and is maintained by, processes of cell division and cell death. In many diseases, such as cancer, diabetes mellitus Type I, and autoimmune disease, the normal balance between cell division and cell death is disrupted, causing either a rapid growth of unwanted and potentially dangerous cells, and/or a loss of cells essential to maintaining the functions of tissue. Inappropriate cell division or cell death can result in serious life-threatening diseases. Diseases associated with increased cell division include cancer and atherosclerosis. Diseases resulting from increased cell death include AIDS, neurodegenerative diseases (e.g., Alzheimer's disease, Parkinson's disease, amyotrophic lateral sclerosis, retinitis pigmentosa), aplastic anemia, atherosclerosis (e.g., myocardial infarction, stroke, reperfusion injury), and toxin-induced liver disease.

The immune system, a complex organization of cells, tissues and organs, serves to protect us from potential harm. Extraordinary advances in our understanding of the immune system have been made in the last hundred years, especially since the discovery of the T cell and B cell [3-5]. Native T-cells require two signals for activation. These are recognition of antigens in Major Histocompatibility Complex-encoded (MHC) molecules [3], and a co-stimulation signal [6-10] provided by the B7/CD28 family members or other co-stimulatory molecules such as Fas (CD95) [11]. Previously activated T cells can be reactivated by co-stimulation alone [12, 13]. In the absence of activation, T-cells disregard the tissue. If a T cell is activated the consequences can be: 1) destruction of the damaged cells or 2) repair of damaged cells by promoting regeneration either directly or indirectly.

A natural question is: why doesn't the immune system destroy tumor cells as they arise? In fact, there is substantial evidence that the immune system does play an extensive role in suppressing cancer. For example, it is known that people on immune-suppressive therapy have a much higher cancer rate as do people with AIDS [14] and the very young and very old. However, it is also clear that the ability of the immune system to control cancer is not perfect.

Researchers have for many years tried to stimulate the immune system as a therapeutic strategy against cancer [15, 16]. These attempts have generally been ineffective, although there have been some recent successes [17]. There are many reasons for this variability. These include: 1) the inability to activate T cells that can destroy the tumor due to the absence of signal one (lack of recognition of the appropriate tumor antigen); 2) the presence of a signal two that results in the production of the wrong cytokines by T cells which may lead to the growth of tumors, or 3) the failure of activated T cells to kill cancerous cells [18].

Anti-cancer agents may work to promote the death of tumor cells in multiple ways. First, these agents may work by direct cytolysis requiring active participation of the tumor cell in the death process [25]. Second, chemotherapeutics may promote the ability of the tumor cell to be recognized by cells of the immune system and to be killed by immune-directed cell death [26]. Third, these agents may work to "rewire" the death inducing receptor/ligand pairs which include Fas and FasL [23, 25, 26]. The second and third possibilities are not mutually exclusive and may work in concert to result in tumor cell death.

It has been discovered that uncoupling protein ("UCP") is normally present in the plasma membrane of rapidly dividing cells, but it is not typically found on the plasma membrane of growth-arrested or chemotherapy-resistant tumor cells. UCP, which is also present in the mitochondria, can regulate cell division by manipulating the manner in which the cell processes and stores energy. It was found that the UCP in the plasma membrane plays an important role in the signal processes that determine whether a cell will undergo cellular division, cellular differentiation, or cellular death. These findings have important implications on the ability to regulate cell division as well as sensitivity and resistance to chemotherapeutic agents and, therefore, for treating diseases associated with excessive cellular division, aberrant differentiation, and premature cellular death, e.g., for the treatment of cancers, autoimmune disease, degenerative diseases, regeneration, etc.

Several cell surface proteins have previously been identified as cell death proteins. These proteins are believed to be involved in initiating a signal which instructs the cell to die. Cell death proteins include, for example, Fas/CD95 (Trauth, et al., *Science*, 245:301, 1989), tumor necrosis factor receptors, immune cell receptors such as CD40, OX40, CD27 and 4-1BB (Smith, et al., *Cell*, 76:959, 1994), and RIP (U.S. Pat. No. 5,674,734). These proteins are believed to be important mediators of cell death. These mediators, however, do not always instruct a cell to die. In some cases, these mediators actually instruct a cell to undergo cell division. The intracellular environment, and particularly the status of the proton motor force and the source of fuel for mitochondrial metabolism, determines whether stimulation of the cell death protein will lead to a signal for death or cell division (see, e.g., U.S. patent application Ser. No. 09/277,575, incorporated herein by reference).

These findings have important implications in the present invention in dealing with drug resistant tumors. Every year at least 6.2 million people die worldwide from cancer [1]. Many cancer patients will be treated by chemotherapy. For some people this treatment will be effective, but it many cases chemotherapy is not successful, in part because of the development of drug resistance. It is commonly observed in treating cancers, that initial treatments, such as with chemotherapy and/or radiation therapy, are effective to destroy significant numbers of tumor cells, only to leave behind a small number of tumor cells that are resistant to the treatment, which then multiply to form newly detected tumors that are increasingly resistant to treatment as new rounds of therapy are tried. The growing popularity of "cocktails" of chemotherapy drugs has given rise to multidrug resistant ("MDR") tumor cells, which are ever more difficult to destroy. Drug sensitive tumor cells, under the selective pressure of treatment with drugs, develop into drug resistant versions of the same tumor cell type. It is the drug resistant cells that take over, and with each round of chemotherapy the proportion of drug resistant cells to drug sensitive cells increases, to the point where recovery becomes more and more difficult, and eventually the cancer becomes untreatable. Indeed, drug resistance, either acquired or inherent, is the leading cause of death in cancer [27]. Mechanisms that have been suggested to account for drug resistance include over-expression of a multi-drug resistance transporter (pgp-1) [27], failure to express death inducing receptors [27, 28], and a metabolic strategy that may provide protection from a variety of stresses. Because drug resistance is such an important problem, one of the goals of the present invention is to provide methods to overcome this problem. Methods for dealing with MDR tumor cells have been proposed, but without practical, clear clinical success at entirely eliminating such cells and providing a cure for patients with MDR tumors. For example, in Lampdis and Priebe U.S. Pat. No. 6,670,330, entitled: "Cancer Chemotherapy with 2-Deoxy-D-Glucose", incorporated herein in its entirety by reference, a class of glucose metabolism inhibitors are described for use in combination with standard chemotherapy protocols in treating solid tumors by attacking anaerobic cells a the center of the tumor.

SUMMARY OF INVENTION

The invention generally relates to systems and methods for treating inflammatory and proliferative diseases, and wounds, using as a pharmacon a UCP and/or Fas antibody or other inhibitor, optionally with a fatty acid metabolism inhibitor and/or a glucose metabolism inhibitor, further optionally in combination with one or more chemotherpeutic agents. In preferred embodiments, the invention uses an antibody against UCP and/or Fas antigen, alone or combined with an oxirane carboxylic acid, represented by etomoxir, and/or with a 2-deoxyglucose compound, represented by 2-deoxy-D-glucose.

The subject matter of this invention involves, in some cases, interrelated products, alternative solutions to a particular problem, and/or a plurality of different uses of one or more systems and/or articles. In contrast to therapies that concentrated primarily on activating the immune system, the present invention can use chemotherapeutics in concert with the immune system and derives some of its effectiveness from the immune response. Tuning the immune response enables an increase in effectiveness of cancer therapy. In the present invention, cellular metabolism plays a dominating role in controlling the intercellular communication between a cancer cell and a T cell and thereby plays a dominant role in T cell activation. In particular there is a significant correlation between cellular metabolism and the expression of cell-surface Fas, one of the key co-stimulatory molecules. Fas is expressed on most rapidly dividing and self-renewing cells, including a wide variety of tumor cells [19]. While Fas is widely known as a "death receptor" and can induce programmed cell death when engaged by Fas Ligand (FasL, CD95L) or anti-Fas antibodies [20, 21], paradoxically, Fas engagement can also result in accelerated proliferation of T lymphocytes, liver cells, nervouse system cells, and some tumor cells [22, 23].

As an example of the connection between metabolism and Fas expression, it has been shown that cell surface Fas expression is upregulated in response to increasing glucose concentrations in vitro, in transformed cell lines and in freshly isolated cells from a variety of tissue origins [19]. Obviously glucose is a key source of fuel and the availability of glucose drives metabolic activity. A further example of the connection between cellular metabolism and Fas is found in the work of Bhushan et al [2] who showed that drug resistant tumor cells fail to express cell surface Fas and the work of Harper et al [24] who showed that drug resistant tumor cells also demonstrated a unique metabolic strategy, quite different from drug-sensitive tumor cells.

In one set of embodiments of the invention, a cell is exposed to a pharmacon of the invention. In another set of embodiments, an immunity profile of a tumor cell is altered by exposing the tumor cell to a pharmacon of the invention. The method, according to yet another set of embodiments, includes acts of increasing the amount of UCP on the surface of a cell, and exposing the cell to at least one of a UCP antibody or inhibitor or a Fas antibody or inhibitor. In another set of embodiments, the method includes an act of administering a pharmacon of the invention to a subject susceptible to or exhibiting symptoms of drug-resistant cancer, in some cases where the subject is not otherwise indicated for treatment with the pharmacon. In another set of embodiments, the method includes an act of administering a pharmacon of the invention to a subject susceptible to or exhibiting symptoms of cancer, in some cases, where the subject is not otherwise indicated for treatment with the compound.

The method, in yet another set of embodiments, includes an act of administering, to a subject susceptible to or exhibiting symptoms of cancer, a therapeutically acceptable amount of a composition comprising an inhibitor of a fatty acid reductase or fatty acid isomerase. The subject, in some cases, may not otherwise be indicated for treatment with the inhibitor of the fatty acid reductase or fatty acid isomerase.

According to another set of embodiments, the method includes an act of administering, to a wound in a subject, a therapeutically acceptable amount of a pharmacon of the invention that includes an agent able to alter production of reactive oxygen in cells located within or proximate the wound.

The method, in yet another set of embodiments, includes acts of surgically removing a tumor from a subject; and inserting a pharmacon of the invention into the subject. In another set of embodiments, the invention provides an act of inserting a pharmacon of the invention into or proximate a tumor. The invention, in still another set of embodiments, includes acts of removing cells from a tumor, exposing the cells to a pharmacon of the invention, and inserting the cells into a subject. In one set of embodiments, the method includes an act of altering an immunity profile of a tumor cell by exposing the tumor cell to a pharmacon of the invention. In another set of embodiments, the method includes an act of administering a pharmacon of the invention to a subject having or at risk of developing an autoimmune disease.

In another aspect, the invention provides a composition that includes a cell exposed to a pharmacon of the invention.

In yet another set of embodiments, the composition includes a pharmacon of the invention and a pharmaceutically acceptable carrier.

In yet another aspect, the invention provides an article that includes a substrate comprising cells exposed to an agent able to alter production of reactive oxygen in a cell. In another set of embodiments, the article includes isolated tumor cells exposed to a pharmacon of the invention.

The invention, in still another aspect, provides a kit. The kit, according to one set of embodiments, includes a pharmacon of the invention.

In another aspect, the present invention is directed to a method of making one or more of the embodiments described herein. In yet another aspect, the present invention is directed to a method of using one or more of the embodiments described herein. In still another aspect, the present invention is directed to a method of promoting one or more of the embodiments described herein.

In particular embodiments, the pharmacon of the invention comprises a UCP or Fas antibody or inhibitor.

In other particular embodiments, the UCP or Fas antibody or inhibitor can be combined with a therapeutically acceptable amount of a fatty acid metabolism inhibitor. A particularly useful type of fatty acid metabolism inhibitor is an oxirane carboxylic acid compound capable of inhibiting fatty acid metabolism, or a pharmacologically acceptable salt thereof. The method is useful for treating cancer that has become drug resistant including cancer that is multi-drug resistant. It has been found that drug resistant cancer cells derive a majority of their metabolic energy through fatty acid metabolism, which is inhibited by the fatty acid metabolism inhibitors used in the methods of this invention, and which are able to bind to a mitochondrial fatty acid transporter to inhibit beta-oxidation. Preferred fatty acid metabolism inhibitors are exemplified by oxirane carboxylic acid compounds.

The oxirane carboxylic acid compound preferably has the formula:

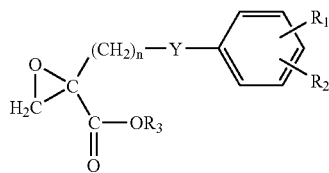

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$(CH_2)_m$—; m is 0 or a whole number from 1 to 4; and n is a whole number from 2 to 8 wherein the sum of m and n is a whole number from 2 to 8.

The oxirane carboxylic acid compound is preferably etomoxir, which is 2-(6-(4-chlorophenoxy)-hexyl)-oxirane-2-carboxylic acid ethyl ester, and a preferred method of treatment for drug resistant cancers comprises administering to a subject susceptible to or exhibiting symptoms of drug-resistant cancer, a therapeutically acceptable amount of etomoxir or a pharmacologically acceptable salt of etomoxir.

Other examples of fatty acid metabolism inhibitors that can be used in the invention include oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, or beta-hydroxy butyrate.

In other particular embodiments, the pharmacon of the invention comprises a therapeutically acceptable amount of a glucose metabolism inhibitor. Preferred glucose metabolism inhibitors are 2-deoxyglucose compounds, defined herein as homologs, analogs, and/or derivatives of 2-deoxy-D-glucose. Glucose metabolism inhibitors particularly useful herein can have the formula:

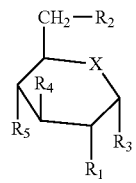

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of $R_3$, $R_4$, and $R_5$ are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group. A preferred glucose metabolism inhibitor is 2-deoxy-D-glucose In still other particular embodiments, an antibody to UCP or an antibody to Fas (CD95) or a UCP or Fas inhibitor can be combined with both a fatty acid metabolism inhibitor and a glucose metabolism inhibitor.

In still other particular embodiments, an anti-cancer agent, such as methotrexate, trimetrexate, adriamycin, taxol, 5-fluoro-uracil, or taxotere, can also administered to the subject, preferably as part of the same treatment regimen. Similarly, immunotherapies, such as tumor cell vaccines, and biotherapies such as cytokine therapies, are useful for stimulating a specific immune response against a cancer antigen. The procedure can be applied along with or after radiation treatment, and after surgically removing a tumor from the subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF DRAWINGS

FIG. 1 illustrates certain compounds for use with the invention;

FIGS. 2A-2D illustrates flow cytometry data, illustrating the treatment of L1210 and l1210DDP cancer cells for 7 hours with or without Cerulenim;

FIG. 15 is a dot plot as a function of live versus dead B16F1 melanoma cells untreated or treated with etomoxir at the indicated concentrations for 48 hours;

FIG. 24 is a dot plot as a function of live versus dead A204 human rhabdomyosarcoma cells untreated or treated with etomoxir at the indicated concentrations for 24, 48, & 72 hours;

FIG. 31 is a dot plot as a function of live versus dead HL60 MDR cells untreated or treated with etomoxir, 2-deoxy-D-glucose, or both, at the indicated concentrations for 48 hours;

FIG. 33 is a dot plot as a function of live versus dead RD cells untreated or treated with etomoxir, 2-deoxy-D-glucose, or both, at the indicated concentrations for 48 hours;

FIG. 35 is a dot plot as a function of live versus dead HL60 MDR cells, treated with anti-UCP2 antibody and otherwise untreated or treated with etomoxir, 2-deoxy-D-glucose, or both, at the indicated concentrations for 48 hours;

FIG. 37 is a dot plot as a function of live versus dead RD cells, treated with anti-UCP2 antibody and otherwise untreated or treated with etomoxir, 2-deoxy-D-glucose, or both, at the indicated concentrations for 48 hours;

FIG. 41-46 show dot plots in their lower halves as functions of live versus dead A204 human rhabdomyosarcoma cells treated with etomoxir and treated or untreated with various antibodies to UCP2;

FIG. 47 shows a comparison of percentage cell deaths with etomoxir alone to cell deaths with etomoxir and antibody;

BRIEF DESCRIPTION OF THE SEQUENCES

Figure 3A:
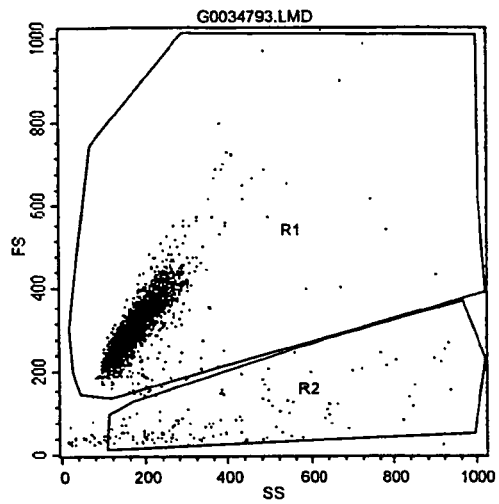
FIGS. 3A-3D illustrates flow cytometry data, illustrating the treatment of L1210 and l1210DDP cancer cells for 24 hours with or without Cerulenim.
Figure 3B:
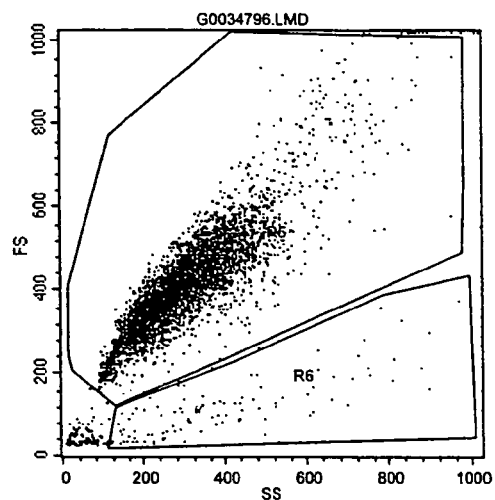
Figure 3C:
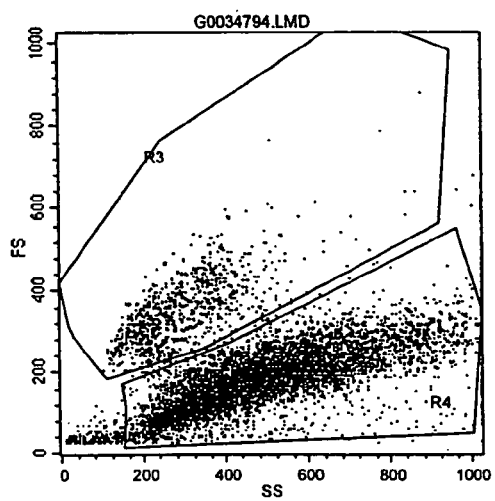
Figure 3D:
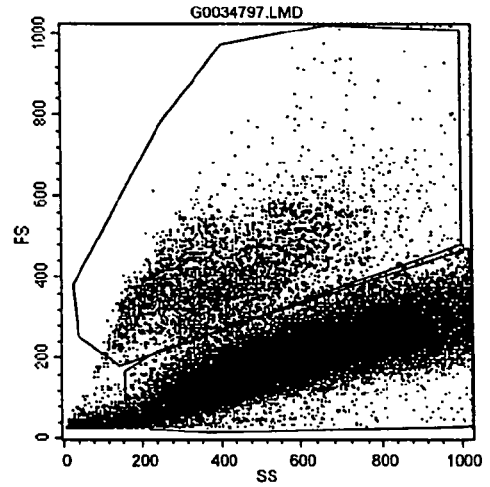
Figure 4A:
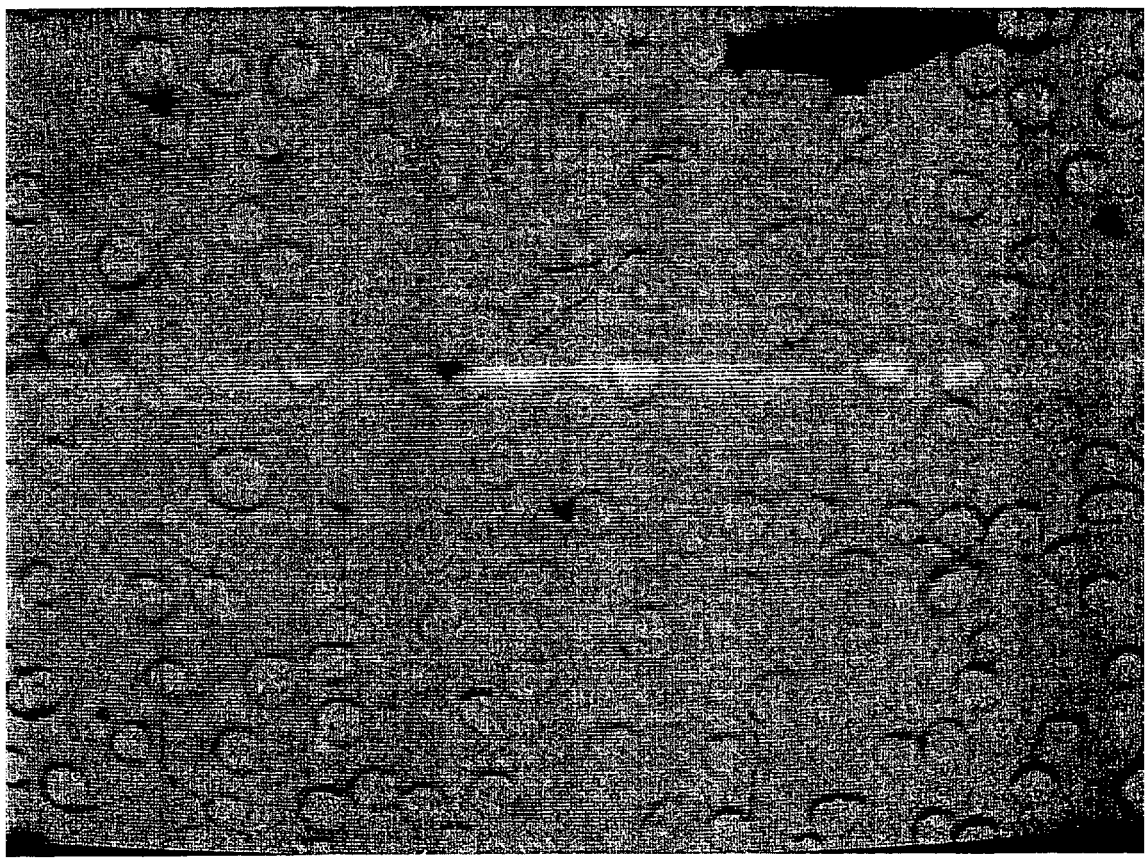
FIGS. 4A-4F illustrates, in vitro, the treatment of HL60 and HL60 MDR multi-drug resistant cancer cells with or without cerulenin.
Figure 4B:
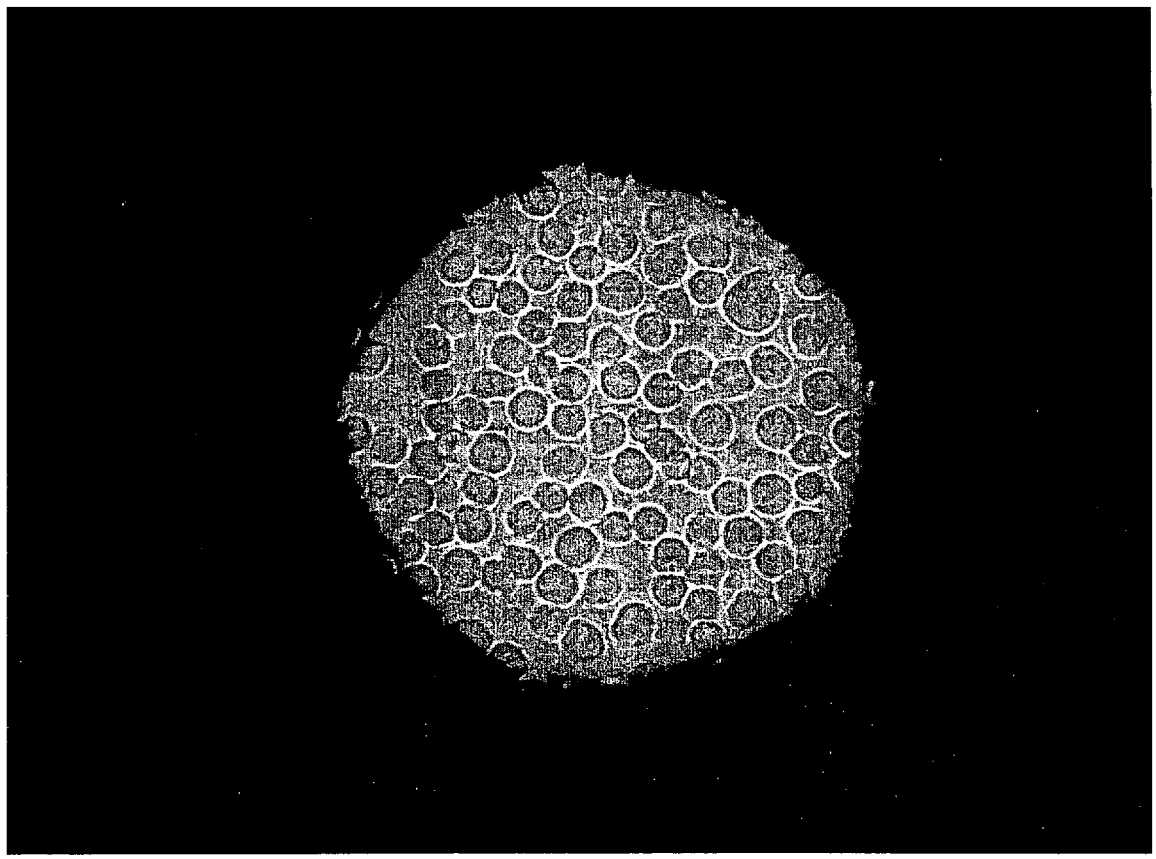
Figure 4C:
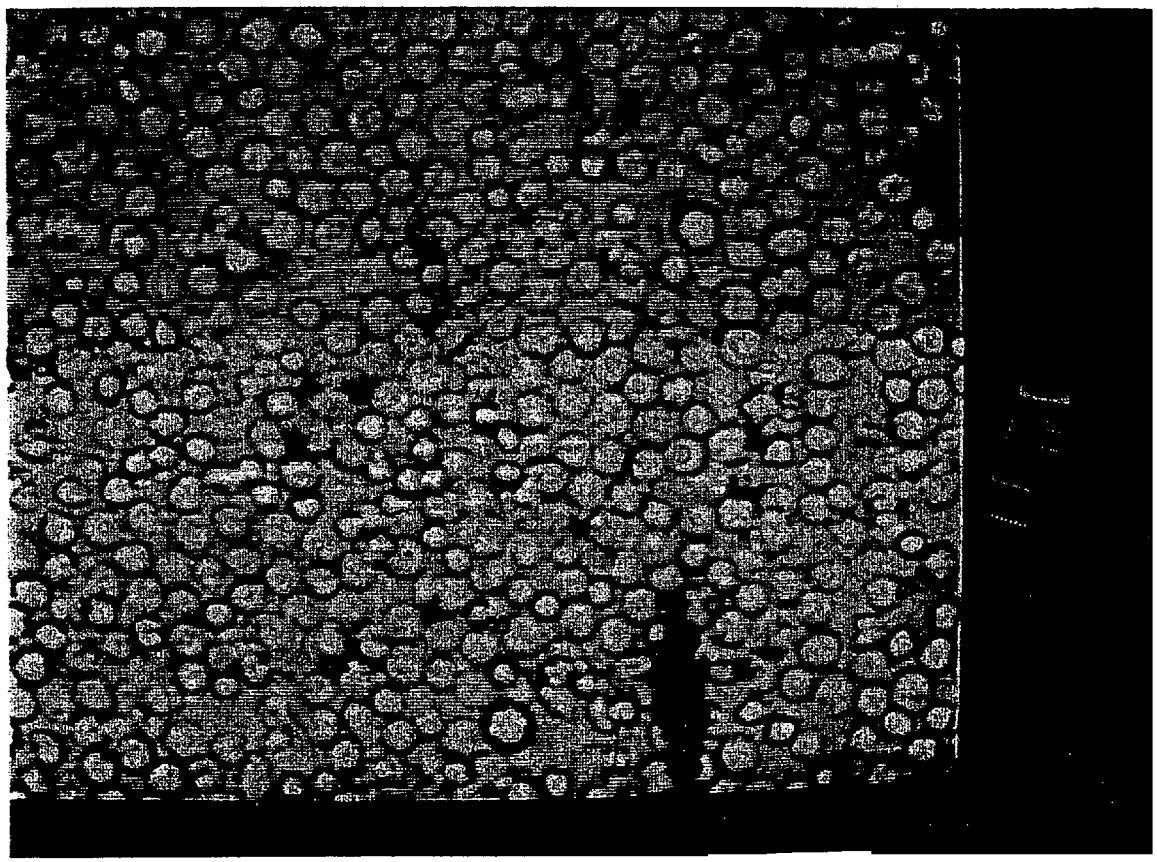
Figure 4D:
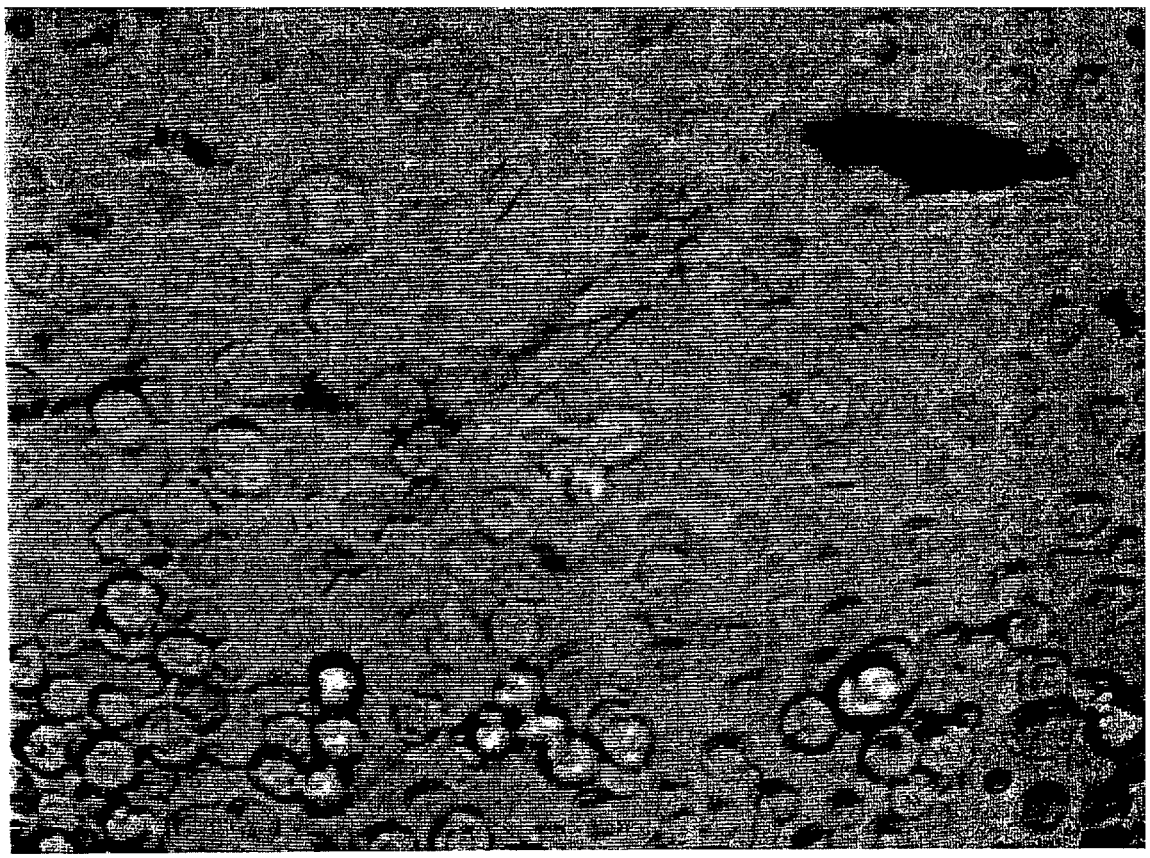
Figure 4E:
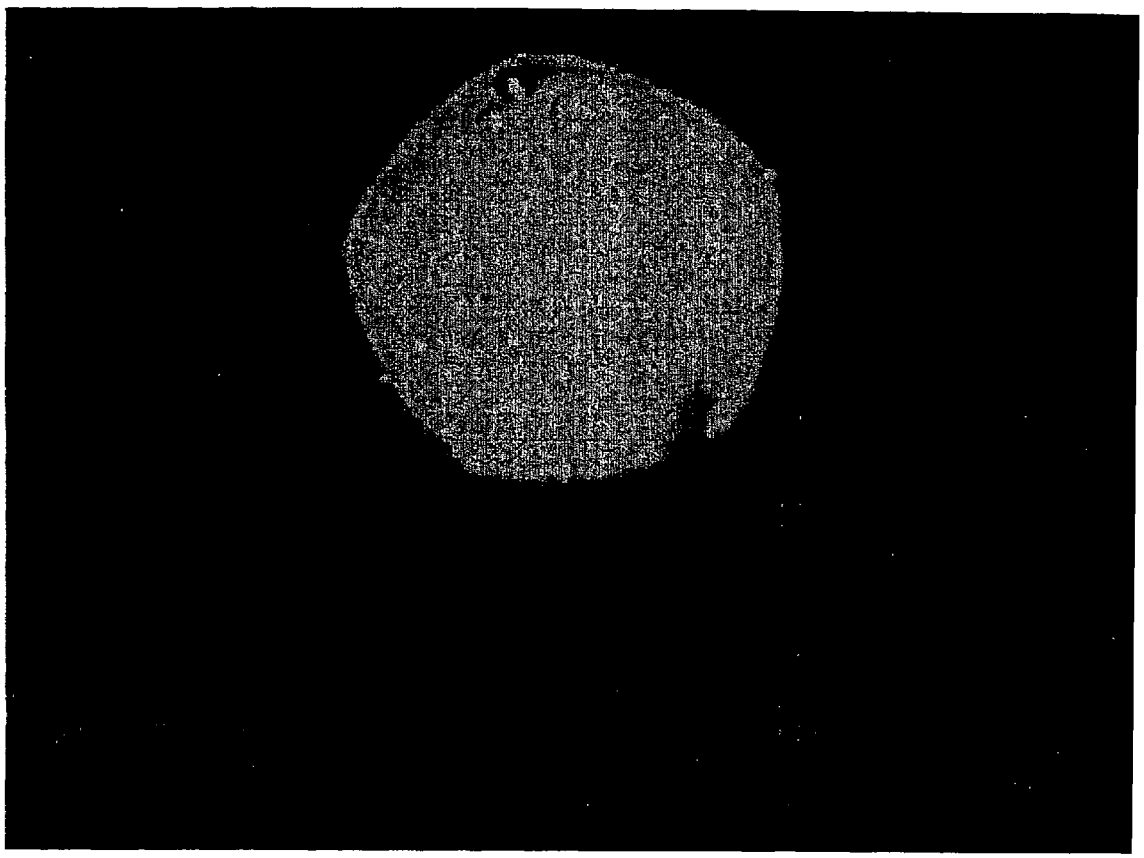
Figure 4F:
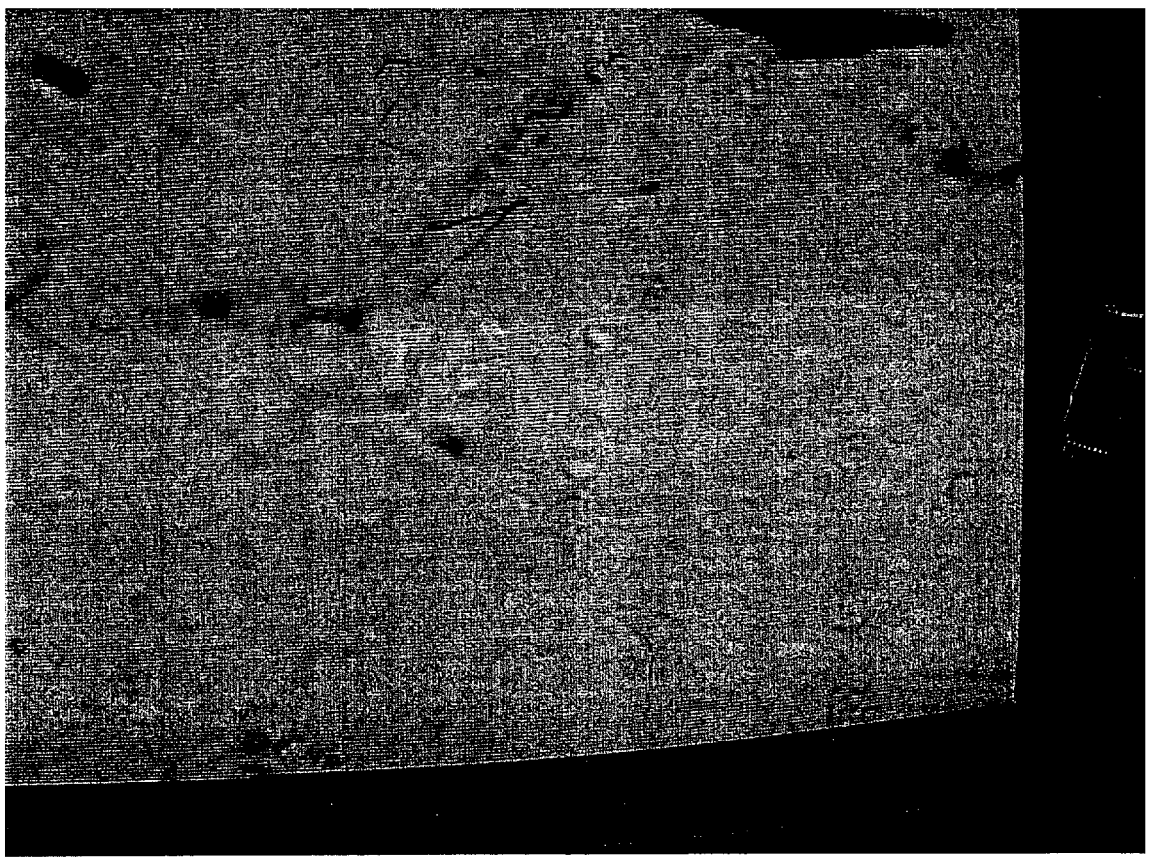

SEQ ID NO: 1 is the nucleotide sequence of the human uncoupling (UCP-1) cDNA with GenBank Acc. No. U28480;

SEQ ID NO: 2 is the predicted amino acid sequence of the translation product of human uncoupling cDNA (UCP-1) (SEQ ID NO:1);

SEQ ID NO: 3 is the nucleotide sequence of the human uncoupling (UCP-2) cDNA with GenBank Acc. No. U82819;

SEQ ID NO: 4 is the predicted amino acid sequence of the translation product of human uncoupling cDNA (UCP-2) (SEQ ID NO:3);

SEQ ID NO: 5 is the nucleotide sequence of the human uncoupling (UCP-3S) cDNA with GenBank Acc. No. U82818;

SEQ ID NO: 6 is the predicted amino acid sequence of the translation product of human uncoupling cDNA (UCP-3S) (SEQ ID NO:5);

SEQ ID NO: 7 is the amino acid sequence of the membrane attachment domain of P-cadherin;

SEQ ID NO: 8 is the amino acid sequence of the membrane attachment domain of CD2;

SEQ ID NO: 9 is the amino acid sequence of the membrane attachment domain of CD40;

SEQ ID NO: 10 is the amino acid sequence of the membrane attachment domain of contacting;

SEQ ID NO: 11 is the amino acid sequence of the membrane attachment domain of IL-4 receptor;

SEQ ID NO: 12 is the amino acid sequence of the membrane attachment domain of mannose receptor;

SEQ ID NO: 13 is the amino acid sequence of the membrane attachment domain of M-CSF receptor;

SEQ ID NO: 14 is the amino acid sequence of the membrane attachment domain of PDGFR beta-chain;

SEQ ID NO: 15 is the amino acid sequence of the membrane attachment domain of PDGFR alpha-chain;

SEQ ID NO: 16 is the amino acid sequence of the membrane attachment domain of P-selecting;

SEQ ID NO: 17 is the amino acid sequence of the membrane attachment domain of rat THY-1;

SEQ ID NO: 18 is the amino acid sequence of the membrane attachment domain of TNFR-1; and SEQ ID NO: 19 is the amino acid sequence of the membrane attachment domain of VCAM-1.

DETAILED DESCRIPTION

The present invention proceeds by recognizing that cells, based on the unique energy demands of each cell, have available to them a number of different metabolic strategies that are brought into play depending on the nature and degree of stress applied to the cells, that cell apoptosis is brought about to a significant extent because the cells energy demands cannot be met, and/or the target cells are recognized by the immune system, and that multi-drug resistant cells are to a significant extent invisible to the immune system and have evolved a unique energetic strategy that protects the cell both from external stresses and from being recognized by the immune system. The invention targets the distinct cellular metabolic pathways of diseased, defective, or pathologic cells, tissues or organs, and the immune system to treat human inflammatory and proliferative diseases, such as cancer, autoimmunity, heart disease, and chronic infectious disease. The methods herein are also useful in tissue regeneration, including neural regeneration, transplantation, and wound healing.

Every cell in the body uses carbohydrates, protein, and fat in different proportions for energy. The cell's choice of fuel, its metabolic strategy, will change depending on its state of activation or differentiation. For example, a cell that is rapidly dividing has different energy demands than one that is not dividing. The same is true for cells that are under stress or are infected. The present invention proceeds from the discovery of a unique metabolic strategy, widely used by drug resistant cells, that is characterized by the ability to burn fat under conditions of stress, including the stress of chemotherapy or radiation. When cells are rapidly dividing, they use glucose at very high rates, but under conditions of stress, cells, if capable, use fat in a greater proportion as a protective strategy. Respiration, oxygen use, and external stresses can generate a variety of toxic by-products (including free radicals) that can cause damage to cells. Tumor cells upregulate proteins that allow them to burn fat as a protective strategy against such by-products. The immune system can monitor the metabolic state of individual cells and destroy those in an inappropriate state. However, tumor cells can survive this surveillance by changing their metabolic strategy to one that protects the tumor cell by causing the cell to be invisible to the immune system.

UCPs are often expressed in the plasma membrane of rapidly dividing cells. According to certain embodiments of this invention, by manipulating UCP expression, inhibition of cellular, metabolic, and/or immunological responses may occur, for example, which may be useful in the treatment of cancers, wounds, or the like. Additionally, cells in cancers or wounds often derive a majority of their metabolic energy through fatty acid metabolism. Thus, the cells may be manipulated to increase the amount of UCP in the plasma membrane (and/or decrease mitochondrial UCP), and/or be manipulated to inhibit UCP function, for example, by exposure of the cells to a UCP inhibitor, a Fas inhibitor, a fatty acid metabolism inhibitor, and/or an agent able to alter cellular production of reactive oxygen, singularly or in combination. Additionally, altered production of reactive oxygen may be associated with changes in cellular immunogenic profiles and thus, in some embodiments, reactive oxygen production may be altered to stimulate or inhibit cellular and/or immunological responses, for example, to cancer cells or wounds. In some cases, the cells may be manipulated to increase the amount of Fas expressed on the cell surface. The ability to manipulate the plasma membrane potential of a cell thus may provide the ability to control or at least influence the fate of the cell. When the plasma membrane potential of a cell is increased in a cell, by causing an increase in the expression of UCP in the plasma membrane, the cell may be able to respond by rapid cell division or cell death, depending on the signal. In certain instances, the systems and methods of the invention can be used in conjunction with conventional therapies.

An increase in UCP levels in the plasma membrane may be related to an increased dependence on UCP for energy production or regulation by the cell. Thus, various systems and methods of the invention provide for the ability to control UCP levels within the cell. As an example, the amount of UCP in the plasma membrane of the cells may be increased by exposing the cells to a composition including a fatty acid metabolism inhibitor, and/or by delivering a nucleic acid to a cell such that the expression of UCP in the plasma membrane is increased, as further described herein.

The present invention generally relates to systems and methods for treating inflammatory or proliferative diseases such as cancers, immunological conditions, autoimmune diseases, and treating wounds. Various aspects of the invention involve the treatment of cells with UCP antibodies or inhibitors or Fas antibodies or inhibitors, alone or in combination with fatty acid metabolism inhibitors, glucose metabolism inhibitors, and/or agents able to alter cellular production of reactive oxygen. The manipulation of the cells may be performed simultaneously or sequentially, in any order. The cells may be manipulated under any suitable condition, i.e., in vivo, ex vivo, in vitro, etc. By inhibiting fatty acid metabolism, the cell is forced to resume glucose metabolism, thus exhibiting UCP and/or Fas on its cell surface to become visible to the immune system. Thus the invention uses a pharmacon of this invention that targets UCP and/or Fas, e.g., a UCP and/or Fas antibody, optionally with a pharmacon that targets one or both of the predominant metabolic pathways: a fatty acid metabolism inhibitor and/or a glucose metabolism inhibitor. As a result of inhibition of fatty acid metabolism, UCP and/or Fas is exposed on the cell surface so that the cell becomes susceptible to attack by the UCP antibody. In another, or further, embodiment, along with, preferably after, treatment of the MDR cell as above, it is subjected to one or more chemotherapeutic agents. In a preferred embodiment, the fatty acid metabolism inhibitor is an oxirane carboxylic acid, exemplified by etomoxir, and the glucose metabolism inhibitor is a 2-deoxyglucose compound, exemplified by 2-deoxy-D-glucose.

The following applications are incorporated by reference. U.S. Provisional Patent Application Ser. No. 60/534,896 filed Jan. 8, 2004, entitled "Systems and Methods for Treating Cancers and Wounds" by M. Karen Newell et al.; U.S. Provisional Patent Application Ser. No. 60/535,077, entitled "Systems and Methods for Treating Cancers and Wounds With Oxirane Carboxylic Acids" by M. Karen Newell; and U.S. Provisional Patent Application Ser. No. 60/566,746, entitled "Systems and Methods for Treating Human Inflammatory and Proliferative Diseases, With a Combination of Fatty Acid Metabolism Inhibitors and Glucose metabolism Inhibitors and/or UCP and/or Fas Antibodies" by M. Karen Newell; U.S. Provisional Patent Application Ser. No. 60/477,873 filed Jun. 12, 2003, entitled "Systems and Methods for Treating Cancers and Wounds," by M. Karen Newell, et al.; U.S. Provisional Patent Application Ser. No. 60/478,646 filed Jun. 12, 2003, entitled "Systems and Methods for Treating Cancers and Wounds," by Martha Karen Newell Rogers, et al.; U.S. Provisional Patent Application Ser. No. 60/490,587, filed Jul. 28, 2003, entitled "Systems and Methods for Treating Cancers and Wounds With Oxirane Carboxylic Acids," by M. Karen Newell, et al.; U.S. Provisional Patent Application Ser. No. 60/534,896 filed Jan. 8, 2004, entitled "Systems and Methods for Treating Cancers and Wounds," by Martha Karen Newell Rogers, et al.; U.S. Provisional Patent Application Ser. No. 60/535,077, filed Jan. 8, 2004, entitled "Systems and Methods for Treating Cancers and Wounds With Oxirane Carboxylic Acids," by M. Karen Newell.; U.S. Provisional Patent Application Ser. No. 60/566,746, filed Apr. 29, 2004, entitled "Systems and Methods for Treating Human Inflammatory and Proliferative Diseases, With a Combination of Fatty Acid Metabolism Inhibitors and Glucose metabolism Inhibitors and/or UCP and/or Fas Antibodies," by Karen Newell; U.S. patent application Ser. No. 10/272,432, filed Oct. 15, 2002, entitled "Methods for Regulating Co-Stimulatory Molecule Expression with Reactive Oxygen," by M. K. Newell, et al., published as 2004/0005291 on Jan. 8, 2004; and International Patent Application No. PCT/US00/17245, filed Jun. 22, 2000, entitled "Methods and Products for Manipulating Uncoupling Protein Expression," by M. K. Newell, et al., published as WO 00/78941 on Dec. 28, 2000.

UCP and/or Fas

According to one set of embodiments, the cells may be exposed to a composition including a UCP or Fas antibody or inhibitor. A "UCP," or an uncoupling protein, is a protein expressed in cells, especially cell membranes, as previously described. An example of a native UCP protein has an amino acid sequence as presented in SEQ ID NO:2. In some cases, UCPs can be expressed in cells using UCP nucleic acid expression vectors for the UCP peptide, prepared and inserted into cells using routine procedures known in the art. "UCP nucleic acid," as used herein, refers to a nucleic acid molecule which: (1) hybridizes under stringent conditions to a nucleic acid having the sequence of SEQ ID NO:1, SEQ ID NO:3, or SEQ ID NO:5 and (2) codes for a UCP polypeptide. An example is the UCP nucleic acid having the nucleic acid sequence of SEQ ID NO:1, SEQ ID NO:3, or SEQ ID NO:5 (the nucleic acids encoding the human UCP-1, UCP-2, and UCP-3 polypeptides respectively). The UCP nucleic acids may be intact UCP nucleic acids which include the nucleic acid sequence of SEQ ID NO:1, SEQ ID NO:3, or SEQ ID NO:5, as well as homologs and alleles of a nucleic acid having the sequences of SEQ ID NO:1, SEQ ID NO:3, or SEQ ID NO:5. Intact UCP nucleic acids further embrace nucleic acid molecules which differ from the sequence of SEQ ID NO:1, SEQ ID NO:3, or SEQ ID NO:5 in the codon sequence due to the degeneracy of the genetic code. The UCP nucleic acids of the invention may also be functionally equivalent variants, analogs and fragments of the foregoing nucleic acids. "Functionally equivalent," in reference to a UCP nucleic acid variant, analog or fragment, refers to a nucleic acid that codes for a UCP polypeptide that is capable of functioning as an UCP.

The UCP nucleic acid molecules can be identified by conventional techniques, e.g., by identifying nucleic acid sequences which code for UCP polypeptides and which hybridize to a nucleic acid molecule having the sequence of SEQ ID NO:1, SEQ ID NO:3, or SEQ ID NO:5 under stringent conditions. The term "stringent conditions," as used herein, refers to parameters with which the art is familiar. As one example, stringent conditions, as used herein, can refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA), where SSC is 0.15 M sodium chloride/0.15 M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C. There are other conditions, reagents, and so forth which can be used, which result in a similar degree of stringency; those of ordinary skill in the art will be familiar with such conditions. It will be understood that those of ordinary skill in the art will be able to manipulate the conditions in a manner to permit the clear identification of homologs and alleles of UCP and UCP nucleic acids. Those of ordinary skill in the art will also be familiar with the methodology for screening cells and libraries for the expression of molecules, such as UCP, which can be isolated, followed by purification and sequencing of the pertinent nucleic acid molecule. For instance, in screening for UCP nucleic acid sequences, a Southern blot may be performed using the foregoing conditions, together with a radioactive probe. After washing the membrane to which the DNA is finally transferred, the membrane can be placed against X-ray film to detect the radioactive signal.

In general, homologs and alleles of a UCP nucleic acid typically will share at least 40% nucleotide identity with SEQ ID NO: 1, SEQ ID NO:3, or SEQ ID NO:5; in some instances, will share at least 50% nucleotide identity; and in still other instances, will share at least 60% nucleotide identity. In some cases, the homologs will have at least 70% sequence homology to SEQ ID NO:1, SEQ ID NO:3, or SEQ ID NO:5. In other cases, the homologs will have at least 80% or at least 90% sequence homology to SEQ ID NO:1, SEQ ID NO:3, or SEQ ID NO:5.

In some cases, the UCP nucleic acid includes degenerate nucleic acids. Examples of degenerate nucleic acids include alternative codons to those present in the naturally occurring nucleic acid that codes for the human UCP polypeptide. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring nucleic acids in codon sequence due to the degeneracy of the genetic code.

In some cases, the UCP nucleic acid is operably linked to a gene expression sequence which directs the expression of the UCP nucleic acid within a eukaryotic cell. The "gene expression sequence" is any regulatory nucleotide sequence, such as a promoter sequence or promoter-enhancer combination, which facilitates the efficient transcription and translation of the UCP nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and beta-actin. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence can include, as necessary, 5' non-transcribing and 5' non-translating sequences involved with the initiation of transcription and translation, respectively, such as a TATA box, capping sequence, CAAT sequence, and the like. Such 5' non-transcribing sequences can include a promoter region which includes a promoter sequence for transcriptional control of the operably joined UCP nucleic acid. The gene expression sequences optionally include enhancer sequences or upstream activator sequences as desired.

In certain instances, the UCP nucleic acid is linked to a gene expression sequence which permits expression of the UCP nucleic acid in the plasma membrane of a cell, e.g. a resistant tumor cell. A sequence which permits expression of the UCP nucleic acid in the plasma membrane of a tumor cell is one which is selectively active in the particular tumor cell and thereby causes the expression of the UCP nucleic acid in the cell. Those of ordinary skill in the art will be able to identify promoters that are capable of expressing a UCP nucleic acid in a tumor cell based on the type of tumor cell, as well as other known cells.

The UCP nucleic acid sequence and the gene expression sequence are said to be "operably linked" when they are covalently linked in such a way as to place the transcription and/or translation of the UCP coding sequence under the influence or control of the gene expression sequence. If it is desired that the UCP sequence be translated into a functional protein, two DNA sequences are said to be operably linked if induction of a promoter in the 5' gene expression sequence results in the transcription of the UCP sequence and if the nature of the linkage between the two DNA sequences does not (1) result in the introduction of a frame-shift mutation, (2) interfere with the ability of the promoter region to direct the transcription of the UCP sequence, or (3) interfere with the ability of the corresponding RNA transcript to be translated into a protein. Thus, a gene expression sequence would be operably linked to a UCP nucleic acid sequence if the gene expression sequence were capable of effecting transcription of that UCP nucleic acid sequence such that the resulting transcript might be translated into the desired protein or polypeptide.

UCP and/or Fas Inhibitors—Generally

As described, the cells may be exposed to a composition including a UCP inhibitor, according to one set of embodiments. A "UCP inhibitor," as used herein, is a molecule that inhibits the expression and/or activity of UCP in the plasma membrane. Examples of UCP inhibitors include, but are not limited to, UCP binding peptides such as anti-UCP antibodies, UCP anti-sense nucleic acids, UCP dominant-negative nucleic acids and nucleotide analogs in an amount effect to inhibit plasma membrane UCP function. In one embodiment, the UCP inhibitor is a nucleotide or a nucleotide analog. In some cases, the nucleotide analog is a purine analog, or a pyrimidine analog. If the UCP inhibitor includes a purine analog, the purine analog may include one or more of guanosine diphosphate, 8-oxo-adenosine, 8-oxo-guanosine, 8-fluoro-adenosine, 8-fluoro-guanosine, 8-methoxy-adenosine, 8-methoxy-guanosine, 8-aza-adenosine and 8-aza-guanosine, azacitidine, fludarabine phosphate, 6-MP, 6-TG, azathiprine, allopurinol, acyclovir, gancylovir, deoxycoformycin, arabinosyladienine (ara-A), guanosine diphosphate fucose, guanosine diphosphate-2-fluorofucose, guanosine diphosphate-beta-L-2-aminofucose, guanosine diphosphate-D-arabinose and 2-aminoadenosine. Those of ordinary skill in the art will know of other suitable analogs. Similarly, if the nucleotide analog includes a pyrimidine analog, the pyrimidine analog may include one or more of uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, floxuridine, uridine, thymine, 3'-azido-3'-deoxythymidine, 2-fluorodeoxycytidine, 3-fluoro-3'-deoxythymidine;

3'-dideoxycytidin-2'-ene; and 3'-deoxy-3'-deoxythymidin-2'-ene, and cytosine arabinoside. Other suitable compounds can be identified by those of ordinary skill in the art.

In certain instances, the analogs are membrane impermeable, and/or are modified in such a way as to render the nucleotide or nucleotide analog membrane impermeable, e.g., to prevent uptake of the nucleotide or nucleotide analog by the cell. By using compounds which are not taken up by a cell, but act on plasma membrane UCP, many toxic side effects may be avoided. Such UCP inhibitors will not have an effect on cells that do not have plasma membrane UCP expressed, as the UCP inhibitors will not have access to intracellular UCP. Additionally, the inhibitors will not be metabolized within cells, which may, in some cases, result in toxic or cytotoxic products.

In some instances, the nucleotide or a nucleotide analog may be modified to include a plasma membrane targeting sequence. For example, the nucleotide or nucleotide analogs can be modified to produce plasma membrane targeted UCP inhibitors by attaching a plasma membrane targeting sequence to the nucleotide or nucleotide analog. This can be accomplished by linking the nucleotide analog to a cell surface targeting molecule. Several non-limiting systems methods for linking molecules are described below and others are known in the art.

Plasma membrane targeting sequences include hydrophobic moieties and membrane attachment domains. Hydrophobic moieties are well known in the art, and include those described herein. Thus, in some cases, the UCP inhibitor includes a hydrophobic moiety; for example, the UCP inhibitor may be a modified nucleotide or nucleotide analog conjugated to a hydrophobic moiety.

In another embodiment, the UCP inhibitor includes a membrane attachment domain, optionally conjugated to a nucleotide or nucleotide analog. A "membrane attachment domain," as used herein, refers to a domain that spans the width of a cell/plasma membrane, or any part thereof. The membrane attachment domain is able to function to attach a UCP inhibitor to a cell membrane in this instance. Membrane attachment domains useful in the invention include those domains that function to attach a UCP inhibitor to a plasma membrane of an eukaryotic cell or the outer membrane of a prokaryotic cell. One of ordinary skill in the art will understand that an appropriate membrane attachment domain can be selected based on the type of cell in which the membrane bound fusion protein is to be expressed. The term "membrane bound," as used herein in reference to a fusion protein, means stably attached to a cellular membrane. The term "fusion protein," as used herein, means a hybrid protein including a synthetic or heterologous amino acid sequence.

In some cases, the membrane attachment domain is a Type I membrane attachment domain, a Type II membrane attachment domain, or a Type III membrane attachment domain. In other cases, the membrane attachment domain is one of P-cadherin (FILPILGAVLALLLLLTLLALLLLV)(SEQ ID NO: 7), CD2 (IYLIIGICGGGSLLMVFVALLVFYIT)(SEQ ID NO: 8), CD40 (ALVVIPIIFGILFAILLVLVFI)(SEQ ID NO: 9), contacting (ISGATAGVPTLLLGLVLPAP)(SEQ ID NO: 10), IL-4 receptor (LLLGVSVSCIVILAV-CLLCYVSIT)(SEQ ID NO: 11), mannose receptor (VAGV-VIIVILLILTGAGLAAYFFY)(SEQ ID NO: 12), M-CSF receptor (FLFTPVVVACMSIMALLLLLLLLLL)(SEQ ID NO: 13), PDGFR beta-chain (VVVISAILALVVLTIISLIIL-IMLWQKKPR)(SEQ ID NO: 14), a PDGFR alpha-chain (ELTVAAAVLVLLVIVSISLIVLVVTW)(SEQ ID NO: 15), P-selecting (LTYFGGAVASTIGLIMGGTLLALL)(SEQ ID NO: 16), rat THY-1 (VKCGGISLLVQNTSWLLLLLLSLS-FLQATDFISL)(SEQ ID NO: 17), TNFR-1 (TVLLPLVIFF-GLCLLSLLFIGLM)(SEQ ID NO: 18), or VCAM-1 (LLV-LYFASSLIIPAIGMIIYFAR)(SEQ ID NO: 19).

A variety of naturally occurring and synthetic membrane attachment domains derived from eukaryotic and prokaryotic cell surface proteins may be useful in the invention. For use in higher eukaryotic cells such as mammalian cells, a membrane attachment domain can be, for example, the membrane-spanning region of an integral membrane protein such as a cell surface receptor or cell adhesion molecule. Membrane attachment domains useful in the invention can be derived, for example, from cell surface receptors including growth factor receptors such as platelet derived growth factor receptor, epidermal growth factor receptor or fibroblast growth factor receptor, hormone receptors, cytokine receptors, or T cell receptor. Membrane attachment domains useful in the invention can also be derived from cell adhesion molecules such as cadherins, integrins, selectins and members of the immunoglobulin superfamily, as well as other integral membrane proteins such as CD antigens. The amino acid sequences of examples of membrane attachment domains are described herein (see also Pigott, et al., *The Adhesion Molecule Facts Book*, Academic Press, Inc., 1993 and Barclay, et al., *The Leukocyte Antigen Facts Book*, Academic Press, Inc., 1993, each of which is incorporated herein by reference). If desired, the fusion protein can include the cytosolic domain, or a portion thereof, of the heterologous protein from which the membrane attachment domain is derived. The term "heterologous," as used herein in reference to a membrane attachment domain operatively fused to a UCP inhibitor, means a membrane attachment domain derived from a source other than the gene encoding the UCP inhibitor. A heterologous membrane attachment domain can be synthetic, or can be encoded by a gene distinct from the gene encoding the UCP inhibitor to which it is fused. The term "operatively fused," as used herein in reference to a UCP inhibitor and a heterologous membrane attachment domain, means that the UCP inhibitor and membrane attachment domain are fused in the correct reading frame such that, under appropriate conditions, a full-length fusion protein is expressed. One of ordinary skill in the art would recognize that such a fusion protein can comprise, for example, an amino-terminal UCP inhibitor operatively fused to a carboxyl-terminal heterologous membrane attachment domain or can comprise an amino-terminal heterologous membrane attachment domain operatively fused to a carboxyl-terminal UCP inhibitor.

Type I membrane attachment domains are typically transmembrane sequences of about 25 hydrophobic amino acid residues usually followed by a cluster of basic amino acids. Amino acids that are usually excluded from such membrane attachment domains include Asn, Asp, Glu, Gln, His, Lys and Arg, although where the domains form a multimeric complex in the membrane, there can be charged residues present. The orientation of a type I membrane attachment domain is such that the amino-terminal portion is extracellular. Such type I membrane attachment domains can be derived, for example, from CD2, CD40 or the IL-4 receptor.

Type II membrane attachment domains typically are transmembrane domains. The orientation of a type II membrane attachment domain is such that the carboxy-terminal portion is extracellular. Examples of type II membrane attachment domains include the transmembrane domain of CD72.

Type III membrane attachment domains, or segments thereof, also can be useful in the invention. Such type III membrane attachment domains are derived from eukaryotic cell surface molecules that cross the lipid bilayer numerous times. A membrane attachment domain useful in the invention can be, for example, one or more transmembrane domains derived from MDR1, a G-protein linked receptor or a protein of the rhodopsin superfamily.

A membrane attachment domain of the invention can also be, in some cases, a phosphatidylinositol-glycan (PI-G) anchor, which is attached to the carboxy-terminal residue of a protein. A PI-G anchor can be derived, for example, from human placental alkaline phosphatase (HPAP), and can function to anchor a fusion protein to the cell surface (see, for example, Whitehom, et al., *Biotechnology*, 13:1215, 1995, incorporated herein by reference). PI-G-anchored molecules have a signal sequence at their carboxy-terminus that is cleaved off and replaced by the PI-G anchor. The residues at the PI-G attachment site and immediately following are typically small amino acids such as Ala, Asn, Asp, Gly, Cys or Ser. After the attachment residue, there is a hydrophobic sequence of about 10 to 20 residues starting 7-10 residues after the attachment point. Such hydrophobic PI-G-signal sequences generally lack the basic charged residues found in type I membrane attachment domains.

In yet another embodiment, the UCP inhibitor includes 5-FU. 5-FU ("FLUOROURACIL" by Roche Labs., a division of Hoffman-LaRoche, Inc., Nutley, N.J.) is a cytotoxic fluoropyrimidine antimetabolic commonly used in the palliative management of carcinoma of the colon, rectum, breast, ovarian, cervix, bladder, stomach, liver and pancreas. 5-FU has been shown to have synergistic interaction with other antineoplastic agents, interferons, and irradiation and is thus commonly used in combination therapy. 5-Fluorouracil (5-FU) has been used continuously since its development in 1957 by Duusinski and Heidelberger (U.S. Pat. No. 2,802,005). 5-FU was originally designed to work as an inhibitor of thymidylate synthetase (TS). TS is the enzyme which converts deoxyuridine 5'-O-monophosphate (dUMP) to deoxythymidine 5'-O-monophosphate (dTMP). 5-FU targeted to the cell membrane and can prevent from entering the cell can function by inhibiting UCP expression in the plasma membrane.

Previous protocols for the administration of 5-FU for treatment of human cancer involve infusion of the drug for long periods of time. 5-FU that is taken up by the cell is rapidly metabolized and excreted with a half-life in vivo of about 18 minutes. The effectiveness of 5-FU is hampered by rapid metabolism and formation of 2-fluoro-beta-alanine (FBAL) which is neurotoxic and cardiotoxic. When 5-FU is used according to the invention, it can be modified to prevent cell uptake or targeted to the plasma membrane so that it is delivered to the plasma membrane and is not taken up by the cell. Thus, use of 5-FU according to certain systems and methods of the invention avoids the metabolic breakdown into toxic compounds that causes the associated side effects.

Screening assays for determining the sensitivity of a cell to 5-fluorouracil and its analogs have been previously described, for example, in Anai H, et al., "Sensitivity Test for 5-Fluorouracil and Its Analogues, 1-(2-Tetrahydrofuryl)-5-fluorouracil, Uracil/1-(2-tetrahydrofuryl)-5-fluorouracil (4:1) and 1-Hexylcarbamoyl-5-fluorouracil, Using the Subrenal Capsule Assay," Oncology,45(3):144-7, 1988. This paper describes the testing of the chemosensitivity of human neoplastic tissues using 5-fluorouracil (5-FU) and its analogs: 1-(2-tetrahydrofuryl)-5-FU (FT), uracil/FT (UFT) and 1-hexylcarbamoyl-5-FU (HCFU), and the in vivo subrenal capsule (SRC) assay. The relative variation of tumor size (delta TS/TSo) was calculated and the chemosensitivity was considered to be sensitive when delta TS/TSo in the treated group was decreased to below 10%. The results of the study suggest that the SRC assay may be useful for predicting the effective drug among 5-FU and 5-FU analog for individual patients with cancer. These assays can also be used with the plasma membrane targeted or membrane impermeable forms of 5-FU to determine which analogs are useful.

In still another embodiment, the UCP inhibitor includes fludarabine phosphate and/or floxuridine. Fludarabine phosphate (e.g., "FLUDARA®" by Berlex Labs., Richmond, Calif. 94804) is a purine analog antimetabolic commonly used in the treatment of chronic lymphocytic leukemia (CLL). Floxuridine (e.g. "FUDR®"by Roche Labs., a division of Hoffman-LaRoche, Inc., Nutley, N.J. 07110) is a cytotoxic drug commonly used in the palliative management of gastrointestinal adenocarcinoma metastatic to the liver and is also used for treating brain, breast, head and neck cancers with liver metastasea. The plasma membrane targeted or membrane impermeable forms of FLUDARA® can also be useful for the treatment of these cancers.

In yet another embodiment, the invention includes the use of antisense oligonucleotides that selectively bind to UCP, for example, to reduce the expression of plasma membrane UCP. Antisense oligonucleotides are useful, for example, for inhibiting plasma membrane UCP in a cell in which it is ordinarily expressed in the plasma membrane. Antisense oligonucleotides are further described below. In some cases, some regions of SEQ ID NO:1, SEQ ID NO:3, and SEQ ID NO:5 will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long).

As used herein, the terms "antisense oligonucleotide" or "antisense" describe an oligonucleotide which hybridizes under physiological conditions to DNA comprising a particular gene, or to an mRNA transcript of that gene, to inhibit the transcription of that gene and/or the translation of the mRNA transcript. The antisense molecules can be designed so as to hybridize with the target gene or target gene product, and interfere with transcription or translation of the target mammalian cell gene. Those of ordinary skill in the art will recognize that the exact length of the antisense oligonucleotide and its degree of complementarity with its target will depend upon the specific target selected, including the sequence of the target, and the particular bases which comprise that sequence. The antisense is often a unique fragment. A unique fragment is one that is a "signature" for a larger nucleic acid. As will be recognized by those of ordinary skill in the art, the size of the unique fragment typically depends upon its conservancy in the genetic code.

In some cases, the antisense oligonucleotide can be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of ordinary skill in the art can easily choose and synthesize any of a number of appropriate antisense molecules for use in accordance with the present invention. In order to be sufficiently selective and potent for inhibition, such antisense oligonucleotides can comprise at least 7, or at least 15 consecutive bases which are complementary to the target. In some cases, the antisense oligonucleotides comprise a complementary sequence of 20 bases to 30 bases. Although oligonucleotides may be chosen which are antisense to any region of the gene or RNA (e.g., mRNA) transcripts, in certain embodiments, the antisense oligonucleotides are complementary to 5' sites, such as translation initiation sites, transcription initiation sites, or promoter sites, that are upstream of the gene targeted for inhibition by the antisense oligonucleotides. In addition, 3'-untranslated regions may be targeted in some cases. Furthermore, 5' or 3' enhancers can be targeted in some applications. Targeting to mRNA splice sites has also been used in the art, but may be less desirable if alternative mRNA splicing occurs. In at least some embodiments, the antisense is targeted, e.g., to sites in which mRNA secondary structure is not expected (see, e.g., Sainio, et al., *Cell Mol. Neurobiol.,* 14(5): 439-457, 1994) and/or at which proteins are not expected to bind. The selective binding of the antisense oligonucleotide to a mammalian target cell nucleic acid can effectively decrease or eliminate the transcription or translation of the mammalian target cell nucleic acid sequence. In some embodiments, reduction in transcription or translation of the nucleic acid molecule may be desirable in preparing an animal model for further defining the role played by the mammalian target cell nucleic acid sequence in modulating an adverse medical condition.

The invention also includes, in another embodiment, the use of a dominant negative plasma membrane UCP polypeptide. The end result of the use (e.g., expression) of a dominant negative polypeptide in a cell is a reduction in plasma membrane expressed UCP. One of ordinary skill in the art can assess the potential for a dominant negative variant of a protein, and using standard mutagenesis techniques to create one or more dominant negative variant polypeptides, e.g., as previously discussed. Other methods for creating and testing dominant negative variants of a protein will be apparent to one of ordinary skill in the art.

As used herein, a "dominant negative" polypeptide is an inactive variant of a protein (e.g., an enzyme), which, by interacting with the cellular machinery, displaces an active protein from its interaction with the cellular machinery and/or competes with the active protein, thereby reducing the effect of the active protein. For example, a dominant negative receptor which binds a ligand, but does not transmit a signal in response to binding of the ligand, can reduce the biological effect of expression of the ligand. Likewise, a dominant negative catalytically-inactive kinase which interacts normally with one or more target proteins, but does not phosphorylate the target proteins, can reduce phosphorylation of the target proteins in response to a cellular signal. Similarly, a dominant negative transcription factor which binds to a promoter site in the control region of a gene, but does not increase gene transcription, can reduce the effect of a normal transcription factor, by occupying promoter binding sites without increasing transcription.

In another set of embodiments, cells may be exposed to a composition including a Fas (CD95) inhibitor. A "Fas inhibitor," as used herein, is any molecule that inhibits Fas function when Fas is expressed on the cell surface. In one embodiment the Fas inhibitor is a Fas binding peptide, such as an antibody, as further described below.

In some embodiments, an inhibitor of the invention is a binding peptide or molecule. For instance, a UCP inhibitor may include a UCP binding peptide or molecule, a Fas inhibitor may include a Fas binding peptide or molecule, etc. The binding peptides or molecules can be delivered directly to a cell, for example, to act on the plasma membrane UCP or Fas. In some cases, UCP binding peptides or molecules can be delivered by a mechanism which will not facilitate uptake of the binding peptides or molecules into the cell, thereby allowing the UCP binding peptide or molecule to be targeted to the plasma membrane UCP, as opposed to mitochondrial or lysosomal UCP. The binding peptide or molecule may also be attached to a targeting molecule which targets the peptide or molecule to the cell of interest, as discussed in more detail herein.

The binding peptides and molecules may be identified by conventional screening methods in some cases, such as binding or activation assays, or phage display procedures (e.g. methods described in Hart, et al., *J. Biol. Chem.,* 269:12468, 1994). Hart, et al. report a filamentous phage display library for identifying novel peptide ligands. In general, phage display libraries using, e.g., M13 or FD phage, can be prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target binding molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding.

In other cases, UCP and Fas binding peptides and molecules can be identified from combinatorial libraries. Many types of combinatorial libraries have been described, for instance, in U.S. Pat. No. 5,712,171 (which describes methods for constructing arrays of synthetic molecular constructs by forming a plurality of molecular constructs having the scaffold backbone of the chemical molecule and modifying at least one location on the molecule in a logically-ordered array), U.S. Pat. No. 5,962,412 (which describes methods for making polymers having specific physiochemical properties), or U.S. Pat. No. 5,962,736 (which describes specific arrayed compounds).

To determine whether a peptide or molecule binds to the appropriate target any known binding assay may be employed. For example, in the case of a peptide that binds to the plasma membrane UCP or Fas, the molecule may be immobilized on a surface and then contacted with a labeled plasma membrane UCP or Fas (or vice versa). The amount of plasma membrane UCP or Fas which interacts with the molecule or the amount that does not bind to the molecule may then be quantified to determine whether the molecule binds to plasma membrane UCP or Fas. A surface having a known molecule that binds to plasma membrane UCP or Fas, such as a commercially available monoclonal antibody immobilized thereto, may serve as a positive control. Several examples of commercially available UCP and Fas antibodies are described below.

Mimics of binding peptides or molecules may also be prepared by known methods, such as: (1) polymerization of functional monomers around a known binding molecule or the binding region of an antibody which also binds to the target (the template) that exhibits the desired activity; (2) removal of the template molecule; and then (3) polymerization of a second class of monomers in the void left by the template, to provide a new molecule which exhibits one or more desired properties which are similar to that of the template. This method is useful for preparing peptides, and other binding molecules which have the same function as binding peptides, such as polysaccharides, nucleotides, nucleoproteins, lipoproteins, carbohydrates, glycoproteins, steroids, lipids and other biologically-active material can also be prepared. Thus, a template, such as a UCP or Fas binding antibody, can be used to identify UCP or Fas inhibitors. It is now routine to produce large numbers of inhibitors based on one or a few peptide sequences or sequence motifs. (See, e.g., Bromme, et al., *Biochem. J.*, 315:85-89, 1996; Palmer, etal., *J. Med. Chem.*, 38:3193-3196, 1995.) For example, if UCP is known to interact with protein X at position Y, an inhibitor of UCP may be chosen or designed as a polypeptide or modified polypeptide having the same sequence as protein X, or structural similarity to the sequence of protein X, in the region adjacent to position Y. In fact, the region adjacent to the cleavage site Y spanning residues removed by 10 residues or 5 residues, N-terminal and C-terminal of position Y, may be defined as a "preferred protein X site" for the choice or design of UCP inhibitors. Thus, a plurality of UCP inhibitors chosen or designed to span the preferred protein X binding site around position Y, may be produced, tested for inhibitory activity, and sequentially modified to optimize or alter activity, stability, and/or specificity in some embodiments of the invention.

These methods may be useful for designing a wide variety of biological mimics that are more stable than the natural counterpart, because they are typically prepared by the free radical polymerization of functional monomers, resulting in a compound with a non-biodegradable backbone. Thus, the created molecules would have the same binding properties as the UCP or Fas antibody but be more stable in vivo, thus preventing UCP or Fas from interacting with components normally available in its native environment. Other methods for designing such molecules include, for example, drug design based on structure activity relationships which require the synthesis and evaluation of a number of compounds and molecular modeling.

In some cases, the UCP or Fas inhibitor may be isolated from natural sources or synthesized or produced by recombinant means. Methods for preparing or identifying molecules which bind to a particular target are well-known in the art. Molecular imprinting, for instance, may be used for the de novo construction of macromolecular structures, such as peptides, which bind to a particular molecule. See, for example, Shea, "Molecular Imprinting of Synthetic Network Polymers: The de novo Synthesis of Macromolecular Binding and Catalytic Sites," *Trends in Polym. Sci.*, 2(5):166, 1994; Mosbach, "Molecular Imprinting," *Trends in Biochem. Sci.*, 19:9, 1994; and Wulff, in *Polymeric Reagents and Catalysts* (Ford, Ed.), *ACS Symposium Series*, No. 308, p. 186-230, Am. Chem. Soc., 1986. Binding peptides, such as antibodies, may easily be prepared by generating antibodies to UCP or Fas (or obtained from commercial sources) or by screening libraries to identify peptides or other compounds which bind to the UCP or Fas.

UCP and/or Fas Inhibitors—Antibodies

Thus, in a particular set of embodiments, the UCP and Fas inhibitors are antibodies or functionally active antibody fragments. Antibodies are well known to those of ordinary skill in the science of immunology. Many of the binding peptides described herein are available from commercial sources as intact functional antibodies, e.g., as described above. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl, et al., *J. Nucl. Med.* 24:316-325, 1983).

As is well-known in the art, the complementarity determining regions (CDRs) of an antibody are the portions of the antibody which are largely responsible for antibody specificity. The CDR's directly interact with the epitope of the antigen. In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody involved in the interaction with the antigen. The CDRs, and in particular the CDR3 regions, and more particularly the heavy chain CDR3, each can contribute to antibody specificity. Because these CDR regions and, in particular, the CDR3 region may confer antigen specificity on the antibody, these regions may be incorporated into other antibodies or peptides, e.g., to confer the identical specificity onto that antibody or peptide.

Many UCP antibodies are commercially available. These include, but are not limited to, those antibodies commercially available from SANTA CRUZ BIOTECHNOLOGY®Inc., e.g., UCP1 (m-17, sc-6529), UCP1 (C-17, sc-6528), UCP2 (A19, sc-6527), UCP2 (N19, sc-6526), UCP2 (c-20, sc-6525), and UCP3 (C-20, sc-7756); antibodies commercially available from Research Diagnostics, Inc., e.g., goat anti-UCP1 human/mouse/rat (RDI-UCP1Cabg); goat anti-UCP1 human/mouse/rat (RDI-MUCP1Cabg); goat anti-UCP2 human/mouse/rat (RDI-UCP2Nabg); goat anti-UCP2 human/mouse/rat (RDI-UCP2Cabg); goat anti-UCP2 human/mouse/rat (RDI-UCP2C 1abg); rabbit anti-murine UCP 1 (RDI-MUCP 1 2abrX); rabbit anti-murine UCP1 (RDI-MUCP19abrX); rabbit anti-murine UCP2 (RDI-MUCP2abrX); rabbit anti-murine UCP2 (RDI-MUCP2CabrX); rabbit anti-human UCP2 (RDI-UCP2MabrX); UCP3L (see Boss, et al., *FEBS Lett.*, 408:38-42, 1997; Vidal-Plug, et al., *Biochem. Biophys. Res. Comm.*, 235:79-82, 1997); rabbit anti-human UCP3 (RDI-UCP3abrX); rabbit anti-human UCP3 (RDI-UCP3CbrX); rabbit anti-human UCP3 (RDI-UCP3MabrX); rabbit anti-rat UCP3 (RDI- RTUCP3MabrX), etc.

Many Fas antibodies are commercially available. These include but are not limited to those antibodies commercially available from : Rabbit polyclonal Fas antibody (ab 2437) (abcam); Rabbit Anti-Human FAS Ligand Anti-Human FAS Ligand Antibody, Polyclonal Antibody (Alpha Diagnostic International Inc); Mouse Anti-CD178 (Fas Ligand) Monoclonal Antibody, Clone 33 (BD Biosciences PHARMINGEN™); Mouse Anti-Fas Monoclonal Antibody, Clone G254-274(BD Biosciences PHARMNGEN™) Mouse Anti-Fas Ligand Monoclonal Antibody, Clone G247-4(BD PHARMINGEN™); Mouse Anti-Fas Ligand Monoclonal Antibody, Clone NOK-2 (BD PHARMINGEN™); Hamster Anti-Human CD178 (Fas Ligand) Monoclonal Antibody, Biotin Labeled, Clone 4H9 (BECKMAN COULTER®); Hamster Anti-Human CD178 (Fas Ligand) Monoclonal Antibody, Clone 4A5 (Beckman COULTER®); Mouse Anti-Human CD95 (APO-1; Fas; TNF receptor family) Monoclonal Antibody, FITC Labeled, Clone UB2 (BECKMAN COULTER®); Mouse Anti-Human CD95 (APO-1; Fas; TNF receptor family) Monoclonal Antibody, Phycoerythrin Labeled, Clone UB2 (BECKMAN COULTER®); Mouse Anti-Human CD95 (APO-1; Fas; TNF receptor family) Monoclonal Antibody, Phycoerythrin Labeled, Clone 7C11 (BECKMAN COULTER®); Mouse Anti-Human CD95 (APO-1; Fas; TNF receptor family) Monoclonal Antibody, Clone ZB4 (BECKMAN COULTER®); Mouse Anti-Human CD95 (APO-1; Fas; TNF receptor family) Monoclonal Antibody, Clone CH11 (BECKMAN COULTER®) Mouse Anti-Human CD95 (APO-1; Fas; TNF receptor family) Monoclonal Antibody, Clone UB2 (BECKMAN COULTER®) Mouse Anti-Human CD95 (APO-1; Fas; TNF receptor family) Monoclonal Antibody, Clone 7C11 (BECKMAN COULTER®) Mouse Anti-Human Fas/CD95/Apo-1 Monoclonal Antibody, Clone B-G27 (BIOSOURCE INTERNATIONAL™); Anti-Human APO-1/Fas Antibody, (CALTAG™); Mouse Anti-Human CD95L (Fas ligand) Antibody (CALTAG™); Anti-Human Fas Ligand Antibody (CALTAG™); Mouse Anti-Fas (CD95/APO-1) Monoclonal Antibody, Labeled or Unconjugated, Clone B-G27, Clone B-D29, Clone ICO-160, Clone SM1/1, Clone SM1/23, Clone 95C02, Clone FSL01 (CHEMICON); Rabbit Anti-Human FAS (APO-1, CD95) Polyclonal Antibody, Unconjugated (Delta Biolabs); Anti-Human CD95 (Fas/APO-1) Antibody, (eBioscience); Rabbit Anti-CD95 (Fas) Ab-4 Polyclonal Antibody (Lab Vision); Mouse Anti-CD95 (Fas) Ab-3 Monoclonal Antibody (Lab Vision); Mouse Anti-CD95 (Fas) Ab-2 Monoclonal Antibody, Clone 95C02 (Lab Vision); Rabbit Anti-Human CD95 (Fas) Ab-5, Epitope Specific Antibody, (Lab Vision); Rabbit Anti-FADD (FAS-Associated Death Domain-containing Protein) Ab-1 Polyclonal Antibody (Lab Vision); Rabbit Anti-Mouse FADD (FAS-Associated Death Domain-containing Protein) Ab-2 Polyclonal Antibody (Lab Vision); Mouse Anti-Human FAP-1 (Fas associated phosphatase-1) Ab-1 Monoclonal Antibody, Clone 2C8 (Lab Vision); Mouse Anti-Fas Ligand Ab-1 Monoclonal Antibody (Lab Vision); Rabbit Anti-Human Fas Ligand Epitope Specific Antibody, (Lab Vision); Anti-Human Fas-Associated Death Domain Protein (FADD) Monoclonal Antibody, Unconjugated, Clone 1F7 (Leinco Technologies, Inc.); Mouse Anti-Human Fas (Apo-1; CD95) Monoclonal Antibody, Clone LT95 (NOVUS BIOLOGICALS™); Rabbit Anti-Human Fas antigen Polyclonal Antibody, (NOVUS BIOLOGICALS™); Mouse Anti-Human Fas antigen Monoclonal Antibody, Clone LOB 3/17 (NOVUS BIOLOGICALS™); Mouse Anti-Human FAS Intracellular Fragment Monoclonal Antibody, Clone GH-9 (NOVUS BIOLOGICALS™); Goat Anti-Human Fas-L (Fas Ligand) Polyclonal Antibody, (PeproTech); Mouse Anti-Human CD95/Fas Monoclonal Antibody, Clone DX-2, Clone DX-3 (Southern-Biotech); Mouse Anti-Fas Monoclonal Antibody, Clone UB2, Clone ZB4 (Stressgen Bioreagents); Mouse Anti-Human CD178 FAS Ligand (CD951) Monoclonal Antibody, (United States Biological); Rabbit Anti-Human FADD (Fas-Associated Death Domain Protein, MORT1) Polyclonal Antibody, (United States Biological); Mouse Anti-Human Fas (CD95, APO-1) Monoclonal Antibody, (United States Biological); Hamster Anti-Human Fas (CD95, APO-1) Monoclonal Antibody, (United States Biological); Mouse Anti-Human Fas, Intracellular Fragment Monoclonal Antibody, (United States Biological); Mouse Anti-Human Fas, Neutralizing (CD95, APO-1) Monoclonal Antibody, (United States Biological); Mouse Anti-Human Fas Activating Monoclonal Antibody, (Upstate); Mouse Anti-Human Fas Neutralizing Monoclonal Antibody, (Upstate); Mouse Anti-Human Fas Ligand Monoclonal Antibody, (Upstate)

Thus, in some cases, the UCP or Fas inhibitor is present as an intact soluble monoclonal antibody in an isolated form and/or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains can be further divided into subregions referred to as variable regions and constant regions. As used herein, the term "monoclonal antibody" refers to a homogenous population of immunoglobulins which specifically bind to an epitope (i.e. antigenic determinant), e.g., of a plasma membrane UCP or Fas.

If the antibody is a monoclonal antibody, in some cases, the antibody may be an intact humanized monoclonal antibody. A "humanized monoclonal antibody," as used herein, is a human monoclonal antibody (or functionally active fragment thereof) having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs, and optionally some of the framework regions, may be covalently joined to human FR and/or Fc/pFc' regions to produce a functional antibody. There are entities which will synthesize humanized antibodies from specific murine antibody regions commercially, such as Protein Design Labs (Mountain View, Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector, including a suitable promoter operably linked to a DNA sequence encoding at least a variable domain of an Ig heavy or light chain, and the variable domain comprising framework regions from a human antibody and a CDR region of a murine antibody, is prepared. Optionally, a second replicable expression vector is prepared, which includes a suitable promoter operably linked to a DNA sequence encoding at least the variable domain of a complementary human Ig light or heavy chain, respectively. A cell line is then transformed with the vectors. In some cases, the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of ordinary skill in the art to produce the humanized antibody.

As set forth in European Patent Application 0239400, several techniques are well known in the art for creating the particular antibody domains to be inserted into the replicable vector. For example, the DNA sequence encoding the domain may be prepared by oligonucleotide synthesis. Alternatively, a synthetic gene lacking the CDR regions in which four framework regions are fused together with suitable restriction sites at the junctions, such that double stranded synthetic or restricted subcloned CDR cassettes with sticky ends could be ligated at the junctions of the framework regions, can be prepared. Another method involves the preparation of the DNA sequence encoding the variable CDR containing domain by oligonucleotide site-directed mutagenesis. Each of these methods is well known in the art. Those of ordinary skill in the art may thus be able to construct humanized antibodies containing a murine CDR region, without destroying the specificity of the antibody for its epitope.

Human monoclonal antibodies may be made by any of the methods known in the art, such as those disclosed in U.S. Pat.

No. 5,567,610; U.S. Pat. No. 5,565,354; U.S. Pat. No. 5,571,893; Kozber, *J. Immunol.*, 133: 3001, 1984; Brodeur, et al., *Monoclonal Antibody Production Techniques and Applications*, p. 51-63, Marcel Dekker, Inc., 1987; and Boemer, et al., *J. Immunol.*, 147:86-95, 1991. In addition to the conventional methods for preparing human monoclonal antibodies, such antibodies may also be prepared by immunizing transgenic animals that are capable of producing human antibodies (e.g., Jakobovits, et al., *Proc. Natl. Acad. Sci. USA*, 90: 2551, 1993; Jakobovits, et al., *Nature*, 362:255-258, 1993; Bruggermann, et al., *Year in Immunol.*, 7:33, 1993; and U.S. Pat. No. 5,569,825.

The UCP and Fas binding peptides may also be functionally active antibody fragments in some cases. For instance, only a small portion of an antibody molecule, the paratope, is often involved in the binding of the antibody to its epitope (see, in general, Clark, *The Experimental Foundations of Modern Immunology*, Wiley & Sons, Inc., 1986; Roitt, *Essential Immunology*, 7th Ed., Blackwell Scientific Publications, 1991). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is often referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation. The terms Fab, Fc, pFc', F(ab')$_2$ and Fv are used consistently with their standard immunological meanings. See, e.g., Klein, *Immunology*, John Wiley, 1982; Clark, *The Experimental Foundations of Modern Immunology*, Wiley & Sons, Inc., 1986; Roitt, *Essential Immunology*, 7th Ed., Blackwell Scientific Publications, 1991.

Fatty Acid Metabolism Inhibitors

According to another set of embodiments, in addition to a UCP and/or Fas antibody or other inhibitor, the cells are exposed to a fatty acid metabolism inhibitor. A "fatty acid metabolism inhibitor," as used herein, is a compound able to inhibit (e.g., prevent, or at least decrease or inhibit the activity by an order of magnitude or more) a reaction within the fatty acid metabolism pathway, such as an enzyme-catalyzed reaction within the pathway. The inhibitor may inhibit the enzyme, e.g., by binding to the enzyme or otherwise interfering with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.).

The fatty acid metabolism pathway includes several enzymatic reactions, which uses various enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc, as further discussed below. In one embodiment, the fatty acid metabolism inhibitor is an inhibitor able to inhibit a beta-oxidation reaction in the fatty acid metabolism pathway. In another embodiment, the inhibitor is an inhibitor for a fatty acid transporter (e.g., a transporter that transports fatty acids into the cell, or from the cytoplasm into the mitochondria for metabolism). In yet another embodiment, the inhibitor may react or otherwise inhibit key steps within the fatty acid metabolism pathway. In still another embodiment, the inhibitor may be an inhibitor of fatty acids as a source of energy in the mitochondria. For example, the inhibitor may inhibit the breakdown of intermediates such as butyryl CoA, glutaryl CoA, or isovaleryl CoA.

2,4-dienoyl-CoA reductase is an enzyme within the fatty acid metabolism pathway that catalyzes reduction reactions involved in the metabolism of polyunsaturated fatty acids. Certain fatty acids are substrates for 2,4-dienoyl-CoA reductases located within the mitochondria. In some cases, fatty acids may be transported into the mitochondria through uncoupling proteins. The uncoupling protein may, in certain instances, increase the mitochondrial metabolism to increase the availability of fatty acids within the mitochondria and/or increase the throughput of beta-oxidation within the mitochondria.

The enzyme 2,4-dienoyl-CoA isomerase is an enzyme within the fatty acid metabolism pathway that catalyzes isomerization of certain fatty acids. One step in the metabolism of certain polyunsaturated fatty acids may be protective against reactive oxygen intermediates ("ROI"). Thus, by generating substrates and antagonists for the activity of 2,4-dienyol-CoA isomerase, the metabolic production of reactive oxygen intermediates may be enhanced and/or reduced. This, in turn, may affect certain disease states, such as cancer.

Thus, it is to be understood that, as used herein, compounds useful for inhibiting fatty acid metabolism (i.e., "fatty acid metabolism inhibitors") are also useful for altering cellular production of reactive oxygen; compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected, since one pathway for a cell to produce reactive oxygen intermediates is through the metabolism of fatty acids. Alteration of the production of reactive oxygen in a cell may be associated with changes in the immune profile of cells, i.e., how immune cells respond to the cell. Thus, in some cases, the production of reactive oxygen can be affected by exposing a cell to, or removing a cell from, a fatty acid metabolism inhibitor. The alteration of the production of reactive oxygen may be useful in treating conditions such as cancers or wounds (as further discussed below), as the alteration of the immune profile of cells within the cancer site or the wound may stimulate the immune system and/or other wound-healing processes.

In a preferred embodiment of the invention, the fatty acid inhibitor is an oxirane carboxylic acid compound. In accordance with a discovery of this invention, such compounds, exemplified by etomoxir, are able to alter cellular production of reactive oxygen. Preferred oxirane carboxylic acid compounds have the formula:

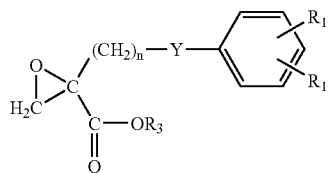

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$CH_2)_m$—; m is 0 or a whole number from 1 to 4; and n is a whole number from 2 to 8 wherein the sum of m and n is a whole number from 2 to 8. More preferred are oxirane carboxylic acid compounds wherein $R_1$ is a halogen atom, $R_2$ is a hydrogen atom, m is 0, and n is 6, and more particulary where $R_3$ is an ethyl group.

It is most particularly preferred to use etomoxir, i.e., 2-(6-(4-chlorophenoxy)-hexyl)-oxirane-2-carboxylic acid ethyl ester. Examples of other oxirane carboxylic acid compounds useful in the invention are 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxy-hexyl)-oxirane-2-carboxylic acid ethyl ester, the corresponding oxirane carboxylic acids, and their pharmacologically acceptable salts.

The foregoing class of oxirane carboxylic acid compounds, including etomoxir, has been described by Horst Wolf and Klaus Eistetter in U.S. Pat. No. 4,946,866 for the prevention and treatmkent of illnesses associated with increased cholesterol and/or triglyceride concentration, and by Horst Wolf in U.S. Pat. No. 5,739,159 for treating heart insufficiency. The preparation of oxirane carboxylic acid compounds, and their use for blood glucose lowering effects as an antidiabetic agent, is described in Jew et al U.S. Pat. No. 6,013,666. Etomoxir has been described as an inhibitor of mitochondrial camitine palmitoyl transferase-I by Mannaerts, G. P., L. J. Debeer, J. Thomas, and P. J. De Schepper. "Mitochondrial and peroxisomal fatty acid oxidation in liver homogenates and isolated hepatocytes from control and clofibrate-treated rats," J. Biol. Chem. 254:4585-4595, 1979. U.S. Patent Application 20030036199 by Bamdad et al, entitled:"Diagnostic tumor markers, drug screening for tumorigenesis inhibition, and compositions and methods for treatment of cancer ", published Feb. 20, 2003, describes treating a subject having a cancer characterized by the aberrant expression of MUC1, comprising administering to the subject etomoxir in an amount effective to reduce tumor growth. In a preferred aspect of this embodiment, subjects for whom the methods of the invention involving treatment with etomoxir are not intended are those diagnosed with diseases which already call for treatment with etomoxir, particularly those subjects who have MUC 1-dependant tumors, nor those diagnosed with diabetes, or diseases associated with increased cholesterol and/or triglyceride concentration, or chronic heart failure (e.g., failing cardiac hypertrophy associated with an inadequate sarcoplasmic reticulum function) calling for treatment with etomoxir.

The foregoing U.S. Pat. Nos. 4,946,866, 5,739,159, and 6,013,666, U.S. Patent Application 20030036199, and the foregoing publication by Mannaerts, G. P., L. J. Debeer, J. Thomas, and P. J. De Schepper, are incorporated herein by reference. In addition, U.S. patent application Ser. No. 10/272,432, filed Oct. 15, 2002, entitled "Methods for Regulating Co-Stimulatory Molecule Expression with Reactive Oxygen," by M. K. Newell, et al. is incorporated herein by reference in its entirety In a specific embodiment, the method includes the step of administering, to a subject susceptible to or exhibiting symptoms of cancer, preferably a subject susceptible to or exhibiting symptoms of drug-resistant cancer, a UCP and/or Fas antibody or other inhibitor, and a therapeutically acceptable amount of the oxirane carboxylic acid compound, exemplified by etomoxir. A "subject," as used herein, means a human or non-human mammal, the latter including, but not limited to, a dog, cat, horse, cow, pig, sheep, goat, chicken, primate, rat, and mouse.

Other, non-limiting examples of fatty acid metabolism inhibitors include fatty acid transporter inhibitors, beta-oxidation process inhibitors, reductase inhibitors, and/or isomerase inhibitors within the fatty acid metabolism pathway. Specific examples of other fatty acid metabolism inhibitors include, but are not limited to, cerulenin, 5-(tetradecyloxy)-2-furoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, and beta-hydroxy butyrate. Structural formulas for these inhibitors are shown in FIGS. 1A-1C. As a another example, the inhibitor may be a non-hydrolyzable analog of carnitine.

In one embodiment, the fatty acid metabolism inhibitor is a carboxylic acid. In some cases, the carboxylic acid may have the structure:

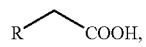

where R comprises an organic moiety, as further described below. In some cases, R may include at least two nitrogen atoms, or R may include an aromatic moiety (as further described below), such as a benzene ring, a furan, etc.

In another embodiment, the fatty acid metabolism inhibitor has the structure:

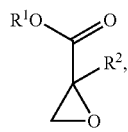

where each of $R^1$ and $R^2$ independently comprises organic moiety. In some instances, either or both of $R^1$ and $R^2$ may independently be an alkyl, such as a straight-chain alkyl, for instance, methyl, ethyl, propyl, etc. In certain cases, $R^2$ may have at least 5 carbon atoms, at least 10 carbon atoms, or at least 15 or more carbon atoms. For example, in one embodiment, $R^2$ may be a tetradecyl moiety. In other cases, $R^2$ may include an aromatic moiety, for example, a benzene ring. In still other cases, R² may have the structure:

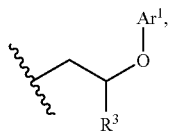

where R³ comprises an organic moiety and Ar¹ comprises an aromatic moiety. R³ may be a an alkyl, such as a straight-chain alkyl. In some instances, Ar¹ may be a benzene ring or a derivative thereof, i.e., having the structure:

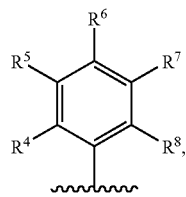

wherein each of $R^4$, $R^5$, $R^6$, $R^7$, and $R^8$ is hydrogen, a halogen, an alkyl, an alkoxy, etc.

In yet another embodiment, the fatty acid metabolism inhibitor has the structure:

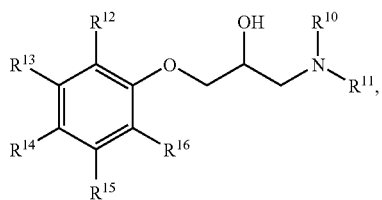

where each of $R^{10}$, $R^{11}$, $R^{12}$, $R^{13}$, $R^{14}$, $R^{15}$ and $R^{16}$ independently comprises hydrogen, a halogen, or an organic moiety, such as an alkyl, an alkoxy, etc. In some cases, $R^{10}$ and $R^{11}$ together may define an organic moiety, such as a cyclic group. For example, the fatty acid metabolism inhibitor may have the structure:

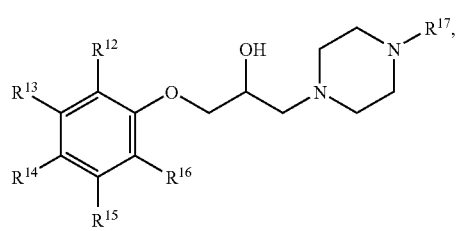

wherein $R^{17}$ comprises an organic moiety, such as an alkyl, an alkoxy, an aromatic moiety, an amide, etc. An example, of $R^{17}$ is:

wherein Ar² comprises an aromatic moiety, such as a benzene ring or a benzene derivative, as previously described.

In still another embodiment, the fatty acid metabolism inhibitor includes a dominant negative plasma membrane polypeptide. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., *Molecular Cloning: A Laboratory Manual*, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

In another set of embodiments, the cells may be exposed to an agent that inhibits the synthesis or production of one or enzymes within the fatty acid metabolism pathway. Exposure of the cells to the agent thus inhibits fatty acid metabolism within the cell. For example, in one embodiment, an antisense oligonucleotide may be used that selectively binds to regions encoding enzymes present within the fatty acid metabolism pathway, such as 2,4-dienoyl-CoA reductase or 2,4-dienoyl-CoA isomerase. Antisense oligonucleotides are discussed in more detail below.

Glucose Metabolism Inhibitor

In other specific embodiments, the method includes the step of administering, to a subject susceptible to or exhibiting symptoms of cancer, preferably a subject susceptible to or exhibiting symptoms of drug-resistant cancer, a UCP and/or Fas antibody or other inhibitor, and (a) a therapeutically acceptable amount of glucose metabolism inhibitor, or (b) therapeutically acceptable amounts of both a fatty acid metabolism inhibitor and a glucose metabolism inhibitor. A glucose metabolism inhibitor inhibits two aspects of glucose metabolism: glycolysis and the burning of carbon derived from glucose in the mitochondria.

Preferred glucose metabolism inhibitors are 2-deoxyglucose compounds, defined herein as 2-deoxy-D-glucos, and homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof. In general glucose metabolism inhibitors can have the formula:

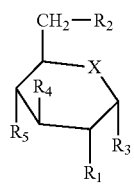

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of $R_3$, $R_4$, and $R_5$ are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

A preferred glucose metabolism inhibitor is 2-deoxy-D-glucose, which has the structure:

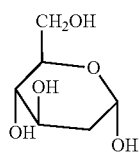

General Considerations

One or more of the UCP or Fas inhibitors and/or the fatty acid metabolism inhibitors and/or the glucose metabolism inhibitors described herein may be an isolated molecule in certain cases. An "isolated molecule," as used herein, is a molecule that is substantially pure and is free of other substances with which it is ordinarily found in nature or in vivo systems to an extent practical and appropriate for its intended use. In particular, the molecular species may be sufficiently pure and may be sufficiently free from other biological constituents of host cells so as to be useful in, for example, producing pharmaceutical preparations, or for sequencing, e.g., if the molecular species is a nucleic acid, peptide, or polysaccharide. Because an isolated molecular species of the invention may be admixed with a pharmaceutically-acceptable carrier in a pharmaceutical preparation, and/or other physiologically-active agents, the molecular species may comprise only a small percentage by weight of the preparation. The molecular species is nonetheless substantially pure in that it has been substantially separated from the substances with which it may be associated in living systems. As an example, the UCP or Fas inhibitor may be associated with other molecules, such as the fatty acid metabolism inhibitor and/or the glucose metabolism inhibitor and/or a pharmaceutically acceptable carrier.

In some aspects of the invention, the systems and methods described herein have broad utility in regulating mammalian cell growth and death in vitro, in vivo, and/or ex vivo. For example, as further discussed below, the systems and methods of the invention may be used in the treatment of cancers, tumors, and other conditions involving rapidly dividing cell populations that may be uncontrolled.

The in vitro methods of the invention are useful for a variety of purposes. For instance, the systems and methods of the invention may be useful for identifying drugs which have an effect, such as a preventative effect, on cellular division, cancers, or cell death, by contacting cells manipulated by the invention to undergo cellular division or death upon exposure to putative compounds.

In addition to in vitro methods, certain methods of the invention may be performed in vivo or ex vivo in a subject to manipulate one or more cell types within a subject. A "subject" as used herein, means a human or non-human mammal, including but not limited to, a dog, cat, horse, cow, pig, sheep, goat, chicken, primate, rat, and mouse. In vivo methods are well known in the art. Thus, the invention is useful for therapeutic purposes as well as research purposes, such as testing in animal or in vitro models of certain medical, physiological or metabolic pathways or conditions. An "ex vivo" method, as used herein, is a method which involves isolation of a cell from a subject, manipulation of the cell outside of the body, and reimplantation of the manipulated cell into the subject. The ex vivo procedure may be used on autologous or heterologous cells, and is typically used on autologous cells. In some embodiments, the ex vivo method is performed on cells that are isolated from bodily fluids, such as peripheral blood or bone marrow; however, the cells may be isolated from any source of cells. When returned to the subject, the manipulated cell can be programmed for cell death or division, depending on the treatment to which it was exposed. Ex vivo manipulation of cells has been described in several references in the art, including Engleman, *Cytotechnology*, 25:1, 1997; Van Schooten, et al., *Molecular Medicine Today*, June, 255, 1997; Steinman, *Experimental Hematology*, 24:849, 1996; and Gluckman, *Cytokines, Cellular and Molecular Therapy*, 3:187, 1997. The ex vivo activation of cells of the invention may be performed by routine ex vivo manipulation steps known in the art.

In addition to the systems and methods of manipulating cells described herein, the invention is also useful, in some embodiments, for screening cells such as cancer cells, tumor cells or other cells that rapidly divide uncontrolled, to determine if those cells are susceptible to cellular division or cellular death, alone or in conjunction with treatment with a chemotherapeutic agent or other cell signal and kits for performing these screening assays. The screening method can be accomplished by isolating a tumor cell from a subject and detecting the ability of the tumor cell to use fat for fuel. The use of fat for fuel indicates the tumor cell is susceptible to treatment with a pharmacon of the invention.

According to one aspect of the invention, the systems and methods described herein are useful in treating cancers, tumors, and other conditions involving rapidly dividing cell populations that are typically uncontrolled. A "rapidly dividing cell," as used herein, is a cell which is undergoing mitotic growth. Such cells are well known in the art and include, but are not limited to, tumor cells, cancer cells, lymphocytes (T cells or B cells), bacteria, and pancreatic beta (β) cells. Rapidly dividing cells, for example, cancer cells such as drug and multi-drug resistant cancer cells, are often able to derive a majority of their metabolic energy through fatty acid metabolism, i.e., the main source of energy (ATP) for the cancer cells comes from the oxidation of fatty acids instead of sugars such as glucose. Thus, in certain embodiments, in addition to a UCP or Fas inhibitor, the invention provides an inhibitor for a reaction of the fatty acid metabolism pathway, which, in some cases, may kill the rapidly dividing cells ("cytotoxic") or at least prevent the cells from further division and/or growth.

Thus, the systems and methods of the invention, in some embodiments, are useful for inducing cell death in many types of mammalian cells, for example, tumor cells. As used herein, the term "cell death" is used to refer to either of the processes of apoptosis or cell lysis. In both apoptosis and cell lysis, the cell dies, but the processes occur through different mechanisms and/or different metabolic states of the cell. Apoptosis is a process of cell death in which the cell undergoes shrinkage and fragmentation, followed by phagocytosis of the cell fragments. Apoptosis is well known in the art and can be assessed by any art-recognized method. For example, apoptosis can easily be determined using flow cytometry, which is able to distinguish between live and dead cells.

In one set of embodiments, the invention includes a method of treating a subject susceptible to or exhibiting symptoms of cancer. In some cases, the cancer is drug-resistant or multi-drug resistant. As used herein, a "drug-resistant cancer" is a cancer that is resistant to conventional commonly-known cancer therapies. Examples of conventional cancer therapies include treatment of the cancer with agents such as methotrexate, trimetrexate, adriamycin, taxotere, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action. In some cases, the subject is not otherwise indicated for treatment with the inhibitor, for example, the subject is not indicated for obesity treatment.

In one embodiment, the systems and methods of the invention can be used in conjunction with one or more other forms of cancer treatment. For example, a UCP inhibitor and/or a Fas inhibitor, together with a fatty acid metabolism inhibitor, and/or a glucose metabolism inhibitor and/or an agent able to alter cellular production of reactive oxygen in cells may be used in conjunction with an anti-cancer agent, chemotherapy, radiotherapy, etc. (e.g., simultaneously, or as part of an overall treatment procedure). As another non-limiting example, a cell may be manipulated to increase the amount of UCP in the plasma membrane or Fas, exposed to a UCP or Fas inhibitor, and also exposed to another form of cancer treatment. The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. One of ordinary skill in the medical arts can determine an appropriate treatment for a subject.

A "tumor cell," as used herein, is a cell which is undergoing unwanted mitotic proliferation. A tumor cell, when used in the in vitro embodiments of the invention, can be isolated from a tumor within a subject, or may be part of an established cell line. A tumor cell in a subject may be part of any type of cancer. Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of a composition for treating a cancer will be that amount necessary to inhibit mammalian cancer cell proliferation in situ. Those of ordinary skill in the art are well-schooled in the art of evaluating effective amounts of anti-cancer agents.

In some cases, the cancer treatment may include treatment with an anti-cancer agent or drug, for example, a conventionally-known anti-cancer agent or drug. Examples of suitable anti-cancer agents and drugs include, but are not limited to, methotrexate, trimetrexate, adriamycin, taxotere, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, and goserelin acetate. Additional examples of suitable anticancer agents and drugs include, but are not limited to, 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermnine, dihydro-5-azacytidine, dioxamycin, diphenyl spiromustine, docosanol, dolasetron, doxifluridine, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, flurocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

In another embodiment, cells may be removed from a tumor or other rapidly dividing cell mass (e.g., a tumor from a subject, a tumor growing in vitro, etc.) and exposed in some fashion to the systems and methods described herein. For example, the cells may be manipulated to increase the amount of UCP in the plasma membrane (e.g., by exposure to a fatty acid metabolic inhibitor) and manipulated to inhibit UCP function (e.g., by exposure to a UCP inhibitor). After suitable exposure, the exposed cells may be introduced into a subject. Exposure of the cells may alter the immunological profile of the tumor cells in some fashion, for example, such that a subject's immune system is able to recognize the tumor cells. The subject's immune system, after interacting with the exposed cells, may then be able to recognize tumors present within the subject, thus causing the cancer (or other rapidly dividing cell mass) to decrease. If the subject has a tumor, the cells may be injected into the tumor, proximate the tumor, and/or systemically or locally delivered in a region of the body away from the tumor. In some cases, a tumor may be removed from a subject, then the exposed cells may be inserted, e.g., into the cavity created upon removal of the tumor, or to another site within the body. Optionally, other cancer treatment methods, such as radiation or exposure to conventional anti-cancer agents, may also be used in conjunction with these methods. In some cases, the subject may not have a cancer or tumor, but the cells may be injected to stimulate the immune system to produce antibodies against future cancers and/or other uncontrolled cellular growths, i.e., "immunizing" the subject from cancer and/or other uncontrolled cellular growths. In some the cancer cells are antigenic and can be targeted by the immune system. Thus, the combined administration of the systems and methods of the invention and cancer medicaments, particularly those which are classified as cancer immunotherapies, can be very useful for stimulating a specific immune response against a cancer antigen. A "cancer antigen" as used herein is a compound, such as a peptide, associated with a tumor or cancer cell surface, and which is capable of provoking an immune response when expressed on the surface of an antigen-presenting cell in the context of an MHC molecule. Cancer antigens, such as those present in cancer vaccines or those used to prepare cancer immunotherapies, can be prepared from crude cancer cell extracts, e.g., as described in Cohen, et al., *Cancer Research*, 54:1055, 1994, or by partially purifying the antigens, using recombinant technology, or de novo synthesis of known antigens. Cancer antigens can be used in the form of immunogenic portions of a particular antigen, or in some instances, a whole cell or a tumor mass can be used as the antigen. Such antigens can be isolated or prepared recombinantly or by any other means known in the art.

The systems and methods of the invention can be used in combination with immunotherapeutics, according to another embodiment. The goal of immunotherapy is to augment a subject's immune response to an established tumor. One method of immunotherapy includes the use of adjuvants. Adjuvant substances derived from microorganisms, such as *bacillus Calmette-Guerin*, can heighten the immune response and enhance resistance to tumors in animals. Immunotherapeutic agents are often medicaments which derive from antibodies or antibody fragments that specifically bind to or otherwise recognize a cancer antigen. Binding of such agents can promote an immune response, such as an antigen-specific immune response. Antibody-based immunotherapy may function by binding to the cell surface of a cancer cell, which can stimulate the endogenous immune system to attack the cancer cell.

As used herein, a "cancer antigen" is broadly defined as an antigen expressed by a cancer cell. The antigen can be expressed at the cell surface of the cancer cell. In many cases, the antigen is one which is not expressed by normal cells, or at least not expressed at the same level or concentration as in cancer cells. As examples, some cancer antigens are normally silent (i.e., not expressed) in normal cells, some are expressed only at certain stages of differentiation, and others are only temporally expressed (such as embryonic and fetal antigens). Other cancer antigens are encoded by mutant cellular genes, such as oncogenes (e.g., activated ras oncogene), suppressor genes (e.g., mutant p53), fusion proteins resulting from internal deletions or chromosomal translocations, or the like. Still other cancer antigens can be encoded by viral genes, such as those carried on RNA and DNA tumor viruses. The differential expression of cancer antigens in normal and cancer cells can be exploited in order to target cancer cells in some cases. As used herein, the terms "cancer antigen" and "tumor antigen" are used interchangeably.

The theory of immune surveillance is that a prime function of the immune system is to detect and eliminate neoplastic cells before a tumor forms. A basic principle of this theory is that cancer cells are antigenically different from normal cells and thus can elicit immune reactions similar to those that cause rejection of immunologically incompatible allografts. Studies have confirmed that tumor cells differ, qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen-dependent, nor MHC-restricted, once activated. Activated macrophages are thought to decrease the growth rate of the tumors they infiltrate. In vitro assays have identified other immune mechanisms such as antibody-dependent, cell-mediated cytotoxic reactions, and lysis by antibody plus complement. However, these immune effector mechanisms are thought to be less important in vivo than the function of NK, CTLs, LAK, and macrophages in vivo (for a review, see Piessens, "Tumor Immunology," in *Scientific American Medicine, Vol. 2*, Scientific American Books, p. 1-13, 1996).

In some cases, the immunotherapeutic agent may function as a delivery system for the specific targeting of toxic substances to cancer cells. For example, the agent may be conjugated to toxins such as ricin (e.g., from castor beans), calicheamicin, maytansinoids, radioactive isotopes such as iodine-131 and yttrium-90, chemotherapeutic agents, and/or to biological response modifiers. In this way, the toxic substances can be concentrated in the region of the cancer and non-specific toxicity to normal cells can be minimized.

In certain instances, the immunotherapeutic agent may be directed towards the binding of vasculature, such as those which bind to endothelial cells. This is because solid tumors are generally dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

In another set of embodiments, the combined administration of the systems and methods of the invention and an apoptotic chemotherapeutic agent may be used. An "apoptotic chemotherapeutic agent," as used herein, includes molecules which function by a variety of mechanisms to induce apoptosis in rapidly dividing cells. Apoptotic chemotherapeutic agents are a class of chemotherapeutic agents which are well known to those of ordinary skill in the art. Chemotherapeutic agents include those agents disclosed in Chapter 52, "Antineoplastic Agents" (Paul Calabresi and Bruce A. Chabner), and the introduction thereto, p. 1202-1263, of Goodman and Gilman's *The Pharmacological Basis of Therapeutics*, Eighth Edition, McGraw-Hill, Inc. Health Professions Division, 1990, incorporated herein by reference. Suitable chemotherapeutic agents may have various mechanisms of action. Classes of suitable chemotherapeutic agents include, but are not limited to: (a) alkylating agents, such as nitrogen mustard (e.g. mechlorethamine, cylophosphamide, ifosfamide, melphalan, chlorambucil), ethylenimines and methylmelamines (e.g. hexamethylmelamine, thiotepa), alkyl sulfonates (e.g. busulfan), nitrosoureas (e.g. carmustine, which is also known as BCNU, lomustine which is also known as CCNU, semustine, which is also known as methyl-CCNU, chlorozoticin, streptozocin), and triazines (e.g. dicarbazine, which is also known as DTIC); (b) antimetabolites, such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin); (c) natural products, such as the vinca alkaloids (e.g. vinblastine, vincristine), epipodophylotoxins (e.g. etoposide, teniposide), antibiotics (e.g. dactinomycin, which is also known as actinomycin-D, daunorubicin, doxorubicin, bleomycin, plicamycin, mitomycin, epirubicin, which is 4-epi-doxorubicin, idarubicin which is 4-dimethoxydaunorubicin, and mitoxanthrone), enzymes (e.g. L-asparaginase), and biological response modifiers (e.g. interferon alfa); (d) miscellaneous agents, such as the platinum coordination complexes (e.g. cisplatin, carboplatin), substituted ureas (e.g. hydroxyurea), methylhydiazine derivatives (e.g. procarbazine), adreocortical suppressants (e.g. mitotane, aminoglutethimide) taxol; (e) hormones and antagonists, such as adrenocorticosteroids (e.g. prednisone or the like), progestins (e.g. hydroxyprogesterone caproate, medroxyprogesterone acetate, megestrol acetate), estrogens (e.g. diethyestilbestrol, ethinyl estradiol, or the like), antiestrogens (e.g. tamoxifen), androgens (e.g. testosterone propionate, fluoxymesterone, or the like), antiandrogens (e.g. flutamide), and gonadotropin-releasing hormone analogs (e.g. leuprolide), and (f) DNA damaging compounds, such as adriamycin. The combined administration of the systems and methods of the invention and an apoptotic chemotherapeutic agent effective to inhibit growth of the tumor cell is that amount effective to induce apoptosis of the tumor cell in some cases.

In yet another set of embodiments, the systems and methods of the invention may be used in conjunction with a vaccine, such as a cancer vaccine. Cancer vaccines are medicaments which are intended to stimulate an endogenous immune response against cancer cells. Currently-produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response in certain cases. Another form of cancer vaccine is a peptide vaccine which uses cancer-specific or cancer-associated small proteins to activate T cells. Cancer-associated proteins are proteins which are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine which includes whole dendritic cells that have been exposed to a cancer antigen or a cancer-associated antigen in vitro. Lysates or membrane fractions of dendritic cells may also be used as cancer vaccines in some instances. Dendritic cell vaccines are able to activate antigen-presenting cells directly. Other non-limiting examples of cancer vaccines include ganglioside vaccines, heat-shock protein vaccines, viral and bacterial vaccines, and nucleic acid vaccines.

Other cancer vaccines can take the form of dendritic cells which have been exposed to cancer antigens in vitro, have processed the antigens and are able to express the cancer antigens at their cell surface in the context of MHC molecules for effective antigen presentation to other immune system cells.

In some embodiments, cancer vaccines may be used along with adjuvants. Adjuvants are substances which activate the subject's immune system, and can be used as an adjunct therapy in any of the systems or methods of the invention. Adjuvants include, for example, alum, QS-Stimulon (Aquila), MF-59 (Chiron), DETOX™ (Ribi), OPTIVAX® (Vaxcels) and LeIF (CORIXA®).

The invention, in still another set of embodiments, is useful for treating other diseases associated with rapidly dividing cells, such as rheumatoid arthritis and scleroderma. Rheumatoid arthritis is associated in its early stages with the rapid division of synoviocytes. This process is referred to a pannus formation. The rapidly dividing cells produce a substance that kills osteocytes leading to the hardening of the tissue.

In another aspect, the systems and methods of the invention are useful for treating or preventing disorders associated with a specific antigenic immune response. Thus, in some embodiments of the invention, the methods are used to treat mammals at risk of, or afflicted with, autoimmune disease. Autoimmune disease is a disorder in which the host's immune response is defective and results in the production of a specific immune response against the individual's own antigens or components. In an autoimmune disease, an individual's own antibodies react with host tissue or in which immune effector T cells are autoreactive to endogenous self peptides and cause destruction of tissue. It is well established that MHC class II alleles act as major genetic elements in susceptibility to a variety of autoimmune diseases. The structures recognized by T cells, the cells that cause autoimmunity, are complexes comprised of class II MHC molecules and antigenic peptides. When the T cells react with the host's class II MHC molecules-peptide complexes derived from a host's own gene products, autoimmune disease can result. If these class II MHC/peptide complexes are inhibited from being formed, the autoimmune response is reduced or suppressed, and thus is inhibited according to the invention. The peptide-antigen of autoimmune disorders are self-antigens. Any autoimmune disease in which class II MHC/peptide complexes play a role may be treated according to the methods of the present invention. Such autoimmune diseases include, but are not limited to, juvenile-onset diabetes (insulin-dependent), multiple sclerosis, pemphigus vulgaris, Graves disease, myasthenia gravis, systemic lupus erythematosus (SLE), celiac disease rheumatoid arthritis, and Hashimoto's thyroiditis. The invention includes a method for determining an individuals susceptibility to developing autoimmune disease. As used herein, "susceptibility to autoimmune disease" indicates a likelihood of at least greater than the average of developing autoimmune disease, and in some embodiments at least about 10% greater. Thus the invention also includes systems and methods for treating a subject having autoimmune disease to reduce associated cell death.

The methods of the invention also include methods for treating a subject having autoimmune disease to reduce associated cell death, according to one set of embodiments. One method is based on the ability to selectively remove gamma delta (γδ) T cells which specifically recognize MHC class II HLA-DR on the surface of a self cell. When the gamma delta T cells recognize a tissue having significant amounts of MHC class II HLA-DR these T cells become activated and proliferate in order to kill more of the recognized cells. The methods of treatment are based on the concept of eliminating the activated gamma delta T cells from the body. These cells can be removed by contacting a gamma delta T cell with an amount of a plasma membrane targeted UCP inhibitor in an amount effective to induce gamma delta T cell death. This selective killing of the gamma delta cells inhibits cell death associated with autoimmune disease.

When used with mammalian cells in vitro, certain systems and methods may have utility for loading of specific antigens within the MHC molecules. Cells with specific antigen loading in class II molecules have utility in a variety of analytical and diagnostic assays. These cells are also useful as therapeutic agents. For instance, the cells can be used in culture to study immune responses or to screen the effect of putative drugs on inhibiting or promoting antigen-specific immune responses. Additionally, the cells could be administered to a mammalian subject to promote an antigen-specific T cell response. When administered to a subject, the class II MHC/antigen complexes on the surface of the cell can interact with endogenous T cells, inducing an immune cascade, and thus can produce an antigen-specific immune response. In some embodiments, the cells manipulated in vitro have been isolated from the same subject ex vivo.

The systems and methods of the invention can also be used for treating a mammalian subject in vivo to induce an antigen-specific immune response, according to another set of embodiments. It is useful to produce antigen-specific immune responses against any foreign antigen, whether it is capable of causing a pathological state and/or any damage to its mammalian host. The terms "foreign antigen" or "antigen" are used synonymously to refer to a molecule capable of provoking an immune response in a host wherein the antigen is not a self-antigen, as defined above. Thus, these terms specifically excludes self-antigens. Self-antigens are used herein to refer to the peptide-antigens of autoimmune disorders. An immune response against the self-antigen results in an autoimmune disorder. The term "self-antigen" does not include, however, antigens such as cancer antigens, which are recognized by the host as foreign and which are not associated with autoimmune disease. Thus, the term "antigen" specifically excludes self-antigens and broadly includes any type of molecule (e.g. associated with a host or foreign cell) which is recognized by a host immune system as being foreign. Antigens include, but are not limited to, cancer antigens and microbial antigens and may be composed of cells, cell extracts, polysaccharides, polysaccharide conjugates, lipids, glycolipids, carbohydrates, peptides, proteins, viruses, viral extracts, etc. A "cancer antigen," as used herein, is a compound which is associated with a tumor or cancer cell surface and which is capable of provoking an immune response when expressed on the surface of an antigen-presenting cell in the context of a class II MHC molecule. Cancers or tumors include those described above.

Cancer antigens include but are not limited to Melan-A/MART-1, Dipeptidyl peptidase IV (DPPIV), adenosine deaminase-binding protein (ADAbp), cyclophilin b, Colorectal associated antigen (CRC)--C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, alpha-fetoprotein, E-cadherin, alpha-catenin, beta-catenin and gamma-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1 and CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, or c-erbB-2.

In some embodiments, cancers or tumors escaping immune recognition and tumor-antigens associated with such tumors (but not exclusively), include acute lymphoblastic leukemia (etv6; aml1; cyclophilin b), B cell lymphoma (Ig-idiotype), glioma (E-cadherin; alpha-catenin; beta-catenin; gamma-catenin; p120ctn), bladder cancer (p21ras), billiary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)--C017-1A/GA733; APC), choriocarcinoma (CEA), epithelial cell-cancer (cyclophilin b), gastric cancer (HER2/neu; c-erbB-2; ga733 glycoprotein), hepatocellular cancer (alpha-fetoprotein), hodgkins lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21 ras), non-small cell lung carcinoma (HER2/neu; c-erbB-2), nasopharyngeal cancer (lmp-1; EBNA-1), ovarian cancer cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins), testicular cancer (NY-ESO-1), T cell leukemia (HTLV-1 epitopes), and melanoma (Melan-A/MART-1; cdc27; MAGE-3; p21ras; gp100$^{Pmel117}$).

For examples of tumor antigens which bind to either or both MHC class I and MHC class II molecules, see the following references: Coulie, *Stem Cells*, 13:393-403, 1995; Traversari, et al., *J. Exp. Med.*, 176:1453-1457, 1992; Chaux, et al., *J. Immunol.*, 163:2928-2936, 1999; Fujie, et al., *Int. J. Cancer*, 80:169-172, 1999; Tanzarella, et al., *Cancer Res.*, 59:2668-2674, 1999; van der Bruggen, et al., *Eur. J. Immunol.*, 24:2134-2140, 1994; Chaux, et al., *J. Exp. Med.*, 189:767-778, 1999; Kawashima et al, *Hum. Immunol.*, 59:1-14, 1998; Tahara, et al., *Clin. Cancer Res.*, 5:2236-2241, 1999; Gaugler, et al., *J. Exp. Med.*, 179:921-930, 1994; van der Bruggen, et al., *Eur. J. Immunol.*, 24:3038-3043, 1994; Tanaka, et al., *Cancer Res.*, 57:4465-4468, 1997; Oiso, et al., *Int. J. Cancer*, 81:387-394, 1999; Herman, et al., *Immunogenetics*, 43:377-383, 1996; Manici, et al., *J. Exp. Med.*, 189:871-876, 1999; Duffour, et al., *Eur. J. Immunol.*, 29:3329-3337, 1999; Zorn, et al., *Eur. J. Immunol.*, 29:602-607, 1999; Huang, et al., *J. Immunol.*, 162:6849-6854, 1999; Böel, et al., *Immunity*, 2:167-175, 1995; Van den Eynde, et al., *J. Exp. Med.*, 182:689-698, 1995; De Backer, et al., *Cancer Res.*, 59:3157-3165, 1999; Jäger, et al., *J. Exp. Med.*, 187:265-270, 1998; Wang, et al., *J. Immunol.*, 161:3596-3606, 1998; Aarnoudse, et al., *Int. J. Cancer*, 82:442-448, 1999; Guilloux, et al., *J. Exp. Med.*, 183:1173-1183, 1996; Lupetti, et al., *J. Exp. Med.*, 188:1005-1016, 1998; Wölfel, et al., *Eur. J Immunol.*, 24:759-764, 1994; Skipper, et al., *J. Exp. Med.*, 183:527-534, 1996; Kang, et al., *J. Immunol.*, 155:1343-1348, 1995; Morel, et al., *Int. J. Cancer*, 83:755-759, 1999; Brichard, et al., *Eur. J. Immunol.*, 26:224-230, 1996; Kittlesen, et al., *J. Immunol.*, 160:2099-2106, 1998; Kawakami, et al., *J. Immunol.*, 161:6985-6992, 1998; Topalian, et al., *J. Exp. Med.*, 183:1965-1971, 1996; Kobayashi, et al., *Cancer Res.*, 58:296-301, 1998; Kawakami, et al., *J. Immunol.*, 154:3961-3968, 1995; Tsai, et al., *J. Immunol.*, 158:1796-1802, 1997; Cox, et al., *Science*, 264:716-719, 1994; Kawakami, et al., *Proc. Natl. Acad. Sci. U.S.A.*, 91:6458-6462, 1994; Skipper, et al., *J. Immunol.*, 157:5027-5033, 1996; Robbins, et al., *J. Immunol.*, 159:303-308, 1997; Castelli et al, *J. Immunol.*, 162:1739-1748, 1999; Kawakami, et al., *J. Exp. Med.*, 180:347-352, 1994; Castelli, et al., *J. Exp. Med.*, 181:363-368, 1995; Schneider, et al., *Int. J. Cancer*, 75:451-458, 1998; Wang, et al., *J. Exp. Med.*, 183:1131-1140, 1996; Wang, et al., *J. Exp. Med.*, 184:2207-2216, 1996; Parkhurst, et al., *Cancer Res.*, 58:4895-4901, 1998; Tsang, et al., *J. Natl. Cancer Inst.*, 87:982-990, 1995; Correale, et al., *J. Natl. Cancer Inst.*, 89:293-300, 1997; Coulie, et al., *Proc. Natl. Acad. Sci. U.S.A.*, 92:7976-7980, 1995; Wölfel, et al., *Science*, 269:1281-1284, 1995; Robbins, et al., *J. Exp. Med.*, 183:1185-1192, 1996; Brändle, et al., *J. Exp. Med.*, 183:2501-2508, 1996; ten Bosch, et al., *Blood*, 88:3522-3527, 1996; Mandruzzato, et al., *J. Exp. Med.*, 186:785-793, 1997; Guéguen, et al., *J. Immunol.*, 160:6188-6194, 1998; Gjertsen, et al., *Int. J. Cancer*, 72:784-790, 1997; Gaudin, et al., *J. Immunol.*, 162:1730-1738, 1999; Chiari, et al., *Cancer Res.*, 59:5785-5792, 1999; Hogan, et al., *Cancer Res.*, 58:5144-5150, 1998; Pieper, et al., *J. Exp. Med.*, 189:757-765, 1999; Wang, et al., *Science*, 284:1351-1354, 1999; Fisk, et al., J. Exp. Med. 181:2109-2117, 1995; Brossart, et al., *Cancer Res.*, 58:732-736, 1998; Röpke, et al., *Proc. Natl. Acad. Sci. U.S.A.*, 93:14704-14707, 1996; Ikeda, et al., *Immunity* 6:199-208, 1997; Ronsin, et al., *J. Immunol.*, 163:483-490, 1999; or Vonderheide, et al., *Immunity*, 10:673-679,1999. These antigens as well as others are disclosed in PCT Application PCT/US98/18601.

The systems and methods of the invention are also useful for treating mammals at risk of, or afflicted with, allergic responses, in yet another set of embodiments. An "allergic response" as used herein is a disorder in which the host's immune response to a particular antigen is unnecessary or disproportionate, resulting in pathology. An allergic response may occur, in part, because a T cell recognizes a particular class II MHC/peptide complex and triggers a cascade of immune response. If the class II MHC/peptide complex is inhibited from being formed, the allergic response is reduced or suppressed. Any allergic response in which class II MHC/peptide complexes play a role may be treated according to the methods of the present invention. Allergies arising from an allergic response include, but are not limited to, allergies to pollen, ragweed, shellfish, domestic animals, (e.g., cats and dogs), B-venom, and the like. A subset of allergic responses produce asthma. Allergic asthmatic responses are also included within the definition of the term "allergic response." It is particularly desirable to treat severe or life-threatening allergic responses, such as those arising during asthmatic attacks or anaphylactic shock, according to the systems and methods of the invention.

In another aspect, the systems and methods of the invention are useful in treating wounds in subjects. As used herein, the term "wound" is used to describe skin wounds as well as tissue wounds. A "skin wound" is defined herein as a break in the continuity of skin tissue which is caused by direct injury to the skin. Skin wounds are generally characterized by several classes including punctures, incisions, including those produced by surgical procedures, excisions, lacerations, abrasions, atrophic skin, or necrotic wounds and burns. The systems and methods of the invention are useful for enhancing the healing of all wounds of the skin.

A "tissue wound," as used herein, is a wound to an internal organ, such as a blood vessel, intestine, colon, etc. The systems and methods of the invention are useful for enhancing the wound healing process in tissue wounds, whether they arise naturally, or as the result of surgery. For instance, during the repair of arteries an artery may need to be sealed and wound healing promoted as quickly as possible. The systems and methods of the invention can speed up that process in many cases. The invention may also be particularly useful for the treatment of damaged tissue in the colon. In addition to promoting wound healing of the damaged colon, in some cases, the systems and methods of the invention can provide an antimicrobial effect.

The cells treated according to the present invention may be used to treat a wound. For example, a UCP inhibitor and/or a Fas inhibitor, together with a fatty acid metabolism inhibitor, and/or a glucose metabolism inhibitor and/or an agent able to alter cellular production of reactive oxygen in cells. As an example, ex vivo cells may be attached to a bandage or other substrate, and the substrate positioned over a wound, at least partially covering the wound. In some cases, the bandage or other substrate may be adhered to the subject, for example, through the use of adhesives. Suitable adhesives can be selected by those of ordinary skill in the art; some suitable adhesives are further described below.

The systems and methods of the invention may also include additional therapeutic and/or pharmacologically acceptable agents. For instance, the compositions or methods may involve other agents for the treatment of wounds such as, for instance, dexpanthenol, growth factors, enzymes or hormones, povidon-iodide, fatty acids, such as cetylphridinium chloride, antibiotics, and analgesics. In some embodiments, the compositions may also include growth factors. Growth factors include, but are not limited to, fibroblast growth factor (FGF), FGF-1, FGF-2, FGF-4, platelet-derived growth factor (PDGF), insulin-binding growth factor (IGF), IGF-1, IGF-2, epidermal growth factor (EGF), transforming growth factor (TGF), TGF-alpha, TGF-beta, cartilage inducing factors-A and -B, osteoid-inducing factors, osteogenin and other bone growth factors, collagen growth factors, heparin-binding growth factor-1 or -2, and/or their biologically active derivatives. The compositions may also include antiseptics in some embodiments.

In another aspect, the systems and methods of the invention are useful for treating mammals which have undergone or about to undergo, an organ transplant or tissue graft. In tissue transplantation (e.g., kidney, lung, liver, heart) or skin grafting, when there is a mismatch between the class II MHC genotypes (HLA types) of the donor and recipient, there may be a severe "allogeneic immune response" against the donor tissues which results from the presence of non-self or allogeneic class II MHC molecules presenting antigenic peptides on the surface of donor cells.

The systems and methods of the invention, in yet another aspect, are useful for treating mammals having an inflammatory disease or condition. An "inflammatory disease or condition," as used herein, refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil activation. These conditions include, but are not limited to, meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

In one aspect, the systems and methods of the invention can also be used in combination with other therapies, such as radiation therapy. When a combination of therapies are used the effective amount to achieve the desired result, inhibition of cell proliferation may be less. This may reduce or eliminate any side effects associated with high concentrations of the individual therapies. One example is a combination of one or more compositions of the invention and radiation therapy. In some cases, the radiation therapy may also contribute to the inhibition of UCP in the plasma membrane. Radiation-sensitive cells are those cells that express UCP in the plasma membrane, and radioresistant cells do not express plasma membrane UCP. The invention also includes, in some instances, systems and methods of treating radioresistant cells by inducing UCP expression in the plasma membrane and treating them with radiation.

Optionally, in some embodiments, a targeting mechanism can be used to target one or more compositions of the invention to a specific cell, tumor, wound, or the like. It is desirable in many instances to specifically target a cell type to increase the efficiency and specificity of administration of the composition, thus avoiding the effects that can damage or destroy unrelated cells. Thus, a delivery system which enables the delivery of such drugs specifically to target cells is provided. The delivery system may increase the efficacy of treatment and reduce the associated "side effects" of such treatment.

Methods of targeting drugs and other compositions to target cells (such as cancer cells or cells within a wound) are well known in the art. One method of targeting involves antibody or receptor targeting. Receptor or antibody targeting involves linking the pharmacon of the invention to a ligand or an antibody which has an affinity for a receptor or cell surface molecule expressed on the desired target cell surface, for example, UCP. Using this approach, a composition of the invention is intended to adhere to the target cell following formation of a ligand-receptor or antibody-cell surface antigen complex on the cell surface. The type of receptor or antibody used to target the cell will depend on the specific cell type being targeted. A target molecule may be attached by a peptide or other type of bond such as a sulfhydryl or disulfide bond. Targeting molecules are described, for instance in U.S. Pat. No. 5,849,718, as well as many other references.

In general, the targeting moiety can be coupled to a composition of the invention. The molecules may be directly coupled to one another, such as by conjugation, or may be indirectly coupled to one another where, for example, the targeting moiety is on the surface of a liposome and one or more compositions of the invention are contained within the liposome. If the molecules are linked to one another, then the targeting moiety can be covalently or noncovalently bound to the pharmacon of the invention in a manner that preserves the targeting specificity of the targeting moiety. As used herein, "linked" or "linkage" means two entities are bound to one another by any physiochemical means. It is important that the linkage be of such a nature that it does not impair substantially the effectiveness of the compositions of the invention or the binding specificity of the targeting moiety. Keeping these parameters in mind, any linkage known to those of ordinary skill in the art may be employed, covalent or noncovalent. Such means and methods of linkage are well known to those of ordinary skill in the art.

Linkages according to the invention need not be direct linkage. The compositions of the invention may be provided with functionalized groups to facilitate their linkage and/or linker groups may be interposed therebetween to facilitate their linkage. In some instances, the components of the present invention may be synthesized in a single process, whereby the composition is regarded as a single entity. For example, a targeting moiety specific for a tumor cell could be synthesized together with a VCP inhibitor and a fatty acid metabolism inhibitor of the invention. These and other modifications are intended to be embraced by the present invention.

Specific examples of covalent bonds include those where bifunctional cross-linker molecules can be used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more of the following groups, such as primary amines, secondary amines, sulfhydriles, carboxyls, carbonyls and carbohydrates.

Non-covalent methods of conjugation also may be used to join the targeting moiety and the composition in some cases. Non-covalent conjugation may be accomplished by direct or indirect means, including hydrophobic interaction, ionic interaction, intercalation, binding to major or minor grooves of a nucleic acid, and other affinity interactions.

Covalent linkages may be noncleavable in physiological environments, or cleavable in physiological environments, such as linkers containing disulfide bonds. Such molecules may resist degradation and/or may be subject to different intracellular transport mechanisms. One of ordinary skill in the art will be able to ascertain, without undue experimentation, the preferred bond for linking the targeting moiety and the compositions of the invention, based on the chemical properties of the molecules being linked and the preferred characteristics of the bond, for a given application.

For indirect linkage, the targeting moiety may be part of a particle, such as a liposome, which is targeted to a specific cell type. The liposome, in turn, may contain the compositions of the invention. The manufacture of liposomes containing compositions of the invention is fully described in the literature. Many for example, are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (i.e., 12 to 20 carbons), for example, naturally occurring fatty acids of between 14 and 18 carbons in length. These molecules can be attached to one or more compositions of the invention, for example, with the lipophilic anchor inserting into the membrane of a liposome and the compositions tethered on the surface of the liposome for targeting the liposome to the cell. In other cases, one or more compositions of the invention may be present in the interior of the liposome.

Each of the compositions described herein (or portions thereof) may optionally be associated with a delivery system or vector, according to one aspect of the invention. In its broadest sense, a "vector" is any vehicle capable of facilitating: (1) delivery of a composition to a target cell or (2) uptake of a composition by a target cell, if uptake is important. Optionally, a "targeting ligand" (in addition to, or the same as, the plasma membrane targeting molecule) can be attached to the vector to selectively deliver the vector to a cell which expresses on its surface the cognate receptor for the targeting ligand. In this manner, the vector (containing one or more compositions of the invention) can be selectively delivered to a cell in, e.g., a tumor, a wound, etc. In general, the vectors useful in the invention are divided into two classes: colloidal dispersion systems and biological vectors. Other example compositions that can be used to facilitate uptake by a target cell of compositions of the invention include calcium phosphate and other chemical mediators of intracellular transport, microinjection compositions, and electroporation.

In general, the vectors useful in the invention include, but are not limited to, plasmids, phagemids, viruses, other vehicles derived from viral or bacterial sources that have been manipulated by the insertion or incorporation of the UCP or UCP or Fas inhibitor nucleic acid sequences. Viral vectors include, but are not limited to, nucleic acid sequences from any of the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named above but known to the art.

In some cases, the viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in the literature, e.g., Kriegler, *Gene Transfer and Expression, A Laboratory Manual*, W. H. Freeman, Co., 1990 and Murry, Ed. *Methods in Molecular Biology*, Vol. 7, Humana Press, Inc., 1991.

A virus useful for certain applications is an adeno-associated virus, which is a double-stranded DNA virus. The adeno-associated virus can be engineered to be replication-deficient and is capable of infecting a wide range of cell types and species in many cases. It further has certain advantages, such as heat and lipid solvent stability; high transduction frequencies in cells of diverse lineages, including hemopoietic cells; and lack of superinfection inhibition, thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other suitable vectors include plasmid vectors. Plasmid vectors have been extensively described in the art and are well-known to those of skill in the art. See e.g., Sambrook, et al., *Molecular Cloning: A Laboratory Manual*, Second Edition, Cold Spring Harbor Laboratory Press, 1989. Plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and/or ligation reactions to remove and add specific fragments of DNA.

It has also been discovered that gene carrying plasmids can be delivered to the cells in vivo using bacteria. Modified forms of bacteria such as *Salmonella* can be transfected with the plasmid and can thus be used as delivery vehicles in some cases. The bacterial delivery vehicles can be administered to a host subject orally or by other administration means. The bacteria in some instances can pass through the gut barrier. High levels of expression have been established using this methodology.

Compaction agents also can be used alone, or in combination with, a vector of the invention. A "compaction agent," as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the compositions in a form that is more efficiently taken up by the cell or, more preferably, in combination with one or more of the above-described vectors.

In one aspect, the invention provides a method of administering any of the compositions described herein to a subject. When administered, the compositions are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. The dose to the subject may be such that a therapeutically effective amount of one or more active pharmacons reaches the active site(s) within the subject. A "therapeutically effective" or an "effective" dose, as used herein, means that amount necessary to delay the onset of, inhibit the progression of, halt altogether the onset or progression of, diagnose a particular condition being treated, or otherwise achieve a medically desirable result, i.e., that amount which is capable of at least partially preventing, reversing, reducing, decreasing, ameliorating, or otherwise suppressing the particular condition being treated. A therapeutically effective amount can be determined on an individual basis and will be based, at least in part, on consideration of the species of mammal, the mammal's age, sex, size, and health; the composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to eliminate or at least control a cancer or a wound, and/or to reduce the severity of the cancer or wound. The pharmaceutical preparations of the invention are administered to subjects in effective amounts. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active pharmacon, when parentally administered, may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day.

In some embodiments, the concentration of the active pharmacon(s) of the composition, if administered systemically, is at a dose of about 1.0 mg to about 2000 mg for an adult of 70 kg body weight, per day. In other embodiments, the dose is about 10 mg to about 1000 mg/70 kg/day. In yet other embodiments, the dose is about 100 mg to about 500 mg/70 kg/day. If applied topically, the concentration may be about 0.1 mg to about 500 mg/g of ointment or other base, about 1.0 mg to about 100 mg/g of base, or about 30 mg to about 70 mg/g of base. The specific concentration partially depends upon the particular composition used, as some are more effective than others. The dosage concentration of the composition actually administered is dependent, at least in part, upon the particular disorder being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously effect the mammal.

The dosage may be given in some cases at the maximum amount while avoiding or minimizing any potentially detrimental side effects within the subject. The dosage actually administered can be dependent upon factors such as the final concentration desired at the active site, the method of administration to the subject, the efficacy of the composition, the longevity of the composition within the subject, the mode and/or timing of administration, the effect of concurrent treatments (e.g., as in a cocktail), etc. The dose delivered may also depend on conditions associated with the subject, and can vary from subject to subject in some cases. For example, the age, sex, weight, size, environment, physical conditions, active site of the cancer or wound, or current state of health of the subject may also influence the dose required and/or the concentration of the composition at the active site. Variations in dosing may occur between different individuals or even within the same individual on different days. These factors are well known to those of ordinary skill in the art and can be addressed with no more than routine experimentation. It is preferred that a maximum dose be used, that is, the highest safe dose according to sound medical judgment.

In the event that the response of a particular subject is insufficient at such doses, even higher doses (or effectively higher doses by a different, more localized delivery route) may be employed to the extent that subject tolerance permits. Multiple doses per day are also contemplated, in some cases, to achieve appropriate systemic levels within the subject or within the active site of the subject. In certain instances, dosing amounts, dosing schedules, routes of administration, and the like may be selected as described herein, whereby therapeutically effective levels of the composition are provided.

In certain embodiments where cancers are being treated, a composition of the invention is administered to a subject who has a family history of cancer, or to a subject who has a genetic predisposition for cancer. In other embodiments, the composition is administered to a subject who has reached a particular age, or to a subject more likely to get cancer. In yet other embodiments, the compositions is administered to subjects who exhibit symptoms of cancer (e.g., early or advanced). In still other embodiments, the composition may be administered to a subject as a preventive measure. In some embodiments, the inventive composition may be administered to a subject based on demographics or epidemiological studies, or to a subject in a particular field or career.

Administration of a composition of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active pharmacon(s) of the composition within the subject without causing clinically unacceptable adverse effects. The administration may be localized (i.e., to a particular region, physiological system, tissue, organ, or cell type) or systemic, depending on the condition being treated. For example, the composition may be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of the composition. Other oral compositions suitable for use with the invention include solutions or suspensions in aqueous or non-aqueous liquids such as a syrup, an elixir, or an emulsion. In one set of embodiments, the composition may be used to fortify a food or a beverage.

Injections can be e.g., intravenous, intradermal, subcutaneous, intramuscular, or interperitoneal. For example, the inhibitor can be injected intravenously or intramuscularly for the treatment of multiple sclerosis, or can be injected directly into the joints for treatment of arthritic disease, or can be injected directly into the lesions for treatment of pemphigus vulgaris. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. For systemic administration, it may be useful to encapsulate the composition in liposomes.

Inhalation includes administering the composition with an aerosol in an inhaler, either alone or attached to a carrier that can be absorbed.

In general, the compositions of the invention may be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those of ordinary skill in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth) acrylic acid, polyamides, copolymers and mixtures thereof.

Bioadhesive polymers of particular interest in some cases include, but are not limited to, the bioerodible hydrogels described by Sawhney, et al., *Macromolecules,* 26:581-587, 1993, the teachings of which are incorporated herein, as well as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The systems and methods of the invention can be administered by any method which allows the composition of the invention to reach the target cells, e.g., tumor cells. These methods include, e.g., injection, infusion, deposition, implantation, anal or vaginal supposition, oral ingestion, inhalation, topical administration, or any other method of administration where access to the target cells by the inhibitor is obtained. In some embodiments, topical administration is preferred, due to the high concentration of APCs in the skin. One method for accomplishing topical administration includes transdermal administration, such as iontophoresis. Iontophoretic transmission can be accomplished by using commercially-available patches which deliver a pharmacon continuously through unbroken skin for periods of hours to days to weeks, depending on the particular patch. This method allows for the controlled delivery of the composition through the skin in relatively high concentrations. One example of an iontophoretic patch is the LECTRO PATCH™ sold by General Medical Company of Los Angeles, Calif. The patch provides dosages of different concentrations which can be continuously or periodically administered across the skin using electronic stimulation of reservoirs containing the composition. Topical administration also includes epidermal administration which involves the mechanical or chemical irritation of the outermost layer of the epidermis sufficiently to provoke an immune response to the irritant. The irritant attracts APCs to the site of irritation where they can then take up the composition. One example of a mechanical irritant is a tyne-containing device. Such a device contains tynes which irritate the skin and deliver the drug at the same time, for instance, the MONO VACC™ manufactured by Pasteur Merieux of Lyon, France. The device contains a syringe plunger at one end and a tyne disk at the other. The tyne disk supports several narrow diameter tynes which are capable of scratching the outermost layer of epidermal cells. Chemical irritants include, for instance, keratinolytic agents, such as salicylic acid, and can be used alone or in conjunction with other irritants such as mechanical irritants.

In certain embodiments of the invention, the administration of the composition of the invention may be designed so as to result in sequential exposures to the composition over a certain time period, for example, hours, days, weeks, months, or years. This may be accomplished, for example, by repeated administration of a composition of the invention by one of the methods described above, and/or by a sustained or controlled release delivery system in which the composition is delivered over a prolonged period, usually without repeated administrations. Administration of the composition using such a delivery system may be, for example, by oral dosage forms, bolus injections, transdermal patches or subcutaneous implants. Maintaining a substantially constant concentration of the composition may be desirable in some cases.

Other delivery systems suitable for use with the present invention include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides, hydrogel release systems, liposome-based systems, phospholipid based-systems, silastic systems, peptide based systems, wax coatings, compressed tablets using conventional binders and excipients, or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and 5,239,660), or diffusional systems in which an active component controls the release rate (for example, as described in U.S. Pat. Nos. 3,832,253, 3,854,480, 5,133,974 and 5,407,686). The formulation may be present as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the composition. In addition, a pump-based hardware delivery system may be used to deliver one or more embodiments of the invention in some cases.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core-degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments of the invention. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

In certain embodiments of the invention, a composition may include a suitable pharmaceutically acceptable carrier, for example, as incorporated into a liposome, incorporated into a polymer release system, or suspended in a liquid, e.g., in a dissolved form or a colloidal form, such as in a colloidal dispersion system. In general, pharmaceutically acceptable carriers suitable for use in the invention are wellknown to those of ordinary skill in the art. As used herein, a "pharmaceutically acceptable carrier" refers to a non-toxic material that does not significantly interfere with the effectiveness of the biological activity of the active pharmacon(s) to be administered, but is used as a formulation ingredient, for example, to stabilize or protect the active pharmacon(s) within the composition before use. The term "carrier" denotes an organic or inorganic ingredient, which may be natural or synthetic, with which one or more active pharmacons of the invention are combined to facilitate the application of the composition. The carrier may be co-mingled or otherwise mixed with one or more active pharmacons of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

As used herein, a "colloidal dispersion system" refers to a natural or synthetic molecule, other than those derived from bacteriological or viral sources, capable of delivering to and releasing the composition in a subject. Colloidal dispersion systems include macromolecular complexes, nanocapsules, microspheres, beads, and lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2 micrometers to 4.0 micrometers can encapsulate large macromolecules within the aqueous interior and these macromolecules can be delivered to cells in a biologically active form (Fraley, et al., *Trends Biochem. Sci.*, 6:77, 1981).

Lipid formulations for transfection are commercially available, e.g., from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2,3-dioleyloxy)-propyl]-N,N,N-trimethylammonium chloride (DOTMA) and dimethyl dioctadecylammonium bromide (DDAB). Methods for making liposomes are well known in the art and have been described in many publications. Some liposomes were described in a review article by Gregoriadis, *Trends in Biotechnol.*, 3:235-241, 1985, which is hereby incorporated by reference.

In one embodiment, the vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System." PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the present invention, the compositions of the invention described herein can be encapsulated or dispersed within the biocompatible, optionally biodegradable polymeric matrix disclosed in PCT/US/03307.

The polymeric matrix can be in the form of a microparticle such as a microsphere (where the composition is dispersed throughout a solid polymeric matrix) or a microcapsule (where the composition is stored in the core of a polymeric shell). Other forms of the polymeric matrix for containing the composition include films, coatings, gels, implants, and stents. The size and composition of the polymeric matrix device can be selected to result in favorable release kinetics in the tissue into which the matrix is introduced. The size of the polymeric matrix can also be selected according to the method of delivery which is to be used, typically injection into a tissue or administration of a suspension by aerosol into the nasal and/or pulmonary areas. When an aerosol route is used the polymeric matrix and composition can be encompassed in a surfactant vehicle. The polymeric matrix composition can be selected to have both favorable degradation rates and/or to be formed of a material which is bioadhesive, e.g., to further increase the effectiveness of transfer when the matrix is administered to a nasal and/or pulmonary surface that has sustained an injury. The matrix composition can also be selected not to degrade, but rather, to release by diffusion over an extended period of time. In another embodiment, the matrix is a biocompatible microsphere that is suitable for oral delivery. Such microspheres are disclosed in Chickering, et al., *Biotech. and Bioeng.*, 52:96-101, 1996, and Mathiowitz, et al., *Nature*, 386:410-414, 1997.

Both non-biodegradable and biodegradable polymeric matrices can be used to deliver the compositions of the invention to the subject. Such polymers may be natural or synthetic polymers. The polymer may be selected based on the period of time over which release is desired, generally in the order of a few hours, to a year or longer. Typically, release over a period ranging from between a few hours and three to twelve months is desirable. The polymer optionally is in the form of a hydrogel that can absorb up to about 90% of its weight in water and further, optionally is cross-linked with multivalent ions or other polymers.

In some embodiments, the compositions of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof, or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in, for example, *Remington's Pharmaceutical Sciences*, Mack Publishing Co. Those of oridnary skill in the art can readily determine the various parameters for preparing and formulating the compositions of the invention without resort to undue experimentation.

In some embodiments, the present invention includes the step of forming a composition of the invention by bringing an active pharmacon into association or contact with a suitable carrier, which may constitute one or more accessory ingredients. The final composition may be prepared by any suitable technique, for example, by uniformly and intimately bringing the composition into association with a liquid carrier, a finely divided solid carrier or both, optionally with one or more formulation ingredients as previously described, and then, if necessary, shaping the product.

In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as alkaline met al salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

In one aspect, the present invention provides any of the above-mentioned compositions in kits, optionally including instructions for use of the composition e.g., for the treatment of cancers or wounds. The "kit" typically defines a package including one or more compositions of the invention and the instructions, or homologs, analogs, derivatives, enantiomers and functionally equivalent compositions thereof. That is, the kit can include a description of use of the composition for participation in any biological or chemical mechanism disclosed herein associated with cancers or wounds. The kits can further include a description of activity of the cancers or wounds in treating the pathology, as opposed to the symptoms. The kit can include a description of use of the compositions as discussed herein. The kit also can include instructions for use of a combination of two or more compositions of the invention, or instruction for use of a combination of a composition of the invention and one or more other compounds indicated for treatment of a cancer, a wound, etc. Instructions also may be provided for administering the composition by any suitable technique as previously described, for example, orally, intravenously, pump or implantable delivery device, or via another known route of drug delivery.

The instructions may be of any form provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting or administering the components to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition and the mode of use or administration. Suitable solvents are well known, for example as previously described, and are available in the literature. The solvent will depend on the compound and the mode of use or administration.

The invention also involves, in another aspect, promotion of the treatment of cancers, wounds, etc. according to any of the systems or methods described herein. In some embodiments, one or more compositions of the invention may be promoted for treatment of cancers or wounds, or include instructions for treatment of cancers or wounds. In some cases, the invention provides a method involving promoting the prevention or treatment of cancers, wounds, etc. via administration of any one of the compositions of the present invention, and homologs, analogs, derivatives, enantiomers and functionally equivalent compositions thereof in which the invention is able to treat cancer, wounds, etc. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cancers or wounds. "Instructions" can define a component of promotion, and typically involve written instructions on or associated with packaging of compositions of the invention. Instructions also can include any oral or electronic instructions provided in any manner.

EXAMPLES

The following examples illustrate the invention with the use of a fatty acid metabolism inhibitor, a glucose metabolism inhibitor, a UCP or Fas inhibitor, and combinations thereof, alone or in combination with a chemotherapeutic, to produce changes in immunologically important co-stimulatory levels, and induce tumor cell death by the action of the immune system. The examples demonstrate efficaceous, synergistic combinations of the foregoing inhibitors, Materials and Methods Except to the extent stated otherwise in the examples, materials and methods used in the examples are as follows:

Cell Culture. All cell lines were cultured in RPMI 1640 culture medium. The medium is supplemented with 5% fetal bovine serum (FBS) (but 10% FBS for A204 human rhabdomyosarcoma cells), 2mM L-Glutamine, 500 units/mL penicillin/500 µg/mL of streptomycin, 10 mM HEPES Buffer, $10^{-5}$M 2-mercaptoethanol (2-ME), 1 mM MEM Sodium Pyruvate, and 0.04 µg/mL of Gentamicin (All reagents from Gibco BRL). Cells were maintained at 37° C. in a humidified atmosphere under 5% $CO_2$ in air.

Flow Cytometry. Cells were harvested, counted, and resuspended at 106 Cells/100 µl of PBS containing 2.5% fetal calf serum in preparation for flow cytometric analysis. Cells were stained for intracellular H202 using 6-carboxy-2',7'-dichlorodihydrofluorescein diacetate (DCF-DA, Molecular Probes, Eugene, Oregon). Briefly, cells were incubated at 37° with 1 mM DCF-DA for 20 minutes, washed twice in PBS containing 2.5 % fetal calf serum and analyzed flow cytometrically. Mitochondrial membrane potential was assessed using MITOTRACKER® Red (CM-H2XROS, Molecular Probes, Eugene, Oreg.). The cells were resuspended in PBS containing 2.5% fetal calf serum containing a final concentration of 0.5 micromolar MITOTRACKER® dye. The cells were incubated at 37° for 20 minutes, washed twice in PBS containing 2.5 % fetal calf serum and analyzed flow cytometrically. Data were acquired on a Coulter Elite Epics, sold under the trademark Coulter EPICS ELITE or Excel flow cytometer (Coulter, Hialeah, Fla.) and analyzed with CELLQUEST™ software, (Becton Dickinson, San Jose, Calif.). COULTER EPICS ELITE™ flow cytometer has a single excitation wavelength (488 nm) and band filters for PE (575 nm), FITC (525 nm) and Red613 (613 nm) that was used to analyze the stained cells. For antibodies that are PE conjugated and for MITOTRACKER® Red, a program for red colored fluorochromes was utilized. For antibodies that are FITC conjugated and for DCFda, LYSOSENSOR™, and LYSOTRACKER™ a program for green colored fluorochromes was used. Each sample population was classified for cell size (forward scatter) and complexity (side scatter), gated on a population of interest and evaluated using 5,000 cells. Each figure describing flow cytometric data represents one of at least four replicate experiments.

Cell Counting. Cells were harvested and resuspended in 1 mL of RPMI medium. A 1:20 dilution of the cell suspension was made by using 50 µL of trypan blue (Sigma chemicals), 45 µL of Phosphate Buffered Saline (PBS) supplemented with 2.5% FBS, and 5 µL of the cell suspension. Live cells were counted using a hemacytometer and the following calculation was used to determine cell number: Average # of Cells×Dilution×$10^4$.

Preparation of Cell for Staining. For staining protocols, between $0.5\times10^6$ and $1.0\times10^6$ cells were used; all staining was done in a 96-well U-bottom staining plate. Cells were harvested by centrifugation for 5 minutes at 300×g, washed with PBS/2.5% FBS, and resuspended into PBS/2% FBS for staining. Cells were plated into wells of a labeled 96-well plate in 100 µL of PBS/2.5% FBS.

Cell Surface Staining. Non-permeabilized cells were stained with antibodies to the cell surface receptors Fas (CD95)(PHARMINGEN®) or with antibodies to uncoupling proteins (anti-UCP2 antibody)(Alpha Diagnostic International). Antibodies for both the isotype control and actual stain were added to the cell suspension, mixed, and then placed on ice for and incubation of 25 minutes in the dark. Subsequently the cells were centrifuged at 300×g for 5 minutes and the supernatant removed. The cells were washed one time with 100 µL of PBS/2.5% FBS and then transferred into flow cyotmetric tubes containing 500 µL of PBS/2.5% FBS for analysis.

Metabolic Activity Assay. Cells were prepared as previously described. The specific metabolic dye was added and mixed into the cell suspension. This plate was then placed into the 37° incubator for a 20-minute incubation. After incubation, the cells were centrifuged at 300×g for 5 minutes, and the supernatant was removed. The cells were then washed once with PBS/2.5% FBS and transferred into flow cytometric tubes containing 500 µL of PBS/2.5% FBS for analysis MITOTRACKER® Red CM-$H_2$XROS (Molecular Probes). One vial of MITOTRACKER® Red provides 10 tests and contains 50 µg. This is unstable and can't be stored. Therefore, when each vial was opened, 43 µL of Dimethysulfoxide (DMSO) were added. Once this was mixed well, 4.0 µL of this was added to each well containing the cells to be tested for their mitochondrial membrane potential. MITOTRACKER® was used at a final concentration of 46 ng for each test.

5-(and-6)-Chloromethyl-2',7'-dichlorodihydrofluorescein diacetate (CMH$_2$DCFDA)(Molecular Probes). One vial of DCFda provides 10 tests and contains 50 µg. This is unstable and can't be stored. Therefore, each vial was opened and 43 µL of DMSO was added. Once this was mixed well, 4.0 µL of this was added to each well containing the cells to be tested. DCFDA was used at a final concentration of 46 ng for each test.

Dot plots as a function of live versus dead cells. The cells were cultured at a concentration of 0.5 to 1 million cells per ml. Cells were untreated or treated with or 2-deoxy-D-glucose and/or etomoxir and/or antibodies to UCP2 and used at dilutions or concentrations as indicated on the figure. The cells were cultured in the presence or absence of etomoxir at 100 micrograms/ml for 24 hours followed by treatment with antibody as indicated for an additional 24 or 48 hours (i.e. totals of 48 hours or 72 hours respectively). Cells were harvested and analyzed by flow cytometry. Each dot on the dot plot represents one cell. Five thousand cells were assessed for forward scatter (FS), as a function of cell size, versus side scatter (SS), as a function of cellular granularity. The upper elipse represents live cells by these criterion and the lower elipse in each dot plot represents the dead cells.

Statistical Analysis, Percents, and Geometric Mean Values Percents. Gating is a tool provided by CELLQUEST™ software and allows for the analysis of a certain population of cells. Gating around both the live and dead cell populations gave a percent of the cell numbers that was in each population. After the gates were drawn, a percent value of dead cells was calculated by taking the number of dead cells divided by the number of total cells and multiplying by one hundred.

Standard Error. When experiments were done in triplicate, a standard error of the mean value was determined using the Excel program (MICROSOFT®). This identified the value given for the error bars seen on some figures.

Geometric Mean Fluorescence. When analyzing data on CELLQUEST™ software, a geometric mean value will be given for each histogram plotted. Once the stained sample was plotted against the control (isotype or unstained), geometric mean fluorescence values were obtained for both histogram peaks. The stained control sample value was subtracted from sample to identify the actual fluorescence of the stained sample over that of the control.

Tumor implantation. Mice were purchased from the Animal Production Program of National Cancer Institute, Frederick, Md. The animals used were Athymic Ncr-nu/nu (strain code 01B74). HL60 MDR cells were harvested and reconstituted at 1 million cells per 100 microliters of phosphate buffered saline. One million tumor cells per injection site were implanted subcutaneously on two sites of the animal's back. Treatments began at exactly seven days post tumor implantation. Tumor size/volume was monitored twice weekly using measurement calipers, with the formula Tumor Volume=π× (short diameter)$^2$×(long diameter)/6.

Mice experiments with fatty acid metabolism and glucose metabolism inhibitors. Fatty acid metabolism inhibitors were exemplified by etomoxir at 200 micrograms/day. Glucose metabolism inhibitors were exemplified by 2-deoxy-D-glucose at 2.5 mM in 100 microliters daily. The combination was administered daily, etomoxir at 200 micrograms and 2-deoxy-D-glucose at 2.5 mM in 100 microliters. All drugs were administered intra-peritoneally. Fluorouracil, at 20 mg per kilogram mouse, was injected intra-peritoneally once a week

Example 1

This example illustrates an embodiment of the invention, where multi-drug resistant cancer cells were exposed to compositions of the invention. Analysis of the cells was performed using flow cytometry. The flow cytometry experiments were performed as follows. The cells were harvested, counted, and resuspended as described above. For DNA staining, the cells were washed and resuspended in ice-cold PBS and fixed by the dropwise addition of 95% ethanol. The cells were then incubated for 30 minutes on ice, washed, and resuspended in PBS containing 1% formaldehyde and 0.01% Tween. The cells were incubated with 50 units of DNAse and washed with PBS containing 5% DNAse. The cells were then incubated with anti DNA Fab (166, kind gift of Dr. Susan Wallace, University of Vermont), then washed and stained with a fluorescein conjugated second step anti-mouse immunoglobulin. The cells were then washed and resuspended in PBS/3% BSA/1% formaldehyde. The cells were stained for intracellular H202 using 6-carboxy- 2',7'-dichlorodihydrofluorescein diacetate (DCF-DA, Molecular Probes, Eugene, Oreg.). The cells were incubated with 1 mM DCF-DA for 20 minutes, washed twice in PBS containing 5% fetal calf serum and analyzed using flow cytometry. The mitochondrial membrane potential was assessed using MITOTRACKER® Red (CM-H$_2$XROS, Molecular Probes, Eugene, Oreg.). The cells were resuspended in warm (37° C.) PBS containing a final concentration of 0.5 micromolar of dye. The cells were then incubated for 30 minutes, pelleted, and resuspended in pre-warmed medium for analysis. The data was acquired on a COULTER EPICS ELITE™ or Excel flow cytometer (Coulter, Hialeah, Fla.) and analyzed with CELLQUEST™ software, (Becton Dickinson, San Jose, Calif.). The COULTER EPICS ELITE™ flow cytometer used in this example had a single excitation wavelength (488 nm) and band filters for PE (575 nm), FITC (525 nm) and Red 613 (613 nm) that was used to analyze the stained cells. Each sample population was classified for cell size (forward scatter) and complexity (side scatter), gated on a population of interest and evaluated using 40,000 cells. Each figure describing flow cytometric data represents one of at least four replicate experiments.

All cell lines in this example were cultured in RPMI 1640 culture medium. The medium was supplemented with 5% fetal bovine serum ("FBS"), 2 mM L-Glutamine, 500 units/mL pennicillin/500 micrograms/mL of streptomycin, 10 mM HEPES Buffer, 10$^{-5}$ M 2-mercaptoethanol ("2-ME"), 1 mM MEM Sodium Pyruvate, and 0.04 micrograms/mL of Gentamicin (All reagents from Gibco BRL). The cells were maintained at 37° C. in a humidified atmosphere under 5% CO$_2$ in air using standard cell culture techniques known to those of ordinary skill in the art.

The cells were counted, prepared for staining, and the cell surfaces were stained, as described above. Techniques used to prepare the cells for intracellular staining are as follows. The cells were prepared as described above with respect to cell surface staining. The cell membranes of the cells then was permeabilized using a Cytofix/Cytoperm kit (Pharmagin). 100 microliters of Cytofix solution was added to all the cell suspensions and mixed. The solutions were then placed on ice for an incubation time of 30 minutes in darkness. The cells were then washed twice with 100 microliters of 1× Perm Wash buffer, then resuspended into 100 microliters of 1× Perm Wash buffer for staining. The cells will be stained according to the cell surface staining protocol, described above. After staining and washing, the cells were then transferred into flow cytometric tubes containing 500 microliters of PBS/2% FBS for further analysis.

A metabolic activity assay was conducted and MITOTRACKER® Red and 5-(and-6)-Chloromethyl-2',7'-dichlorodihydrofluorescein diacetate molecular probes were prepared, as described above. LYSOSENSOR™ Green DND-189 molecular probes were provided by the manufacturer at a concentration of 1 mM in 50 microliters of DMSO. The LYSOSENSOR™ Solution was thawed to room temperature immediately before use and 0.5 microliters was added to each well containing the cells to be tested. The LYSONSENSOR™ Solution was used at a final concentration of 5 nM for each test.

For all death assays between 0.5×10$^6$ and 1.0×10$^6$ cells were used. Cells were harvested and placed into a 48-well plate in 1 mL of RPMI medium. To a first well, no treatment was added. To a second well 20 microliters of 37% hydrochloric acid was added. To a third well 1 microliter of purified mouse IgG1 kappa isotype control NA/LE was added (to a final concentration of 1 microgram/mL). To a fourth well, 1 microliter of purified anti-human CD95 (Fas) antibody NA/LE was added (to a final concentration of 1 microgram/mL). These treatment groups were incubated at 37° C. for 24 hours. After the incubation, the cells were examined for viability using flow cytometry.

For all death assays between 0.5×10$^6$ and 1.0×10$^6$ cells were used. Cells were harvested and placed into a 48-well plate in 1 mL of RPMI medium. The plate was prepared for this assay by adding 10 micrograms/mL of purified mouse IgG1 kappa isotype control NA/LE to a control well and 10 micrograms/mL of purified CD95 (Fas) antibody NA/LE to an experimental well. This antibody dilution solution was plated in the control and experimental wells and incubated for 1 hour at 37° C. The wells were then washed twice with 1 mL of PBS/2% FBS. The cell suspension was then added to the treated wells in complete RPMI medium and placed into the 37° C. incubator for a 24-hour period. After the incubation, the cells were examined for viability using flow cytometry.

The flow cytometry experiments were performed as follows. Once the samples were prepared and transferred into flow cytometric tubes, the samples were analyzed on a Becton/Dickinson Flow Cytometer. For antibodies that were PE conjugated and for the MITOTRACKER® Red experiments, a program for red-colored fluorochromes was utilized. For antibodies that were FITC-conjugated and for the DCFDA, LYSOSENSOR™, and LYSOTRACKER™ experiments, a program for green-colored fluorochromes was used. Statistical analysis, percents, and geometric mean values percents were calculated as described above.

As the experiments were performed in triplicate, a standard error of the mean value was determined using the Excel program (MICROSOFT®). This is shown as error bars in some of the figures.

The geometric mean fluorescence was determined as follows. When analyzing data on CELLQUEST™ software, a geometric mean value was calculated for each histogram plotted. The stained sample was plotted against the control (isotype or unstained), and the geometric mean fluorescence values was obtained for both histogram peaks. The stained sample value was divided by the control sample to identify the actual fluorescence of the stained sample over that of the control.

Flow cytometry profiles from these experiments are shown in FIGS. 2A-2D and 3A-3D. The experimental protocols and the % of cell death for these experiments are shown in Tables 1 and 2. In these experiments, multidrug resistant cancer cells (HL60 MDR and L1210 DDP) showed greater amounts of cell death after treatment with cerulenin, compared to control and non-multidrug resistant cancer cells.

TABLE 1

| Time Frame | No Treatment | Treated |
| --- | --- | --- |
| B16F1 % Death Data Treated or Not with 25 ug/mL Cerulenin | | |
| 5.0 Hours | 44 | 61 |
| 24 Hours | 50 | 90 |
| HL60 % Death Data Treated or Not with 25 ug/mL Cerulenin | | |
| 2.0 Hours | 10 | 11 |
| 24 Hours | 7 | 44 |
| HL60 MDR % Death Data Treated or Not with 25 ug/mL Cerulenin | | |
| 2.0 Hours | 6.3 | 13 |
| 24 Hours | 6.1 | 99.6 |

TABLE 2

| Time Frame | No Treatment | Treated |
| --- | --- | --- |
| B16F1 % Death Data Treated or Not with 25 ug/mL Cerulenin | | |
| 5.0 Hours | 43 | 67 |
| 24 Hours | 39 | 72 |
| L1210 % Death Data Treated or Not with 25 ug/mL Cerulenin | | |
| 7.0 Hours | 1.7 | 27 |
| 24 Hours | 2.3 | 89 |
| L1210 DDP % Death Data Treated or Not with 25 ug/mL Cerulenin | | |
| 7.0 Hours | 1.4 | 14 |
| 24 Hours | 2 | 92 |

In FIG. 4, microscopy images of HL60 and HL60 MDR ("multi-drug resistant") cells treated with cerulenin ("Treated") and not treated with cerulenin ("No Stn") are shown. FIG. 4A-4B show non-treated HL60 cells, while FIG. 4C shows HL60 cells treated with cerulenin. For the HL60 cells, large numbers of the cells survived treatment with cerulenin. In contrast, FIG. 4D shows non-treated HL60 MDR, and FIGS. 4E and 4F show HL60 MDR cells treated with cerulenin. In these figures, exposure of drug-resistant HL60 MDR cells to cerulenin resulted in large numbers of cell death.

Example 2

In this example, in vivo experiments were performed on mice in accordance with one embodiment of the invention.

Highly carcinogenic B16F1 melanoma cells were either exposed ("treated") or not exposed to cerulenin, then injected into male mice. Experimental protocols, data, and observations from these experiments are shown in Table 3. It was found that mice exposed to untreated melanoma cells developed lethal cancers within a few days. In contrast, mice exposed to melanoma cells treated with cerulenin did not develop lethal cancers during the experiment.

TABLE 3

Control Group

Mouse #1

Figure 5A:
FIGS. 5A-5D illustrates, in vivo, the treatment of mice injected with highly carcinogenic B16F1 melanoma cells, exposed or not to cerulenin.

Day 0 @ 2:45 pm injected with PBS only
Day 9 No apparent tumors active
Day 12 Picture - see FIG. 5A
Day 13 Still no apparent tumors still active
Day 14 Still no apparent tumors still active
Mouse #2

Day 0 @ 2:45 pm injected with PBS only
Day 9 No apparent tumors - active
Day 13 Still no apparent tumors-active
Day 14 Still no apparent tumors still active
Mouse #3

Figure 5B:

Day 0 @ 2:45 pm injected with PBS only
Day 9 no apparent tumors - active
Day 13 still no apparent tumors-active (FIG. 5B)
Day 14 Still no apparent tumors still active No treatment group Mouse #4

Day 0 @ 2:45 pm injected with B16F1 $10^6$ cells in PBS, No Treatment
Day 9 possible start of tumor behind R shoulder and upper R leg - relatively active
Day 10 tumor development lower belly near left leg - still active
Day 12 tumor progressing inactive possibly in process of dying
Day 13Very inactive, labored breathing, close to death
Mouse #5

Day 0 @ 2:45 pm injected with B16F1 $10^6$ cells with PBS, No Treatment
Day 9 no apparent tumors - active
Day 10 Tumor developing
Day 12 tumor still progressing still active
Day 13 tumor same, still active
Mouse #6

Figure 5C:

Day 0 @ 2:45 pm injected B16F1 $10^6$ cells with PBS, No Treatment
Day 9 tumor developing lower belly, near genitals left side - active
Day 12 tumor still progressing also second tumor appeared on right side-still active (FIG. 5C)
Day 13 Tumors larger, beginning to be inactive Treatment group Mouse #7

Day 0 @2:45 pm injected with B16F1 $10^6$ cells in PBS, Treatment w/ 25 ug/ml cerulenin 5.0 hrs
Day 9 no visible tumors - very active
Day 12 no visible tumors - very active
Day 13 no visible tumors - very active
Mouse #8

Figure 5D:
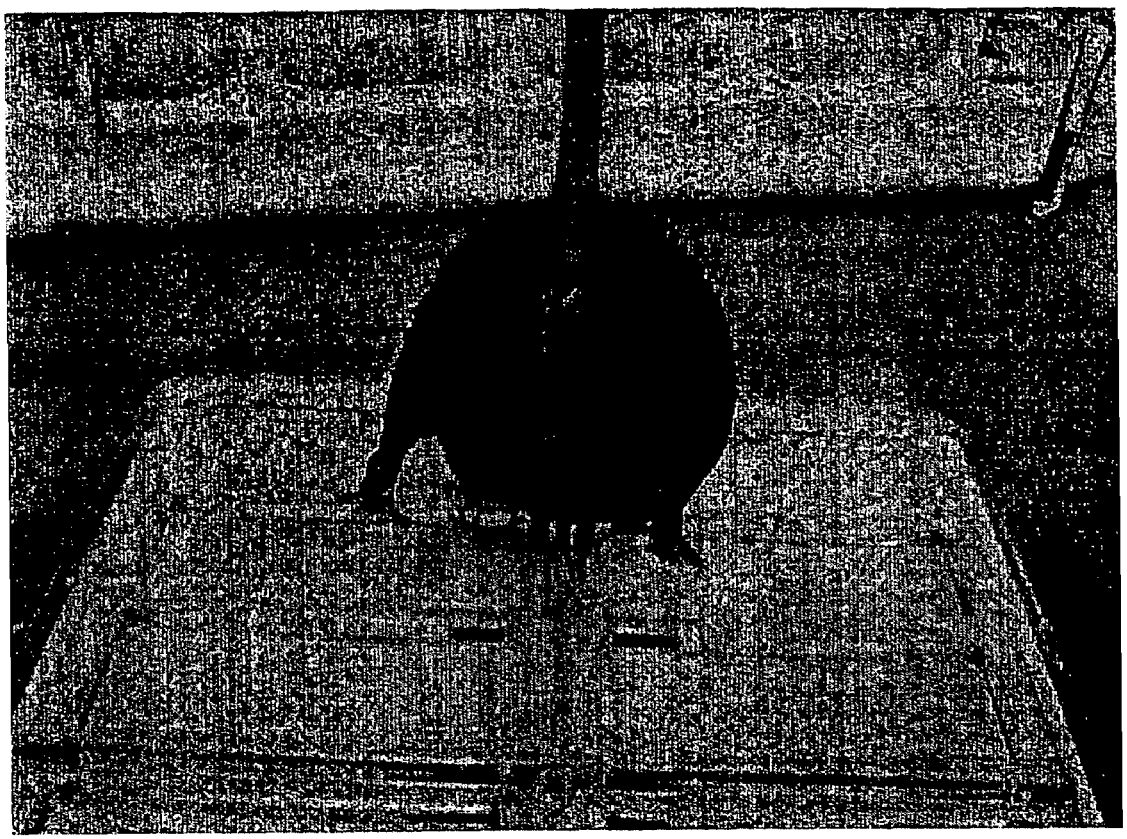

Day 0 injected w/ B16F1 $10^6$ cells in PBS, Treatment w/ 25 ug/ml cerulenin 5.0 h
Day 9 no visible tumors - very active
Day 12 no visible tumors - very active (FIG. 5D)
Day 13 no visible tumors - very active TABLE 3-continued Mouse #9

Day 0 @ 2:45 pm injected w/ B16F1 ($10^6$ cells in PBS) Treatment w/ 25 ug/ml cerulenin 5 h
Day 9 no visible sign of tumors - very active
Day 12 no visible tumors - very active
Day 13 no visible tumors - very active It was found that mice exposed to untreated melanoma cells developed lethal cancers within a few days. In contrast, mice exposed to melanoma cells treated with cerulenin did not develop lethal cancers during the experiment.

Example 3

Figure 6A:
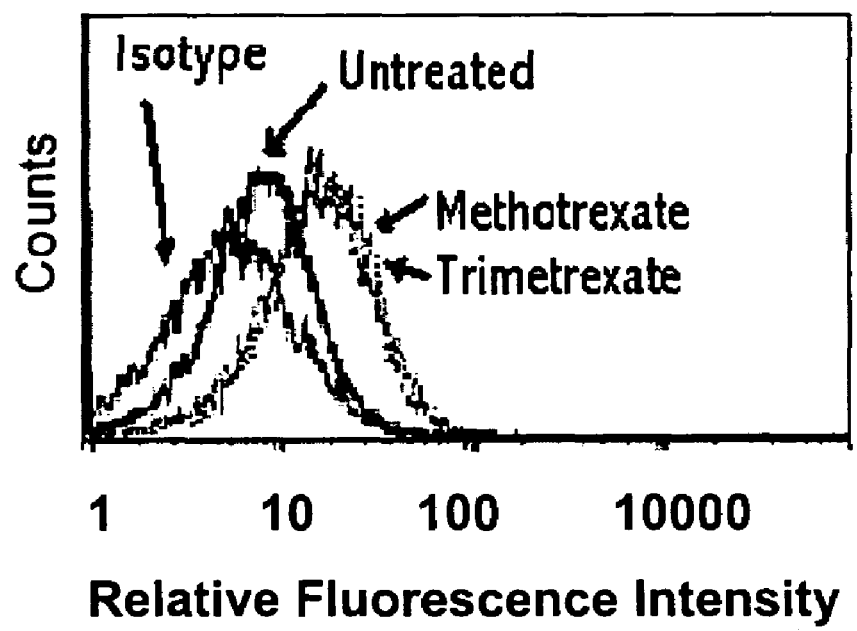
FIG. 6A is a plot showing levels of cell-surface Fas expression on drug sensitive L1210 cells as measured by flow cytometry.
Figure 6B:
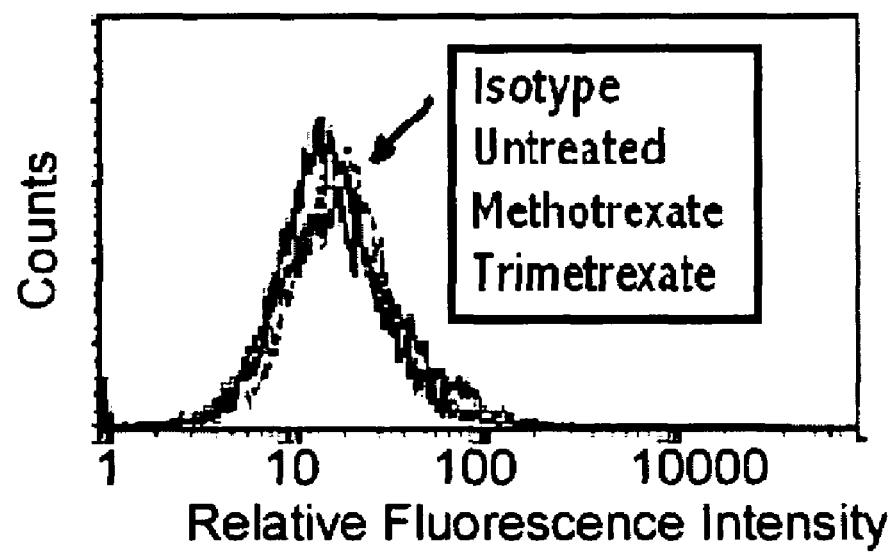
FIG. 6B is a plot showing levels of cell-surface Fas expression on drug resistant L12100/DDP cells as measured by flow cytometry.

Drug sensitive L1210 cells and drug resistant L12100/DDP cells were cultured in the presence of chemotherapeutic agents overnight. FIGS. 6A and 6B show the levels of cell-surface Fas expression on the drug sensitive L1210 cells (FIG. 6A) and on the drug resistant L12100/DDP cells (FIG. 6B), as measured by flow cytometry. The drug sensitive cells show increases in Fas as a result of the drug. In contrast, the drug resistant cells are unchanged with treatment. The horizontal axis in each panel shows intensity of the fluorescence and the vertical axis shows the number of cells at each intensity. Peaks which appear farther to the right have higher levels of Fas per cell. Note that the drug sensitive cells have significantly higher levels of cell surface Fas.

Example 4

Figure 7:
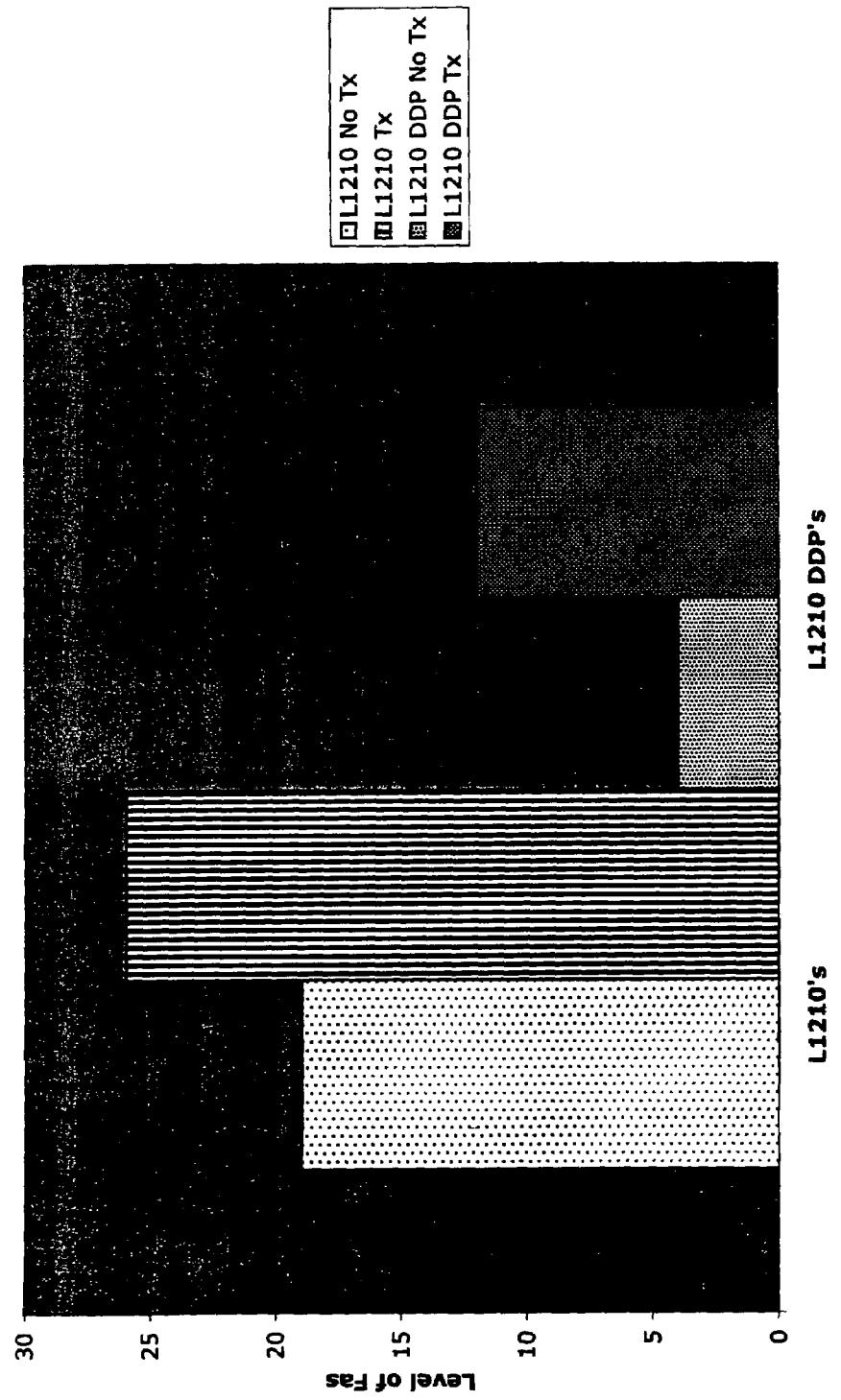
FIG. 7 is a chart showing the levels of cell surface Fas expression on L1210 and L1210DDP cells after 23 hours of incubation with etomoxir.

Drug sensitive L1210 cells and drug resistant L1210/DDP cells were cultured with etomoxir for 24 hours (Tx indicates treatment with etomoxir). The level of cell-surface Fas was determined using fluorochrome conjugated anti-Fas antibodies and flow cytometry. The Fas levels are measured relative to a control for staining artifacts. Percent values indicate % per cent dead cells. FIG. 7 shows the expression of cell-surface Fas as a function of treatment with etomoxir. The etomoxir induced significant increases in cell surface Fas in both cell lines.

Example 5

Figure 8:
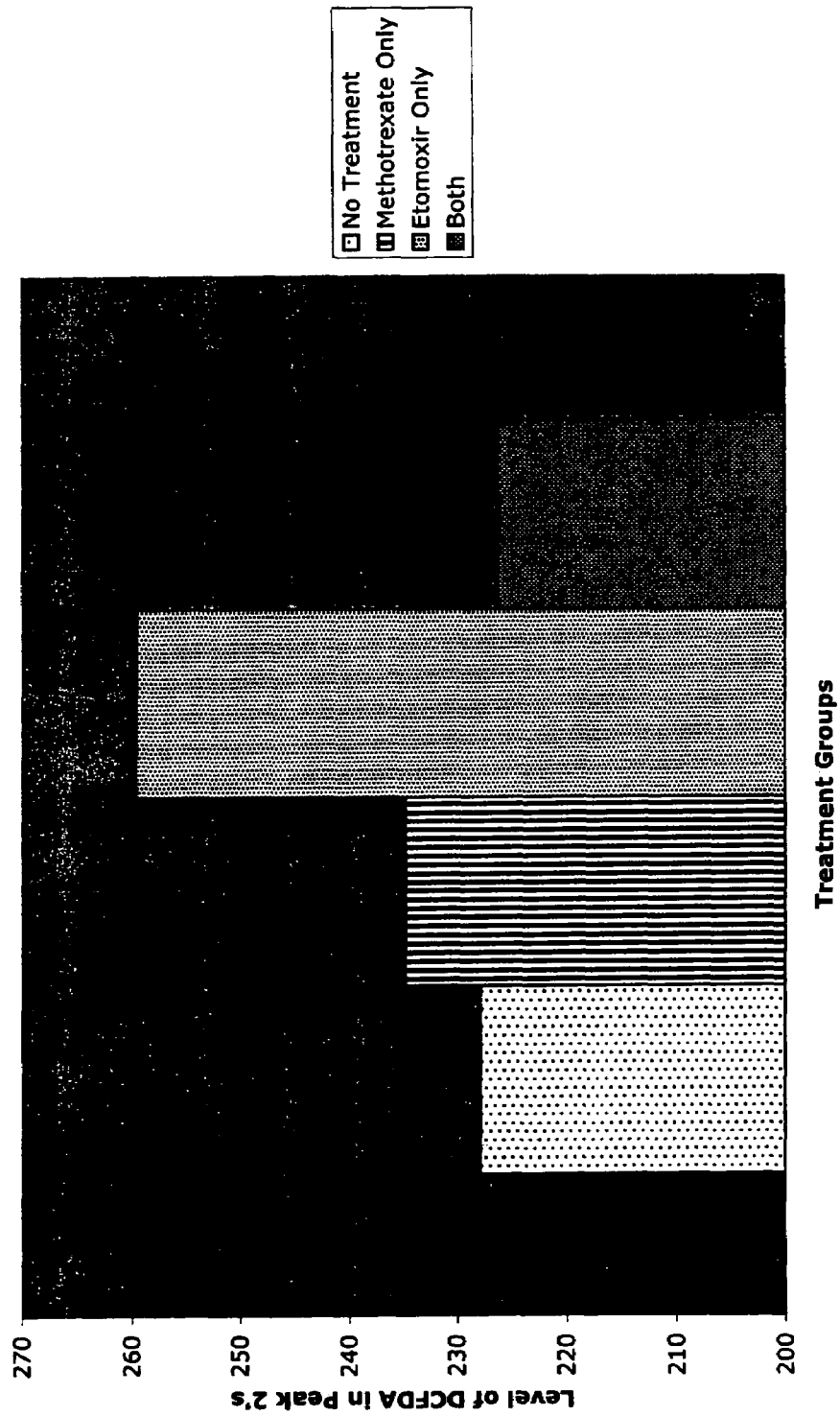
FIG. 8 is a chart showing the levels of DCFDA staining on L1210 DDP cells treated (or not) with methotrexate, etomoxir, or both, after 24 hours of incubation.

In a third series of experiments, we used etomoxir with and without methotrexates to determine the effects of combination therapy on Fas expression, FIG. 8.

In FIG. 8, we see that etomoxir increases the methotrexate-induced increases in Fas on L1210 and promotes increases in cell surface Fas on methotrexate-treated L1210 DDP, drug resistant, tumor cells.

Example 6

Figure 9:
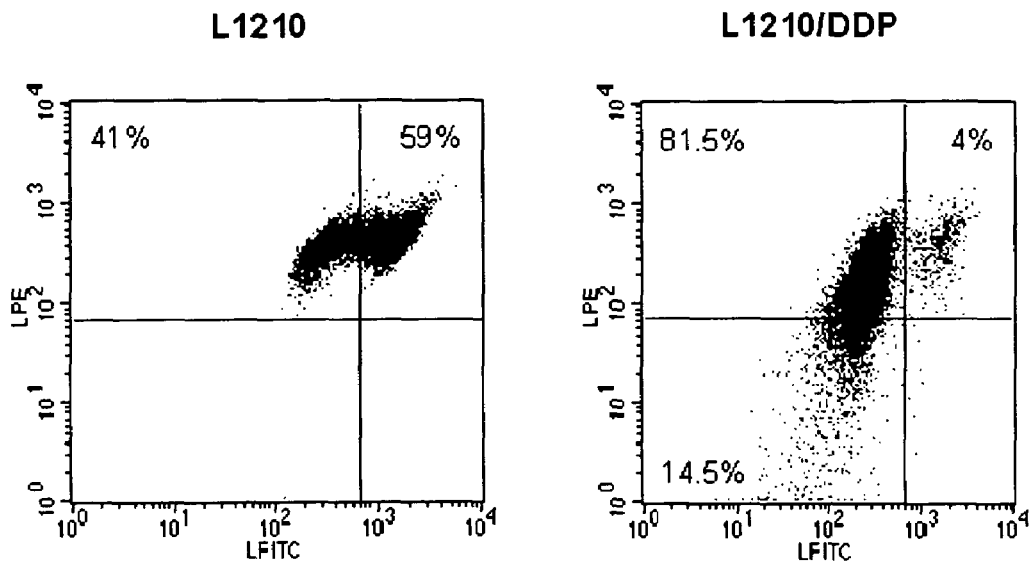
FIG. 9 shows scatter diagrams for drug sensitive and drug resistant tumor cells in which change in pH across the inner mitochondrial membrane is plotted against mitochondrial membrane potential.

The foregoing examples demonstrate that treatment of some cancer cells by etomoxir and chemotherapeutics produces substantially enhanced co-stimulatory signals, and that the treatment of cancer cells by chemotherapeutics and immune system involvement results in substantially higher membrane potential and levels of intracellular reactive intermediates—thereby resulting in tumor cell death. Thus, drug sensitive cancer cells and drug resistant tumor cells have been shown to have very different metabolic properties. As is well known, cell metabolism is largely governed by the action of the mitochondria. This, in turn, depends on some key parameters including the potential difference across the inner mitochondrial membrane and the change in acidity across the same membrane. FIG. 9 shows scatter diagrams for drug sensitive and drug resistant tumor cells in which the horizontal axis is a measure of the change in pH across the inner mitochondrial membrane and the vertical axis measures mitochondrial membrane potential, and indicates the range of both of these parameters. FIG. 9 shows that the drug resistant cells, in general, have a lower membrane potential and the pH gradient is also significantly reduced for these cells. These data have been substantiated and extended to other cell lines (including HL60 and HL60/MDR) by other measurements, providing strong evidence that drug resistance is correlated with altered metabolic behavior.

Example 7

Figure 10:
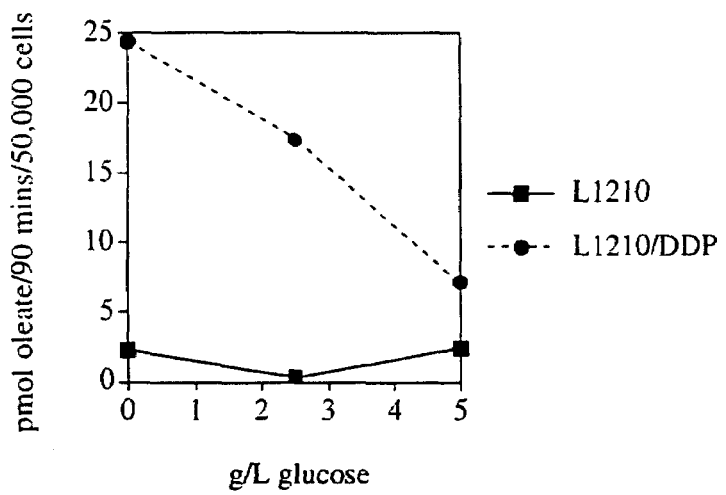
FIG. 10 is a plot showing the rates of oleate oxidation with glucose competition.

A second example of how drug resistant cells exhibit a different metabolic behavior compared to drug sensitive cells is provided by the rate of mitochondrial oleate consumption in the two different types of cells, L1210 and L1210 DDP. FIG. 10 is a plot showing the rates of oleate oxidation with glucose competition and shows that the oxidation rates for drug resistant cells are generally higher than those for drug sensitive cells and this becomes more pronounced at low glucose levels. The drug resistant cells typically have higher levels of oleate consumption, and as glucose becomes limited, the rate of consumption increases dramatically in the drug resistant cells only. This demonstrates that the ability to "burn fat" is substantially different between the two types of cells. These data provided the rationale for the use of etomoxir as etomoxir has been reported to inhibit an enzyme, carnitine palmitoyl transferase (CPT) that is used when cells burn fat for fuel.

Example 8

Figure 11:
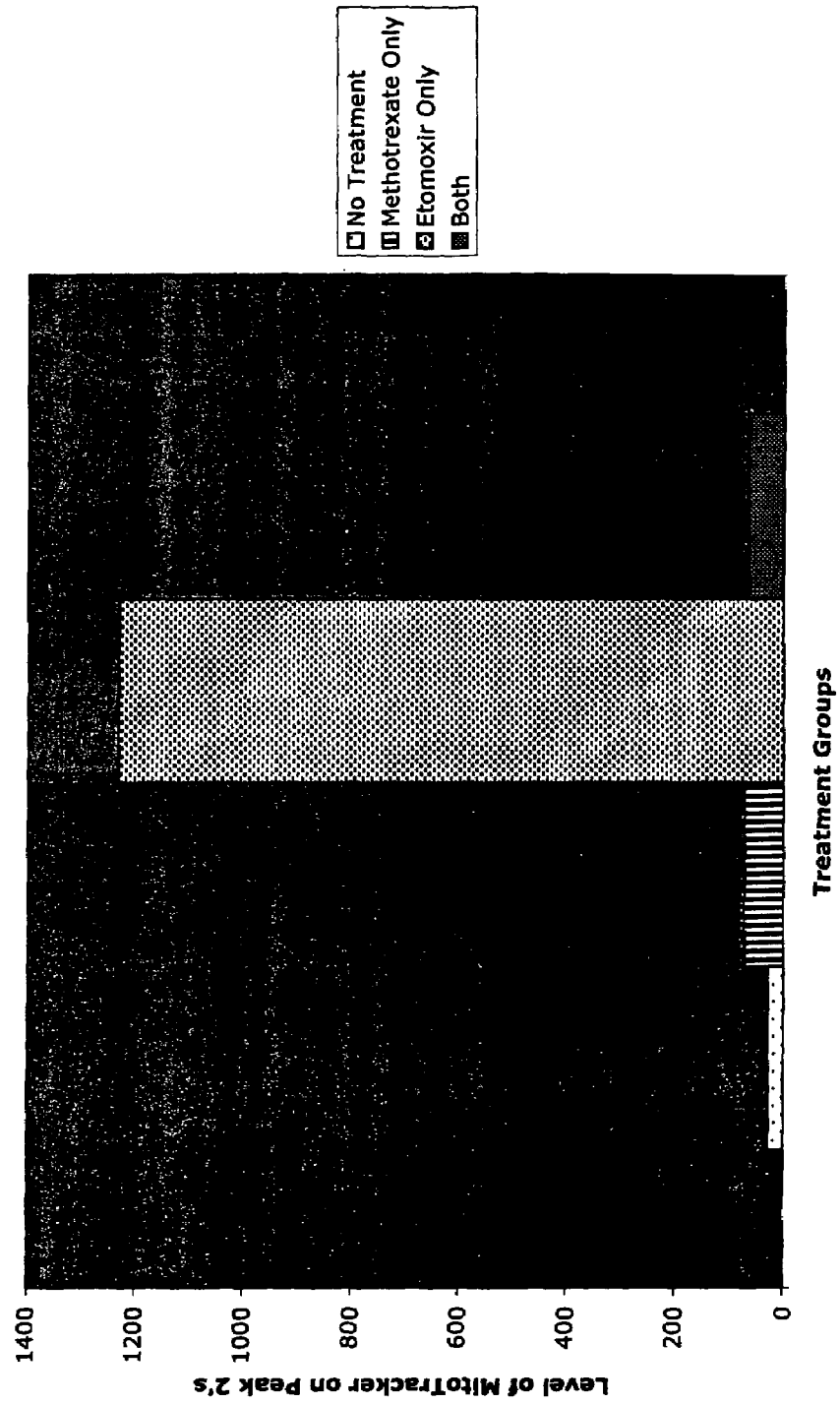
FIG. 11 is a chart showing the levels of mitochondrial membrane potenial (by MITOTRACKER®) of L1210 DDP cells treated (or not) with methotrexate, etomoxir, or both, after 24 hours of incubation.

We measured the effects of etomoxir on metabolism by measuring mitochondrial membrane potential with a fluorescent dye (MITOTRACKER® Red, Molecular Probes, Eugene, Oreg.) which fluoresces as a function of mitochondrial potential. We also measured levels of reactive intermediates using dichloro-difluoro-diacetate ester (DCF-da, Molecular Probes, Eugene, Oreg.) which fluoresces as a function of intracellular reactive intermediates. We expected and, referring to FIG. 11, found that etomoxir would increase the mitochondrial membrane potential of the drug resistant cells to a point that correlates with the potential of drug sensitive cells. FIG. 11 is a chart showing the levels of mitochondrial membrane potential (by MITOTRACKER®) of L1210 DDP cells treated (or not) with methotrexate, etomoxir, or both, after 24 hours of incubation.

Example 9

Figure 12A:
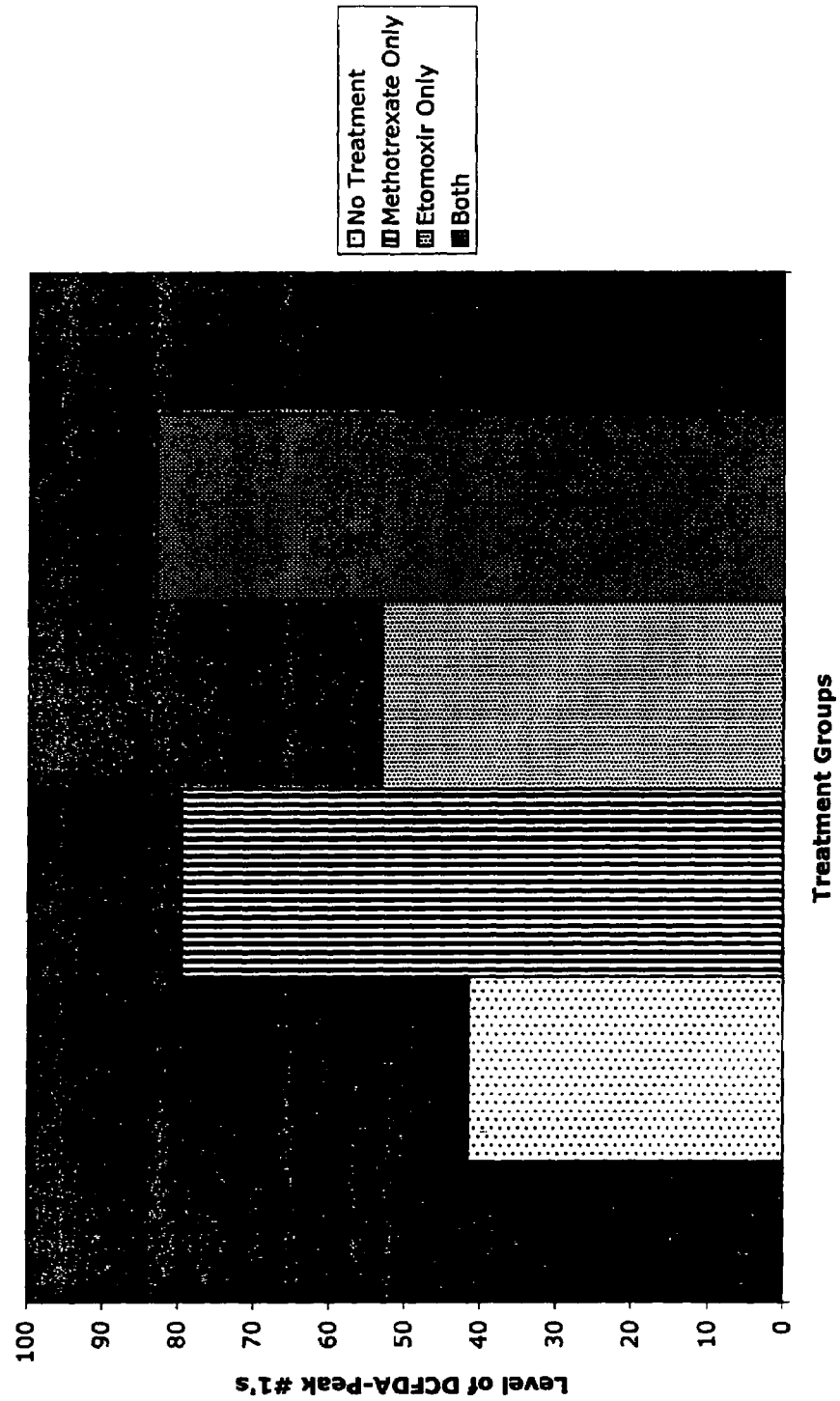
FIG. 12A is a chart showing the levels of DCFDA staining on L1210 cells treated (or not) with methotrexate, etomoxir, or both, after 24 hours of incubation.
Figure 12B:
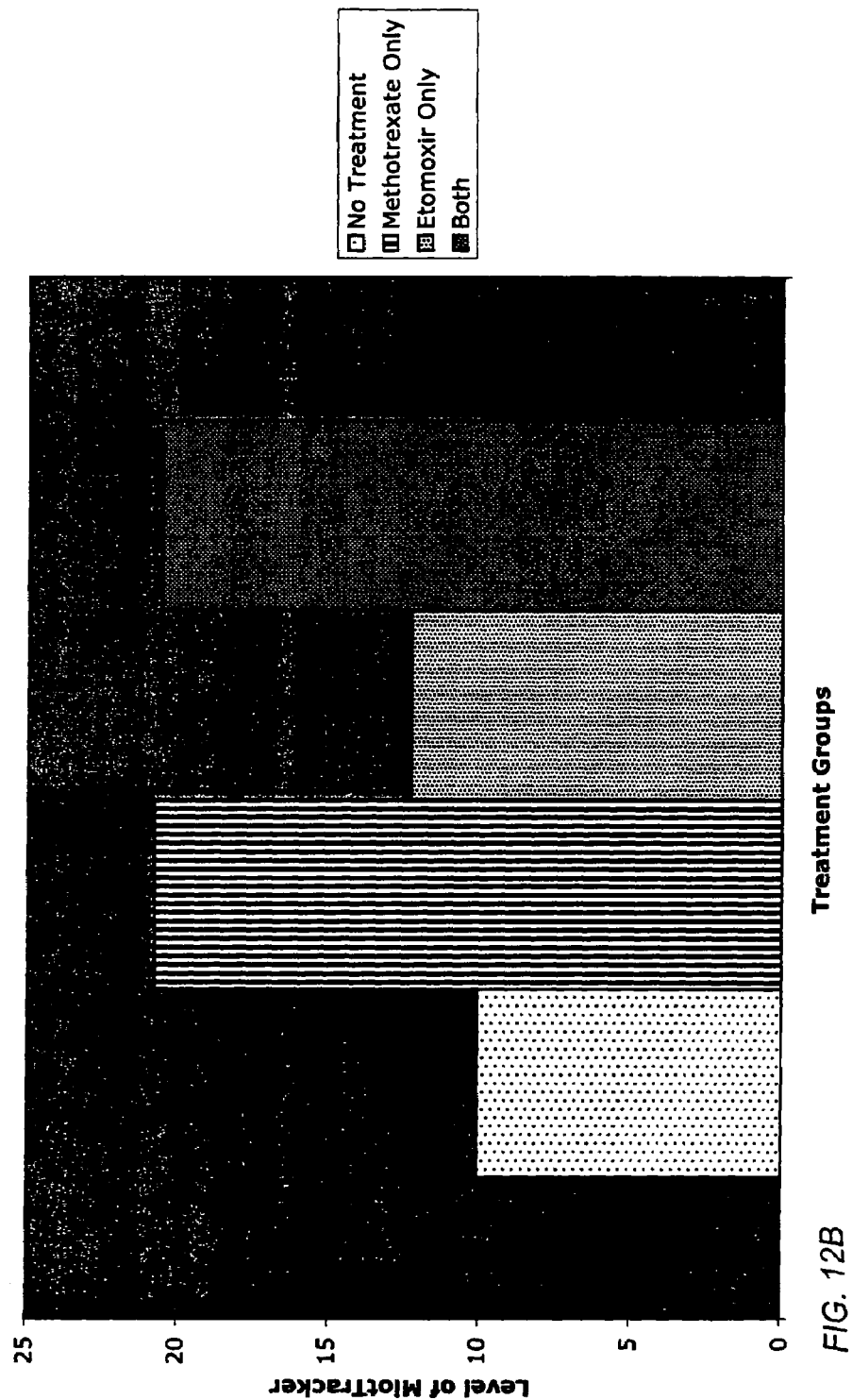
FIG. 12B is a chart showing the levels of mithochondrial membrane potenial (by MITOTRACKER®) of L1210 cells treated (or not) with methotrexate, etomoxir, or both, after 24 hours of incubation.

FIG. 12A is a chart showing the levels of DCFDA staining on L1210 cells and FIG. 12B is a chart showing the levels of mitochondrial membrane potential (by MITOTRACKER®) of L1210 cells, in each case treated (or not) with methotrexate, etomoxir, or both, after 24 hours of incubation. As expected etomoxir caused an increase in free radicals (reactive intermediates), an important aspect in susceptibility of the cells to immune mediated cell death.

Example 10

Figure 13:
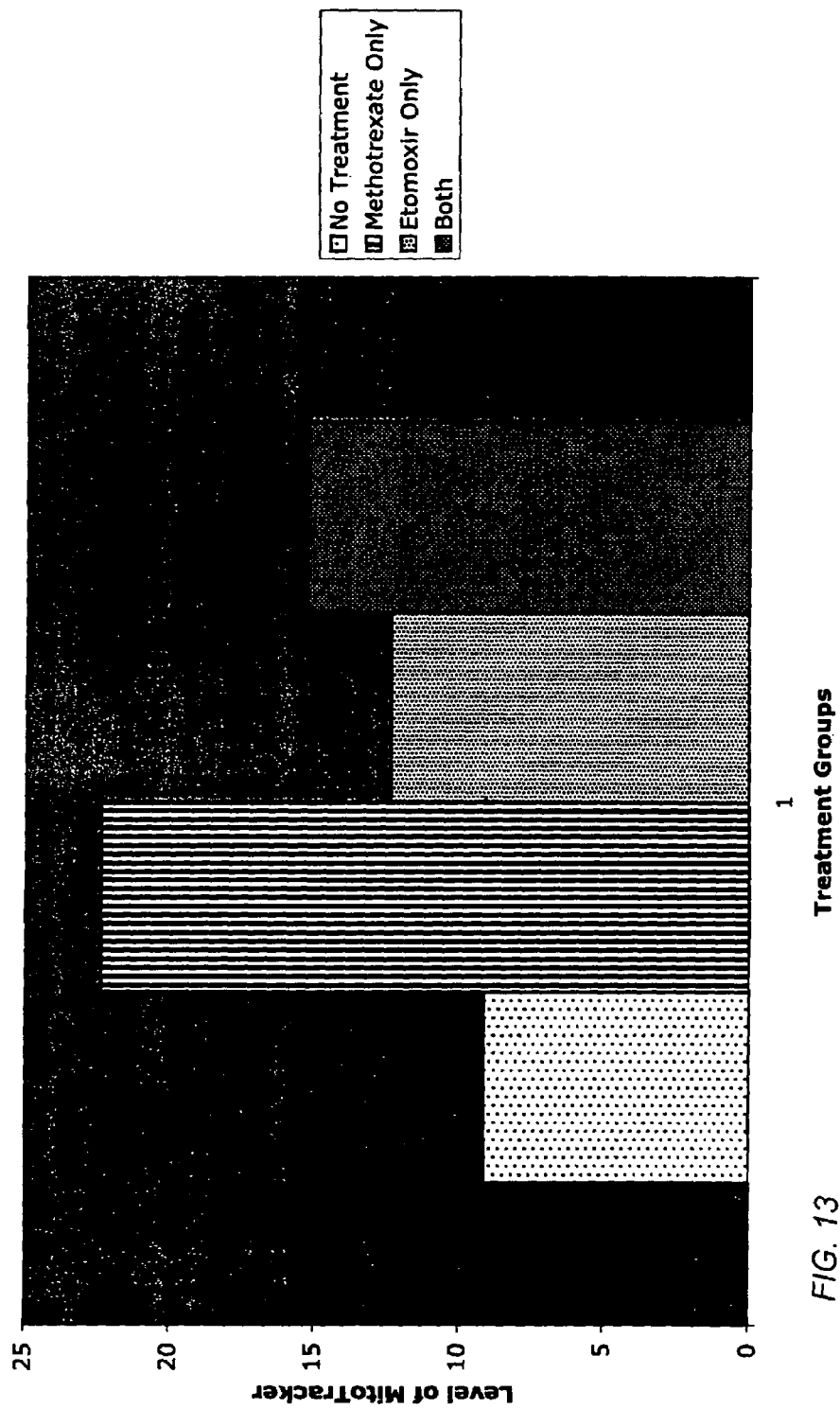
FIG. 13 is a chart showing the levels of mithochondrial membrane potenial (by MITOTRACKER®) of RU937 human leukemia cells treated (or not) with methotrexate, etomoxir, or both, after 24 hours of incubation.

The effects of etomoxir on human leukemia RU937 cells was determined. FIG. 13 is a chart showing the levels of mitochondrial membrane potential (by MITOTRACKER®) of RU937 cells treated (or not) with methotrexate, etomoxir, or both, after 24 hours of incubation. Etomoxir increased the levels of mitochondrial membrane potential in human leukemia RU937.

Example 11

Figure 14:
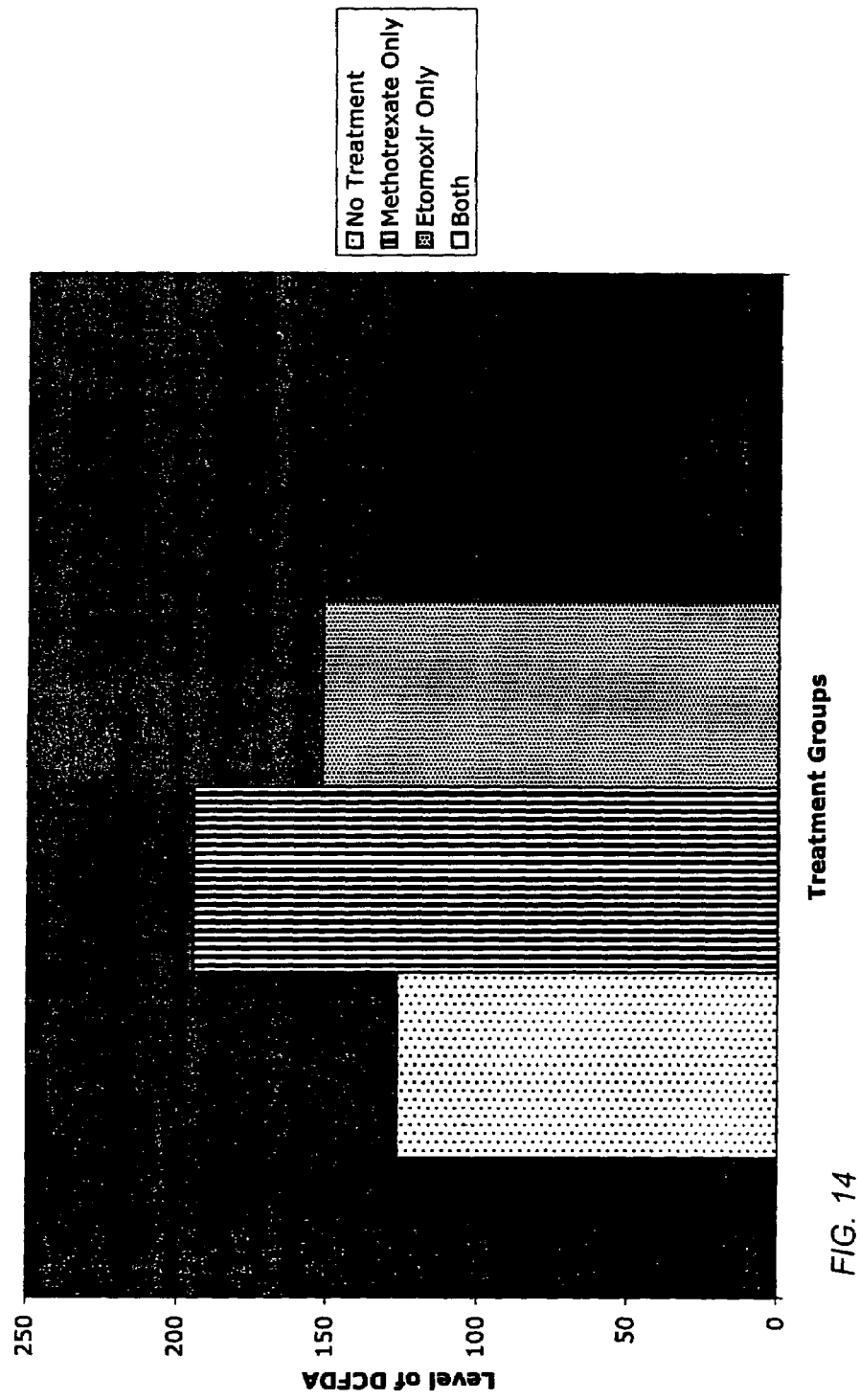
FIG. 14 is a chart showing the levels of DCFDA staining on HL60 human leukemia cells treated (or not) with methotrexate or etomoxir after 24 hours of incubation.

The effects of etomoxir on human leukemia HL60 cells was determined. FIG. 14 is a chart showing the levels of DCFDA staining on HL60 cells treated (or not) with methotrexate or etomoxir after 24 hours of incubation. Etomoxir induces increases in reactive oxygen intermediates in human leukemia HL60.

Example 12

Figure 16:
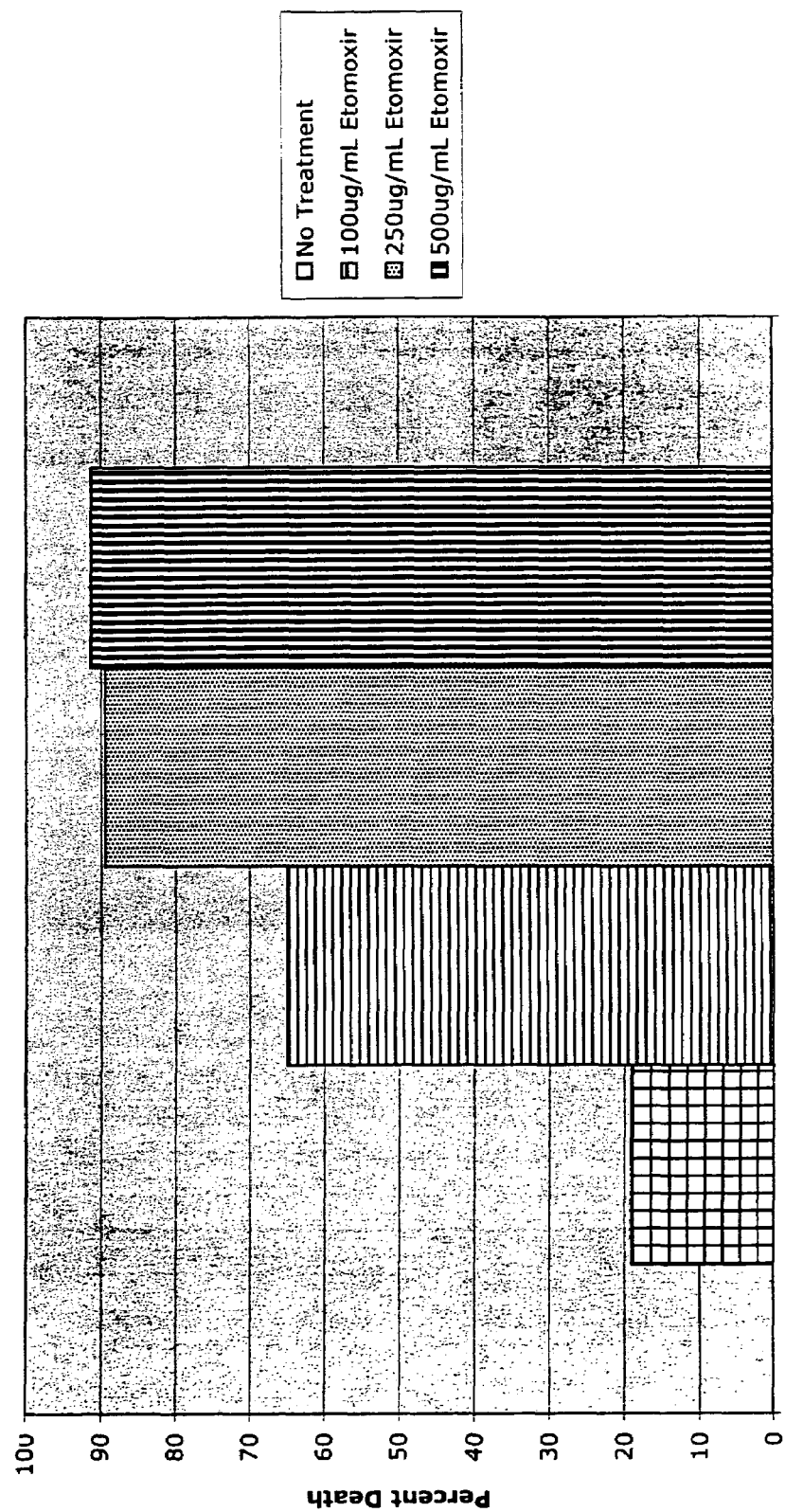
FIG. 16 shows the percent death of B16F1 melanoma cells after 48 hours of treatment with indicated concentrations of etomoxir.

B16F1 melanoma cells were cultured at a concentration of 0.5 to 1 million cells per ml. Cells were untreated or treated with etomoxir at concentrations indicated in FIG. 15 for 48 hours. Cells were harvested and analyzed by flow cytometry. Dot plots are shown in FIG. 15 as functions of live versus dead cells. Each dot on the dot plot represents one cell. Five thousand cells were assessed for forward scatter (FS), as a function of cell size, versus side scatter (SS), as a function of cellular granularity. The upper elipse represents live cells by these criterion and the lower elipse in each dot plot represents the dead cells. FIG. 16 shows the percent death of the B16F1 melanoma cells, calculated by taking the number of dead cells divided by the total number of cells and multiplying by 100.

Example 13

Figure 17:
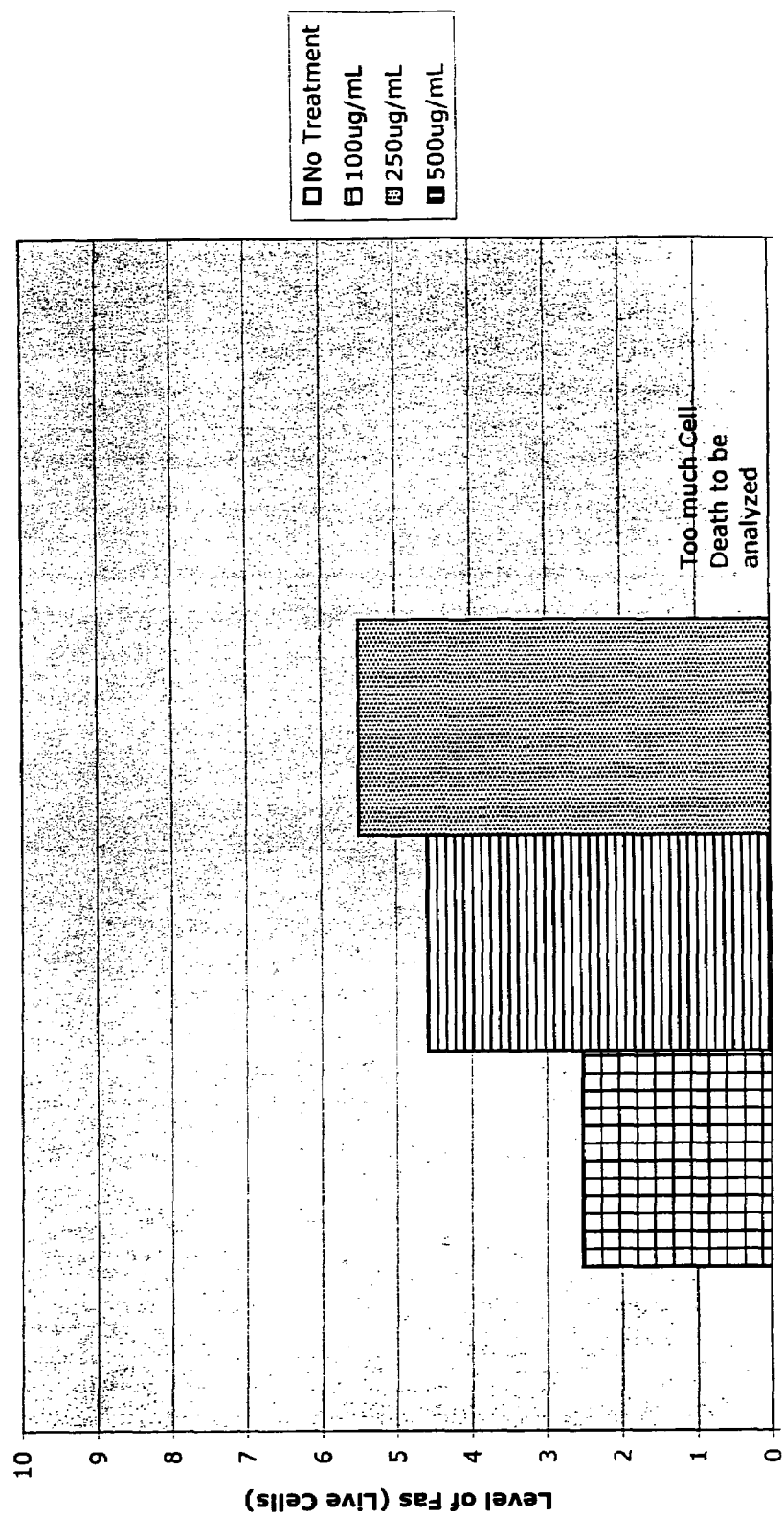
FIG. 17 shows cell surface Fas (CD95) expression on live B16F1 melanoma cells after 48 hours in etomoxir.
Figure 18:
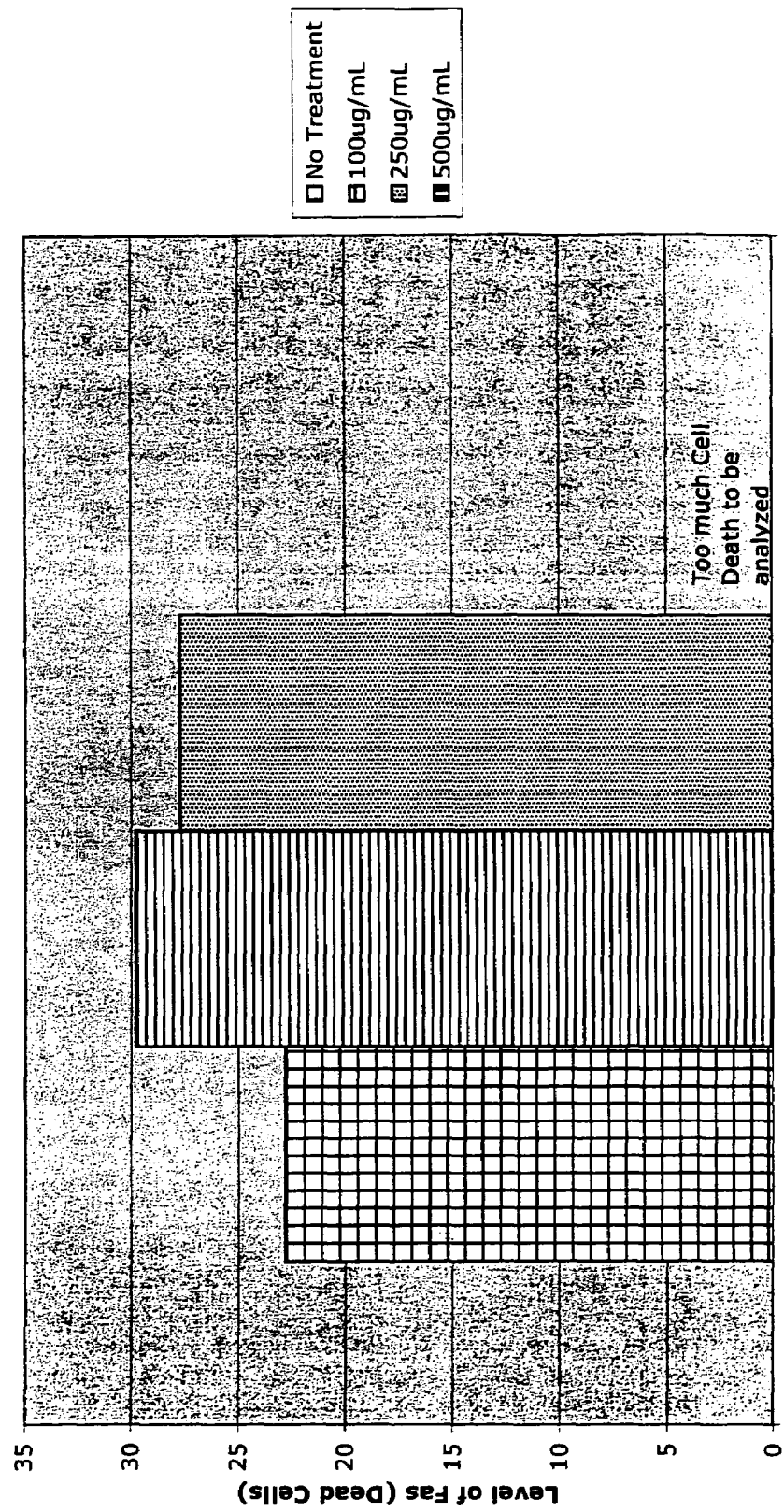
FIG. 18 shows cell surface Fas (CD95) expression on dead B16F1 melanoma cells after 48 hours in etomoxir.

Referring to FIGS. 17 and 18, B16F1 melanoma cells of Example 12 were untreated or treated with etomoxir at the indicated concentrations for 48 hours. Cells were harvested, stained with fluorochrome conjugated anti-Fas antibody (PHARMINGEN®,) and analyzed by flow cytometry. Results indicate etomoxir induced a dose dependent increase in cell surface Fas expression in the live cell (1b) or dead cell (1c) populations after 48 hours.

Example 14

Figure 19:
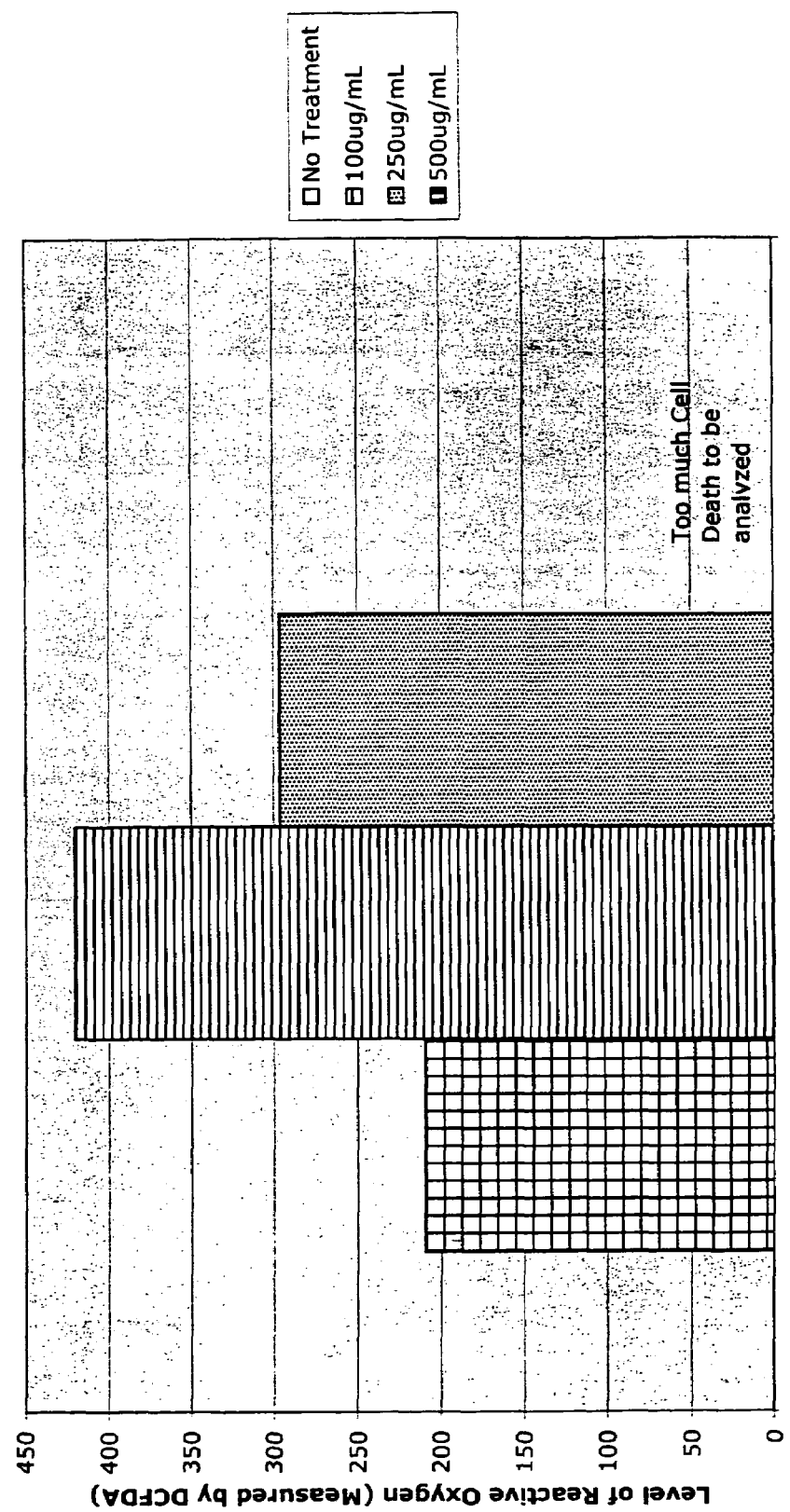
FIG. 19 shows intracellular reactive intermediates in B16F1 melanoma cells untreated or treated with etomoxir at the indicated concentrations for 24 hours.

B16F1 melanoma cells of Example 12 were untreated or treated with etomoxir at the indicated concentrations for 48 hours. Cells were harvested, stained with DCFDA as described in Materials and Methods, and analyzed by flow cytometry. The value of DCFDA was then calculated as described in Materials and Methods. Referring to FIG. 19, etomoxir induced a dose dependent increase the reactive oxygen species as measured by DCFDA.

Example 15

Figure 20:
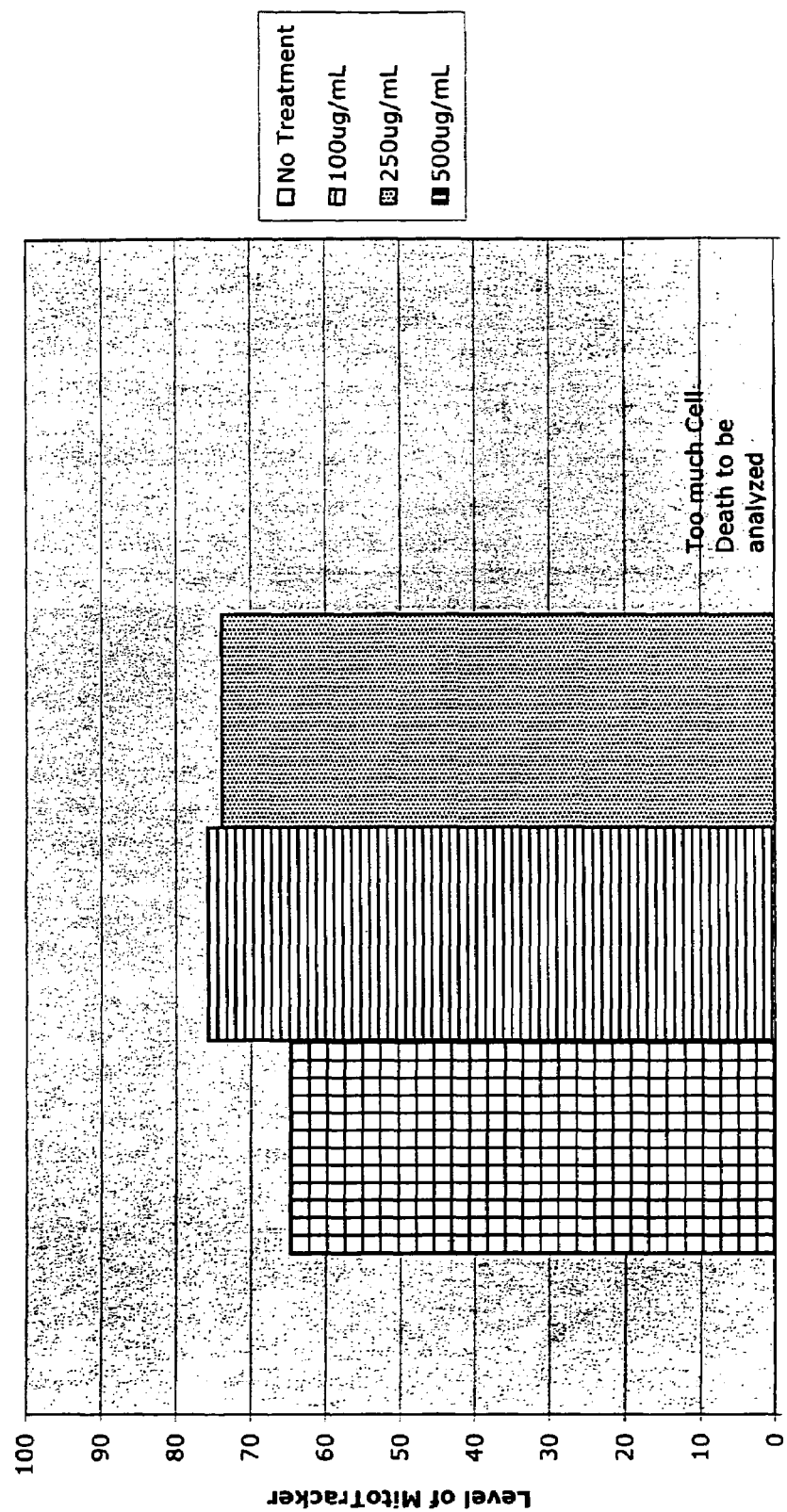
FIG. 20 shows mitochondrial membrane potential in B16F1 melanoma cells untreated or treated with etomoxir at the indicated concentrations for 24 hours.

B16F1 melanoma cells of Example 12 were untreated or treated with etomoxir at the indicated concentrations for 48 hours. Cells were harvested, stained with MITOTRACKER® Red (Molecular Probes) as described in Materials and Methods, and analyzed by flow cytometry. The value of MITOTRACKER® Red was then calculated as described in Materials and Methods. Referring to FIG. 20, etomoxir induced an increase in mitochondrial membrane potential as measured by MITOTRACKER® Red.

Example 16

Figure 21:
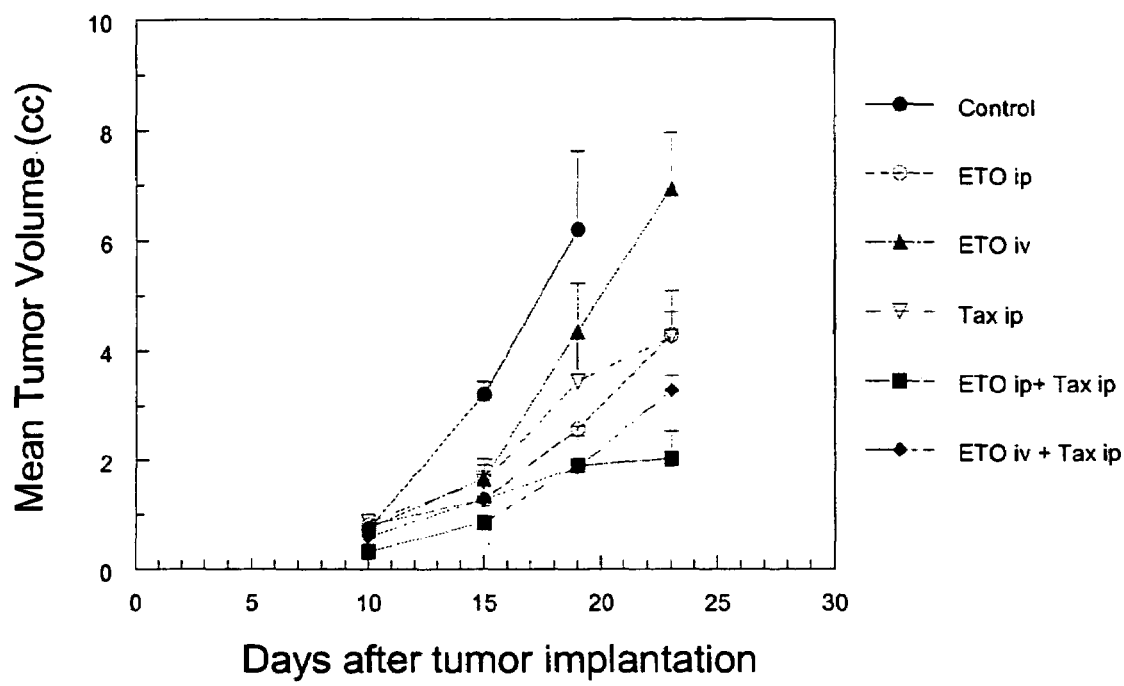
FIG. 21 shows the effects of etomoxir and/or taxol on tumor size in vivo tumor transplantation and treatment with etomoxir and taxol.

C57 black 6 mice were injected with 750,000 tumor cells intradermally in two locations on the back. One week later the animals were treated with etomoxir and taxol as indicated in FIG. 21 and tumor size was monitored for three to four weeks. The results, as shown in FIG. 21, indicate the effects of etomoxir at 50 µg/dose and/or taxol at 480 µg/dose on tumor size.

Example 17

Figure 22:
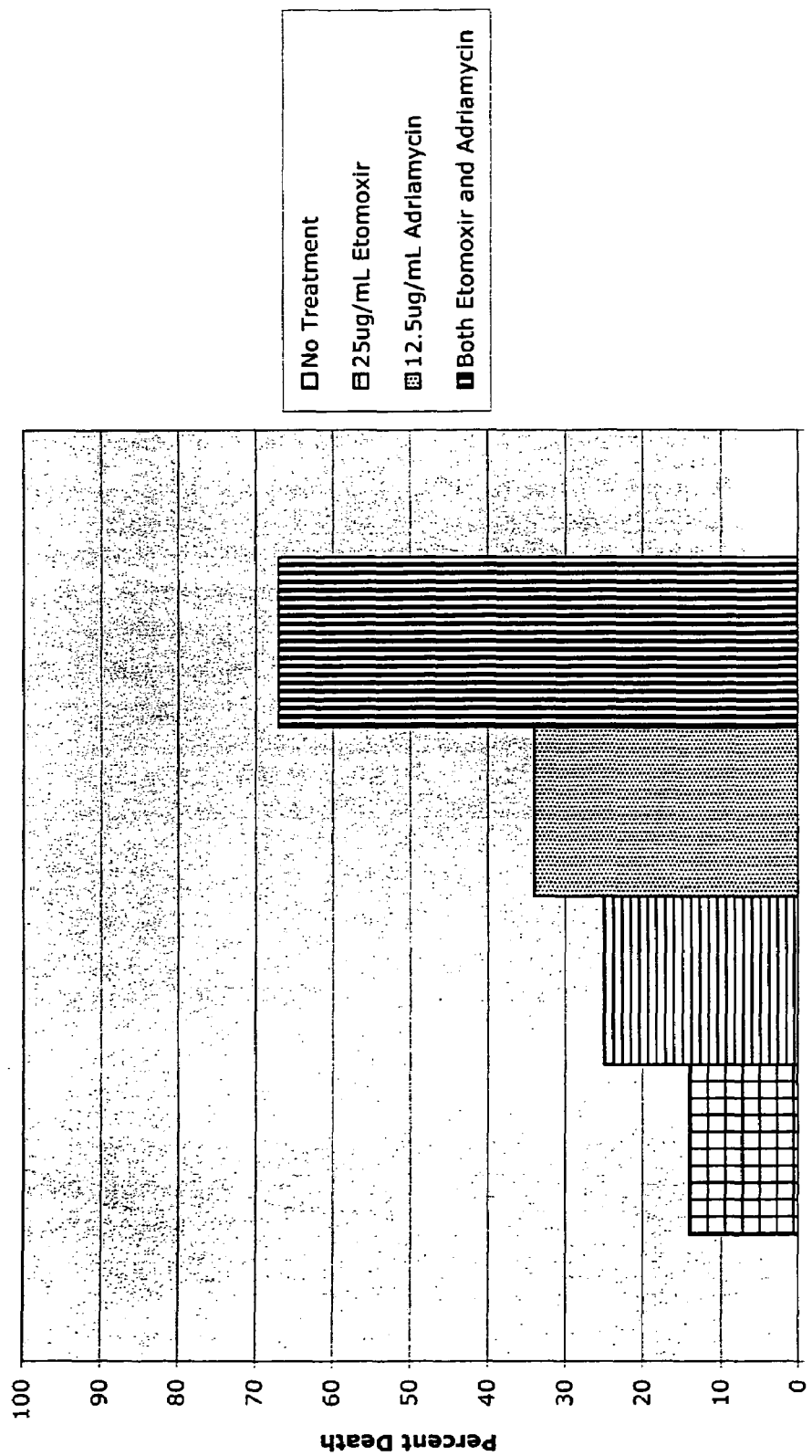
FIG. 22. shows percent death after 72 hours in etomoxir with or without 24 hours of adriamycin treatment on the human leukemic cell HL60.

HL60 cells were cultured at a concentration of 0.5 to 1 million cells per ml. Referring to FIG. 22, cells were untreated or treated with etomoxir with or without adriamycin at the indicated concentrations for 24 to 72 hours. Cells were harvested and analyzed by flow cytometry. Results shown in FIG. 22 represent percent death after 72 hours in etomoxir with or without 24 hours of adriamycin treatment.

Example 18

Figure 23:
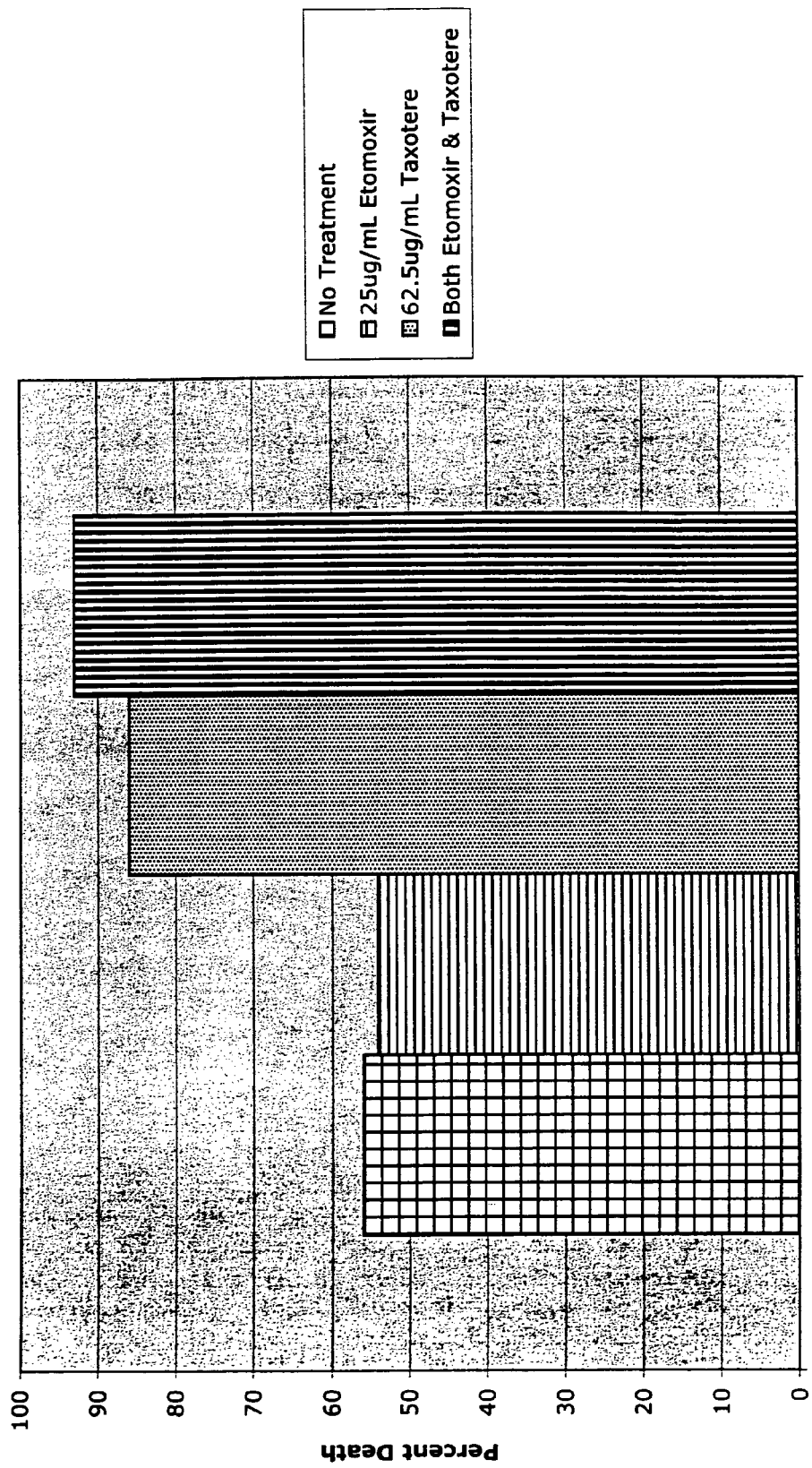
FIG. 23 shows percent death after 72 hours in etomoxir with or without 24 hours of taxotere treatment on the multidrug resistant human leukemic cell HL60MDR.

HL60MDR cells were cultured at a concentration of 0.5 to 1 million cells per ml. Referring to FIG. 23, cells were untreated or treated with etomoxir with or without taxotere at the indicated concentrations for 24 to 72 hours. Cells were harvested and analyzed by flow cytometry. Results shown in FIG. 23 represent per cent death after 72 hours in etomoxir with or without 24 hours of taxotere treatment.

Example 19

Figure 25:
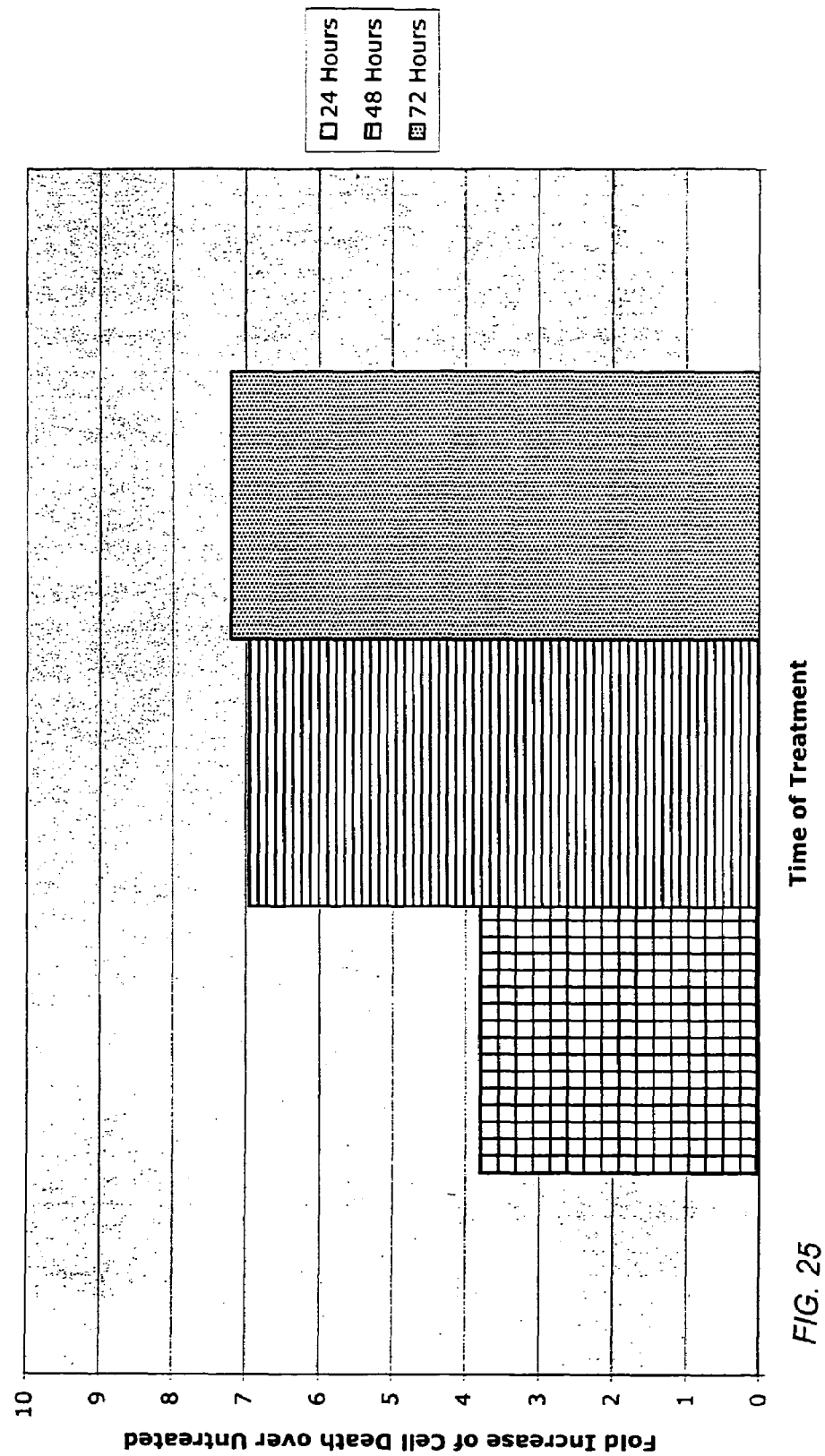
FIG. 25 shows the "fold" increases in death of A204 human rhabdomyosarcoma cells after 24, 48, & 72 hours of treatment with indicated concentrations of etomoxir.

A204 human rhabdomyosarcoma cells were cultured at a concentration of 0.5 to 1 million cells per ml. Cells were untreated or treated with etomoxir at concentrations indicated in FIG. 24 for 24, 48, & 72 hours. Cells were harvested and analyzed by flow cytometry. Dot plots are shown in FIG. 24 as functions of live versus dead cells. Each dot on the dot plot represents one cell. Five thousand cells were assessed for forward scatter (FS), as a function of cell size, versus side scatter (SS), as a function of cellular granularity. The upper elipse represents live cells by these criterion and the lower elipse in each dot plot represents the dead cells. FIG. 25 shows the "fold" increases in death of the B16F1 melanoma cells.

Example 20

Figure 26:
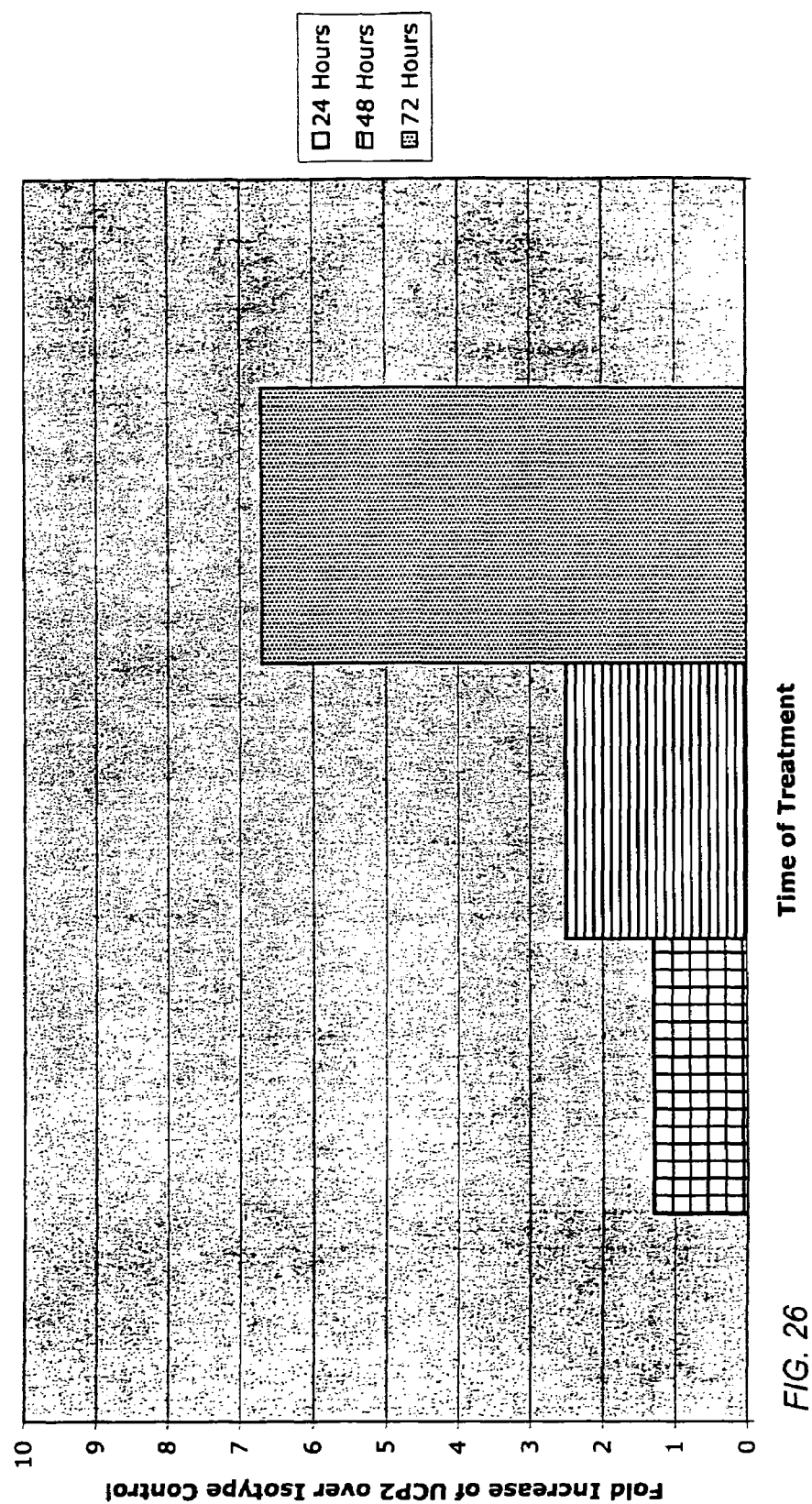
FIG. 26 shows the "fold" increases in cell surface UCP2 expression on A-204 human rhabdomyosarcoma cells after 24, 48, & 72 hours in etomoxir.

Cells were untreated or treated with etomoxir at the concentration indicated in FIG. 26 at the indicated concentration for 24, 48, & 72 hours. Cells were harvested, stained with fluorochrome conjugated with anti-UCP2 antibody and analyzed by flow cytometry. Results shown in FIG. 26 indicate etomoxir induced a time dependent "fold" increases in cell surface UCP2 expression in the live cells.

Example 21

Figure 27:
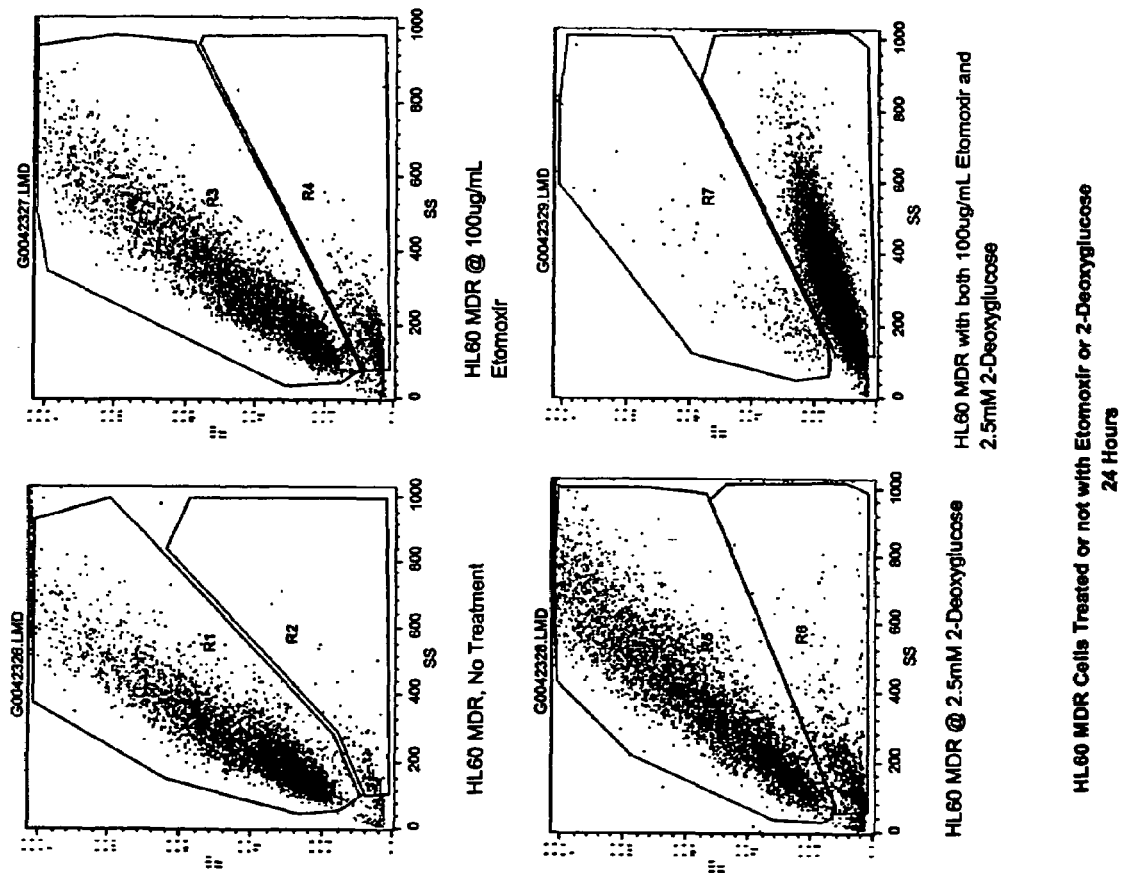
FIG. 27 is a dot plot as a function of live versus dead multidrug resistant human leukemia cell HL60 MDR untreated or treated with etomoxir, 2-deoxy-D-glucose, or both, at the indicated concentrations for 24 hours.
Figure 28:
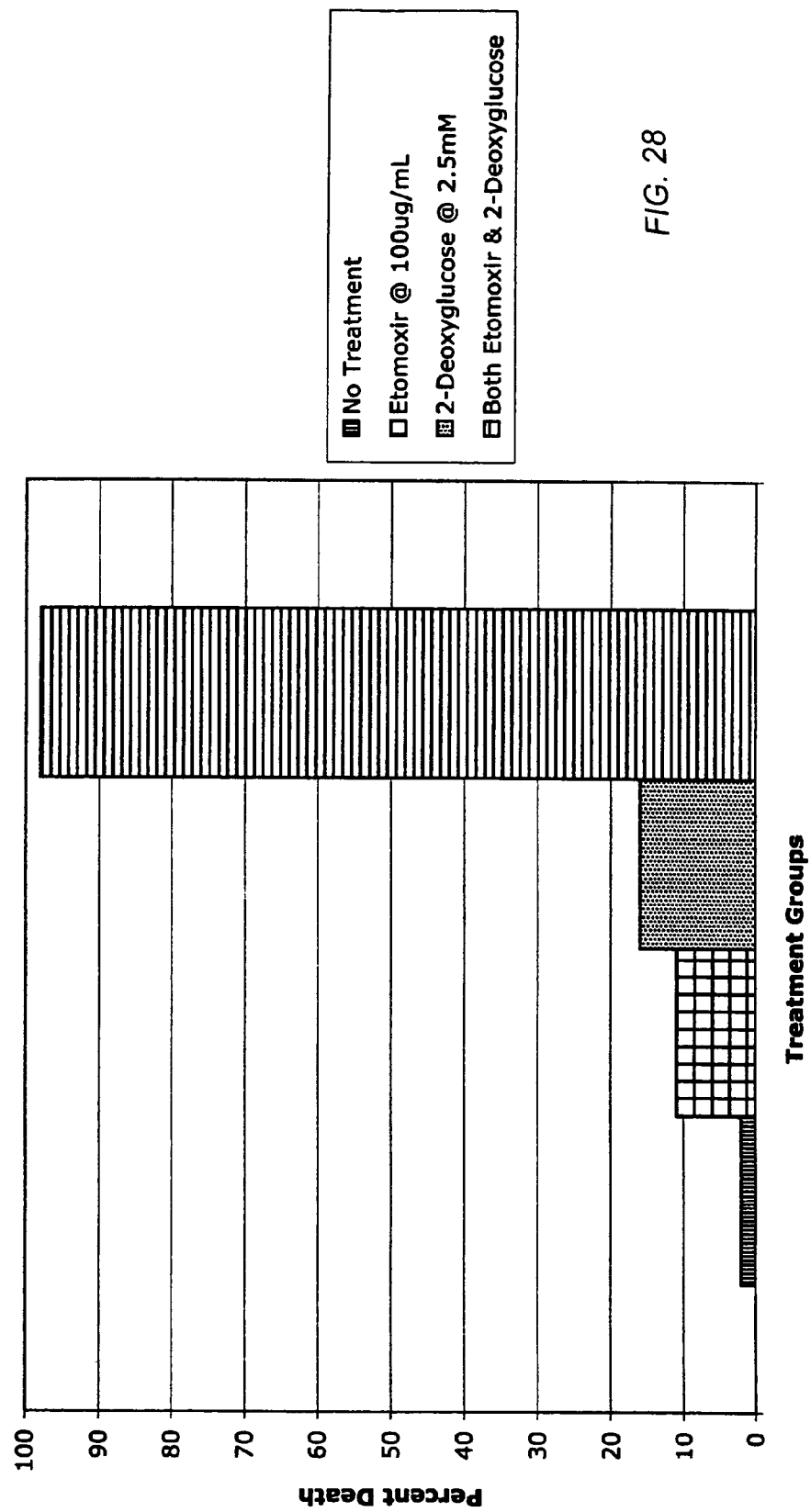
FIG. 28 shows the percent death of HL60 MDR cells untreated or treated for 24 hours with etomoxir, 2-deoxy-D-glucose, or both, at the indicated concentrations.

HL60 MDR human leukemia cells were cultured as described above under "Materials and Methods". Cells were untreated or treated with etomoxir, with 2-deoxy-D-glucose, or with a combination of etomoxir and 2-deoxy-D-glucose, at concentrations indicated in FIG. 27 for 24 hours. Cells were harvested and analyzed by flow cytometry. Dot plots are shown in FIG. 27 as functions of live versus dead cells, as described above under "Materials and Methods"—"Dot plots as a function of live versus dead cells". FIG. 28 shows the percent death of the HL60 MDR cells, calculated as described above under "Materials and Methods"—"Statistical Analysis, Percents." The percent of cell deaths for HL60 MDR cells after 24 hours was: (a) 2% when untreated, (b) 11% when treated with etomoxir alone, (c) 16% when treated with 2-deoxy-D-glucose alone, and (d) 98% when treated with the combination of etomoxir and 2-deoxy-D-glucose. Thus the combination of glucose metabolism inhibitor and fatty acid metabolism inhibitor had a dramatically synergistic effect in killing the multi drug resistant HL60 MDR human leukemia cells.

Example 22

Figure 29:
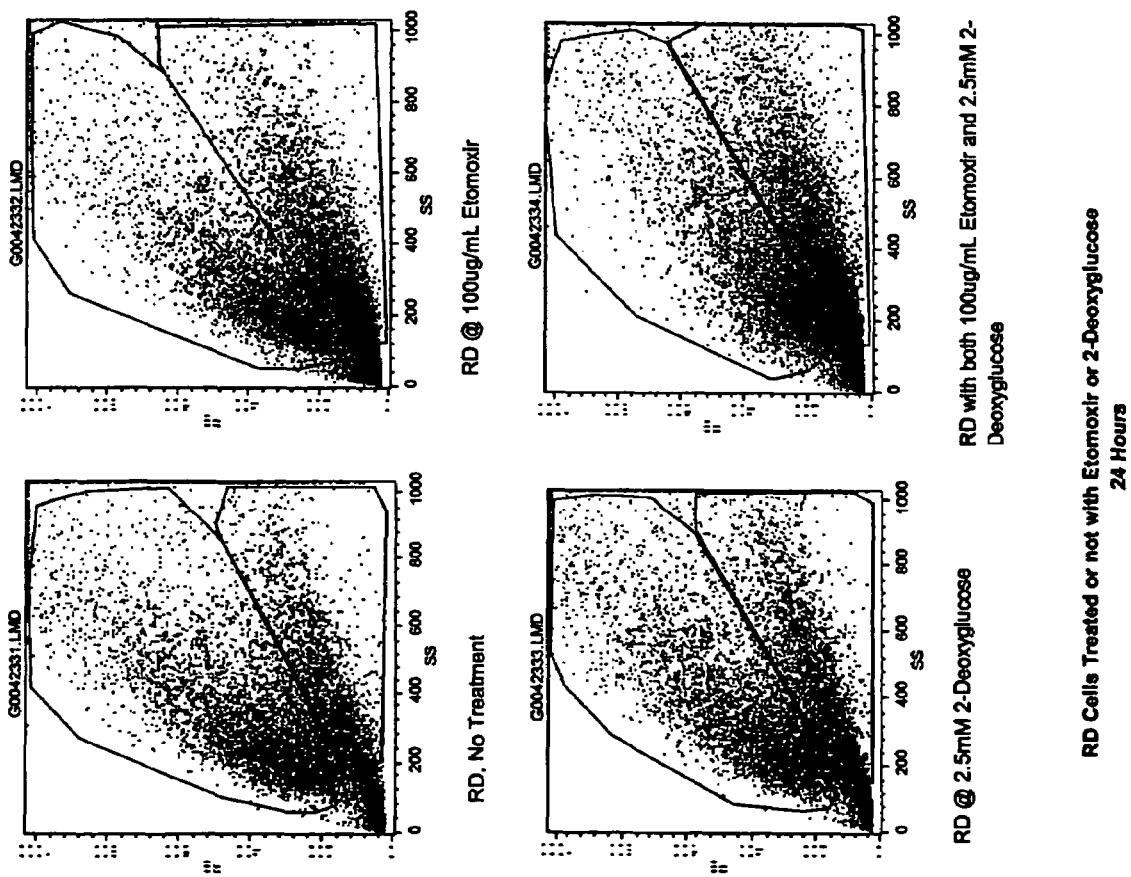
FIG. 29 is a dot plot as a function of live versus dead RD cells untreated or treated with etomoxir, 2-deoxy-D-glucose, or both, at the indicated concentrations for 24 hours.
Figure 30:
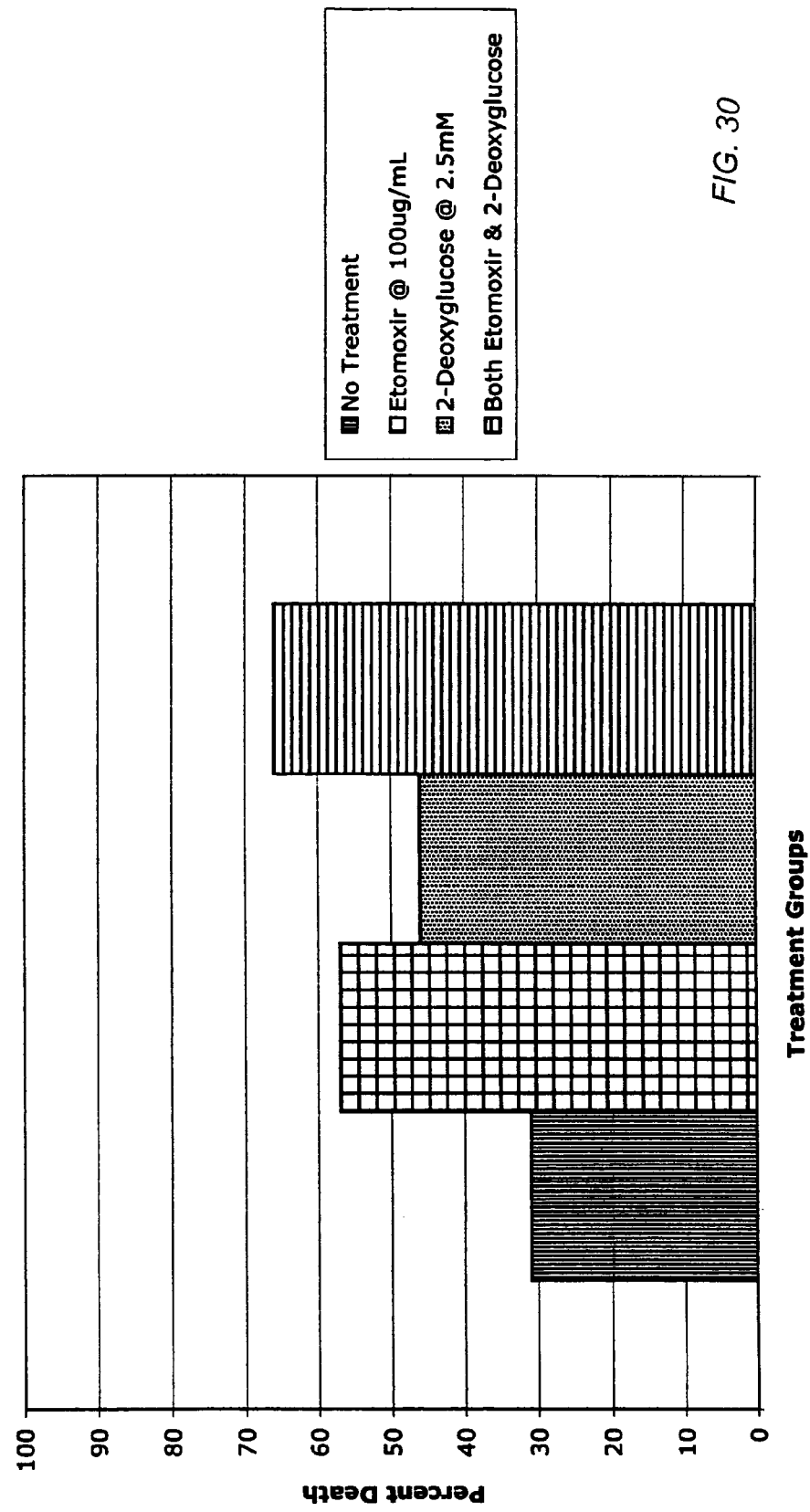
FIG. 30 shows the percent death of RD cells untreated or treated for 24 hours with etomoxir, 2-deoxy-D-glucose, or both, at the indicated concentrations.

Referring to FIGS. 29 and 30, RD cells (rhabdomyosarcoma cells—not drug resistant), cultured as described above under "Materials and Methods" were untreated or treated with etomoxir, with 2-deoxy-D-glucose, or with a combination of etomoxir and 2-deoxy-D-glucose, at concentrations indicated in FIG. 29 for 24 hours. Cells were harvested and analyzed by flow cytometry. Dot plots are shown in FIG. 29. FIG. 30 shows the percent death of the RD cells. The percent of cell deaths for RD cells after 24 hours was: (a) 31% when untreated, (b) 57% when treated with etomoxir alone, (c) 46% when treated with 2-deoxy-D-glucose alone, and (d) 66% when treated with the combination of etomoxir and 2-deoxy-D-glucose. The combination of glucose metabolism inhibitor and fatty acid metabolism inhibitor still had a synergistic effect in killing the RD cells but not nearly as much as with the multi drug resistant cells in Example 21.

Example 23

Figure 32:
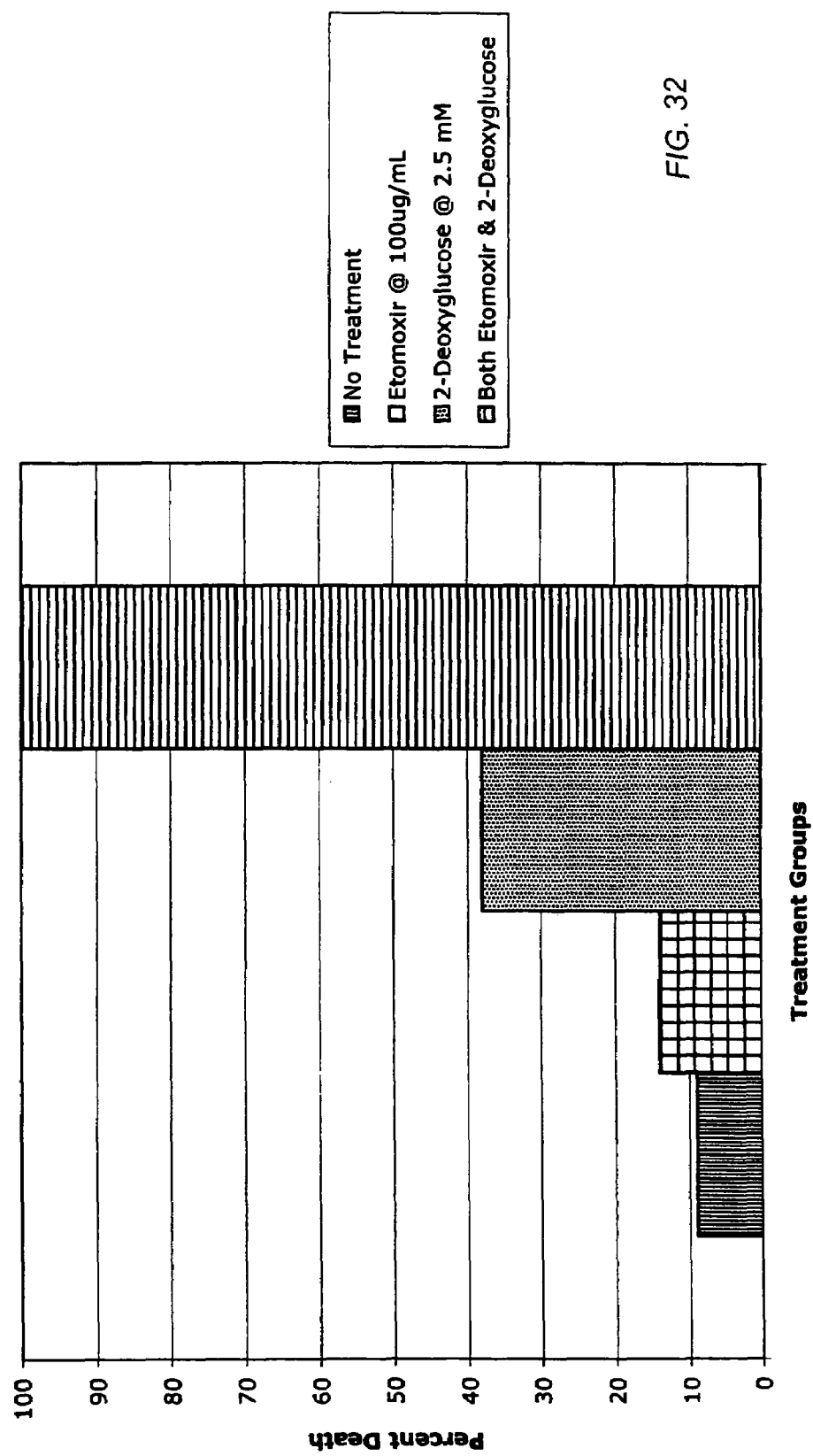
FIG. 32 shows the percent death of HL60 MDR cells untreated or treated for 48 hours with etomoxir, 2-deoxy-D-glucose, or both, at the indicated concentrations.

Referring to FIGS. 31 and 32, HL60 MDR cells, cultured as described in Example 21, were untreated or treated with etomoxir, with 2-deoxy-D-glucose, or with a combination of etomoxir and 2-deoxy-D-glucose, at concentrations indicated in FIG. 31 for 48 hours. Cells were harvested and analyzed by flow cytometry. Dot plots are shown in FIG. 31. FIG. 32 shows the percent death of the HL60 cells. The percent of cell deaths for HL60 MDR cells after 48 hours was: (a) 9% when untreated, (b) 14% when treated with etomoxir alone, (c) 38% when treated with 2-deoxy-D-glucose alone, and (d) 100% when treated with the combination of etomoxir and 2-deoxy-D-glucose. Thus, increasing exposure time increased cell deaths generally, but most dramatically with the combination of glucose metabolism inhibitor and fatty acid metabolism inhibitor, where 100% of the HL60 MDR cells were killed.

Example 24

Figure 34:
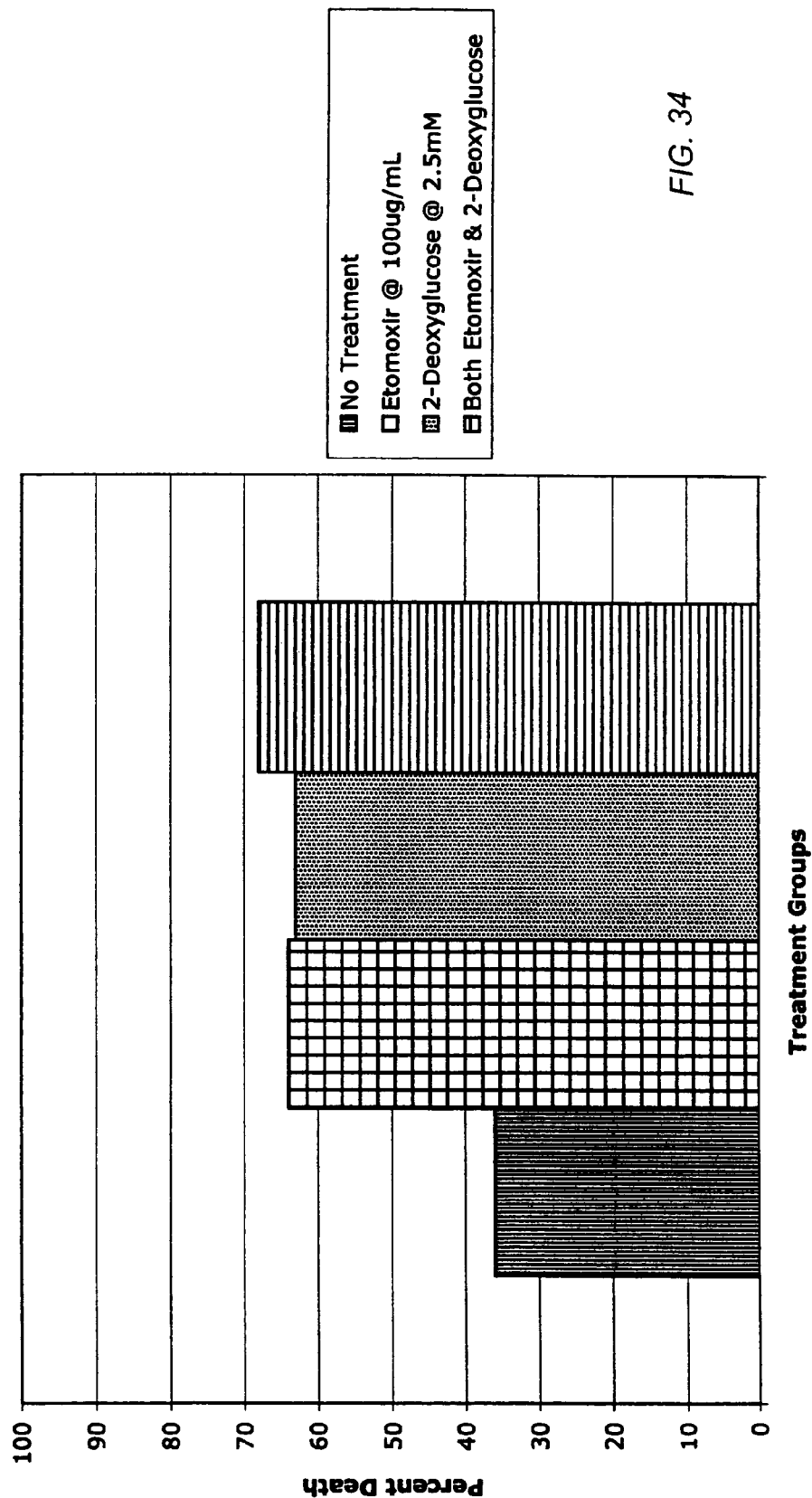
FIG. 34 shows the percent death of RD cells untreated or treated for 48 hours with etomoxir, 2-deoxy-D-glucose, or both, at the indicated concentrations.

Referring to FIGS. 33 and 34, RD cells, cultured as described in Example 22, were untreated or treated with etomoxir, with 2-deoxy-D-glucose, or with a combination of etomoxir and 2-deoxy-D-glucose, at concentrations indicated in FIG. 33 for 48 hours. Cells were harvested and analyzed by flow cytometry. Dot plots are shown in FIG. 33. FIG. 34 shows the percent death of the RD cells. The percent of cell deaths for RD cells after 48 hours was: (a) 36% when untreated, (b) 64% when treated with etomoxir alone, (c) 63% when treated with 2-deoxy-D-glucose alone, and (d) 68% when treated with the combination of etomoxir and 2-deoxy-D-glucose. Increasing the treatment time for RD cells only modestly increased the number of cells killed.

Example 25

Figure 36:
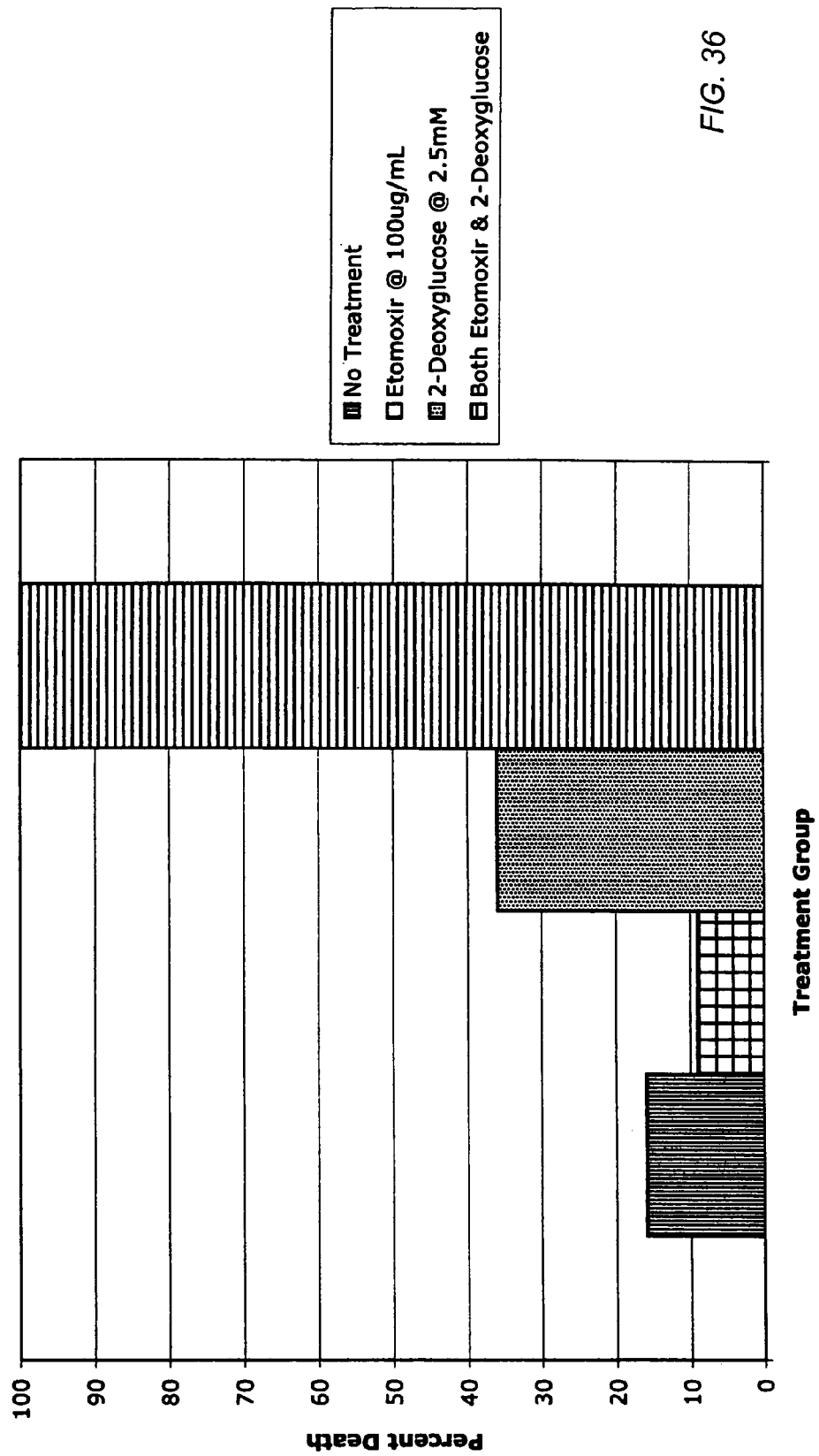
FIG. 36. shows the percent death of HL60 MDR cells treated for 48 hours with anti-UCP2 antibody and otherwise untreated or treated with etomoxir, 2-deoxy-D-glucose, or both, at the indicated concentrations.

Referring to FIGS. 35 and 36, HL60 MDR cells, cultured as described in Example 21, were treated with anti-UCP2 antibody and otherwise untreated or treated simultaneously with etomoxir, 2-deoxy-D-glucose, or both, at concentrations indicated in FIG. 35 for 48 hours. Cells were harvested and analyzed by flow cytometry. Dot plots are shown in FIG. 35. FIG. 36 shows the percent death of the HL60 cells. The percent of cell deaths for HL60 MDR cells after 48 hours was: (a) 16% when treated only with the antibody, (b) 9% when treated with the antibody and etomoxir, (c) 36% when treated with the antibody and 2-deoxy-D-glucose alone, and (d) 100% when treated with the combination of antibody, etomoxir and 2-deoxy-D-glucose. Thus, treatment with the antibody had a minor effect when the cells were otherwise untreated, but otherwise little effect, a result that is attributed to the fact that it was administered at the same time as the etomoxir. As shown in this example and in Example 3, the combination of glucose metabolism inhibitor and fatty acid metabolism inhibitor resulted in a 100% kill rate with or without the antibody.

Example 26

Figure 38:
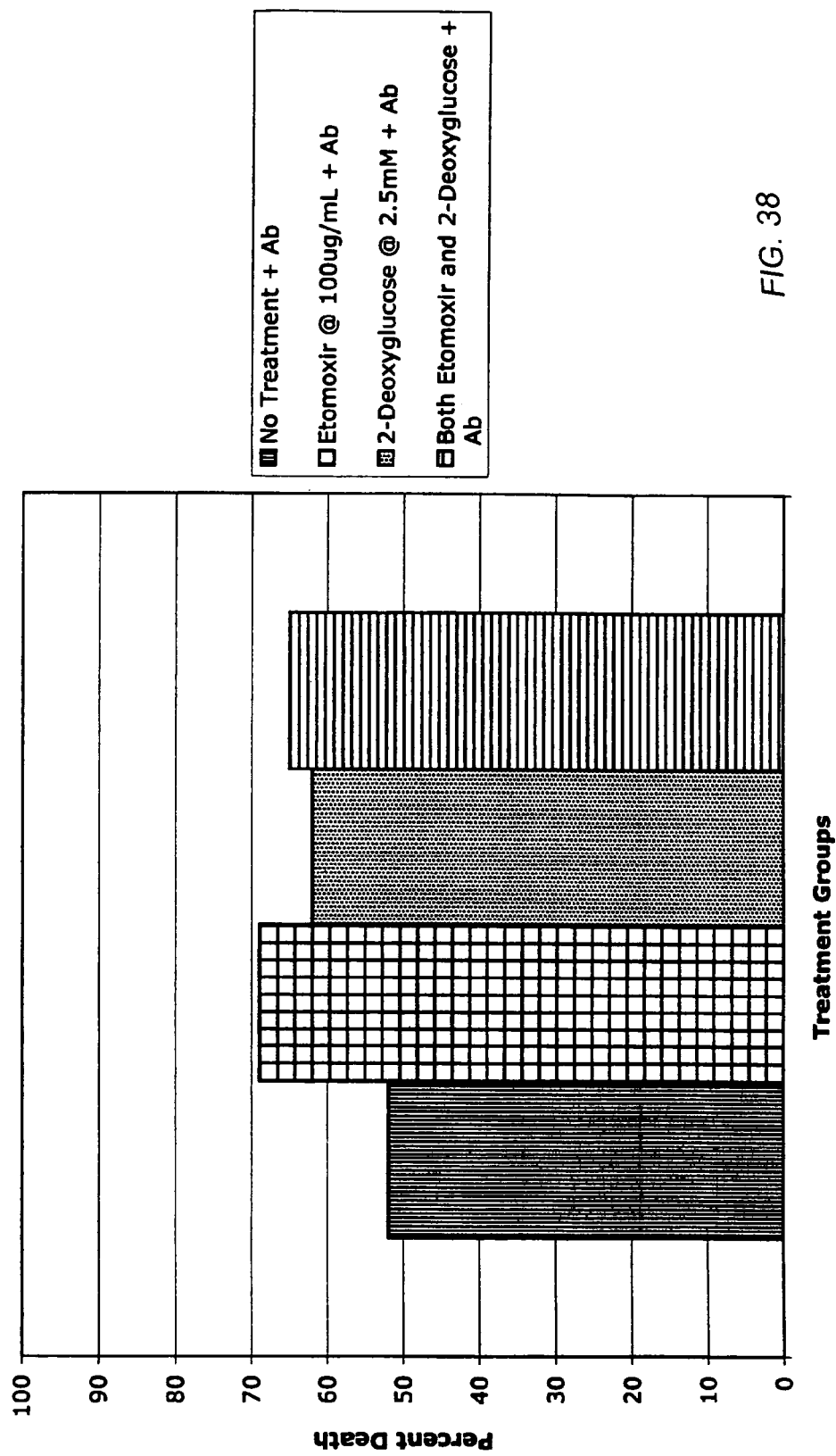
FIG. 38 shows the percent death of RD cells treated for 48 hours with anti-UCP2 antibody and otherwise untreated or treated with etomoxir, 2-deoxy-D-glucose, or both, at the indicated concentrations.

Referring to FIGS. 37 and 38, RD cells, cultured as described in Example 22, were treated with anti-UCP2 antibody and otherwise untreated or treated simultaneously with etomoxir, 2-deoxy-D-glucose, or both, at concentrations indicated in FIG. 37 for 48 hours. Cells were harvested and analyzed by flow cytometry. Dot plots are shown in FIG. 37. FIG. 38 shows the percent death of the RD cells. The percent of cell deaths for RD cells after 48 hours was: (a) 52% when treated only with the antibody, (b)69% when treated with the antibody and etomoxir, (c) 62% when treated with the antibody and 2-deoxy-D-glucose alone, and (d) 65% when treated with the combination of antibody, etomoxir and 2-deoxy-D-glucose. Treatment of the RD cells with the antibody had some effect when the cells were otherwise untreated, but otherwise, as in Example 25, had little effect Example 27

HL60 MDR human leukemia cells were cultured and implanted in nude mice as described above under "Materials and Methods". The mice were given 200 ug of Etomoxir, 2.5 mM 2-Deoxy-D-glucose, or both 200 ug of Etomoxir and 2.5 mM 2-Deoxy-D-glucose given daily by IP injection. Treatment began exactly one week after tumor implantation. Tumor growth was observed for 21 days with tumor volume measured on days 7, 9, 15 and 21. The following shows the tumor volume in mm$^3$ for the four classes of mice over the 21 day period:

|  | Day 7 | Day 9 | Day 15 | Day 21 |
| --- | --- | --- | --- | --- |
| Control | 26 | 58.12 | 171.27 | 728.87 |
| Etomoxir only | 36 | 71.73 | 261.35 | 895.09 |
| 2-Deoxy-D-glucose only | 35 | 51.56 | 158.55 | 1,181.61 |
| Etomoxir and 2-deoxy-D-glucose | 24 | 37.72 | 99.76 | 296.83 |

Figure 39:
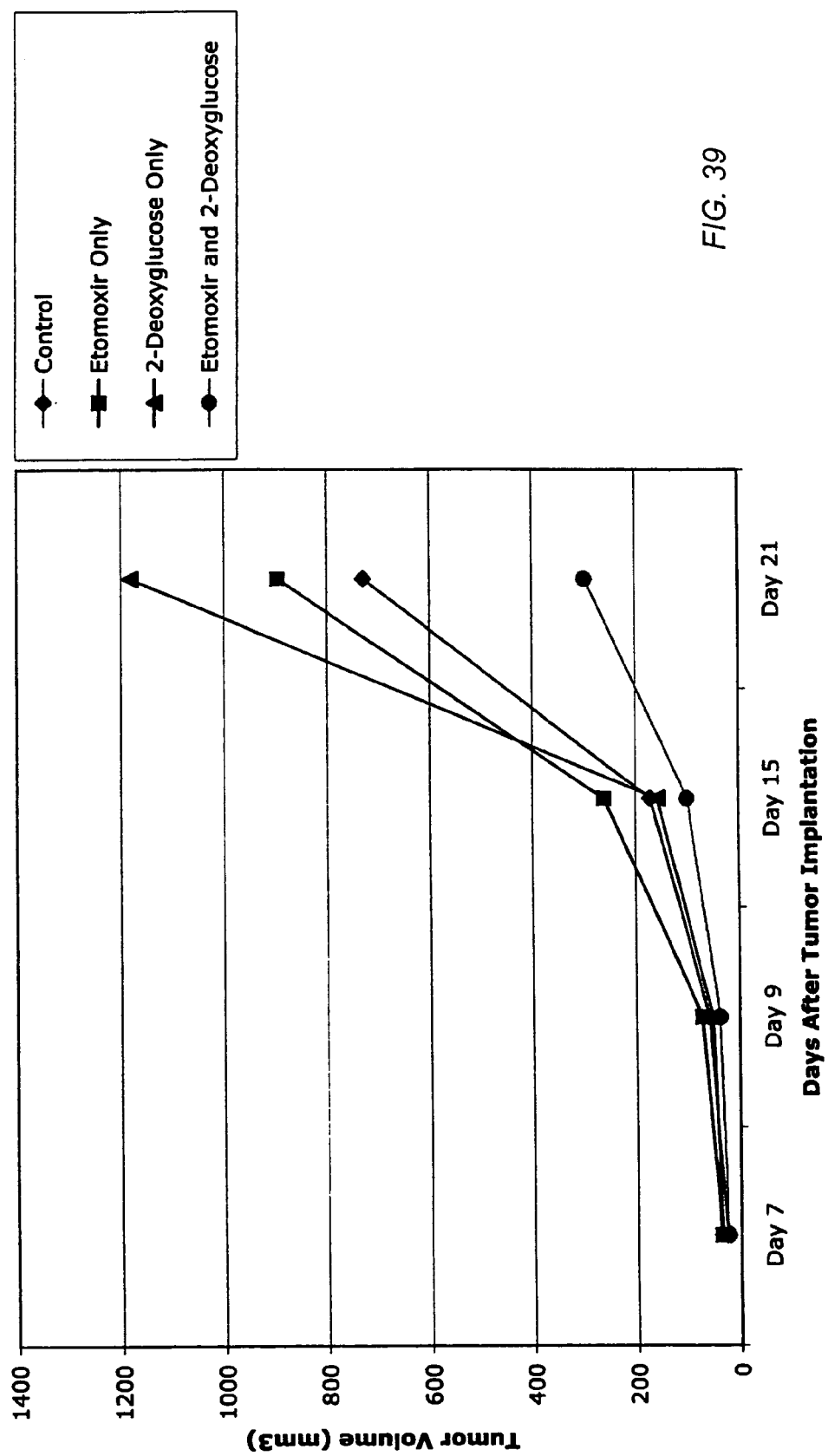
FIG. 39 shows tumor volume of an HL60 MDR tumor implanted in nude mice, treated with etomoxir, 2-deoxy-D-glucose, or both, at the indicated days after tumor implantation.

FIG. 39 shows plots of the observed tumor volume over the 21 day period. The etomoxir alone and the 2-deoxy-D-glucose alone each caused an increase in tumor growth, likely because by each restricting only one of the fatty acid and glucose metabolism pathways, the other pathway became dominant. However, the combination of fatty acid metabolism inhibitor and glucose metabolism inhibitor had a dramatically synergistic effect, limiting tumor growth to 40% of the growth of the control.

Example 28

Mice were purchased from National Cancer Institute, Animal Production Program (Frederick, Md.). The animals used were Athymic Ncr-nu/nu (Strain code 01B74). HL60 MDR cells were harvested and reconstituted at 1 million cells per 100 microliters of phosphate buffered saline. One million tumor cells/per injection site were implanted subcutaneously on two sites of the animal's back. Treatments began at exactly seven days post tumor implantation. Tumor size/volume was monitored twice weekly using measurement calipers with the formula for Tumor Volume=$\pi$(short diameter)$^2$(long diameter)/(divided by )6.

HL60 MDR human leukemia cells were cultured and implanted in nude mice, as described above. The mice were given anti-UCP2 Antibody (Alpha Diagnostics, UCP23-S) at a concentration of 50 ug/mouse by IP injection. Treatment began exactly one week after tumor implantation. Tumor growth was observed for 20 days with tumor volume measured on days 2, 6, 10, 12, 18, and 20. The following shows the tumor volume in cm$^3$ for the mice over the 20day period:

|  | Day 2 | Day 6 | Day 10 | Day 12 | Day 18 | Day 20 |
| --- | --- | --- | --- | --- | --- | --- |
| Control | 0 | 0.05 | 0.15 | 0.5 | 0.9 | 1.46 |
| Anti-UCP2 antibody | 0 | 0.01 | 0.04 | 0.1 | 0.3 | 0.75 |

Figure 40:
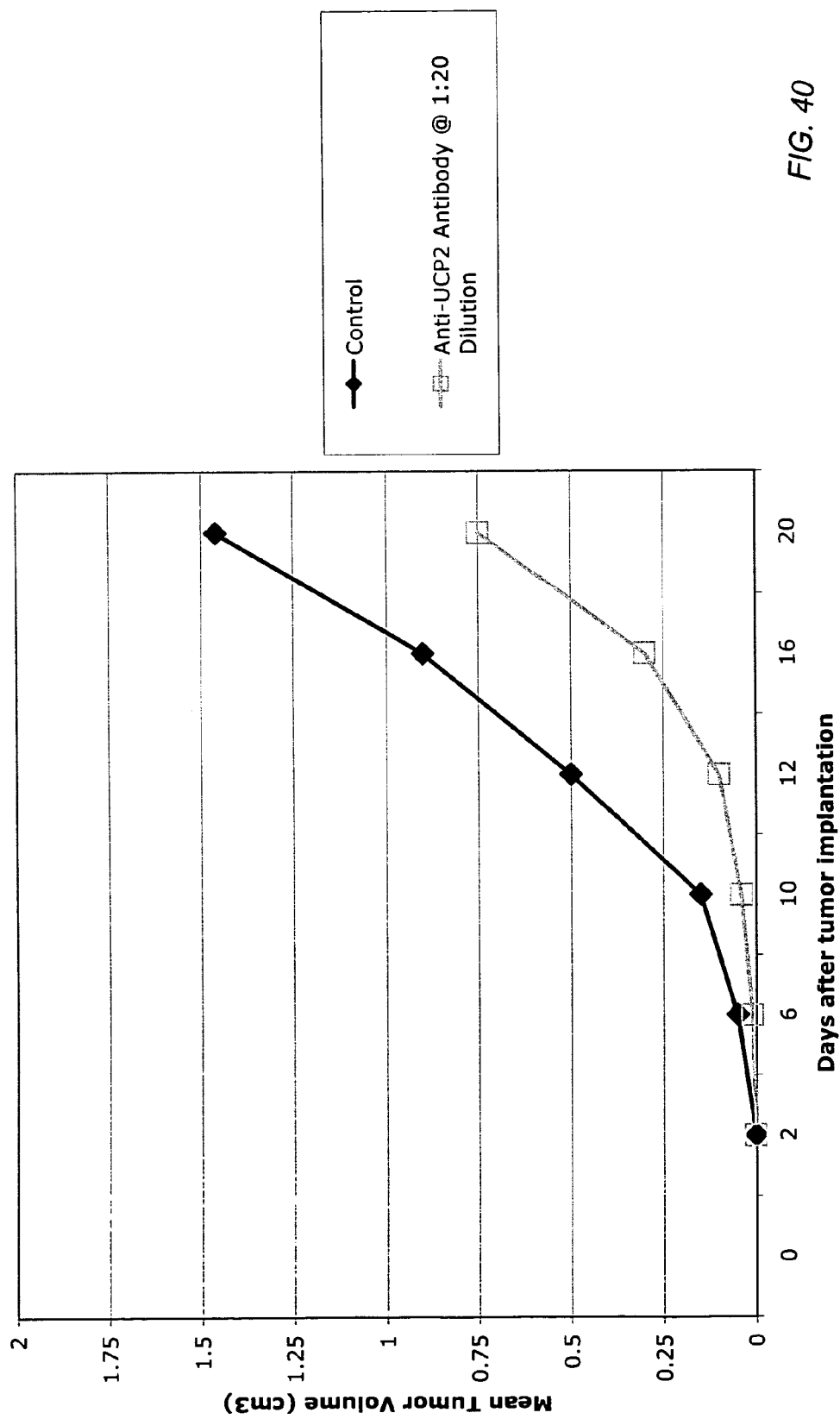
FIG. 40 shows tumor volume of an HL60 MDR tumor implanted in nude mice, treated anti-UCP2 antibody, at the indicated days after tumor implantation.
Figure 41:
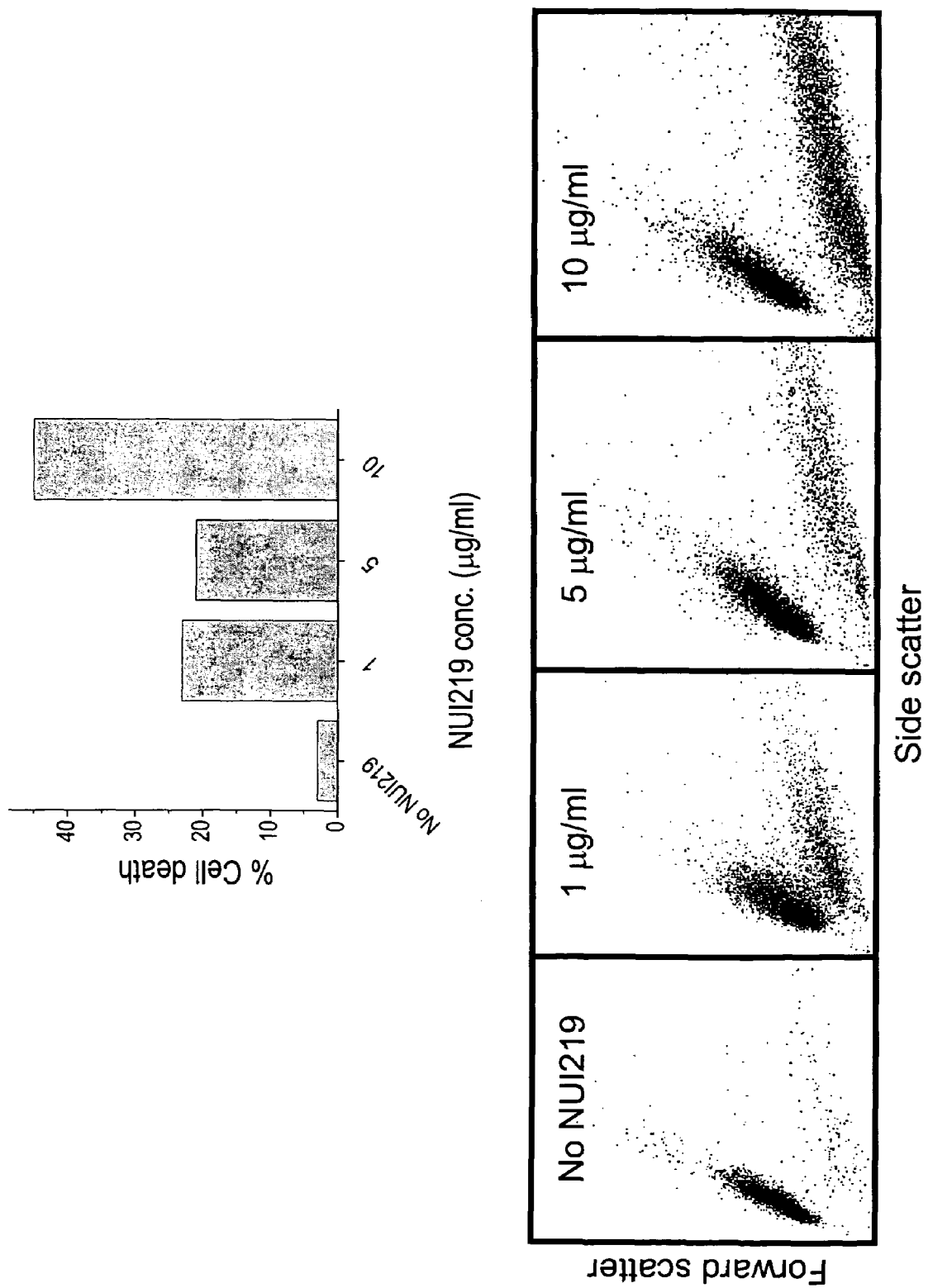
Figure 42:
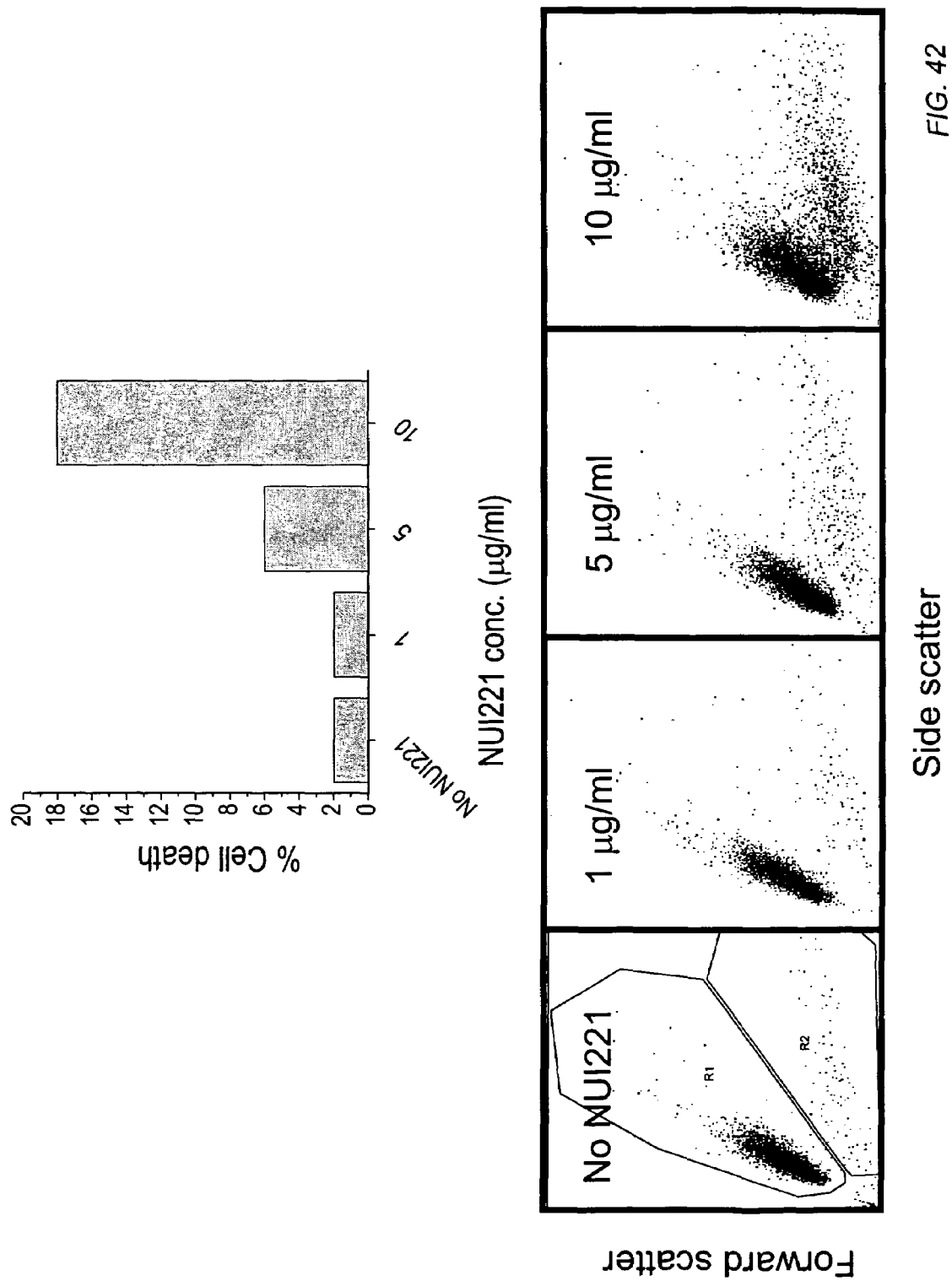
Figure 43:
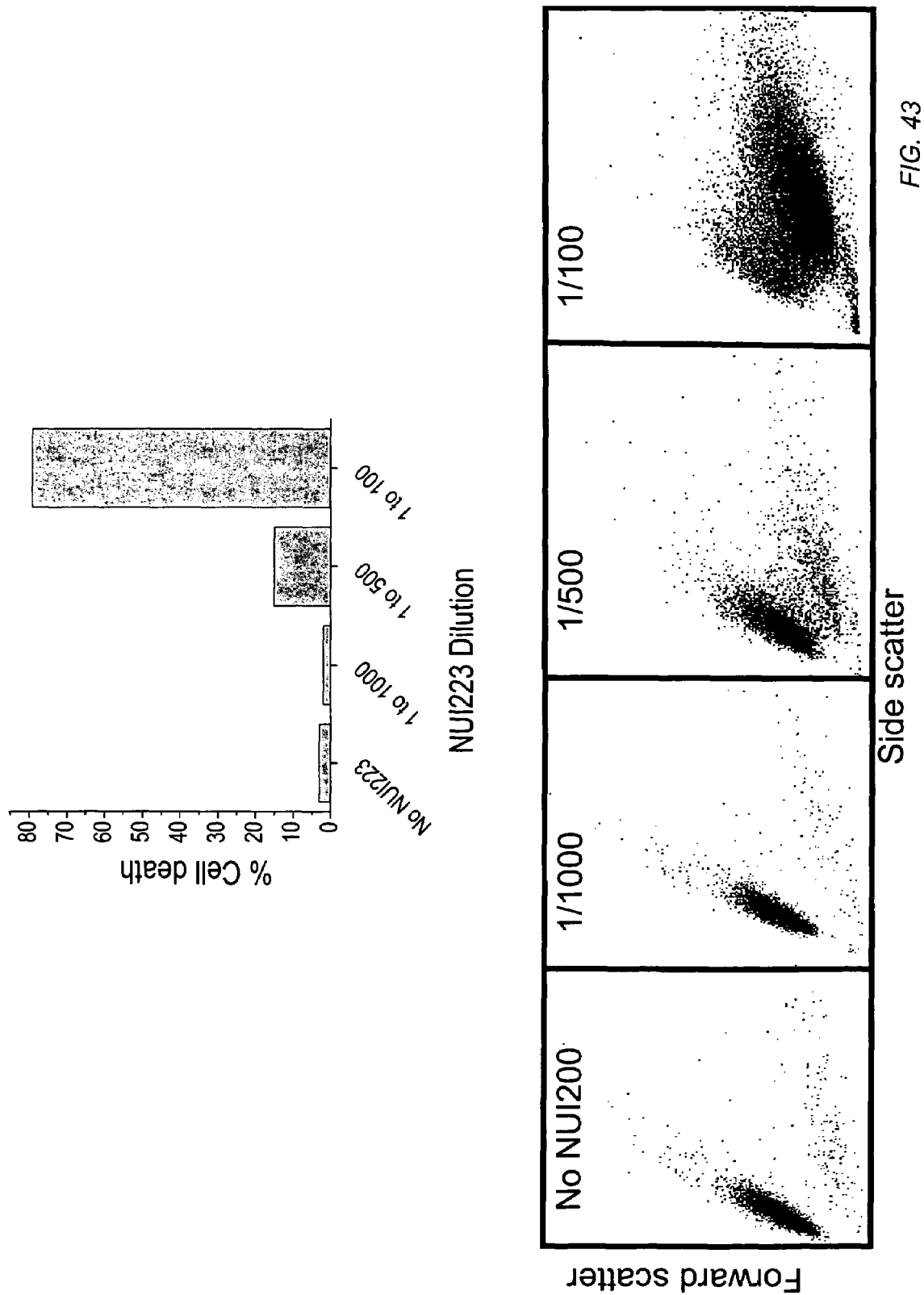

FIG. 40 shows plots of the observed tumor volume over the 20-day period. Over this three-week period, a two-fold inhibition of tumor growth was observed with weekly anti-UCP2 antibody injections at a concentration of 50 ug/mouse.

Example 29

A204 human rhabdomyosarcoma cells were cultured at a concentration of 0.5 to 1 million cells per ml. Cells were treated with etomoxir (NUI100) and treated or untreated with antibodies to UCP2, including NUI219 (Santa Cruz, antibody to the N-19 portion of the UCP2 molecule), NUI221 (Alpha Diagnostics, antibody to mouse UCP2), and NUI223 (Alpha Diagnostics, an anti-human UCP2 antibody) as indicated on the charts and used at dilutions or concentrations as indicated on the figure. The cells were cultured in the presence or absence of etomoxir at 100 micrograms/ml for 24 hours followed by treatment with antibody as indicated for an additional 24 or 48 hours (i.e. totals of 48 hours or 72 hours respectively). Cells were harvested and analyzed by flow cytometry. Dot plots are shown in the lower halves of FIGS. 41 through 46 as functions of live versus dead cells. Each dot on the dot plot represents one cell. Five thousand cells were assessed for forward scatter (FS), as a function of cell size, versus side scatter (SS), as a function of cellular granularity. The upper ellipse represents live cells by these criterion and the lower ellipse in each dot plot represents the dead cells. "Fold" increases in death of the cells are shown in the upper halves of FIGS. 41 through 46. FIG. 47 compares percentage cell deaths with etomoxir alone to cell deaths with etomoxir and the antibody. Except at the highest dilution (1 to 100) dramatic increases in effectiveness were obtained with the combination of UCP2 antibody and etomoxir.

Example 30

Mouse melanoma B16F1 tumor cells were implanted in syngenic mouse host, C57Black6. The procedure was otherwise the same as described in Example 27. The mice were given both 200 ug of Etomoxir and 2.5 mM 2-Deoxy-D-glucose daily by IP injection, or anti-UCP2 Antibody (Alpha Diagnostics, UCP23-S) at a concentration of 50 ug/mouse twice weekly by IP injection. Tumor growth was observed for 19 days with tumor volume measured on days 9, 12, 16 and 19, except that none of the controls survived past day 16. The following shows the tumor volume in mm$^3$ for the four classes of mice over the 21 day period:

|  | Day 9 | Day 12 | Day 16 | Day 19 |
| --- | --- | --- | --- | --- |
| Control | 0.736 | 1.202 | 3.535 | — |
| Etomoxir and 2-deoxy-D-glucose | 0.225 | 0.606 | 1.493 | 1.757 |
| Anti-UCP2 antibody | 0.446 | 0.823 | 1.878 | 2.648 |

Figure 48:
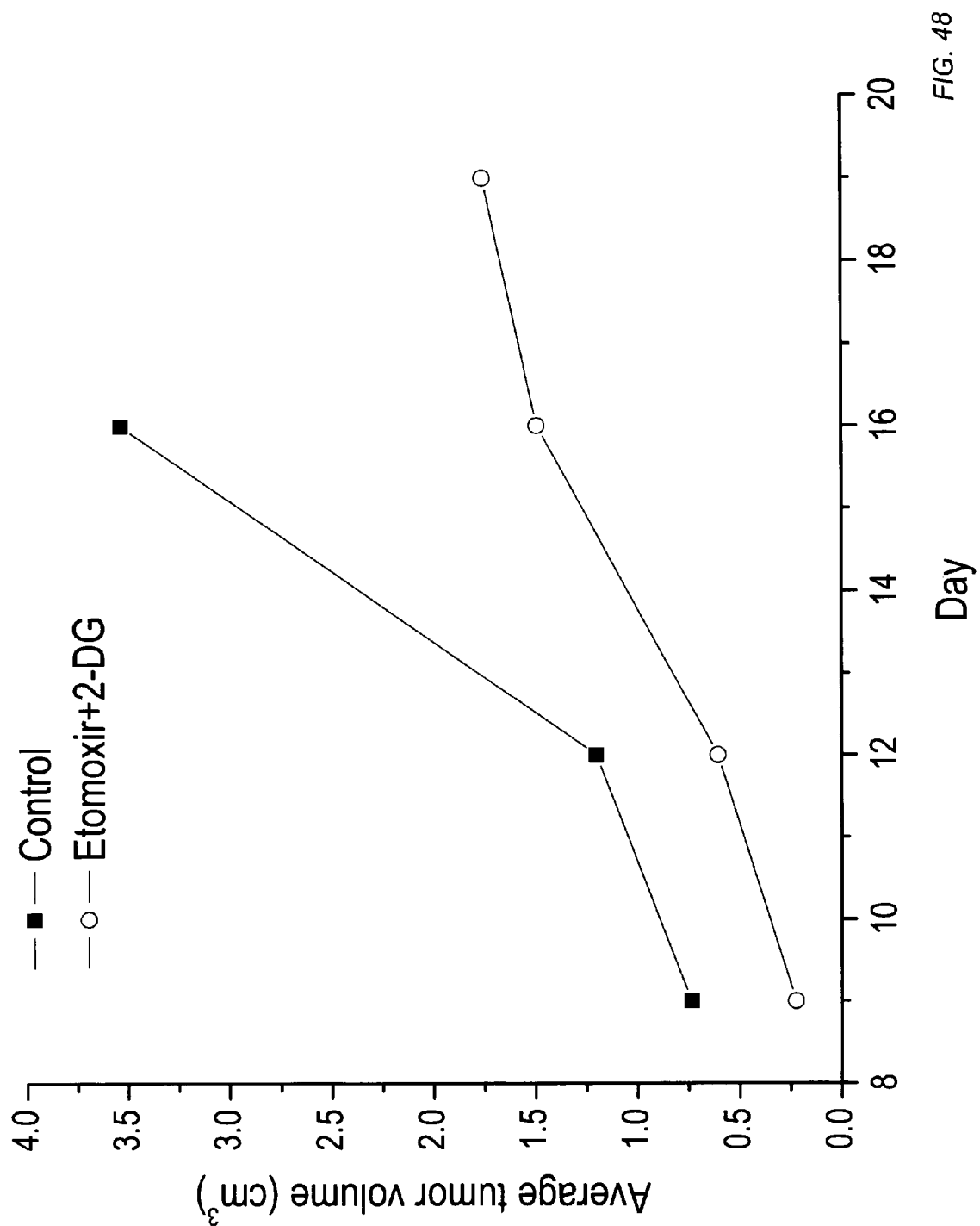
FIG. 48 shows tumor volume of a mouse melanoma B16F1 tumor implanted in syngeneic mouse hosts, treated with both etomoxir and 2-deoxy-D-glucose at the indicated days after tumor implantation.
Figure 49:
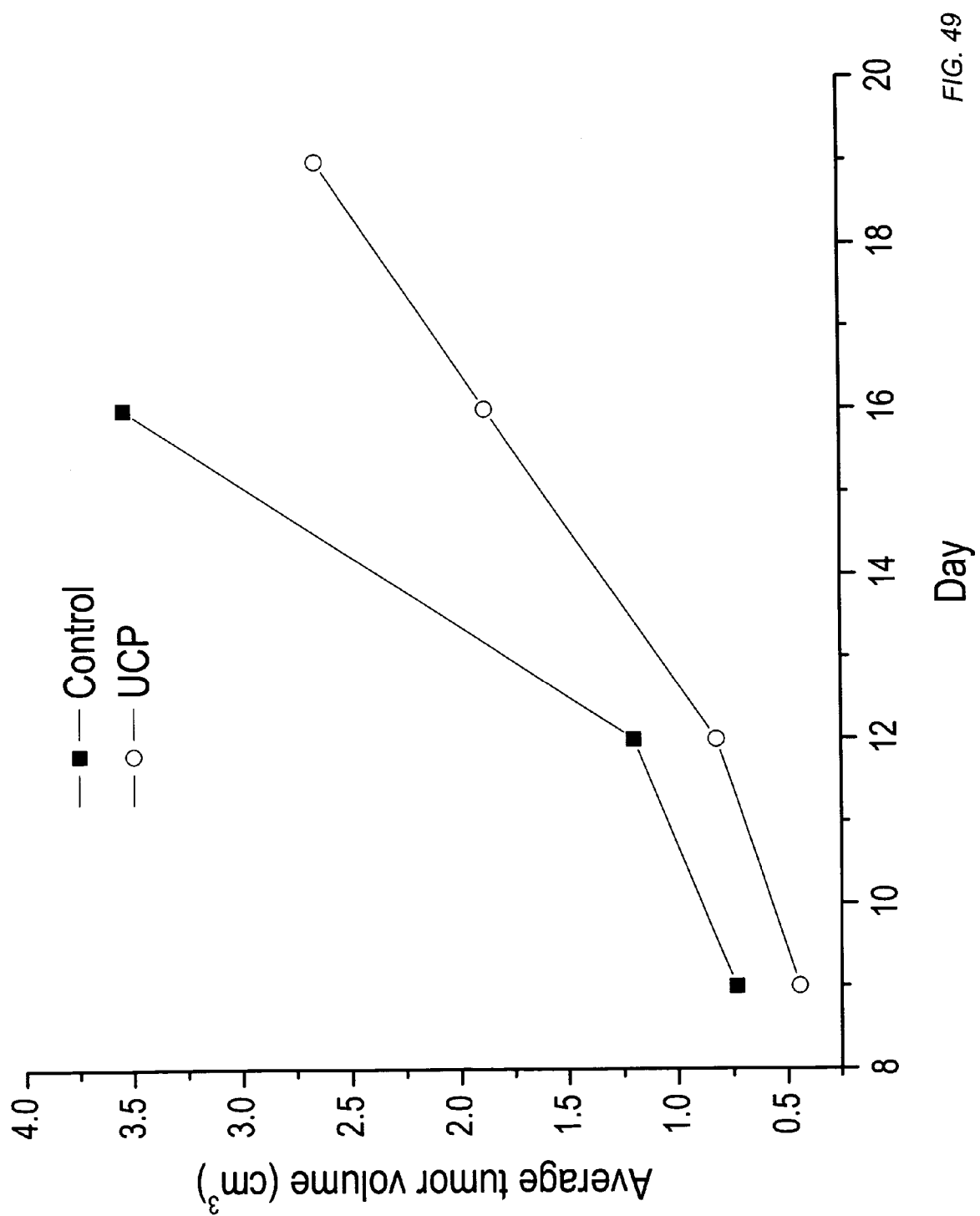
FIG. 49 shows tumor volume of a mouse melanoma B16F1 tumor implanted in syngeneic mouse hosts, treated with anti-mouse UCP2 antibody at the indicated days after tumor implantation.

FIGS. 48 and 49 show plots of the observed tumor volume over the 19 day period. Both the combination of fatty acid metabolism inhibitor and glucose metabolism inhibitor and the anti-UCP antibody had significant effects in limiting tumor growth.

DEFINITIONS

Following are several definitions which will aid in understanding of the scope of the compounds described above and in understanding the invention. All definitions, as defined and used herein, should be understood to control over dictionary definitions, definitions in documents incorporated by reference, and/or ordinary meanings of the defined terms.

As used herein, the term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine; fluorine and chlorine; chlorine and bromine, or a single type of halogen atom.

As used herein, "alkyl" is given its ordinary meaning as used in the field of organic chemistry. Alkyl (i.e., aliphatic) moieties useful for practicing the invention can contain any of a wide number of carbon atoms, for example, between and 1 and 25 carbon atoms, between 1 and 20 carbon atoms, between 1 and 15 carbon atoms, between 1 and 10 carbon atoms, or between 1 and 5 carbon atoms. In some embodiments, the alkyl moiety will contain at least 1 carbon atom, at least 3 carbon atoms, at least 5 carbon atoms, or at least 10 carbon atoms; in other embodiments, the alkyl moiety will have at most 10 carbon atoms, at most 5 carbon atoms, or at most 3 carbon atoms. Typically, an alkyl moiety is a non-cyclic moiety.

The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, etc.) or a branched chain, i.e., a chain where there is at least one carbon atom that is covalently bonded to at least three carbon atoms (e.g., a t-butyl moiety, an isoalkyl moiety such as an isopropyl moiety or an isobutyl moiety, etc.). The alkyl moiety may contain only single bonds, or may contain one or more double and/or triple bonds within its structure, for example, as in an alkene, an alkyne, an alkadiene, an alkadiyne, an alkenyne, etc. In some cases, the alkyl moiety contains only carbon and hydrogen atoms; however, in other embodiments, the alkyl moiety may also contain one or more substituents, i.e., a non-carbon and non-hydrogen moiety may be present within the alkyl moiety. For example, in certain embodiments, the alkyl moiety can include a halogen, an alkoxy moiety (e.g., methoxy or ethoxy), an amine moiety (e.g., a primary, secondary, or tertiary amine), a carbonyl (e.g., an aldehyde and/or a ketone) or a hydroxide as a substituent. If more than substituent is present within the alkyl moiety, then the substituents may each be the same or different.

Similarly, a "cyclic" moiety, as used herein, is given its ordinary definition as used in the field of organic chemistry, i.e., a moiety structure that contains at least one ring of atoms, and may contain more than one ring of atoms that is, a cyclic structure has at least one chain of atoms that does not have a terminal end. The chain may have, for example, three, four, five, six, or more atoms arranged to form a ring. In some embodiments, the cyclic moiety has a maximum size of at most ten atoms, at most eight atoms, or at most seven atoms. In some cases, the cyclic moiety may only include carbon and hydrogen atoms; however, in other cases, the atoms within the ring may also include, besides carbon atoms, nitrogen atoms, oxygen atoms, sulfur atoms, silicon atoms, or any other atom able to covalently bond to at least two different atoms (i.e., a "heterocyclic" moiety). If the cyclic moiety contains more than one ring, the rings may be arranged in any orientation with respect to each other, e.g., the rings may be fused (i.e., at least two rings have more than one atom in common, for example, as in bicyclic moieties, tricyclic moieties, etc.), spiro (i.e., two rings have only one atom in common), a ring may be a substituent on another ring, two or more rings may be connected through an alkyl moiety, etc. In some embodiments of the invention, one or more substituents may be present on the cyclic moiety. The substituents may be any substituent, as previously described in connection with alkyl moieties, for example, a halogen, an alkoxy, an amine, a hydroxide, or the like. In some embodiments, the substituents may also be alkyl moieties, as previously described, for example, methyl, ethyl, propyl, etc.

The cyclic moiety may be a saturated cyclic moiety (i.e., a moiety not containing any double or triple bonds, such as a cyclopentyl moiety, a cyclohexyl moiety, a cycloheptyl moiety, a cyclooctyl moiety, etc.) or an unsaturated cyclic moiety (i.e., a moiety containing at least one double or triple bond, such as a cycloalkenyl moiety, a cycloalkynyl moiety, an aromatic moiety, etc.). An "aromatic" moiety is given its ordinary meaning as used in the art, i.e., a moiety having at least one ring in which some electrons are delocalized in the ring. For instance, the aromatic moiety may include a benzene moiety, a naphthalenyl moiety, an anthracenyl moiety, a pyridinyl moiety, a furanyl moiety, etc. Similarly, a "non-aromatic" structure is a structure in which aromaticity of the cyclic moiety is not present. For example, a non-aromatic cyclic structure may be a saturated cyclic structure, a cycloalkenyl moiety such as a cyclopentenyl moiety or a cyclohexenyl moiety, a cycloalkynyl moiety such as a cyclooctynyl moiety or a cyclodecynyl moiety, etc.

Some of the compounds described herein are commercially available compounds, are derived from commercially available compounds, or are synthesized de novo using routine chemical synthetic procedures known to those of ordinary skill in the art and/or described herein.

In some embodiments, the systems and methods of the invention described herein may include homologs, analogs, derivatives, enantiomers and/or functionally equivalent compositions thereof of the compositions described herein, for example, as shown in FIG. 1. Such homologs, analogs, derivatives, enantiomers and functionally equivalent compositions thereof may be used in any of the systems and methods described herein. "Functionally equivalent" also refers to compositions capable of treatment of a subject that is wounded or exhibits symptoms of cancer (or other conditions described herein), a subject susceptible to or otherwise at increased risk for cancer, or a subject not exhibiting symptoms of cancer, but for whom it is desired to decrease the risk of cancer (e.g., a vaccination or a prophylactic treatment), etc. It will be understood that one of ordinary skill in the art will be able to manipulate the conditions in a manner to prepare such homologs, analogs, derivatives, enantiomers and functionally equivalent compositions as necessary. Homologs, analogs, derivatives, enantiomers and/or functionally equivalent compositions that are about as effective or more effective than the parent compound are also intended for use in the systems and methods of the invention. The synthesis of such compositions may be accomplished through typical chemical modification methods such as those routinely practiced by those of ordinary skill in the art.

The indefinite articles "a" and "an," as used herein in the specification and in the claims, unless clearly indicated to the contrary, should be understood to mean "one or more."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc.

As used herein in the specification and in the claims, unless clearly indicated to the contrary, "or" should be understood to have the same meaning as "and/or" as defined above. For example, when separating items in a list, "or" and "and/or" each shall be interpreted as being inclusive, i.e., the inclusion of at least one, but also including more than one, of a number or list of elements, and, optionally, additional unlisted items. In general, the term "or" as used herein shall only be interpreted as indicating exclusive alternatives (i.e. "one or the other but not both") when preceded by terms of exclusivity, such as "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and " consisting essentially of" shall be closed or semi-closed transitional phrases, respectively, as set forth in the United States Patent Office Manual of Patent Examining Procedures, Section 2111.03.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

REFERENCES

1. Brundtland, G. H., World Cancer Report, ed. B. W. Stewart and P. Kleihues. 2003, Lyon: International Agency for Research on Cancer, World Health Organization. 352.
2. Bhushan, A., et al., Drug resistance results in alterations in expression of immune recognition molecules and failure to express Fas (CD95). 1998, 1998. 76: p. 350-356.
3. Marrack, P. and J. Kappler, *The T cell receptor*. Science, 1987. 238: p. 1073-1079.
4. Bretscher, P. A. and M. Cohn, *A theory of self-nonself discrimination*. Science, 1970. 169: p. 1042-1049.
5. Linsley, P. S. and J. A. Ledbetter, *The role of the CD28 receptor during T cell responses to antigen*. Ann. Rev. Immunol., 1993. 11: p. 191-212.
6. Linsley, P. S., et al., *Human B7-1 (CD80) and B7-2 (CD86) bind with similar avidities but distinct kinetics to CD28 and CTLA4*. Immunity, 1994. 1: p. 793-801.
7. June, C. H., et al., *The B7 and CD28 receptor families*. Immunol. Today, 1994. 15: p. 321-330.
8. Kuchroo, V. K., et al., *B7-1 and B7-2 costimulatory molecules activate differentially the Th1/Th2 developmental pathways: application to autoimmune disease therapy*. Cell, 1995. 80: p. 707-718.
9. Lanier, L. L., et al., *CD80(B7) and CD86(B70) provide similiar costimulatory signals for T cell proliferation, cytokine production, and generation of CTL*. Journal of Immunology, 1995. 154: p. 97-105.
10. Alderson, M. R., et al., *Fas transduces activation signals in normal human T lymphocytes*. J. Exp. Med., 1993. 178: p. 2231-2235.
11. Nagata, S., *Human autoimmune lymphoproliferative syndrome, a defect in the apoptosis-inducing Fas receptor: a lesson from the mouse model*. J. Human Genetics, 1998. 43(1): p. 2-8.
12. Desbarats, J., et al., *Dichotomy between naive and memory $CD4^+$ T cell responses to Fas (CD95) engagement*. Proc. Natl. Acad. Sci. USA, 1999. 96: p. 8104-8109.
13. Desbarats, J. and M. K. Newell, *Fas engagement accelerates liver regeneration after partial hepatectomy*. Nature Medicine, 2000. 6(8): p. 920-923.
14. Pollock, B. H., et al., *Risk factors for pediatric human immunodeficiency virus-related malignancy*. JAMA, 2003. 289(18): p. 2393-9.
15. Mavligit, G. M., et al., *Cell-mediated immunity to human solid tumors: in vitro detection by lymphocyte blastogenic responses to cell-associated and solubilized tumor antigens*. Natl Cancer Inst Monogr, 1973. 37: p. 167-76.
16. Whelan, M., et al., *Cancer immunotherapy: an embarrassment of riches?* Drug Discov Today, 2003. 8(6): p. 253-8.
17. Martindale, D., *T Cell Triumph. Immunotherapy may have finally turned a corner*. Sci Am, 2003. 288(2): p. 18-19.
18. Tsuruo, T., et al., *Molecular targeting therapy of cancer: drug resistance, apoptosis and survival signal*. Cancer Sci, 2003. 94(1): p. 15-21.
19. Newell, M. K., et al., *Does the Oxidative/Glycolytic Ratio Determine Proliferation or Death in Immune Recognition?* Ann. of the New York Acad. of Sciences, 1999. 887: p. 77-82.
20. Nagata, S. and P. Golstein, *The Fas death factor*. Science, 1995. 267: p. 1449-1456.
21. Nagata, S., *Apoptosis by death factor*. Cell, 1997. 88: p. 355-365.
22. Schneider, P. and J. Tschopp, *Apoptosis induced by death receptors*. Pharm Acta Helv, 2000. 74(2-3): p. 281-6.
23. Kataoka, T., et al., *Expression level of c-FLIP versus Fas determines susceptibility to Fas ligand-induced cell death in murine thymoma EL-4 cells*. Exp Cell Res, 2002. 273(2): p. 256-64.
24. Harper, M.-E., et al., *Characterization of a novel metabolic strategy used by drug-resistant tumor cells*. FASEB, 2002. 16: p. in press.
25. Sinkovics, J. G. and J. C. Horvath, *Virological and immunological connotations of apoptotic and anti-apoptotic-forces in neoplasia*, Int J Oncol, 2001. 19(3): p. 473-88.
26. Green, D. R. and G. I. Evan, *A matter of life and death*. Cancer Cell, 2002. 1(1): p. 19-30.
27. Tolomeo, M. and D. Simoni, *Drug resistance and apoptosis in cancer treatment: development of new apoptosis-inducing agents active in drug resistant malignancies*. Curr Med Chem Anti-Canc Agents, 2002. 2(3): p. 387-401.
28. Landowski, T. H., et al., *Myeloma cells selected for resistance to CD95-mediated apoptosis are not cross-resistant to cytotoxic drugs: evidence for independent mechanisms of caspase activation*. Blood, 1999. 94(1): p. 265-74.

What is claimed is:

1. A composition, comprising:
a therapeutically acceptable combination, suitable for administration to a patient, of an isolated fatty acid metabolism inhibitor, wherein the isolated fatty acid metabolism inhibitor is etomoxir, or a pharmacologically acceptable salt thereof and an isolated glucose metabolism inhibitor, wherein the isolated glucose metabolism inhibitor is a 2-deoxy-D-glucose compound.

2. The composition of claim 1, further comprising a colloidal dispersion system.

3. The composition of claim 2 wherein the colloidal dispersion system is a liposome.

4. The composition of claim 1 further comprising a pharmaceutically acceptable carrier.

5. The composition of claim 4 further comprising one or more chemotherapeutic agents.

6. The composition of claim 5 wherein one or more of the chemotherapeutic agents is selected from the group consisting of methotrexate, trimetrexate, adriamycin, taxotere, doxorubicin, 5-flurouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, and goserelin acetate.

* * * * *